United States Patent
Davis et al.

(10) Patent No.: US 11,421,030 B2
(45) Date of Patent: Aug. 23, 2022

(54) BTLA ANTIBODIES

(71) Applicants: Oxford University Innovation Limited, Oxford (GB); MiroBio Limited, Oxford (GB)

(72) Inventors: Simon John Davis, Oxford (GB); Richard John Cornall, Oxford (GB); Christopher Douglas Paluch, Oxford (GB)

(73) Assignees: MiroBio Limited, Oxford (GB); Oxford University Innovation Limited, Oxford (GB)

( * ) Notice: Subject to any disclaimer, the term of this patent is extended or adjusted under 35 U.S.C. 154(b) by 57 days.

(21) Appl. No.: 17/330,168

(22) Filed: May 25, 2021

(65) Prior Publication Data

US 2021/0277123 A1 Sep. 9, 2021

Related U.S. Application Data

(63) Continuation of application No. PCT/GB2019/053569, filed on Dec. 17, 2019.

(30) Foreign Application Priority Data

Dec. 17, 2018 (GB) ..................... 1820554

(51) Int. Cl.
| | | |
|---|---|---|
| C07K 16/00 | (2006.01) | |
| C07K 16/28 | (2006.01) | |
| A61P 37/06 | (2006.01) | |
| A61P 1/00 | (2006.01) | |
| A61K 39/00 | (2006.01) | |

(52) U.S. Cl.
CPC ............ *C07K 16/2818* (2013.01); *A61P 1/00* (2018.01); *A61P 37/06* (2018.01); *A61K 2039/505* (2013.01); *C07K 2317/24* (2013.01); *C07K 2317/33* (2013.01); *C07K 2317/51* (2013.01); *C07K 2317/515* (2013.01); *C07K 2317/55* (2013.01); *C07K 2317/565* (2013.01); *C07K 2317/75* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 4,816,567 A | 3/1989 | Cabilly et al. | |
| 5,312,335 A | 5/1994 | McKinnon et al. | |
| 5,770,429 A | 6/1998 | Lonberg et al. | |
| 5,807,715 A | 9/1998 | Morrison et al. | |
| 6,075,181 A | 6/2000 | Kucherlapati et al. | |
| 6,150,584 A | 11/2000 | Kucherlapati et al. | |
| 6,331,415 B1 | 12/2001 | Cabilly et al. | |
| 6,620,135 B1 | 9/2003 | Weston et al. | |
| 6,982,321 B2 | 1/2006 | Winter | |
| 7,041,870 B2 | 5/2006 | Tomizuka et al. | |
| 7,087,409 B2 | 8/2006 | Barbas, III et al. | |
| 7,189,826 B2 | 3/2007 | Rodman | |
| 2007/0061900 A1 | 3/2007 | Murphy et al. | |

FOREIGN PATENT DOCUMENTS

| | | |
|---|---|---|
| WO | WO-9704801 A1 | 2/1997 |
| WO | WO-2008076560 A2 | 6/2008 |
| WO | WO-2010106051 A1 | 9/2010 |
| WO | WO-2011014438 A1 | 2/2011 |
| WO | WO-2016176583 A1 | 11/2016 |
| WO | WO-2017004213 A1 | 1/2017 |
| WO | WO-2017096017 A1 | 6/2017 |
| WO | WO-2018213113 A1 | 11/2018 |

OTHER PUBLICATIONS

Meibohm (Pharmacokinetics and Pharmacodynamics of Biotech Drugs, Wiley-VHC, 2006, chapter 3, p. 45-91) (Year: 2006).*
White et al. (2001, Ann. Rev. Med., 2001, 52:125-145) (Year: 2001).*
Kulkarni-Kale et al. Nucleic Acid Research, 2005, 33:W168-W171 (Year: 2005).*
Corada (Blood, 2001; 97:1679-84) (Year: 2001).*
Berglund et al, Protein Science, 2008, 17:606-613 (Year: 2008).*
Padlan (Advances in Protein Chemistry, 1996, 49:57-133) (Year: 1996).*
Almagro & Fransson, Frontiers in Bioscience 2008; 13:1619-33 (Year: 2008).*
Albring et al.: Targeting of B and T lymphocyte associated (BTLA) prevents graft-versus-host disease without global immunosuppression. J Exp Med. 207(12):2551-2559 (2010).
Altschul et al., "Basic Local Alignment Search Tool," J. Mol. Biol. 215:403-410 (1990).
Argos, An investigation of oligopeptides linking domains in protein tertiary structures and possible candidates for general gene fusion., 1990, J Mol. Biol. 211:943-58, doi:10.1016/0022-2836(90)90085-.
Bird, et al. Single-chain antigen-binding proteins. Science. Oct. 21, 1988;242(4877):423-426.
Boerner, et al. Production of antigen-specific human monoclonal antibodies from in vitro-primed human splenocytes. J Immunol. Jul. 1, 1991;147(1):86-95.
Brodeur et al., Monoclonal Antibody Production Techniques and Applications, pp. 51-63 (Marcel Dekker, Inc., New York, 1987).
Clackson et al. Making antibody fragments using phage display libraries. Nature 352(6336):624-628 (1991).
Clynes, et al. Inhibitory Fc receptors modulate in vivo cytotoxicity against tumour targets. Nat Med. Apr. 2000;6(4):443-6.

(Continued)

*Primary Examiner* — Meera Natarajan
(74) *Attorney, Agent, or Firm* — Wilson Sonsini Goodrich & Rosati

(57) ABSTRACT

This invention relates generally to antibodies or antigen binding fragments that bind to human B and T lymphocyte attenuator (BTLA) and uses thereof. More specifically, the invention relates to agonistic antibodies that bind human BTLA and modulate its activity, and their use in treating inflammatory, autoimmune and proliferative diseases and disorders.

28 Claims, 13 Drawing Sheets

Specification includes a Sequence Listing.

(56) References Cited

OTHER PUBLICATIONS

Cockett et al.: High level expression of tissue inhibitor of metalloproteinases in Chinese hamster ovary cells using glutamine synthetase gene amplification. Biotechnology (NY) 8(7):662-667 (1990).
Compaan et al. Attenuating lymphocyte activity: the crystal structure of the BTLA-HVEM complex. J Biol Chem 280(47):39553-39561 (2005).
Crawford et al.: Editorial: Therapeutic potential of targeting BTLA. J Leukoc Biol. 86(1):5-8 (2009).
Davis et al.: The role of charged residues mediating low affinity protein-protein recognition at the cell surface by CD2. Proc Natl Acad Sci USA 95(10):5490-5494 (1998).
Del Rio et al.: Detection of protein on BTLAlow cells and in vivo antibody-mediated downmodulation of BTLA on lymphoid and myeloid cells of C57BL/6 and BALB/c BTLA allelic variants. Immunobiology 215(7):570-578 (2010).
Foecking et al.: Powerful and versatile enhancer-promoter unit for mammalian expression vectors. Gene 45(1):101-105 (1986).
GenBank: AJ717664.1: *Homo sapiens* mRNA for B and T lymphocyte attenuator (BTLA gene), https://www.ncbi.nlm.nih.gov/nuccore/AJ717664.1 (Published Oct. 8, 2008).
George, et al. An analysis of protein domain linkers: their classification and role in protein folding. Protein Eng. Nov. 2002;15(11):871-9.
Gurka et al.: Generation of novel anti-BTLA monoclonal antibodies for in vivo use and their functional testing at near-physiological conditions. Hybridoma 28(6):405-414 (2009).
Han et al.: An inhibitory Ig superfamily protein expressed by lymphocytes and APCs is also an early marker of thymocyte positive selection. J Immunol. 172 (10):5931-5939 (2004).
Harris: Production of humanized monoclonal antibodies for in vivo imaging and therapy. Biochem Soc Trans. 23(4):1035-1038 (1995).
Hollinger et al., "Diabodies": Small bivalent and bispecific antibody fragments. Proc. Natl. Acad. Sci. USA 90:6444 6448 (1993).
Hurle, et al. Protein engineering techniques for antibody humanization. Curr Opin Biotechnol. Aug. 1994;5(4):428-33.
Jones et al. Replacing the complementarity-determining regions in a human antibody with those from a mouse. Nature, 321.6069 (1986): 522-5.
Kohler et al. Continuous cultures of fused cells secreting antibody of predefined specificity. Nature. Aug. 7, 1975;256(5517):495-7.
Kostelny et al. Formation of a bispecific antibody by the use of leucine zippers. J. Immunol. 148(5):1547-1553 (1992).
Kozbor et al.: A human hybrid myeloma for production of human monoclonal antibodies. J Immunol. 133(6):3001-3005 (1984).
Krieg et al.: Functional analysis of B and T lymphocyte attenuator engagement on CD4+ and CD8+ T cells. J Immunol. 175(10):6420-6427 (2005).
Leath et al.: Single-chain antibodies: A therapeutic modality for cancer gene therapy (review). Int J Oncol. 24(4):765-771 (2004).
Leitner et al.: T cell stimulator cells, an efficient and versatile cellular system to assess the role of costimulatory ligands in the activation of human T cells. J Immunol Methods. 362:131-141 (2010).
Li, et al. Human antibodies for immunotherapy development generated via a human B cell hybridoma technology. Proc Natl Acad Sci USA. Mar. 7, 2006;103(10):3557-62. Epub Feb. 27, 2006.
Lonberg et al., Human antibodies from transgenic animals. Nature Biotechnology 23(9):1117-1125 (2005).
Marks, et al. By-passing immunization. Human antibodies from V-gene libraries displayed on phage. J Mol Biol. 222(3):581-97, 1991.
Mauro et al.: A critical analysis of codon optimization in human therapeutics. Trends Mol Med. 20(11):604-613 (2014).
Milstein et al.: Hybrid hybridomas and their use in immunohistochemistry. Nature 305(5934):537-540 (1983).
Murphy et al.: Slow down and survive: enigmatic immunoregulation by BTLA and HVEM. Ann Rev Immunol 28:389-411 (2010).
NCBI Reference Sequence: XP_005548224.1: Predicted: B- and T-lymphocyte attenuator isoform X3 [Macaca fascicularis], https://www.ncbi.nlm.nih.gov/protein/XP_005548224 (Published Jan. 25, 2016).
Ostanin et al. T cell transfer model of chronic colitis: concepts, considerations, and tricks of the trade. Am J Physiol Gastrointest Liver Physiol. Feb. 2009; 296(2): G135-G146. Published online Nov. 25, 2008. doi: 10.1152/ajpgi.90462.2008.
Otsuki et al. Expression and function of the B and T lymphocyte attenuator (BTLA/CD272) on human T cells. Biochem Biophys Res Comm 344:1121-1127 (2006).
Oya et al.: Development of autoimmune hepatitis-like disease and production of autoantibodies to nuclear antigens in mice lacking B and T lymphocyte attenuator. Arthritis Rheum. 58(8):2498-2510 (2008).
Paluch: Manipulating immune checkpoint signalling pathways with antibodies. Thesis, University of Oxford [1-231] (2019).
PCT/GB2019/053569 International Search Report and Written Opinion dated Jun. 23, 2020.
Presta: Antibody Engineering. Curr Op Struct Biol 2:593-596 (1992).
Riechmann et al., "Reshaping human antibodies fortherapy," Nature 332:323-327 (1988).
Sakoda et al.: Dichotomous regulation of GVHD through bidirectional functions of the BTLA-HVEM pathway. Blood 117(8):2506-2514 (2011).
Sedy et al.: B and T lymphocyte attenuator regulates T cell activation through interaction with herpesvirus entry mediator. Nat Immunol. 6(1):90-98 (2005).
Shui et al.: Regulation of inflammation, autoimmunity, and infection immunity by HVEM-BTLA signaling. J Leukoc Biol. 89(4):517-523 (2011).
Smith et al. Identification of common molecular subsequences. J Mol Biol 147:195-197 (1981).
Songsivilai et al.: Bispecific antibody: a tool for diagnosis and treatment of disease. Clin. Exp. Immunol. 79(3):315-321 (1990).
Tiller et al.: Cloning and expression of murine Ig genes from single B cells. J Immunol Methods 350(1-2):183-193 (2009).
Traunecker et al. Bispecific single chain molecules (Janusins) target cytotoxic lymphocytes on HIV infected cells. EMBO J. 10(12):3655-9 (1991).
Traunecker et al.: Janusin: new molecular design for bispecific reagents. Int J Cancer Suppl. 7:51-52 (1992).
Vaswani et al.: Humanized antibodies as potential therapeutic drugs. Ann Allergy Asthma Immunol. 81(2):105-119 (1998).
Vollmers, et al. Death by stress: natural IgM-induced apoptosis. Methods Find Exp Clin Pharmacol. Apr. 2005;27(3):185-91.
Vollmers et al.: The "early birds": natural IgM antibodies and immune surveillance. Histol Histopathol. 20(3):927-937 (2005).
Watanabe et al. BTLA is a lymphocyte inhibitory receptor with similarities to CTLA-4 and PD-1. Nat Immunol 4(7):670-679 (2003).

\* cited by examiner a b

SEQUENCE LISTING

```
<160> NUMBER OF SEQ ID NOS: 390

<210> SEQ ID NO 1
<211> LENGTH: 8
<212> TYPE: PRT
<213> ORGANISM: Mus musculus

<400> SEQUENCE: 1

Gly Asp Ser Ile Thr Ser Ala Tyr
1               5

<210> SEQ ID NO 2
<211> LENGTH: 7
<212> TYPE: PRT
<213> ORGANISM: Mus musculus

<400> SEQUENCE: 2

Ile Ser Tyr Ser Gly Ser Thr
1               5

<210> SEQ ID NO 3
<211> LENGTH: 12
<212> TYPE: PRT
<213> ORGANISM: Mus musculus

<400> SEQUENCE: 3

Ala Arg Ser His Tyr Tyr Gly Tyr Tyr Phe Asp Tyr
1               5                   10

<210> SEQ ID NO 4
<211> LENGTH: 10
<212> TYPE: PRT
<213> ORGANISM: Mus musculus

<400> SEQUENCE: 4

Glu Thr Ile Asp Ser Tyr Gly Asp Ser Leu
1               5                   10

<210> SEQ ID NO 5
```

```
<211> LENGTH: 3
<212> TYPE: PRT
<213> ORGANISM: Mus musculus

<400> SEQUENCE: 5

Arg Ala Ser
1

<210> SEQ ID NO 6
<211> LENGTH: 9
<212> TYPE: PRT
<213> ORGANISM: Mus musculus

<400> SEQUENCE: 6

Gln Gln Thr Asp Glu Asp Pro Tyr Thr
1               5

<210> SEQ ID NO 7
<211> LENGTH: 8
<212> TYPE: PRT
<213> ORGANISM: Mus musculus

<400> SEQUENCE: 7

Gly Phe Ser Leu Thr Thr Tyr Gly
1               5

<210> SEQ ID NO 8
<211> LENGTH: 7
<212> TYPE: PRT
<213> ORGANISM: Mus musculus

<400> SEQUENCE: 8

Met Trp Pro Gly Gly Arg Thr
1               5

<210> SEQ ID NO 9
<211> LENGTH: 14
<212> TYPE: PRT
<213> ORGANISM: Mus musculus

<400> SEQUENCE: 9

Val Arg Gly Asp Tyr Glu Tyr Asp Tyr Tyr Ala Met Asp Tyr
1               5                   10

<210> SEQ ID NO 10
<211> LENGTH: 5
<212> TYPE: PRT
<213> ORGANISM: Mus musculus

<400> SEQUENCE: 10

Ser Ser Val Ser Tyr
1               5

<210> SEQ ID NO 11
<211> LENGTH: 3
<212> TYPE: PRT
<213> ORGANISM: Mus musculus

<400> SEQUENCE: 11

Ala Thr Ser
1

<210> SEQ ID NO 12
<211> LENGTH: 9
<212> TYPE: PRT
```

```
<213> ORGANISM: Mus musculus

<400> SEQUENCE: 12

His Gln Trp Ser Ser Asn Pro Tyr Thr
1               5

<210> SEQ ID NO 13
<211> LENGTH: 120
<212> TYPE: PRT
<213> ORGANISM: Artificial Sequence
<220> FEATURE:
<223> OTHER INFORMATION: Humanised antibody 2.8.6 VH region

<400> SEQUENCE: 13

Gln Val Thr Leu Lys Glu Ser Gly Pro Ala Leu Val Lys Pro Thr Gln
1               5                   10                  15

Thr Leu Thr Leu Thr Cys Thr Val Ser Gly Phe Ser Leu Thr Thr Tyr
            20                  25                  30

Gly Val His Trp Ile Arg Gln Pro Pro Gly Lys Ala Leu Glu Trp Leu
        35                  40                  45

Gly Val Met Trp Pro Gly Gly Arg Thr Ser Tyr Asn Pro Ser Leu Lys
    50                  55                  60

Ser Arg Leu Thr Ile Thr Lys Asp Asn Ser Lys Ser Gln Val Val Leu
65                  70                  75                  80

Thr Met Thr Asn Met Asp Pro Val Asp Thr Ala Thr Tyr Tyr Cys Val
                85                  90                  95

Arg Gly Asp Tyr Glu Tyr Asp Tyr Tyr Ala Met Asp Tyr Trp Gly Gln
            100                 105                 110

Gly Thr Leu Val Thr Val Ser Ser
        115                 120

<210> SEQ ID NO 14
<211> LENGTH: 106
<212> TYPE: PRT
<213> ORGANISM: Artificial Sequence
<220> FEATURE:
<223> OTHER INFORMATION: Humanised antibody 2.8.6 VL region

<400> SEQUENCE: 14

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Ser Ser Val Ser Tyr Met
            20                  25                  30

His Trp Tyr Gln Gln Lys Pro Gly Gln Ala Pro Arg Pro Leu Ile Tyr
        35                  40                  45

Ala Thr Ser Asn Arg Ala Thr Gly Ile Pro Ala Arg Phe Ser Gly Ser
    50                  55                  60

Gly Ser Gly Thr Asp Tyr Thr Leu Thr Ile Ser Ser Leu Glu Pro Glu
65                  70                  75                  80

Asp Phe Ala Val Tyr Tyr Cys His Gln Trp Ser Ser Asn Pro Tyr Thr
                85                  90                  95

Phe Gly Gln Gly Thr Lys Leu Glu Ile Lys
            100                 105

<210> SEQ ID NO 15
<211> LENGTH: 106
<212> TYPE: PRT
<213> ORGANISM: Mus musculus

<400> SEQUENCE: 15
```

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Val Ser Tyr Met
            20                  25                  30

His Trp Tyr Gln Gln Lys Pro Gly Ser Ser Pro Lys Pro Trp Ile Tyr
                35                  40                  45

Ala Thr Ser Asn Leu Ala Ser Gly Val Pro Ala Arg Phe Ser Gly Ser
        50                  55                  60

Gly Ser Gly Thr Ser Tyr Ser Leu Thr Ile Ser Arg Met Glu Ala Glu
65              70                  75                  80

Asp Ala Ala Thr Tyr Tyr Cys His Gln Trp Ser Asn Pro Tyr Thr
                85                  90                  95

Phe Gly Gly Gly Thr Lys Leu Glu Ile Lys
            100                 105

<210> SEQ ID NO 16
<211> LENGTH: 319
<212> TYPE: DNA
<213> ORGANISM: Mus musculus

<400> SEQUENCE: 16
caaattgttc tctcccagtc tccagcaatc ctgtctgcat ctccagggga gaaggtcaca    60
atgacttgca gggccagttc aagtgtaagt tacatgcact ggtaccagca gaagccagga   120
tcctccccca aaccctggat ttatgccaca tccaacctgg cttctggagt ccctgctcgc   180
ttcagtggca gtgggtctgg gacctcttac tctctcacaa tcagcagaat ggaggctgaa   240
gatgctgcca cttattactg ccaccagtgg agtagtaacc cgtacacgtt cggagggggg   300
accaagctgg aaataaaac                                                319

<210> SEQ ID NO 17
<211> LENGTH: 120
<212> TYPE: PRT
<213> ORGANISM: Mus musculus

<400> SEQUENCE: 17

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Thr Tyr
            20                  25                  30

Gly Val His Trp Val Arg Gln Ser Pro Gly Lys Gly Leu Glu Trp Leu
                35                  40                  45

Gly Val Met Trp Pro Gly Gly Arg Thr Ser Tyr Asn Pro Ala Pro Met
        50                  55                  60

Ser Arg Leu Ser Ile Ser Lys Asp Asn Ser Lys Ser Gln Val Phe Leu
65              70                  75                  80

Lys Met Asn Ser Leu Gln Thr Asp Asp Thr Ala Met Tyr Tyr Cys Val
                85                  90                  95

Arg Gly Asp Tyr Glu Tyr Asp Tyr Tyr Ala Met Asp Tyr Trp Gly Gln
                100                 105                 110

Gly Thr Ser Val Thr Val Ser Ser
        115                 120

<210> SEQ ID NO 18
<211> LENGTH: 361
<212> TYPE: DNA
<213> ORGANISM: Mus musculus

<400> SEQUENCE: 18

```
caggtgcagc tgaaggagtc tggacctggc ctggtggcgc cctcacagag cctgtccatc    60
acttgcactg tctctgggtt ttcattaacc acctatggtg tacactgggt tcgccagtct   120
ccaggaaagg gtctggagtg gctgggagta atgtggcctg gtggaagaac aagttataat   180
ccggctccca tgtccagact gagcatcagc aaagacaact ccaagagcca gttttcttta   240
aaaatgaaca gtctgcaaac tgatgacacg gccatgtact actgtgtcag aggggactat   300
gaatacgatt actatgctat ggactactgg ggtcaaggaa cctcagtcac cgtctcctca   360
g                                                                   361
```

<210> SEQ ID NO 19
<211> LENGTH: 111
<212> TYPE: PRT
<213> ORGANISM: Mus musculus

<400> SEQUENCE: 19

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Thr Ile Asp Ser Tyr
            20                  25                  30

Gly Asp Ser Leu Met His Trp Tyr Gln Gln Lys Ala Gly Gln Pro Pro
        35                  40                  45

Lys Leu Leu Ile Tyr Arg Ala Ser Asn Leu Glu Ser Gly Ile Pro Ala
    50                  55                  60

Arg Phe Ser Gly Ser Gly Ser Arg Thr Asp Phe Thr Leu Thr Ile Asn
65                  70                  75                  80

Pro Val Glu Ala Asp Asp Val Ala Thr Tyr Tyr Cys Gln Gln Thr Asp
                85                  90                  95

Glu Asp Pro Tyr Thr Phe Gly Gly Gly Thr Lys Leu Glu Ile Lys
            100                 105                 110

<210> SEQ ID NO 20
<211> LENGTH: 333
<212> TYPE: DNA
<213> ORGANISM: Mus musculus

<400> SEQUENCE: 20

```
gacattgtgc tgacccaatc tccagcttct ttggctgtgt ctctagggca gagggccacc    60
atatcctgca gagccagtga aactattgat agttatggcg atagtttaat gcactggtac   120
cagcagaaag caggacagcc acccaaactc ctcatctatc gtgcatccaa cctagaatct   180
gggatccctg ccaggttcag tggcagtggg tctcggacag acttcaccct caccattaat   240
cctgtggagg ctgatgatgt tgcaacctat tactgtcagc aaactgatga ggatccgtac   300
acgttcggag gggggaccaa gctggaaata aaa                                333
```

<210> SEQ ID NO 21
<211> LENGTH: 118
<212> TYPE: PRT
<213> ORGANISM: Mus musculus

<400> SEQUENCE: 21

Glu Val Gln Leu Gln Glu Ser Gly Pro Ser Leu Val Lys Pro Ser Gln
1               5                   10                  15

Thr Leu Ser Leu Thr Cys Ser Val Thr Gly Asp Ser Ile Thr Ser Ala
            20                  25                  30

Tyr Trp Asn Trp Ile Arg Lys Phe Pro Gly Asn Lys Leu Glu Tyr Met
         35                  40                  45

Gly Tyr Ile Ser Tyr Ser Gly Ser Thr Tyr Phe Asn Pro Ser Leu Lys
 50                  55                  60

Ser Arg Ile Ser Ile Thr Arg Asn Thr Ser Lys Asn Gln Tyr Tyr Leu
65                   70                  75                  80

Gln Leu Asn Ser Val Thr Thr Glu Asp Thr Ala Thr Tyr Tyr Cys Ala
                 85                  90                  95

Arg Ser His Tyr Tyr Gly Tyr Tyr Phe Asp Tyr Trp Gly His Gly Thr
                 100                 105                 110

Thr Leu Thr Val Ser Ser
         115

<210> SEQ ID NO 22
<211> LENGTH: 354
<212> TYPE: DNA
<213> ORGANISM: Mus musculus

<400> SEQUENCE: 22
gaggtgcagc ttcaggagtc aggacctagc ctcgtgaaac cttctcagac tctgtccctc    60
acctgttctg tcactggcga ctccatcacc agtgcttact ggaactggat ccggaaattc   120
ccagggaata acttgagta catggggtac ataagctaca gtggtagcac ttacttcaat    180
ccatctctca aaagtcgaat ctccatcact cgaaacacat ccaagaacca gtactacctg   240
cagttgaatt ctgtgactac tgaggacaca gccacatatt actgtgcaag atctcattac   300
tacggctact actttgacta ctggggccat ggcaccactc tcacagtctc ctca          354

<210> SEQ ID NO 23
<211> LENGTH: 289
<212> TYPE: PRT
<213> ORGANISM: Homo sapiens
<220> FEATURE:
<221> NAME/KEY: MISC_FEATURE
<222> LOCATION: (1)..(30)
<223> OTHER INFORMATION: signal sequence
<220> FEATURE:
<221> NAME/KEY: MISC_FEATURE
<222> LOCATION: (31)..(151)
<223> OTHER INFORMATION: extracellular region
<220> FEATURE:
<221> NAME/KEY: MISC_FEATURE
<222> LOCATION: (152)..(178)
<223> OTHER INFORMATION: transmembrane region
<220> FEATURE:
<221> NAME/KEY: MISC_FEATURE
<222> LOCATION: (179)..(289)
<223> OTHER INFORMATION: intracellular region

<400> SEQUENCE: 23

Met Lys Thr Leu Pro Ala Met Leu Gly Thr Gly Lys Leu Phe Trp Val
1               5                   10                  15

Phe Phe Leu Ile Pro Tyr Leu Asp Ile Trp Asn Ile His Gly Lys Glu
                20                  25                  30

Ser Cys Asp Val Gln Leu Tyr Ile Lys Arg Gln Ser Glu His Ser Ile
             35                  40                  45

Leu Ala Gly Asp Pro Phe Glu Leu Glu Cys Pro Val Lys Tyr Cys Ala
         50                  55                  60

Asn Arg Pro His Val Thr Trp Cys Lys Leu Asn Gly Thr Thr Cys Val
65                   70                  75                  80

Lys Leu Glu Asp Arg Gln Thr Ser Trp Lys Glu Glu Lys Asn Ile Ser

```
                    85                  90                  95
Phe Phe Ile Leu His Phe Glu Pro Val Leu Pro Asn Asp Asn Gly Ser
            100                 105                 110
Tyr Arg Cys Ser Ala Asn Phe Gln Ser Asn Leu Ile Glu Ser His Ser
            115                 120                 125
Thr Thr Leu Tyr Val Thr Asp Val Lys Ser Ala Ser Glu Arg Pro Ser
            130                 135                 140
Lys Asp Glu Met Ala Ser Arg Pro Trp Leu Leu Tyr Arg Leu Leu Pro
145                 150                 155                 160
Leu Gly Gly Leu Pro Leu Leu Ile Thr Thr Cys Phe Cys Leu Phe Cys
                165                 170                 175
Cys Leu Arg Arg His Gln Gly Lys Gln Asn Glu Leu Ser Asp Thr Ala
            180                 185                 190
Gly Arg Glu Ile Asn Leu Val Asp Ala His Leu Lys Ser Glu Gln Thr
            195                 200                 205
Glu Ala Ser Thr Arg Gln Asn Ser Gln Val Leu Leu Ser Glu Thr Gly
            210                 215                 220
Ile Tyr Asp Asn Asp Pro Asp Leu Cys Phe Arg Met Gln Glu Gly Ser
225                 230                 235                 240
Glu Val Tyr Ser Asn Pro Cys Leu Glu Glu Asn Lys Pro Gly Ile Val
                245                 250                 255
Tyr Ala Ser Leu Asn His Ser Val Ile Gly Pro Asn Ser Arg Leu Ala
                260                 265                 270
Arg Asn Val Lys Glu Ala Pro Thr Glu Tyr Ala Ser Ile Cys Val Arg
            275                 280                 285
Ser

<210> SEQ ID NO 24
<211> LENGTH: 289
<212> TYPE: PRT
<213> ORGANISM: Macaca fascicularis

<400> SEQUENCE: 24

Met Lys Thr Leu Pro Ala Met Leu Gly Ser Gly Arg Leu Phe Trp Val
1               5                   10                  15
Val Phe Leu Ile Pro Tyr Leu Asp Ile Trp Asn Ile His Gly Lys Glu
            20                  25                  30
Ser Cys Asp Val Gln Leu Tyr Ile Lys Arg Gln Ser Tyr His Ser Ile
            35                  40                  45
Phe Ala Gly Asp Pro Phe Lys Leu Glu Cys Pro Val Lys Tyr Cys Ala
        50                  55                  60
His Arg Pro Gln Val Thr Trp Cys Lys Leu Asn Gly Thr Thr Cys Val
65                  70                  75                  80
Lys Leu Glu Gly Arg His Thr Ser Trp Lys Gln Glu Lys Asn Leu Ser
                85                  90                  95
Phe Phe Ile Leu His Phe Glu Pro Val Leu Pro Ser Asp Asn Gly Ser
            100                 105                 110
Tyr Arg Cys Ser Ala Asn Phe Leu Ser Ala Ile Ile Glu Ser His Ser
            115                 120                 125
Thr Thr Leu Tyr Val Thr Asp Val Lys Ser Ala Ser Glu Arg Pro Ser
            130                 135                 140
Lys Asp Glu Met Ala Ser Arg Pro Trp Leu Leu Tyr Ser Leu Leu Pro
145                 150                 155                 160
Leu Gly Gly Leu Pro Leu Leu Ile Thr Thr Cys Phe Cys Leu Phe Cys
```

```
                      165                 170                 175
Phe Leu Arg Arg His Gln Gly Lys Gln Asn Glu Leu Ser Asp Thr Thr
                180                 185                 190
Gly Arg Glu Ile Thr Leu Val Asp Val Pro Phe Lys Ser Glu Gln Thr
            195                 200                 205
Glu Ala Ser Thr Arg Gln Asn Ser Gln Val Leu Leu Ser Glu Thr Gly
        210                 215                 220
Ile Tyr Asp Asn Glu Pro Asp Phe Cys Phe Arg Met Gln Glu Gly Ser
225                 230                 235                 240
Glu Val Tyr Ser Asn Pro Cys Leu Glu Glu Asn Lys Pro Gly Ile Ile
                245                 250                 255
Tyr Ala Ser Leu Asn His Ser Ile Ile Gly Leu Asn Ser Arg Gln Ala
                260                 265                 270
Arg Asn Val Lys Glu Ala Pro Thr Glu Tyr Ala Ser Ile Cys Val Arg
            275                 280                 285
Ser

<210> SEQ ID NO 25

<400> SEQUENCE: 25

000

<210> SEQ ID NO 26

<400> SEQUENCE: 26

000

<210> SEQ ID NO 27

<400> SEQUENCE: 27

000

<210> SEQ ID NO 28

<400> SEQUENCE: 28

000

<210> SEQ ID NO 29

<400> SEQUENCE: 29

000

<210> SEQ ID NO 30

<400> SEQUENCE: 30

000

<210> SEQ ID NO 31
<211> LENGTH: 5
<212> TYPE: PRT
<213> ORGANISM: Mus musculus

<400> SEQUENCE: 31

Ser Tyr Gly Ile Ser
1               5
```

```
<210> SEQ ID NO 32
<211> LENGTH: 17
<212> TYPE: PRT
<213> ORGANISM: Mus musculus

<400> SEQUENCE: 32

Glu Ile Tyr Pro Arg Ser Gly Asn Thr Tyr Tyr Asn Glu Lys Phe Lys
1               5                   10                  15

Gly

<210> SEQ ID NO 33
<211> LENGTH: 10
<212> TYPE: PRT
<213> ORGANISM: Mus musculus

<400> SEQUENCE: 33

Asn Tyr Gly Ser Ser Tyr Pro Phe Ala Tyr
1               5                   10

<210> SEQ ID NO 34
<211> LENGTH: 12
<212> TYPE: PRT
<213> ORGANISM: Mus musculus

<400> SEQUENCE: 34

Ser Ala Ser Ser Ser Val Ser Ser Ser Tyr Leu His
1               5                   10

<210> SEQ ID NO 35
<211> LENGTH: 7
<212> TYPE: PRT
<213> ORGANISM: Mus musculus

<400> SEQUENCE: 35

Arg Thr Ser Asn Leu Ala Ser
1               5

<210> SEQ ID NO 36
<211> LENGTH: 9
<212> TYPE: PRT
<213> ORGANISM: Mus musculus

<400> SEQUENCE: 36

Gln Gln Trp Ser Gly Tyr Pro Phe Thr
1               5

<210> SEQ ID NO 37
<211> LENGTH: 5
<212> TYPE: PRT
<213> ORGANISM: Mus musculus

<400> SEQUENCE: 37

Asp Tyr Tyr Met Asn
1               5

<210> SEQ ID NO 38
<211> LENGTH: 17
<212> TYPE: PRT
<213> ORGANISM: Mus musculus

<400> SEQUENCE: 38

Asp Ile Asn Pro Asn Asn Gly Gly Thr Ser Tyr Asn Gln Lys Phe Lys
1               5                   10                  15

Gly
```

<210> SEQ ID NO 39
<211> LENGTH: 8
<212> TYPE: PRT
<213> ORGANISM: Mus musculus

<400> SEQUENCE: 39

Trp Arg Gln Leu Arg Ser Asp Tyr
1               5

<210> SEQ ID NO 40
<211> LENGTH: 11
<212> TYPE: PRT
<213> ORGANISM: Mus musculus

<400> SEQUENCE: 40

Leu Ala Ser Gln Thr Ile Gly Thr Trp Leu Ala
1               5                   10

<210> SEQ ID NO 41
<211> LENGTH: 7
<212> TYPE: PRT
<213> ORGANISM: Mus musculus

<400> SEQUENCE: 41

Ala Ala Thr Ser Leu Ala Asp
1               5

<210> SEQ ID NO 42
<211> LENGTH: 9
<212> TYPE: PRT
<213> ORGANISM: Mus musculus

<400> SEQUENCE: 42

Gln Gln Leu Tyr Ser Thr Pro Leu Thr
1               5

<210> SEQ ID NO 43
<211> LENGTH: 5
<212> TYPE: PRT
<213> ORGANISM: Mus musculus

<400> SEQUENCE: 43

Ser Tyr Trp Met His
1               5

<210> SEQ ID NO 44
<211> LENGTH: 17
<212> TYPE: PRT
<213> ORGANISM: Mus musculus

<400> SEQUENCE: 44

Met Ile His Pro Asn Asn Gly Ile Pro Asn Tyr Asn Glu Lys Phe Lys
1               5                   10                  15

Ser

<210> SEQ ID NO 45
<211> LENGTH: 12
<212> TYPE: PRT
<213> ORGANISM: Mus musculus

<400> SEQUENCE: 45

Glu Gly Tyr Tyr Gly Ser Glu Gly Tyr Phe Asp Val
1               5                   10

```
<210> SEQ ID NO 46
<211> LENGTH: 10
<212> TYPE: PRT
<213> ORGANISM: Mus musculus

<400> SEQUENCE: 46

Ser Ala Ser Ser Ser Ile Ser Tyr Ile His
1               5                   10

<210> SEQ ID NO 47
<211> LENGTH: 7
<212> TYPE: PRT
<213> ORGANISM: Mus musculus

<400> SEQUENCE: 47

Asp Thr Ser Lys Leu Ala Ser
1               5

<210> SEQ ID NO 48
<211> LENGTH: 9
<212> TYPE: PRT
<213> ORGANISM: Mus musculus

<400> SEQUENCE: 48

His Gln Arg Ser Thr Tyr Pro Tyr Thr
1               5

<210> SEQ ID NO 49

<400> SEQUENCE: 49

000

<210> SEQ ID NO 50

<400> SEQUENCE: 50

000

<210> SEQ ID NO 51

<400> SEQUENCE: 51

000

<210> SEQ ID NO 52

<400> SEQUENCE: 52

000

<210> SEQ ID NO 53

<400> SEQUENCE: 53

000

<210> SEQ ID NO 54

<400> SEQUENCE: 54

000

<210> SEQ ID NO 55
```

```
<400> SEQUENCE: 55

000

<210> SEQ ID NO 56
<211> LENGTH: 17
<212> TYPE: PRT
<213> ORGANISM: Mus musculus

<400> SEQUENCE: 56

Met Ile His Pro Asn Ser Gly Ser Thr Asn Tyr Asn Glu Lys Phe Lys
1               5                   10                  15

Ser

<210> SEQ ID NO 57
<211> LENGTH: 8
<212> TYPE: PRT
<213> ORGANISM: Mus musculus

<400> SEQUENCE: 57

Lys Arg Gly Gly Leu Gly Asp Tyr
1               5

<210> SEQ ID NO 58
<211> LENGTH: 15
<212> TYPE: PRT
<213> ORGANISM: Mus musculus

<400> SEQUENCE: 58

Arg Ala Ser Lys Ser Val Ser Thr Ser Gly Tyr Ser Tyr Met His
1               5                   10                  15

<210> SEQ ID NO 59
<211> LENGTH: 7
<212> TYPE: PRT
<213> ORGANISM: Mus musculus

<400> SEQUENCE: 59

Leu Ala Ser Asn Leu Glu Ser
1               5

<210> SEQ ID NO 60
<211> LENGTH: 9
<212> TYPE: PRT
<213> ORGANISM: Mus musculus

<400> SEQUENCE: 60

Gln His Ser Arg Glu Leu Pro Tyr Thr
1               5

<210> SEQ ID NO 61
<211> LENGTH: 5
<212> TYPE: PRT
<213> ORGANISM: Mus musculus

<400> SEQUENCE: 61

Ser Ser Trp Met Asn
1               5

<210> SEQ ID NO 62
<211> LENGTH: 17
<212> TYPE: PRT
<213> ORGANISM: Mus musculus

<400> SEQUENCE: 62
```

```
Arg Ile Tyr Pro Gly Asp Gly Asp Thr Asn Tyr Asn Gly Lys Phe Lys
1               5                   10                  15
Gly

<210> SEQ ID NO 63
<211> LENGTH: 8
<212> TYPE: PRT
<213> ORGANISM: Mus musculus

<400> SEQUENCE: 63

Arg Gly Tyr Gly Tyr Leu Ala Tyr
1               5

<210> SEQ ID NO 64
<211> LENGTH: 11
<212> TYPE: PRT
<213> ORGANISM: Mus musculus

<400> SEQUENCE: 64

Lys Ala Ser Gln Asp Val Ser Thr Ala Val Ala
1               5                   10

<210> SEQ ID NO 65
<211> LENGTH: 7
<212> TYPE: PRT
<213> ORGANISM: Mus musculus

<400> SEQUENCE: 65

Ser Ala Ser Tyr Arg Tyr Thr
1               5

<210> SEQ ID NO 66
<211> LENGTH: 9
<212> TYPE: PRT
<213> ORGANISM: Mus musculus

<400> SEQUENCE: 66

Gln Gln His Tyr Ser Thr Pro Tyr Thr
1               5

<210> SEQ ID NO 67

<400> SEQUENCE: 67

000

<210> SEQ ID NO 68

<400> SEQUENCE: 68

000

<210> SEQ ID NO 69
<211> LENGTH: 10
<212> TYPE: PRT
<213> ORGANISM: Mus musculus

<400> SEQUENCE: 69

Gly Tyr Gly Ser Ser Tyr Gly Phe Ala Tyr
1               5                   10

<210> SEQ ID NO 70

<400> SEQUENCE: 70
```

000

<210> SEQ ID NO 71

<400> SEQUENCE: 71

000

<210> SEQ ID NO 72
<211> LENGTH: 9
<212> TYPE: PRT
<213> ORGANISM: Mus musculus

<400> SEQUENCE: 72

Gln Gln Trp Ser Gly Tyr Pro Trp Thr
1               5

<210> SEQ ID NO 73
<211> LENGTH: 6
<212> TYPE: PRT
<213> ORGANISM: Mus musculus

<400> SEQUENCE: 73

Ser Gly Tyr Tyr Trp Asn
1               5

<210> SEQ ID NO 74
<211> LENGTH: 16
<212> TYPE: PRT
<213> ORGANISM: Mus musculus

<400> SEQUENCE: 74

Tyr Ile Ser Tyr Asp Gly Ser Asn Asn Tyr Asn Pro Ser Leu Lys Asn
1               5                   10                  15

<210> SEQ ID NO 75
<211> LENGTH: 10
<212> TYPE: PRT
<213> ORGANISM: Mus musculus

<400> SEQUENCE: 75

Ile Tyr Gly Asn Tyr Tyr Ala Met Asp Tyr
1               5                   10

<210> SEQ ID NO 76
<211> LENGTH: 10
<212> TYPE: PRT
<213> ORGANISM: Mus musculus

<400> SEQUENCE: 76

Ser Ala Ser Ser Ser Val Ser Tyr Met His
1               5                   10

<210> SEQ ID NO 77

<400> SEQUENCE: 77

000

<210> SEQ ID NO 78
<211> LENGTH: 9
<212> TYPE: PRT
<213> ORGANISM: Mus musculus

<400> SEQUENCE: 78

```
Gln Gln Trp Ser Ser Asn Pro Pro Thr
1               5

<210> SEQ ID NO 79
<211> LENGTH: 5
<212> TYPE: PRT
<213> ORGANISM: Mus musculus

<400> SEQUENCE: 79

Asp Tyr Tyr Met Ile
1               5

<210> SEQ ID NO 80
<211> LENGTH: 17
<212> TYPE: PRT
<213> ORGANISM: Mus musculus

<400> SEQUENCE: 80

Asn Ile Asn Pro Asn Asn Gly Gly Thr Thr Tyr Asn Gln Lys Phe Lys
1               5                   10                  15

Gly

<210> SEQ ID NO 81
<211> LENGTH: 10
<212> TYPE: PRT
<213> ORGANISM: Mus musculus

<400> SEQUENCE: 81

Gly Gly Leu Arg Pro Leu Tyr Phe Asp Tyr
1               5                   10

<210> SEQ ID NO 82
<211> LENGTH: 11
<212> TYPE: PRT
<213> ORGANISM: Mus musculus

<400> SEQUENCE: 82

Lys Ala Ser Glu Asn Val Asp Thr Tyr Val Ser
1               5                   10

<210> SEQ ID NO 83
<211> LENGTH: 7
<212> TYPE: PRT
<213> ORGANISM: Mus musculus

<400> SEQUENCE: 83

Gly Ala Ser Asn Arg Tyr Thr
1               5

<210> SEQ ID NO 84
<211> LENGTH: 9
<212> TYPE: PRT
<213> ORGANISM: Mus musculus

<400> SEQUENCE: 84

Gly Gln Ser Tyr Ser Tyr Pro Leu Thr
1               5

<210> SEQ ID NO 85
<211> LENGTH: 5
<212> TYPE: PRT
<213> ORGANISM: Mus musculus

<400> SEQUENCE: 85
```

```
Asn Thr Tyr Met His
1               5

<210> SEQ ID NO 86
<211> LENGTH: 17
<212> TYPE: PRT
<213> ORGANISM: Mus musculus

<400> SEQUENCE: 86

Arg Ile Asp Pro Ala Asn Gly Asn Thr Lys Tyr Asp Pro Lys Phe Gln
1               5                   10                  15

Gly

<210> SEQ ID NO 87
<211> LENGTH: 12
<212> TYPE: PRT
<213> ORGANISM: Mus musculus

<400> SEQUENCE: 87

Thr Tyr Tyr Gly Ser Ser Gln His Tyr Phe Asp Tyr
1               5                   10

<210> SEQ ID NO 88
<211> LENGTH: 16
<212> TYPE: PRT
<213> ORGANISM: Mus musculus

<400> SEQUENCE: 88

Lys Ser Ser Gln Ser Leu Leu Asp Ser Asp Gly Lys Thr Tyr Leu Asn
1               5                   10                  15

<210> SEQ ID NO 89
<211> LENGTH: 7
<212> TYPE: PRT
<213> ORGANISM: Mus musculus

<400> SEQUENCE: 89

Leu Val Ser Lys Leu Asp Ser
1               5

<210> SEQ ID NO 90
<211> LENGTH: 9
<212> TYPE: PRT
<213> ORGANISM: Mus musculus

<400> SEQUENCE: 90

Trp Gln Asp Thr His Phe Pro Gln Thr
1               5

<210> SEQ ID NO 91

<400> SEQUENCE: 91

000

<210> SEQ ID NO 92
<211> LENGTH: 17
<212> TYPE: PRT
<213> ORGANISM: Mus musculus

<400> SEQUENCE: 92

Arg Ile Tyr Pro Gly Asp Gly Asp Ala Asn Tyr Asn Gly Lys Phe Lys
1               5                   10                  15
```

Gly

<210> SEQ ID NO 93
<211> LENGTH: 15
<212> TYPE: PRT
<213> ORGANISM: Mus musculus

<400> SEQUENCE: 93

Glu Gly His Tyr Tyr Gly Ser Gly Tyr Arg Trp Tyr Leu Asp Val
1               5                   10                  15

<210> SEQ ID NO 94
<211> LENGTH: 11
<212> TYPE: PRT
<213> ORGANISM: Mus musculus

<400> SEQUENCE: 94

Arg Ala Ser Glu Asn Ile Tyr Ser Asn Leu Ala
1               5                   10

<210> SEQ ID NO 95
<211> LENGTH: 7
<212> TYPE: PRT
<213> ORGANISM: Mus musculus

<400> SEQUENCE: 95

Ala Ala Thr Asn Leu Ala Asp
1               5

<210> SEQ ID NO 96
<211> LENGTH: 9
<212> TYPE: PRT
<213> ORGANISM: Mus musculus

<400> SEQUENCE: 96

Gln His Phe Arg Gly Ala Pro Phe Thr
1               5

<210> SEQ ID NO 97
<211> LENGTH: 5
<212> TYPE: PRT
<213> ORGANISM: Mus musculus

<400> SEQUENCE: 97

Asp Tyr Glu Ile His
1               5

<210> SEQ ID NO 98
<211> LENGTH: 17
<212> TYPE: PRT
<213> ORGANISM: Mus musculus

<400> SEQUENCE: 98

Pro Ile Asp Pro Asp Thr Gly Asn Thr Ala Tyr Asn Gln Asn Leu Lys
1               5                   10                  15

Gly

<210> SEQ ID NO 99
<211> LENGTH: 11
<212> TYPE: PRT
<213> ORGANISM: Mus musculus

<400> SEQUENCE: 99

Gly Gly Tyr Asp Ser Asp Trp Gly Phe Ala Tyr

```
                       1               5                   10

<210> SEQ ID NO 100
<211> LENGTH: 16
<212> TYPE: PRT
<213> ORGANISM: Mus musculus

<400> SEQUENCE: 100

Arg Ser Ser Lys Ser Leu Leu His Ser Asn Gly Asn Thr Phe Leu Phe
1               5                   10                  15

<210> SEQ ID NO 101
<211> LENGTH: 7
<212> TYPE: PRT
<213> ORGANISM: Mus musculus

<400> SEQUENCE: 101

Arg Met Ser Asp Leu Ala Ser
1               5

<210> SEQ ID NO 102
<211> LENGTH: 9
<212> TYPE: PRT
<213> ORGANISM: Mus musculus

<400> SEQUENCE: 102

Met Gln His Leu Glu Tyr Pro Phe Thr
1               5

<210> SEQ ID NO 103
<211> LENGTH: 5
<212> TYPE: PRT
<213> ORGANISM: Mus musculus

<400> SEQUENCE: 103

Asp Tyr Tyr Leu Asn
1               5

<210> SEQ ID NO 104
<211> LENGTH: 17
<212> TYPE: PRT
<213> ORGANISM: Mus musculus

<400> SEQUENCE: 104

Leu Ile Asp Pro Tyr Asn Gly Gly Ser Ser Cys Asn Gln Lys Phe Lys
1               5                   10                  15

Gly

<210> SEQ ID NO 105
<211> LENGTH: 6
<212> TYPE: PRT
<213> ORGANISM: Mus musculus

<400> SEQUENCE: 105

Gly Asn Ala Met Asp Tyr
1               5

<210> SEQ ID NO 106

<400> SEQUENCE: 106

000

<210> SEQ ID NO 107
```

```
<211> LENGTH: 7
<212> TYPE: PRT
<213> ORGANISM: Mus musculus

<400> SEQUENCE: 107

Trp Ala Ser Thr Arg His Thr
1               5

<210> SEQ ID NO 108
<211> LENGTH: 9
<212> TYPE: PRT
<213> ORGANISM: Mus musculus

<400> SEQUENCE: 108

Gln Gln His Tyr Ile Ile Pro Tyr Met
1               5

<210> SEQ ID NO 109
<211> LENGTH: 5
<212> TYPE: PRT
<213> ORGANISM: Mus musculus

<400> SEQUENCE: 109

Asn Thr Tyr Met Tyr
1               5

<210> SEQ ID NO 110
<211> LENGTH: 17
<212> TYPE: PRT
<213> ORGANISM: Mus musculus

<400> SEQUENCE: 110

Arg Ile Asp Pro Ala Asn Gly Asn Thr Lys Tyr Ala Pro Lys Phe Gln
1               5                   10                  15

Gly

<210> SEQ ID NO 111
<211> LENGTH: 12
<212> TYPE: PRT
<213> ORGANISM: Mus musculus

<400> SEQUENCE: 111

Leu Tyr Tyr Gly Ser Ser Tyr Asp Tyr Phe Asp Tyr
1               5                   10

<210> SEQ ID NO 112

<400> SEQUENCE: 112

000

<210> SEQ ID NO 113

<400> SEQUENCE: 113

000

<210> SEQ ID NO 114
<211> LENGTH: 9
<212> TYPE: PRT
<213> ORGANISM: Mus musculus

<400> SEQUENCE: 114

Trp Gln Gly Thr His Phe Pro Gln Thr
1               5
```

<210> SEQ ID NO 115

<400> SEQUENCE: 115

000

<210> SEQ ID NO 116

<400> SEQUENCE: 116

000

<210> SEQ ID NO 117
<211> LENGTH: 12
<212> TYPE: PRT
<213> ORGANISM: Mus musculus

<400> SEQUENCE: 117

Thr Tyr Tyr Gly Ser Ser Gln Tyr Tyr Phe Asp Tyr
1               5                   10

<210> SEQ ID NO 118

<400> SEQUENCE: 118

000

<210> SEQ ID NO 119

<400> SEQUENCE: 119

000

<210> SEQ ID NO 120

<400> SEQUENCE: 120

000

<210> SEQ ID NO 121
<211> LENGTH: 5
<212> TYPE: PRT
<213> ORGANISM: Mus musculus

<400> SEQUENCE: 121

Asp Tyr Tyr Ile Asn
1               5

<210> SEQ ID NO 122
<211> LENGTH: 17
<212> TYPE: PRT
<213> ORGANISM: Mus musculus

<400> SEQUENCE: 122

Arg Ile Tyr Pro Gly Ser Gly Asn Thr Tyr Tyr Asn Glu Lys Phe Lys
1               5                   10                  15

Gly

<210> SEQ ID NO 123
<211> LENGTH: 7
<212> TYPE: PRT
<213> ORGANISM: Mus musculus

<400> SEQUENCE: 123

```
Gly Tyr Gly Asn Ser Asp Tyr
1               5

<210> SEQ ID NO 124
<211> LENGTH: 11
<212> TYPE: PRT
<213> ORGANISM: Mus musculus

<400> SEQUENCE: 124

Arg Ala Ser Gln Ser Ile Gly Thr Arg Ile His
1               5                   10

<210> SEQ ID NO 125
<211> LENGTH: 7
<212> TYPE: PRT
<213> ORGANISM: Mus musculus

<400> SEQUENCE: 125

Tyr Ala Ser Glu Ser Ile Ser
1               5

<210> SEQ ID NO 126
<211> LENGTH: 9
<212> TYPE: PRT
<213> ORGANISM: Mus musculus

<400> SEQUENCE: 126

Gln Gln Ser Asn Ser Trp Pro Tyr Thr
1               5

<210> SEQ ID NO 127
<211> LENGTH: 5
<212> TYPE: PRT
<213> ORGANISM: Mus musculus

<400> SEQUENCE: 127

Ser Tyr Ala Ile Arg
1               5

<210> SEQ ID NO 128
<211> LENGTH: 17
<212> TYPE: PRT
<213> ORGANISM: Mus musculus

<400> SEQUENCE: 128

Glu Ile Tyr Pro Arg Ser Gly Asn Thr Tyr Tyr Asn Glu Asn Phe Lys
1               5                   10                  15

Gly

<210> SEQ ID NO 129
<211> LENGTH: 10
<212> TYPE: PRT
<213> ORGANISM: Mus musculus

<400> SEQUENCE: 129

Ser Gly Gly Ala Ser Tyr Thr Met Asp Tyr
1               5                   10

<210> SEQ ID NO 130

<400> SEQUENCE: 130

000
```

<210> SEQ ID NO 131

<400> SEQUENCE: 131

000

<210> SEQ ID NO 132

<400> SEQUENCE: 132

000

<210> SEQ ID NO 133
<211> LENGTH: 5
<212> TYPE: PRT
<213> ORGANISM: Mus musculus

<400> SEQUENCE: 133

Ser Tyr Gly Leu Ile
1               5

<210> SEQ ID NO 134
<211> LENGTH: 17
<212> TYPE: PRT
<213> ORGANISM: Mus musculus

<400> SEQUENCE: 134

Glu Ile Tyr Pro Arg Ser Gly Ser Thr Tyr Tyr Asn Glu Trp Phe Lys
1               5                   10                  15

Gly

<210> SEQ ID NO 135
<211> LENGTH: 10
<212> TYPE: PRT
<213> ORGANISM: Mus musculus

<400> SEQUENCE: 135

Arg Arg Gly Thr Gly Asp Gly Phe Asp Tyr
1               5                   10

<210> SEQ ID NO 136
<211> LENGTH: 11
<212> TYPE: PRT
<213> ORGANISM: Mus musculus

<400> SEQUENCE: 136

Ser Ala Ser Gln Gly Ile Ser Asn Tyr Leu Asn
1               5                   10

<210> SEQ ID NO 137
<211> LENGTH: 7
<212> TYPE: PRT
<213> ORGANISM: Mus musculus

<400> SEQUENCE: 137

Tyr Thr Ser Ser Leu His Ser
1               5

<210> SEQ ID NO 138
<211> LENGTH: 9
<212> TYPE: PRT
<213> ORGANISM: Mus musculus

<400> SEQUENCE: 138

Gln Gln Tyr Ile Glu Leu Pro Phe Thr

```
1               5

<210> SEQ ID NO 139
<211> LENGTH: 5
<212> TYPE: PRT
<213> ORGANISM: Mus musculus

<400> SEQUENCE: 139

Asp Tyr Tyr Met His
1               5

<210> SEQ ID NO 140
<211> LENGTH: 17
<212> TYPE: PRT
<213> ORGANISM: Mus musculus

<400> SEQUENCE: 140

Tyr Ile Tyr Pro Asn Asn Gly Gly Asn Gly Tyr Asn Gln Lys Phe Lys
1               5                   10                  15

Gly

<210> SEQ ID NO 141
<211> LENGTH: 13
<212> TYPE: PRT
<213> ORGANISM: Mus musculus

<400> SEQUENCE: 141

Gly Asp Tyr Tyr Gly Ser Leu Arg Leu Thr Phe Ala Tyr
1               5                   10

<210> SEQ ID NO 142
<211> LENGTH: 17
<212> TYPE: PRT
<213> ORGANISM: Mus musculus

<400> SEQUENCE: 142

Lys Ser Ser Gln Ser Leu Leu Tyr Ser Ser Asn Gln Lys Asn Tyr Leu
1               5                   10                  15

Ala

<210> SEQ ID NO 143
<211> LENGTH: 7
<212> TYPE: PRT
<213> ORGANISM: Mus musculus

<400> SEQUENCE: 143

Trp Ala Ser Thr Arg Glu Ser
1               5

<210> SEQ ID NO 144
<211> LENGTH: 9
<212> TYPE: PRT
<213> ORGANISM: Mus musculus

<400> SEQUENCE: 144

Gln Gln Tyr Tyr Ser Tyr Pro Leu Thr
1               5

<210> SEQ ID NO 145
<211> LENGTH: 5
<212> TYPE: PRT
<213> ORGANISM: Mus musculus

<400> SEQUENCE: 145
```

```
Thr Tyr Gly Val Ser
1               5

<210> SEQ ID NO 146
<211> LENGTH: 17
<212> TYPE: PRT
<213> ORGANISM: Mus musculus

<400> SEQUENCE: 146

Trp Ile Asn Thr Tyr Ser Gly Val Pro Thr Tyr Ala Asp Asp Phe Lys
1               5                   10                  15

Gly

<210> SEQ ID NO 147
<211> LENGTH: 11
<212> TYPE: PRT
<213> ORGANISM: Mus musculus

<400> SEQUENCE: 147

Val Thr Thr Ile Leu His Trp Tyr Phe Asp Val
1               5                   10

<210> SEQ ID NO 148
<211> LENGTH: 11
<212> TYPE: PRT
<213> ORGANISM: Mus musculus

<400> SEQUENCE: 148

Arg Ala Ser Gln Glu Ile Ser Gly Tyr Leu Ser
1               5                   10

<210> SEQ ID NO 149
<211> LENGTH: 7
<212> TYPE: PRT
<213> ORGANISM: Mus musculus

<400> SEQUENCE: 149

Ala Ala Ser Thr Leu Asp Ser
1               5

<210> SEQ ID NO 150
<211> LENGTH: 9
<212> TYPE: PRT
<213> ORGANISM: Mus musculus

<400> SEQUENCE: 150

Leu Gln Tyr Ala Ser Tyr Pro Phe Thr
1               5

<210> SEQ ID NO 151

<400> SEQUENCE: 151

000

<210> SEQ ID NO 152

<400> SEQUENCE: 152

000

<210> SEQ ID NO 153

<400> SEQUENCE: 153
```

<210> SEQ ID NO 154

<400> SEQUENCE: 154

000

<210> SEQ ID NO 155

<400> SEQUENCE: 155

000

<210> SEQ ID NO 156

<400> SEQUENCE: 156

000

<210> SEQ ID NO 157

<400> SEQUENCE: 157

000

<210> SEQ ID NO 158

<400> SEQUENCE: 158

000

<210> SEQ ID NO 159
<211> LENGTH: 10
<212> TYPE: PRT
<213> ORGANISM: Mus musculus

<400> SEQUENCE: 159

Arg Arg Gly Ala Gly Asp Gly Phe Asp Tyr
1               5                   10

<210> SEQ ID NO 160

<400> SEQUENCE: 160

000

<210> SEQ ID NO 161

<400> SEQUENCE: 161

000

<210> SEQ ID NO 162
<211> LENGTH: 9
<212> TYPE: PRT
<213> ORGANISM: Mus musculus

<400> SEQUENCE: 162

Gln Gln Tyr Ser Lys Leu Pro Phe Thr
1               5

<210> SEQ ID NO 163

<400> SEQUENCE: 163

```
000

<210> SEQ ID NO 164
<400> SEQUENCE: 164

000

<210> SEQ ID NO 165
<400> SEQUENCE: 165

000

<210> SEQ ID NO 166
<400> SEQUENCE: 166

000

<210> SEQ ID NO 167
<400> SEQUENCE: 167

000

<210> SEQ ID NO 168
<400> SEQUENCE: 168

000

<210> SEQ ID NO 169
<211> LENGTH: 5
<212> TYPE: PRT
<213> ORGANISM: Mus musculus

<400> SEQUENCE: 169

Asp His Thr Ile His
1               5

<210> SEQ ID NO 170
<211> LENGTH: 17
<212> TYPE: PRT
<213> ORGANISM: Mus musculus

<400> SEQUENCE: 170

Tyr Ile Tyr Pro Arg Asp Gly Ser Thr Lys Tyr Asn Glu Lys Phe Lys
1               5                   10                  15

Gly

<210> SEQ ID NO 171
<211> LENGTH: 7
<212> TYPE: PRT
<213> ORGANISM: Mus musculus

<400> SEQUENCE: 171

Ser Asn Trp Asn Phe Asp Tyr
1               5

<210> SEQ ID NO 172
<211> LENGTH: 11
<212> TYPE: PRT
<213> ORGANISM: Mus musculus

<400> SEQUENCE: 172
```

```
Lys Ala Ser Gln Asp Val Gly Thr Ala Val Ala
1               5                   10

<210> SEQ ID NO 173
<211> LENGTH: 7
<212> TYPE: PRT
<213> ORGANISM: Mus musculus

<400> SEQUENCE: 173

Trp Ala Ser Thr Arg Arg Thr
1               5

<210> SEQ ID NO 174
<211> LENGTH: 9
<212> TYPE: PRT
<213> ORGANISM: Mus musculus

<400> SEQUENCE: 174

Gln Gln Tyr Ser Ser Tyr Pro Leu Thr
1               5

<210> SEQ ID NO 175

<400> SEQUENCE: 175

000

<210> SEQ ID NO 176

<400> SEQUENCE: 176

000

<210> SEQ ID NO 177

<400> SEQUENCE: 177

000

<210> SEQ ID NO 178

<400> SEQUENCE: 178

000

<210> SEQ ID NO 179

<400> SEQUENCE: 179

000

<210> SEQ ID NO 180
<211> LENGTH: 9
<212> TYPE: PRT
<213> ORGANISM: Mus musculus

<400> SEQUENCE: 180

Gln Gln His Tyr Ser Thr Pro Trp Thr
1               5

<210> SEQ ID NO 181

<400> SEQUENCE: 181

000
```

<210> SEQ ID NO 182
<211> LENGTH: 17
<212> TYPE: PRT
<213> ORGANISM: Mus musculus

<400> SEQUENCE: 182

Glu Ile Tyr Pro Arg Ser Gly Thr Thr Tyr Tyr Asn Glu Lys Phe Lys
1               5                   10                  15
Gly

<210> SEQ ID NO 183
<211> LENGTH: 10
<212> TYPE: PRT
<213> ORGANISM: Mus musculus

<400> SEQUENCE: 183

Arg Ile Ser Ser Gly Ser Gly Val Asp Tyr
1               5                   10

<210> SEQ ID NO 184

<400> SEQUENCE: 184

000

<210> SEQ ID NO 185

<400> SEQUENCE: 185

000

<210> SEQ ID NO 186
<211> LENGTH: 9
<212> TYPE: PRT
<213> ORGANISM: Mus musculus

<400> SEQUENCE: 186

Gln Gln Tyr Ser Glu Leu Pro Trp Thr
1               5

<210> SEQ ID NO 187
<211> LENGTH: 6
<212> TYPE: PRT
<213> ORGANISM: Mus musculus

<400> SEQUENCE: 187

Ser Gly Tyr Asp Trp His
1               5

<210> SEQ ID NO 188
<211> LENGTH: 16
<212> TYPE: PRT
<213> ORGANISM: Mus musculus

<400> SEQUENCE: 188

Tyr Ile Ser Tyr Ser Gly Ser Thr Asn Tyr Asn Pro Ser Leu Lys Ser
1               5                   10                  15

<210> SEQ ID NO 189
<211> LENGTH: 12
<212> TYPE: PRT
<213> ORGANISM: Mus musculus

<400> SEQUENCE: 189

Gly Thr Pro Val Val Ala Glu Asp Tyr Phe Asp Tyr
1               5                   10

<210> SEQ ID NO 190
<211> LENGTH: 14
<212> TYPE: PRT
<213> ORGANISM: Mus musculus

<400> SEQUENCE: 190

Arg Ser Ser Thr Gly Ala Val Thr Thr Ser Asn Tyr Ala Asn
1               5                   10

<210> SEQ ID NO 191
<211> LENGTH: 7
<212> TYPE: PRT
<213> ORGANISM: Mus musculus

<400> SEQUENCE: 191

Ala Thr Asn Asn Arg Ala Pro
1               5

<210> SEQ ID NO 192
<211> LENGTH: 9
<212> TYPE: PRT
<213> ORGANISM: Mus musculus

<400> SEQUENCE: 192

Ala Leu Trp Tyr Ser Asn His Leu Val
1               5

<210> SEQ ID NO 193
<211> LENGTH: 5
<212> TYPE: PRT
<213> ORGANISM: Mus musculus

<400> SEQUENCE: 193

Thr Tyr Gly Val His
1               5

<210> SEQ ID NO 194
<211> LENGTH: 16
<212> TYPE: PRT
<213> ORGANISM: Mus musculus

<400> SEQUENCE: 194

Val Met Trp Pro Gly Arg Thr Ser Tyr Asn Pro Ala Pro Met Ser
1               5                   10                  15

<210> SEQ ID NO 195
<211> LENGTH: 12
<212> TYPE: PRT
<213> ORGANISM: Mus musculus

<400> SEQUENCE: 195

Gly Asp Tyr Glu Tyr Asp Tyr Tyr Ala Met Asp Tyr
1               5                   10

<210> SEQ ID NO 196
<211> LENGTH: 10
<212> TYPE: PRT
<213> ORGANISM: Mus musculus

<400> SEQUENCE: 196

Arg Ala Ser Ser Ser Val Ser Tyr Met His
1               5                   10

```
<210> SEQ ID NO 197
<211> LENGTH: 7
<212> TYPE: PRT
<213> ORGANISM: Mus musculus

<400> SEQUENCE: 197

Ala Thr Ser Asn Leu Ala Ser
1               5

<210> SEQ ID NO 198

<400> SEQUENCE: 198

000

<210> SEQ ID NO 199
<211> LENGTH: 5
<212> TYPE: PRT
<213> ORGANISM: Mus musculus

<400> SEQUENCE: 199

Ser Ala Tyr Trp Asn
1               5

<210> SEQ ID NO 200
<211> LENGTH: 16
<212> TYPE: PRT
<213> ORGANISM: Mus musculus

<400> SEQUENCE: 200

Tyr Ile Ser Tyr Ser Gly Ser Thr Tyr Phe Asn Pro Ser Leu Lys Ser
1               5                   10                  15

<210> SEQ ID NO 201
<211> LENGTH: 10
<212> TYPE: PRT
<213> ORGANISM: Mus musculus

<400> SEQUENCE: 201

Ser His Tyr Tyr Gly Tyr Tyr Phe Asp Tyr
1               5                   10

<210> SEQ ID NO 202
<211> LENGTH: 15
<212> TYPE: PRT
<213> ORGANISM: Mus musculus

<400> SEQUENCE: 202

Arg Ala Ser Glu Thr Ile Asp Ser Tyr Gly Asp Ser Leu Met His
1               5                   10                  15

<210> SEQ ID NO 203
<211> LENGTH: 7
<212> TYPE: PRT
<213> ORGANISM: Mus musculus

<400> SEQUENCE: 203

Arg Ala Ser Asn Leu Glu Ser
1               5

<210> SEQ ID NO 204

<400> SEQUENCE: 204
```

000

<210> SEQ ID NO 205
<211> LENGTH: 5
<212> TYPE: PRT
<213> ORGANISM: Mus musculus

<400> SEQUENCE: 205

Ser Tyr Gly Met Ser
1               5

<210> SEQ ID NO 206
<211> LENGTH: 16
<212> TYPE: PRT
<213> ORGANISM: Mus musculus

<400> SEQUENCE: 206

Ser Ile Arg Ser Asp Gly Asn Thr Tyr Tyr Pro Asp Ser Val Lys Gly
1               5                   10                  15

<210> SEQ ID NO 207
<211> LENGTH: 10
<212> TYPE: PRT
<213> ORGANISM: Mus musculus

<400> SEQUENCE: 207

Gly Gly Tyr Tyr Gly Ser Ser Pro Tyr Tyr
1               5                   10

<210> SEQ ID NO 208

<400> SEQUENCE: 208

000

<210> SEQ ID NO 209
<211> LENGTH: 7
<212> TYPE: PRT
<213> ORGANISM: Mus musculus

<400> SEQUENCE: 209

Trp Ala Ser Thr Arg Asp Ser
1               5

<210> SEQ ID NO 210
<211> LENGTH: 8
<212> TYPE: PRT
<213> ORGANISM: Mus musculus

<400> SEQUENCE: 210

Gln Gln Tyr Tyr Asn Tyr Leu Thr
1               5

<210> SEQ ID NO 211
<211> LENGTH: 6
<212> TYPE: PRT
<213> ORGANISM: Mus musculus

<400> SEQUENCE: 211

Ser Gly Tyr Ser Trp His
1               5

<210> SEQ ID NO 212
<211> LENGTH: 16
<212> TYPE: PRT

-continued

<213> ORGANISM: Mus musculus

<400> SEQUENCE: 212

Tyr Ile His Tyr Ser Gly Ser Thr Asn Tyr Asn Pro Ser Leu Lys Ser
1               5                   10                  15

<210> SEQ ID NO 213
<211> LENGTH: 12
<212> TYPE: PRT
<213> ORGANISM: Mus musculus

<400> SEQUENCE: 213

Gly Pro His Arg Tyr Asp Gly Val Trp Phe Ala Tyr
1               5                   10

<210> SEQ ID NO 214
<211> LENGTH: 12
<212> TYPE: PRT
<213> ORGANISM: Mus musculus

<400> SEQUENCE: 214

Ser Ala Ser Ser Ser Ile Ser Ser Asn Tyr Leu His
1               5                   10

<210> SEQ ID NO 215

<400> SEQUENCE: 215

000

<210> SEQ ID NO 216
<211> LENGTH: 9
<212> TYPE: PRT
<213> ORGANISM: Mus musculus

<400> SEQUENCE: 216

Gln Gln Gly Thr Asn Ile Pro Leu Thr
1               5

<210> SEQ ID NO 217

<400> SEQUENCE: 217

000

<210> SEQ ID NO 218

<400> SEQUENCE: 218

000

<210> SEQ ID NO 219

<400> SEQUENCE: 219

000

<210> SEQ ID NO 220

<400> SEQUENCE: 220

000

<210> SEQ ID NO 221

<400> SEQUENCE: 221

000

<210> SEQ ID NO 222

<400> SEQUENCE: 222

000

<210> SEQ ID NO 223

<400> SEQUENCE: 223

000

<210> SEQ ID NO 224

<400> SEQUENCE: 224

000

<210> SEQ ID NO 225

<400> SEQUENCE: 225

000

<210> SEQ ID NO 226

<400> SEQUENCE: 226

000

<210> SEQ ID NO 227

<400> SEQUENCE: 227

000

<210> SEQ ID NO 228

<400> SEQUENCE: 228

000

<210> SEQ ID NO 229

<400> SEQUENCE: 229

000

<210> SEQ ID NO 230

<400> SEQUENCE: 230

000

<210> SEQ ID NO 231

<400> SEQUENCE: 231

000

<210> SEQ ID NO 232

<400> SEQUENCE: 232

000

-continued

<210> SEQ ID NO 233
<400> SEQUENCE: 233
000

<210> SEQ ID NO 234
<400> SEQUENCE: 234
000

<210> SEQ ID NO 235
<400> SEQUENCE: 235
000

<210> SEQ ID NO 236
<400> SEQUENCE: 236
000

<210> SEQ ID NO 237
<400> SEQUENCE: 237
000

<210> SEQ ID NO 238
<400> SEQUENCE: 238
000

<210> SEQ ID NO 239
<400> SEQUENCE: 239
000

<210> SEQ ID NO 240
<400> SEQUENCE: 240
000

<210> SEQ ID NO 241
<400> SEQUENCE: 241
000

<210> SEQ ID NO 242
<400> SEQUENCE: 242
000

<210> SEQ ID NO 243
<400> SEQUENCE: 243
000

<210> SEQ ID NO 244
<400> SEQUENCE: 244
000

<210> SEQ ID NO 245
<400> SEQUENCE: 245
000

<210> SEQ ID NO 246
<400> SEQUENCE: 246
000

<210> SEQ ID NO 247
<400> SEQUENCE: 247
000

<210> SEQ ID NO 248
<400> SEQUENCE: 248
000

<210> SEQ ID NO 249
<400> SEQUENCE: 249
000

<210> SEQ ID NO 250
<400> SEQUENCE: 250
000

<210> SEQ ID NO 251
<400> SEQUENCE: 251
000

<210> SEQ ID NO 252
<400> SEQUENCE: 252
000

<210> SEQ ID NO 253
<400> SEQUENCE: 253
000

<210> SEQ ID NO 254
<400> SEQUENCE: 254
000

<210> SEQ ID NO 255

<400> SEQUENCE: 255

000

<210> SEQ ID NO 256

<400> SEQUENCE: 256

000

<210> SEQ ID NO 257

<400> SEQUENCE: 257

000

<210> SEQ ID NO 258

<400> SEQUENCE: 258

000

<210> SEQ ID NO 259

<400> SEQUENCE: 259

000

<210> SEQ ID NO 260

<400> SEQUENCE: 260

000

<210> SEQ ID NO 261

<400> SEQUENCE: 261

000

<210> SEQ ID NO 262

<400> SEQUENCE: 262

000

<210> SEQ ID NO 263

<400> SEQUENCE: 263

000

<210> SEQ ID NO 264

<400> SEQUENCE: 264

000

<210> SEQ ID NO 265

<400> SEQUENCE: 265

000

<210> SEQ ID NO 266

<400> SEQUENCE: 266

000

<210> SEQ ID NO 267

<400> SEQUENCE: 267

000

<210> SEQ ID NO 268

<400> SEQUENCE: 268

000

<210> SEQ ID NO 269

<400> SEQUENCE: 269

000

<210> SEQ ID NO 270

<400> SEQUENCE: 270

000

<210> SEQ ID NO 271

<400> SEQUENCE: 271

000

<210> SEQ ID NO 272

<400> SEQUENCE: 272

000

<210> SEQ ID NO 273

<400> SEQUENCE: 273

000

<210> SEQ ID NO 274

<400> SEQUENCE: 274

000

<210> SEQ ID NO 275

<400> SEQUENCE: 275

000

<210> SEQ ID NO 276

<400> SEQUENCE: 276

000

<210> SEQ ID NO 277

<400> SEQUENCE: 277

000

-continued

<210> SEQ ID NO 278
<400> SEQUENCE: 278
000

<210> SEQ ID NO 279
<400> SEQUENCE: 279
000

<210> SEQ ID NO 280
<400> SEQUENCE: 280
000

<210> SEQ ID NO 281
<400> SEQUENCE: 281
000

<210> SEQ ID NO 282
<400> SEQUENCE: 282
000

<210> SEQ ID NO 283
<400> SEQUENCE: 283
000

<210> SEQ ID NO 284
<400> SEQUENCE: 284
000

<210> SEQ ID NO 285
<400> SEQUENCE: 285
000

<210> SEQ ID NO 286
<400> SEQUENCE: 286
000

<210> SEQ ID NO 287
<400> SEQUENCE: 287
000

<210> SEQ ID NO 288
<400> SEQUENCE: 288
000

<210> SEQ ID NO 289

```
<400> SEQUENCE: 289

000

<210> SEQ ID NO 290
<400> SEQUENCE: 290

000

<210> SEQ ID NO 291
<400> SEQUENCE: 291

000

<210> SEQ ID NO 292
<400> SEQUENCE: 292

000

<210> SEQ ID NO 293
<400> SEQUENCE: 293

000

<210> SEQ ID NO 294
<400> SEQUENCE: 294

000

<210> SEQ ID NO 295
<400> SEQUENCE: 295

000

<210> SEQ ID NO 296
<400> SEQUENCE: 296

000

<210> SEQ ID NO 297
<400> SEQUENCE: 297

000

<210> SEQ ID NO 298
<400> SEQUENCE: 298

000

<210> SEQ ID NO 299
<400> SEQUENCE: 299

000

<210> SEQ ID NO 300
<400> SEQUENCE: 300
```

-continued

```
000

<210> SEQ ID NO 301
<211> LENGTH: 119
<212> TYPE: PRT
<213> ORGANISM: Mus musculus

<400> SEQUENCE: 301

Gln Val Gln Leu Gln Gln Ser Gly Ala Glu Leu Ala Arg Pro Gly Ala
1               5                   10                  15

Ser Val Lys Leu Ser Cys Lys Ala Ser Gly Tyr Thr Phe Thr Ser Tyr
            20                  25                  30

Gly Ile Ser Trp Val Lys Gln Arg Thr Gly Gln Gly Leu Glu Trp Ile
        35                  40                  45

Gly Glu Ile Tyr Pro Arg Ser Gly Asn Thr Tyr Tyr Asn Glu Lys Phe
    50                  55                  60

Lys Gly Lys Ala Thr Leu Thr Ala Asp Lys Ser Ser Ser Thr Ala Tyr
65                  70                  75                  80

Met Glu Leu Arg Ser Leu Thr Ser Glu Asp Ser Ala Val Tyr Phe Cys
                85                  90                  95

Ala Arg Asn Tyr Gly Ser Ser Tyr Pro Phe Ala Tyr Trp Gly Gln Gly
            100                 105                 110

Thr Leu Val Thr Val Ser Ala
        115

<210> SEQ ID NO 302
<211> LENGTH: 117
<212> TYPE: PRT
<213> ORGANISM: Mus musculus

<400> SEQUENCE: 302

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Asp Tyr
            20                  25                  30

Tyr Met Asn Trp Val Lys Gln Ser His Gly Lys Ser Leu Glu Trp Ile
        35                  40                  45

Gly Asp Ile Asn Pro Asn Asn Gly Gly Thr Ser Tyr Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Trp Arg Gln Leu Arg Ser Asp Tyr Trp Gly Gln Gly Thr Thr
            100                 105                 110

Leu Thr Val Ser Ser
        115

<210> SEQ ID NO 303
<211> LENGTH: 121
<212> TYPE: PRT
<213> ORGANISM: Mus musculus

<400> SEQUENCE: 303

Gln Val Gln Leu Gln Gln Pro Gly Ala Glu Leu Val Lys Pro Arg Ala
1               5                   10                  15

Ser Val Lys Leu Ser Cys Lys Ala Ser Gly Tyr Thr Phe Thr Ser Tyr
```

```
                    20                  25                  30

Trp Met His Trp Val Lys Gln Arg Pro Gly Gln Gly Leu Glu Trp Ile
             35                  40                  45

Gly Met Ile His Pro Asn Asn Gly Ile Pro Asn Tyr Asn Glu Lys Phe
         50                  55                  60

Lys Ser Lys Ala Thr Leu Thr Val Asp Lys Ser Ser Thr Thr Ala Tyr
 65                  70                  75                  80

Met Gln Leu Ser Ser Leu Thr Ser Glu Asp Ser Ala Val Tyr His Cys
                 85                  90                  95

Ala Arg Glu Gly Tyr Tyr Gly Ser Gly Gly Tyr Phe Asp Val Trp Gly
            100                 105                 110

Thr Gly Thr Thr Val Thr Val Ser Ser
            115                 120

<210> SEQ ID NO 304

<400> SEQUENCE: 304

000

<210> SEQ ID NO 305
<211> LENGTH: 117
<212> TYPE: PRT
<213> ORGANISM: Mus musculus

<400> SEQUENCE: 305

Gln Val Gln Leu Gln Gln Pro Gly Ala Glu Leu Val Lys Pro Gly Ala
 1               5                  10                  15

Ser Val Lys Leu Ser Cys Lys Ala Ser Gly Tyr Thr Phe Thr Ser Tyr
                 20                  25                  30

Trp Met His Trp Val Lys Gln Arg Pro Gly Gln Gly Leu Glu Trp Ile
             35                  40                  45

Gly Met Ile His Pro Asn Ser Gly Ser Thr Asn Tyr Asn Glu Lys Phe
         50                  55                  60

Lys Ser Lys Ala Thr Leu Thr Val Asp Lys Ser Ser Ser Thr Ala Tyr
 65                  70                  75                  80

Met Gln Leu Ser Ser Leu Thr Ser Glu Asp Ser Ala Val Tyr Tyr Cys
                 85                  90                  95

Ala Arg Lys Arg Gly Gly Leu Gly Asp Tyr Trp Gly Gln Gly Thr Ser
            100                 105                 110

Val Thr Val Ser Ser
            115

<210> SEQ ID NO 306
<211> LENGTH: 117
<212> TYPE: PRT
<213> ORGANISM: Mus musculus

<400> SEQUENCE: 306

Gln Val Gln Leu Gln Gln Ser Gly Pro Glu Leu Val Lys Pro Gly Ala
 1               5                  10                  15

Ser Val Lys Ile Ser Cys Lys Ala Ser Gly Tyr Ala Phe Ser Ser Ser
                 20                  25                  30

Trp Met Asn Trp Val Lys Gln Arg Pro Gly Lys Gly Leu Glu Trp Ile
             35                  40                  45

Gly Arg Ile Tyr Pro Gly Asp Gly Asp Thr Asn Tyr Asn Gly Lys Phe
         50                  55                  60
```

-continued

Lys Gly Lys Ala Thr Leu Thr Ala Asp Lys Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Arg Gly Tyr Gly Tyr Leu Ala Tyr Trp Gly Gln Gly Thr Leu
            100                 105                 110

Val Thr Val Ser Ala
        115

<210> SEQ ID NO 307
<211> LENGTH: 119
<212> TYPE: PRT
<213> ORGANISM: Mus musculus

<400> SEQUENCE: 307

Gln Val Gln Leu Gln Gln Ser Gly Ala Glu Leu Ala Arg Pro Gly Ala
1               5                   10                  15

Ser Val Lys Leu Ser Cys Lys Ala Ser Gly Tyr Thr Phe Thr Ser Tyr
            20                  25                  30

Gly Ile Ser Trp Val Lys Gln Arg Thr Gly Gln Gly Leu Glu Trp Ile
        35                  40                  45

Gly Glu Ile Tyr Pro Arg Ser Gly Asn Thr Tyr Tyr Asn Glu Lys Phe
    50                  55                  60

Lys Gly Lys Ala Thr Leu Thr Ala Asp Lys Ser Ser Thr Ala Tyr
65                  70                  75                  80

Met Glu Leu Arg Ser Leu Thr Ser Glu Asp Ser Ala Val Tyr Phe Cys
                85                  90                  95

Ala Arg Gly Tyr Gly Ser Ser Tyr Gly Phe Ala Tyr Trp Gly Gln Gly
            100                 105                 110

Thr Leu Val Thr Val Ser Ala
        115

<210> SEQ ID NO 308
<211> LENGTH: 119
<212> TYPE: PRT
<213> ORGANISM: Mus musculus

<400> SEQUENCE: 308

Asp Val Gln Leu Gln Glu Ser Gly Pro Gly Leu Val Lys Pro Ser Gln
1               5                   10                  15

Ser Leu Ser Leu Thr Cys Ser Val Thr Gly Tyr Ser Ile Thr Ser Gly
            20                  25                  30

Tyr Tyr Trp Asn Trp Ile Arg Gln Phe Pro Gly Asn Lys Leu Glu Trp
        35                  40                  45

Met Gly Tyr Ile Ser Tyr Asp Gly Ser Asn Asn Tyr Asn Pro Ser Leu
    50                  55                  60

Lys Asn Arg Ile Ser Ile Thr Arg Asp Thr Ser Lys Asn Gln Phe Phe
65                  70                  75                  80

Leu Lys Leu Asn Ser Val Thr Thr Glu Asp Thr Ala Thr Tyr Tyr Cys
                85                  90                  95

Ala Ser Ile Tyr Gly Asn Tyr Tyr Ala Met Asp Tyr Trp Gly Gln Gly
            100                 105                 110

Thr Ser Val Thr Val Ser Ser
        115

<210> SEQ ID NO 309
<211> LENGTH: 119

```
<212> TYPE: PRT
<213> ORGANISM: Mus musculus

<400> SEQUENCE: 309

Glu Val Gln Leu Gln Gln Ser Gly Pro Glu Leu Val Gln Pro Gly Ala
1               5                   10                  15

Ser Val Lys Ile Ser Cys Lys Ala Ser Gly Tyr Thr Phe Thr Asp Tyr
            20                  25                  30

Tyr Met Ile Trp Val Lys Gln Ser His Gly Lys Ser Leu Glu Trp Ile
        35                  40                  45

Gly Asn Ile Asn Pro Asn Asn Gly Gly Thr Thr Tyr Asn Gln Lys Phe
    50                  55                  60

Lys Gly Lys Ala Thr Leu Thr Val Asp Lys Ser Ser Ser Thr Ala Tyr
65                  70                  75                  80

Met Gly Leu Pro Ser Leu Thr Ser Glu Asp Ser Ala Val Tyr Tyr Cys
                85                  90                  95

Ala Arg Gly Gly Leu Arg Pro Leu Tyr Phe Asp Tyr Trp Gly Gln Gly
            100                 105                 110

Thr Thr Leu Thr Val Ser Ser
        115

<210> SEQ ID NO 310
<211> LENGTH: 121
<212> TYPE: PRT
<213> ORGANISM: Mus musculus

<400> SEQUENCE: 310

Glu Val Gln Leu Gln Gln Ser Val Ala Glu Leu Val Arg Pro Gly Ala
1               5                   10                  15

Ser Val Lys Leu Ser Cys Thr Ala Ser Gly Phe Asn Ile Lys Asn Thr
            20                  25                  30

Tyr Met His Trp Val Lys Gln Arg Pro Glu Gln Gly Leu Glu Trp Ile
        35                  40                  45

Gly Arg Ile Asp Pro Ala Asn Gly Asn Thr Lys Tyr Asp Pro Lys Phe
    50                  55                  60

Gln Gly Lys Ala Thr Ile Thr Ala Asp Thr Ser Ser Asn Thr Ala Tyr
65                  70                  75                  80

Val Gln Leu Ser Ser Leu Thr Ser Glu Asp Thr Ala Ile Tyr Tyr Cys
                85                  90                  95

Ala Leu Thr Tyr Tyr Gly Ser Ser Gln His Tyr Phe Asp Tyr Trp Gly
            100                 105                 110

Gln Gly Thr Thr Leu Thr Val Ser Ser
        115                 120

<210> SEQ ID NO 311
<211> LENGTH: 124
<212> TYPE: PRT
<213> ORGANISM: Mus musculus

<400> SEQUENCE: 311

Gln Ile Gln Leu Gln Gln Ser Gly Pro Glu Leu Val Lys Pro Gly Ala
1               5                   10                  15

Ser Val Lys Ile Ser Cys Lys Ala Ser Gly Tyr Ala Phe Ser Ser Ser
            20                  25                  30

Trp Met Asn Trp Val Lys Lys Arg Pro Gly Lys Gly Leu Glu Trp Ile
        35                  40                  45

Gly Arg Ile Tyr Pro Gly Asp Gly Asp Ala Asn Tyr Asn Gly Lys Phe
```

```
                    50                  55                  60
Lys Gly Lys Ala Thr Leu Thr Ala Asp Lys Ser Ser Thr Ala Tyr
 65                  70                  75                  80

Met Gln Leu Ser Ser Leu Thr Ser Glu Asp Ser Ala Val Tyr Phe Cys
                 85                  90                  95

Ala Gly Glu Gly His Tyr Tyr Gly Ser Gly Tyr Arg Trp Tyr Leu Asp
            100                 105                 110

Val Trp Gly Thr Gly Thr Thr Val Thr Val Ser Ser
            115                 120
```

<210> SEQ ID NO 312
<211> LENGTH: 120
<212> TYPE: PRT
<213> ORGANISM: Mus musculus

<400> SEQUENCE: 312

```
Gln Val Gln Leu Gln Gln Ser Gly Ala Glu Leu Val Arg Pro Gly Ala
 1               5                  10                  15

Ser Val Thr Leu Ser Cys Lys Ala Ser Gly Tyr Thr Phe Thr Asp Tyr
                20                  25                  30

Glu Ile His Trp Val Lys Gln Thr Leu Val His Gly Leu Glu Trp Ile
            35                  40                  45

Gly Pro Ile Asp Pro Asp Thr Gly Asn Thr Ala Tyr Asn Gln Asn Leu
     50                  55                  60

Lys Gly Lys Ala Ile Leu Thr Ala Asp Lys Ser Ser Thr Ala Tyr
 65                  70                  75                  80

Met Glu Leu Arg Ser Leu Thr Ser Glu Asp Ser Ala Val Tyr Tyr Cys
                 85                  90                  95

Thr Arg Gly Gly Tyr Asp Ser Asp Trp Gly Phe Ala Tyr Trp Gly Gln
            100                 105                 110

Gly Thr Leu Val Thr Val Ser Ala
            115                 120
```

<210> SEQ ID NO 313
<211> LENGTH: 115
<212> TYPE: PRT
<213> ORGANISM: Mus musculus

<400> SEQUENCE: 313

```
Glu Val Gln Leu Gln Gln Ser Gly Pro Val Leu Val Lys Pro Gly Ala
 1               5                  10                  15

Ser Val Lys Met Ser Cys Lys Ala Ser Gly Tyr Thr Phe Thr Asp Tyr
                20                  25                  30

Tyr Leu Asn Trp Val Lys Gln Ser His Gly Lys Ser Leu Glu Trp Ile
            35                  40                  45

Gly Leu Ile Asp Pro Tyr Asn Gly Ser Ser Cys Asn Gln Lys Phe
     50                  55                  60

Lys Gly Lys Ala Thr Leu Thr Val Asp Lys Ser Ser Thr Ala Tyr
 65                  70                  75                  80

Met Asp Leu Asn Ser Leu Thr Ser Glu Asp Ser Ala Val Tyr Tyr Cys
                 85                  90                  95

Ala Arg Gly Asn Ala Met Asp Tyr Trp Gly Gln Gly Thr Ser Val Thr
            100                 105                 110

Val Ser Ser
    115
```

<210> SEQ ID NO 314
<211> LENGTH: 121
<212> TYPE: PRT
<213> ORGANISM: Mus musculus

<400> SEQUENCE: 314

Glu Val Gln Leu Gln Gln Ser Val Ala Glu Leu Val Arg Pro Gly Ala
1               5                   10                  15

Ser Val Lys Leu Ser Cys Thr Ala Ser Gly Phe Asn Ile Lys Asn Thr
            20                  25                  30

Tyr Met Tyr Trp Val Lys Gln Arg Pro Glu Gln Gly Leu Glu Trp Ile
        35                  40                  45

Gly Arg Ile Asp Pro Ala Asn Gly Asn Thr Lys Tyr Ala Pro Lys Phe
50                  55                  60

Gln Gly Lys Ala Thr Ile Thr Ala Asp Thr Ser Ser Asn Thr Ala Tyr
65                  70                  75                  80

Leu Gln Leu Ser Ser Leu Thr Ser Glu Asp Thr Ala Ile Tyr Tyr Cys
                85                  90                  95

Ala Leu Leu Tyr Tyr Gly Ser Ser Tyr Asp Tyr Phe Asp Tyr Trp Gly
            100                 105                 110

Gln Gly Thr Thr Leu Thr Val Ser Ser
        115                 120

<210> SEQ ID NO 315
<211> LENGTH: 121
<212> TYPE: PRT
<213> ORGANISM: Mus musculus

<400> SEQUENCE: 315

Glu Val Gln Leu Gln Gln Ser Val Ala Glu Leu Val Arg Pro Gly Ala
1               5                   10                  15

Ser Val Lys Leu Ser Cys Thr Ala Ser Gly Phe Asn Ile Lys Asn Thr
            20                  25                  30

Tyr Met His Trp Val Lys Gln Arg Pro Glu Gln Gly Leu Glu Trp Ile
        35                  40                  45

Gly Arg Ile Asp Pro Ala Asn Gly Asn Thr Lys Tyr Ala Pro Lys Phe
50                  55                  60

Gln Gly Lys Ala Thr Ile Thr Ala Asp Thr Ser Ser Asn Thr Ala Tyr
65                  70                  75                  80

Leu Gln Leu Ser Ser Leu Thr Ser Glu Asp Thr Ala Ile Tyr Tyr Cys
                85                  90                  95

Ala Leu Thr Tyr Tyr Gly Ser Ser Gln Tyr Tyr Phe Asp Tyr Trp Gly
            100                 105                 110

Gln Gly Thr Thr Leu Thr Val Ser Ser
        115                 120

<210> SEQ ID NO 316
<211> LENGTH: 116
<212> TYPE: PRT
<213> ORGANISM: Mus musculus

<400> SEQUENCE: 316

Gln Val Gln Leu Lys Gln Ser Gly Ala Glu Leu Val Arg Pro Gly Ala
1               5                   10                  15

Ser Val Lys Leu Ser Cys Lys Ala Ser Gly Tyr Thr Phe Thr Asp Tyr
            20                  25                  30

Tyr Ile Asn Trp Val Lys Gln Arg Pro Gly Gln Gly Leu Glu Trp Ile
        35                  40                  45

Ala Arg Ile Tyr Pro Gly Ser Gly Asn Thr Tyr Tyr Asn Glu Lys Phe
            50                  55                  60

Lys Gly Lys Ala Thr Leu Thr Ala Glu Lys Ser Ser Thr Ala Tyr
 65                  70                  75                  80

Met Gln Leu Ser Ser Leu Thr Ser Glu Asp Ser Ala Val Tyr Phe Cys
                85                  90                  95

Ala Arg Gly Tyr Gly Asn Ser Asp Tyr Trp Gly Gln Gly Thr Thr Leu
            100                 105                 110

Thr Val Ser Ser
        115

<210> SEQ ID NO 317
<211> LENGTH: 119
<212> TYPE: PRT
<213> ORGANISM: Mus musculus

<400> SEQUENCE: 317

Gln Val Gln Leu Gln Ser Gly Ala Glu Leu Ala Arg Pro Gly Ala
 1               5                  10                  15

Ser Val Arg Leu Ser Cys Lys Ala Ser Gly Tyr Thr Phe Thr Ser Tyr
                20                  25                  30

Ala Ile Arg Trp Val Lys Gln Arg Thr Gly Gln Gly Leu Glu Trp Ile
            35                  40                  45

Gly Glu Ile Tyr Pro Arg Ser Gly Asn Thr Tyr Tyr Asn Glu Asn Phe
            50                  55                  60

Lys Gly Lys Ala Thr Leu Thr Ala Asp Lys Ser Ser Ser Thr Ala Tyr
 65                  70                  75                  80

Met Glu Leu Arg Ser Leu Thr Ser Glu Asp Ser Ala Val Tyr Phe Cys
                85                  90                  95

Ala Arg Ser Gly Gly Ala Ser Tyr Thr Met Asp Tyr Trp Gly Gln Gly
            100                 105                 110

Thr Ser Val Thr Val Ser Ser
        115

<210> SEQ ID NO 318
<211> LENGTH: 119
<212> TYPE: PRT
<213> ORGANISM: Mus musculus

<400> SEQUENCE: 318

Gln Val Gln Leu Gln Ser Gly Ala Glu Leu Ala Arg Pro Gly Ala
 1               5                  10                  15

Ser Val Arg Leu Ser Cys Lys Ala Ser Gly Tyr Thr Phe Thr Ser Tyr
                20                  25                  30

Gly Leu Ile Trp Leu Lys Gln Arg Thr Gly Gln Gly Leu Glu Trp Ile
            35                  40                  45

Gly Glu Ile Tyr Pro Arg Ser Gly Ser Thr Tyr Tyr Asn Glu Trp Phe
            50                  55                  60

Lys Gly Lys Ala Thr Leu Thr Ala Asp Lys Ser Ser Asn Thr Ala Phe
 65                  70                  75                  80

Met Glu Leu Arg Ser Leu Thr Ser Glu Asp Ser Ala Val Tyr Phe Cys
                85                  90                  95

Ala Arg Arg Arg Gly Thr Gly Asp Gly Phe Asp Tyr Trp Gly Gln Gly
            100                 105                 110

Thr Ile Leu Thr Val Ser Ser
        115

<210> SEQ ID NO 319
<211> LENGTH: 122
<212> TYPE: PRT
<213> ORGANISM: Mus musculus

<400> SEQUENCE: 319

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asp Tyr
            20                  25                  30

Tyr Met His Trp Val Lys Gln Ser His Gly Lys Ser Leu Glu Trp Ile
        35                  40                  45

Gly Tyr Ile Tyr Pro Asn Asn Gly Gly Asn Gly Tyr Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Ile Gly Asp Tyr Tyr Gly Ser Leu Arg Leu Thr Phe Ala Tyr Trp
            100                 105                 110

Gly Gln Gly Thr Leu Val Thr Val Ser Ala
        115                 120

<210> SEQ ID NO 320
<211> LENGTH: 120
<212> TYPE: PRT
<213> ORGANISM: Mus musculus

<400> SEQUENCE: 320

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Thr Tyr
            20                  25                  30

Gly Val Ser Trp Val Lys Gln Ala Pro Gly Lys Val Leu Lys Trp Met
        35                  40                  45

Gly Trp Ile Asn Thr Tyr Ser Gly Val Pro Thr Tyr Ala Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Ser Asn Leu Lys Asn Glu Asp Thr Ala Thr Tyr Phe Cys
                85                  90                  95

Ala Pro Val Thr Thr Ile Leu His Trp Tyr Phe Asp Val Trp Gly Thr
            100                 105                 110

Gly Thr Thr Val Thr Val Ser Ser
        115                 120

<210> SEQ ID NO 321
<211> LENGTH: 119
<212> TYPE: PRT
<213> ORGANISM: Mus musculus

<400> SEQUENCE: 321

Gln Val Gln Leu Gln Gln Ser Gly Ala Glu Leu Ala Arg Pro Gly Ala
1               5                   10                  15

Ser Val Arg Leu Ser Cys Lys Ala Ser Gly Tyr Thr Phe Thr Ser Tyr
            20                  25                  30

```
Gly Ile Ser Trp Val Lys Gln Arg Thr Gly Gln Gly Leu Glu Trp Ile
        35                  40                  45

Gly Glu Ile Tyr Pro Arg Ser Gly Asn Thr Tyr Tyr Asn Glu Lys Phe
 50                  55                  60

Lys Gly Lys Ala Thr Leu Thr Ala Asp Lys Ser Ser Ser Thr Ala Tyr
 65                  70                  75                  80

Met Glu Leu Arg Ser Leu Thr Ser Glu Asp Ser Ala Val Tyr Phe Cys
                 85                  90                  95

Ala Arg Asn Tyr Gly Ser Ser Tyr Pro Phe Ala Tyr Trp Gly Gln Gly
                100                 105                 110

Thr Leu Val Thr Val Ser Ala
        115
```

<210> SEQ ID NO 322
<211> LENGTH: 119
<212> TYPE: PRT
<213> ORGANISM: Mus musculus

<400> SEQUENCE: 322

```
Gln Val Gln Leu Gln Gln Ser Gly Ala Glu Leu Ala Arg Pro Gly Ala
 1               5                  10                  15

Ser Val Lys Leu Ser Cys Lys Ala Ser Gly Tyr Thr Phe Thr Ser Tyr
                20                  25                  30

Gly Ile Ser Trp Val Lys Gln Arg Thr Gly Gln Gly Leu Glu Trp Ile
        35                  40                  45

Gly Glu Ile Tyr Pro Arg Ser Gly Asn Thr Tyr Tyr Asn Glu Lys Phe
 50                  55                  60

Lys Gly Lys Ala Thr Leu Thr Ala Asp Lys Ser Ser Ser Thr Ala Tyr
 65                  70                  75                  80

Met Glu Leu Arg Ser Leu Thr Ser Glu Asp Ser Ala Val Tyr Phe Cys
                 85                  90                  95

Ala Arg Arg Arg Gly Ala Gly Asp Gly Phe Asp Tyr Trp Gly Gln Gly
                100                 105                 110

Thr Thr Leu Thr Val Ser Ser
        115
```

<210> SEQ ID NO 323

<400> SEQUENCE: 323

000

<210> SEQ ID NO 324
<211> LENGTH: 116
<212> TYPE: PRT
<213> ORGANISM: Mus musculus

<400> SEQUENCE: 324

```
Gln Asp Gln Leu Gln Gln Ser Asp Ala Glu Leu Val Lys Pro Gly Ala
 1               5                  10                  15

Ser Val Lys Ile Ser Cys Lys Val Ser Gly Tyr Thr Phe Thr Asp His
                20                  25                  30

Thr Ile His Trp Met Lys Gln Arg Pro Glu Gln Gly Leu Glu Trp Ile
        35                  40                  45

Gly Tyr Ile Tyr Pro Arg Asp Gly Ser Thr Tyr Tyr Asn Glu Lys Phe
 50                  55                  60

Lys Gly Lys Ala Thr Leu Thr Ala Asp Lys Ser Ser Ser Thr Ala Tyr
 65                  70                  75                  80
```

```
Met Gln Leu Asn Ser Leu Thr Ser Glu Asp Ser Ala Val Tyr Phe Cys
                85                  90                  95

Ala Ser Ser Asn Trp Asn Phe Asp Tyr Trp Gly Gln Gly Thr Thr Leu
            100                 105                 110

Thr Val Ser Ser
        115

<210> SEQ ID NO 325

<400> SEQUENCE: 325

000

<210> SEQ ID NO 326
<211> LENGTH: 119
<212> TYPE: PRT
<213> ORGANISM: Mus musculus

<400> SEQUENCE: 326

Gln Val Gln Leu Gln Gln Ser Gly Ala Glu Leu Ala Arg Pro Gly Ala
1               5                   10                  15

Ser Val Lys Leu Pro Cys Lys Ala Ser Gly Tyr Thr Phe Thr Ser Tyr
            20                  25                  30

Gly Ile Ser Trp Val Lys Gln Arg Thr Gly Gln Gly Leu Glu Trp Ile
        35                  40                  45

Gly Glu Ile Tyr Pro Arg Ser Gly Thr Thr Tyr Tyr Asn Glu Lys Phe
    50                  55                  60

Lys Gly Lys Ala Thr Leu Thr Ala Asp Lys Ser Ser Thr Ala Tyr
65                  70                  75                  80

Met Glu Leu Arg Ser Leu Thr Ser Glu Asp Ser Ala Val Tyr Phe Cys
                85                  90                  95

Ala Arg Arg Ile Ser Ser Gly Ser Gly Val Asp Tyr Trp Gly Gln Gly
            100                 105                 110

Thr Thr Leu Thr Val Ser Ser
        115

<210> SEQ ID NO 327
<211> LENGTH: 121
<212> TYPE: PRT
<213> ORGANISM: Mus musculus

<400> SEQUENCE: 327

Asp Val Gln Leu Gln Glu Ser Gly Pro Gly Met Val Lys Pro Ser Gln
1               5                   10                  15

Ser Leu Ser Leu Thr Cys Thr Val Thr Gly Tyr Ser Ile Thr Ser Gly
            20                  25                  30

Tyr Asp Trp His Trp Ile Arg His Phe Pro Gly Asn Lys Leu Glu Trp
        35                  40                  45

Met Gly Tyr Ile Ser Tyr Ser Gly Ser Thr Asn Tyr Asn Pro Ser Leu
    50                  55                  60

Lys Ser Arg Ile Ser Ile Thr His Asp Thr Ser Lys Asn His Phe Phe
65                  70                  75                  80

Leu Lys Leu Asn Ser Val Thr Thr Glu Asp Thr Ala Thr Tyr Tyr Cys
                85                  90                  95

Ala Arg Gly Thr Pro Val Val Ala Glu Asp Tyr Phe Asp Tyr Trp Gly
            100                 105                 110

Gln Gly Thr Thr Leu Thr Val Ser Ser
```

<210> SEQ ID NO 328

<400> SEQUENCE: 328

000

<210> SEQ ID NO 329

<400> SEQUENCE: 329

000

<210> SEQ ID NO 330
<211> LENGTH: 118
<212> TYPE: PRT
<213> ORGANISM: Mus musculus

<400> SEQUENCE: 330

Glu Val Lys Leu Val Glu Ser Gly Gly Gly Leu Val Lys Pro Gly Gly
 1               5                  10                  15

Ser Leu Lys Leu Ser Cys Ala Ala Ser Gly Phe Thr Leu Ser Ser Tyr
            20                  25                  30

Gly Met Ser Trp Val Arg Gln Ile Pro Glu Lys Arg Leu Glu Trp Val
        35                  40                  45

Ala Ser Ile Arg Ser Asp Gly Asn Thr Tyr Tyr Pro Asp Ser Val Lys
    50                  55                  60

Gly Arg Phe Ile Ile Ser Arg Asp Asn Ala Arg Asn Ile Leu Tyr Leu
65                  70                  75                  80

Gln Met Ser Ser Leu Arg Ser Glu Asp Thr Ala Met Tyr Tyr Cys Thr
                85                  90                  95

Arg Gly Gly Tyr Tyr Gly Ser Ser Pro Tyr Tyr Trp Gly Gln Gly Thr
            100                 105                 110

Thr Leu Thr Val Ser Ser
        115

<210> SEQ ID NO 331
<211> LENGTH: 121
<212> TYPE: PRT
<213> ORGANISM: Mus musculus

<400> SEQUENCE: 331

Asp Val Gln Leu Gln Glu Ser Gly Pro Asp Leu Val Lys Pro Ser Gln
 1               5                  10                  15

Ser Leu Ser Val Thr Cys Thr Val Thr Gly Tyr Ser Ile Thr Ser Gly
            20                  25                  30

Tyr Ser Trp His Trp Ile Arg Gln Phe Pro Gly Asn Lys Leu Glu Trp
        35                  40                  45

Met Gly Tyr Ile His Tyr Ser Gly Ser Thr Asn Tyr Asn Pro Ser Leu
    50                  55                  60

Lys Ser Arg Ile Ser Ile Thr Arg Asp Thr Ser Lys Asn Gln Phe Phe
65                  70                  75                  80

Leu Gln Leu Ser Ser Val Thr Thr Glu Asp Thr Ala Thr Tyr Tyr Cys
                85                  90                  95

Ala Ser Gly Pro His Arg Tyr Asp Gly Val Trp Phe Ala Tyr Trp Gly
            100                 105                 110

Gln Gly Thr Leu Val Thr Val Ser Ser
        115                 120

<210> SEQ ID NO 332

<400> SEQUENCE: 332

000

<210> SEQ ID NO 333

<400> SEQUENCE: 333

000

<210> SEQ ID NO 334

<400> SEQUENCE: 334

000

<210> SEQ ID NO 335

<400> SEQUENCE: 335

000

<210> SEQ ID NO 336

<400> SEQUENCE: 336

000

<210> SEQ ID NO 337

<400> SEQUENCE: 337

000

<210> SEQ ID NO 338

<400> SEQUENCE: 338

000

<210> SEQ ID NO 339

<400> SEQUENCE: 339

000

<210> SEQ ID NO 340

<400> SEQUENCE: 340

000

<210> SEQ ID NO 341

<400> SEQUENCE: 341

000

<210> SEQ ID NO 342

<400> SEQUENCE: 342

000

<210> SEQ ID NO 343

<400> SEQUENCE: 343

000

<210> SEQ ID NO 344

<400> SEQUENCE: 344

000

<210> SEQ ID NO 345

<400> SEQUENCE: 345

000

<210> SEQ ID NO 346

<400> SEQUENCE: 346

000

<210> SEQ ID NO 347

<400> SEQUENCE: 347

000

<210> SEQ ID NO 348

<400> SEQUENCE: 348

000

<210> SEQ ID NO 349

<400> SEQUENCE: 349

000

<210> SEQ ID NO 350

<400> SEQUENCE: 350

000

<210> SEQ ID NO 351
<211> LENGTH: 108
<212> TYPE: PRT
<213> ORGANISM: Mus musculus

<400> SEQUENCE: 351

```
Glu Asn Val Leu Thr Gln Ser Pro Ala Ile Met Ala Ala Ser Leu Gly
1               5                   10                  15

Gln Lys Val Thr Met Thr Cys Ser Ala Ser Ser Ser Val Ser Ser Ser
            20                  25                  30

Tyr Leu His Trp Tyr Gln Gln Lys Ser Gly Ala Ser Pro Lys Pro Leu
        35                  40                  45

Ile His Arg Thr Ser Asn Leu Ala Ser Gly Val Pro Ala Arg Phe Ser
    50                  55                  60

Gly Ser Gly Ser Gly Thr Ser Tyr Ser Leu Thr Ile Ser Ser Val Glu
65                  70                  75                  80

Ala Glu Asp Asp Ala Thr Tyr Tyr Cys Gln Gln Trp Ser Gly Tyr Pro
```

```
                         85                  90                  95

Phe Thr Phe Gly Gly Gly Thr Lys Leu Glu Ile Lys
            100                 105

<210> SEQ ID NO 352
<211> LENGTH: 107
<212> TYPE: PRT
<213> ORGANISM: Mus musculus

<400> SEQUENCE: 352

Asp Ile Gln Met Thr Gln Ser Pro Ala Ser Gln Ser Ala Ser Leu Gly
1               5                   10                  15

Glu Ser Val Thr Ile Thr Cys Leu Ala Ser Gln Thr Ile Gly Thr Trp
            20                  25                  30

Leu Ala Trp Tyr Gln Gln Lys Pro Gly Lys Ser Pro Gln Leu Leu Ile
        35                  40                  45

Tyr Ala Ala Thr Ser Leu Ala Asp Gly Val Pro Ser Arg Phe Ser Gly
    50                  55                  60

Ser Gly Ser Gly Thr Lys Phe Ser Phe Lys Ile Ser Ser Leu Gln Ala
65                  70                  75                  80

Glu Asp Phe Val Ser Tyr Tyr Cys Gln Gln Leu Tyr Ser Thr Pro Leu
                85                  90                  95

Thr Phe Gly Ala Gly Thr Lys Leu Glu Leu Lys
            100                 105

<210> SEQ ID NO 353
<211> LENGTH: 106
<212> TYPE: PRT
<213> ORGANISM: Mus musculus

<400> SEQUENCE: 353

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Ile Ser Tyr Ile
            20                  25                  30

His Trp Tyr Gln Gln Lys Pro Gly Thr Ser Pro Lys Arg Trp Ile Tyr
        35                  40                  45

Asp Thr Ser Lys Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys His Gln Arg Ser Thr Tyr Pro Tyr Thr
                85                  90                  95

Phe Gly Gly Gly Thr Lys Leu Glu Ile Lys
            100                 105

<210> SEQ ID NO 354

<400> SEQUENCE: 354

000

<210> SEQ ID NO 355
<211> LENGTH: 111
<212> TYPE: PRT
<213> ORGANISM: Mus musculus

<400> SEQUENCE: 355

Asp Ile Val Leu Thr Gln Ser Pro Ala Ser Leu Ala Val Ser Leu Gly
```

-continued

```
                1               5                  10                  15
        Gln Arg Ala Thr Ile Ser Cys Arg Ala Ser Lys Ser Val Ser Thr Ser
                            20                  25                  30

Gly Tyr Ser Tyr Met His Trp Tyr Gln Gln Lys Pro Gly Gln Pro Pro
                    35                  40                  45

Lys Leu Leu Ile Tyr Leu Ala Ser Asn Leu Glu Ser Gly Val Pro Ala
                50                  55                  60

Arg Phe Ser Gly Ser Gly Ser Gly Thr Asp Phe Thr Leu Asn Ile His
        65                  70                  75                  80

Pro Val Glu Glu Glu Asp Ala Ala Thr Tyr Tyr Cys Gln His Ser Arg
                            85                  90                  95

Glu Leu Pro Tyr Thr Phe Gly Gly Gly Thr Lys Leu Glu Ile Lys
                        100                 105                 110
```

<210> SEQ ID NO 356
<211> LENGTH: 107
<212> TYPE: PRT
<213> ORGANISM: Mus musculus

<400> SEQUENCE: 356

```
        Asp Ile Val Met Thr Gln Ser His Lys Phe Met Ser Thr Ser Val Gly
        1               5                  10                  15

Asp Arg Val Ser Ile Thr Cys Lys Ala Ser Gln Asp Val Ser Thr Ala
                            20                  25                  30

Val Ala Trp Tyr Gln Gln Lys Pro Gly Gln Ser Pro Lys Leu Leu Ile
                    35                  40                  45

Tyr Ser Ala Ser Tyr Arg Tyr Thr Gly Val Pro Asp Arg Phe Thr Gly
                50                  55                  60

Ser Gly Ser Gly Thr Asp Phe Thr Phe Thr Ile Ser Ser Val Gln Ala
        65                  70                  75                  80

Glu Asp Leu Ala Val Tyr Tyr Cys Gln Gln His Tyr Ser Thr Pro Tyr
                            85                  90                  95

Thr Phe Gly Gly Gly Thr Lys Leu Glu Ile Lys
                        100                 105
```

<210> SEQ ID NO 357
<211> LENGTH: 108
<212> TYPE: PRT
<213> ORGANISM: Mus musculus

<400> SEQUENCE: 357

```
        Glu Asn Val Leu Thr Gln Ser Pro Ala Ile Met Ala Ala Ser Leu Gly
        1               5                  10                  15

Gln Lys Val Thr Met Thr Cys Ser Ala Ser Ser Ser Val Ser Ser Ser
                            20                  25                  30

Tyr Leu His Trp Tyr Gln Gln Lys Ser Gly Ala Ser Pro Lys Pro Leu
                    35                  40                  45

Ile His Arg Thr Ser Asn Leu Ala Ser Gly Val Pro Ala Arg Phe Ser
                50                  55                  60

Gly Ser Gly Ser Gly Thr Ser Tyr Ser Leu Thr Ile Ser Ser Val Glu
        65                  70                  75                  80

Ala Glu Asp Asp Ala Thr Tyr Tyr Cys Gln Gln Trp Ser Gly Tyr Pro
                            85                  90                  95

Trp Thr Phe Gly Gly Gly Thr Lys Leu Glu Ile Lys
                        100                 105
```

<210> SEQ ID NO 358
<211> LENGTH: 106
<212> TYPE: PRT
<213> ORGANISM: Mus musculus

<400> SEQUENCE: 358

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Val Ser Tyr Met
            20                  25                  30

His Trp Tyr Gln Gln Lys Ser Gly Thr Ser Pro Lys Arg Trp Ile Tyr
        35                  40                  45

Asp Thr Ser Lys Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Pro Thr
                85                  90                  95

Phe Gly Ser Gly Thr Lys Leu Glu Ile Lys
            100                 105

<210> SEQ ID NO 359
<211> LENGTH: 107
<212> TYPE: PRT
<213> ORGANISM: Mus musculus

<400> SEQUENCE: 359

Asn Ile Val Met Thr Gln Ser Pro Lys Ser Met Ser Met Ser Val Gly
1               5                   10                  15

Glu Arg Val Thr Leu Ser Cys Lys Ala Ser Glu Asn Val Asp Thr Tyr
            20                  25                  30

Val Ser Trp Tyr Gln Gln Lys Pro Glu Gln Ser Pro Lys Leu Leu Ile
        35                  40                  45

Tyr Gly Ala Ser Asn Arg Tyr Thr Gly Val Pro Asp Arg Phe Thr Gly
    50                  55                  60

Ser Gly Ser Ala Thr Asp Phe Thr Leu Thr Ile Ser Ser Val Gln Ala
65                  70                  75                  80

Glu Asp Leu Ala Asp Tyr His Cys Gly Gln Ser Tyr Ser Tyr Pro Leu
                85                  90                  95

Thr Phe Gly Ala Gly Thr Lys Leu Glu Leu Ile
            100                 105

<210> SEQ ID NO 360
<211> LENGTH: 112
<212> TYPE: PRT
<213> ORGANISM: Mus musculus

<400> SEQUENCE: 360

Asp Val Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

```
Ser Arg Val Glu Ala Glu Asp Leu Gly Val Tyr Tyr Cys Trp Gln Asp
            85                  90                  95

Thr His Phe Pro Gln Thr Phe Gly Gly Gly Thr Lys Leu Glu Ile Lys
            100                 105                 110

<210> SEQ ID NO 361
<211> LENGTH: 107
<212> TYPE: PRT
<213> ORGANISM: Mus musculus

<400> SEQUENCE: 361

Asp Ile Gln Met Thr Gln Ser Pro Ala Ser Leu Ser Val Ser Val Gly
1               5                   10                  15

Glu Thr Val Thr Ile Thr Cys Arg Ala Ser Glu Asn Ile Tyr Ser Asn
            20                  25                  30

Leu Ala Trp Tyr Gln Gln Lys Gln Gly Lys Ser Pro Gln Leu Leu Val
            35                  40                  45

Tyr Ala Ala Thr Asn Leu Ala Asp Gly Val Pro Ser Arg Phe Ser Gly
        50                  55                  60

Ser Gly Ser Gly Thr Gln Tyr Ser Leu Lys Ile Asn Ser Leu Gln Ser
65                  70                  75                  80

Glu Asp Phe Gly Ser Tyr Tyr Cys Gln His Phe Arg Gly Ala Pro Phe
                85                  90                  95

Thr Phe Gly Ser Gly Thr Lys Leu Glu Ile Lys
            100                 105

<210> SEQ ID NO 362
<211> LENGTH: 112
<212> TYPE: PRT
<213> ORGANISM: Mus musculus

<400> SEQUENCE: 362

Asp Ile Val Met Thr Gln Ala Thr Pro Ser Val Pro Val Thr Pro Gly
1               5                   10                  15

Glu Ser Val Ser Ile Ser Cys Arg Ser Ser Lys Ser Leu Leu His Ser
            20                  25                  30

Asn Gly Asn Thr Phe Leu Phe Trp Phe Leu Gln Arg Pro Gly Gln Ser
            35                  40                  45

Pro Gln Leu Leu Ile Tyr Arg Met Ser Asp Leu Ala Ser Gly Val Pro
        50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Ile Tyr Tyr Cys Met Gln His
                85                  90                  95

Leu Glu Tyr Pro Phe Thr Phe Gly Ser Gly Thr Lys Leu Glu Ile Lys
            100                 105                 110

<210> SEQ ID NO 363
<211> LENGTH: 107
<212> TYPE: PRT
<213> ORGANISM: Mus musculus

<400> SEQUENCE: 363

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Ser Thr Ala
            20                  25                  30
```

```
Val Ala Trp Tyr Gln Glu Lys Pro Gly Gln Ser Pro Lys Leu Leu Ile
            35                  40                  45

Tyr Trp Ala Ser Thr Arg His Thr Gly Val Pro Asp Arg Phe Thr Gly
 50                  55                  60

Ser Gly Ser Gly Thr Asp Tyr Ile Leu Asn Ile Ser Ser Val Gln Ala
 65                  70                  75                  80

Glu Asp Leu Ala Leu Tyr Tyr Cys Gln Gln His Tyr Ile Ile Pro Tyr
                 85                  90                  95

Met Phe Gly Gly Gly Thr Lys Leu Glu Ile Lys
                100                 105

<210> SEQ ID NO 364
<211> LENGTH: 112
<212> TYPE: PRT
<213> ORGANISM: Mus musculus

<400> SEQUENCE: 364

Asp Val Val Met Thr Gln Thr Pro Leu Thr Leu Ser Val Thr Ile Gly
 1               5                  10                  15

Gln Pro Ala Ser Ile Ser Cys Lys Ser Ser Gln Ser Leu Leu Asp Ser
                 20                  25                  30

Asp Gly Lys Thr Tyr Leu Asn Trp Leu Leu Gln Arg Pro Gly Gln Ser
             35                  40                  45

Pro Lys Arg Leu Ile Tyr Leu Val Ser Lys Leu Asp Ser Gly Val Pro
 50                  55                  60

Asp Arg Phe Thr Gly Ser Gly Ser Gly Thr Asp Phe Thr Leu Lys Ile
 65                  70                  75                  80

Ser Arg Val Glu Ala Glu Asp Leu Gly Val Tyr Tyr Cys Trp Gln Gly
                 85                  90                  95

Thr His Phe Pro Gln Thr Phe Gly Gly Gly Thr Lys Leu Glu Ile Lys
                100                 105                 110

<210> SEQ ID NO 365

<400> SEQUENCE: 365

000

<210> SEQ ID NO 366
<211> LENGTH: 107
<212> TYPE: PRT
<213> ORGANISM: Mus musculus

<400> SEQUENCE: 366

Asp Ile Leu Leu Thr Gln Ser Pro Ala Ile Leu Ser Val Ser Pro Gly
 1               5                  10                  15

Glu Arg Val Ser Phe Ser Cys Arg Ala Ser Gln Ser Ile Gly Thr Arg
                 20                  25                  30

Ile His Trp Tyr Gln Gln Arg Thr Asn Gly Ser Pro Arg Leu Leu Ile
             35                  40                  45

Lys Tyr Ala Ser Glu Ser Ile Ser Gly Ile Pro Ser Arg Phe Ser Gly
 50                  55                  60

Ser Gly Ser Gly Thr Asp Phe Thr Leu Ser Ile Asn Ser Val Glu Ser
 65                  70                  75                  80

Glu Asp Ile Ala Asp Tyr Tyr Cys Gln Gln Ser Asn Ser Trp Pro Tyr
                 85                  90                  95

Thr Phe Gly Gly Gly Thr Lys Leu Glu Ile Lys
                100                 105
```

<210> SEQ ID NO 367
<211> LENGTH: 108
<212> TYPE: PRT
<213> ORGANISM: Mus musculus

<400> SEQUENCE: 367

Glu Asn Val Leu Thr Gln Ser Pro Ala Ile Met Ala Ala Ser Leu Gly
1               5                   10                  15

Gln Lys Val Thr Met Thr Cys Ser Ala Ser Ser Ser Val Ser Ser
            20                  25                  30

Tyr Leu His Trp Tyr Gln Gln Lys Ser Gly Ala Ser Pro Lys Pro Leu
        35                  40                  45

Ile His Arg Thr Ser Asn Leu Ala Ser Gly Val Pro Ala Arg Phe Ser
    50                  55                  60

Gly Ser Gly Ser Gly Thr Ser Tyr Ser Leu Thr Ile Ser Ser Val Glu
65                  70                  75                  80

Ala Glu Asp Asp Ala Thr Tyr Tyr Cys Gln Gln Trp Ser Gly Tyr Pro
                85                  90                  95

Phe Thr Phe Gly Ser Gly Thr Lys Leu Glu Ile Lys
            100                 105

<210> SEQ ID NO 368
<211> LENGTH: 107
<212> TYPE: PRT
<213> ORGANISM: Mus musculus

<400> SEQUENCE: 368

Asp Ile Gln Met Thr Gln Thr Thr Ser Ser Leu Ser Ala Ser Leu Gly
1               5                   10                  15

Asp Arg Val Thr Ile Ser Cys Ser Ala Ser Gln Gly Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Ser Leu His Ser Gly Val Pro Ser Arg Phe Ser Gly
    50                  55                  60

Ser Gly Ser Gly Thr Asp Tyr Ser Leu Thr Ile Ser Asn Leu Glu Pro
65                  70                  75                  80

Glu Asp Ile Ala Thr Tyr Tyr Cys Gln Gln Tyr Ile Glu Leu Pro Phe
                85                  90                  95

Thr Phe Gly Ser Gly Thr Lys Leu Glu Ile Lys
            100                 105

<210> SEQ ID NO 369
<211> LENGTH: 113
<212> TYPE: PRT
<213> ORGANISM: Mus musculus

<400> SEQUENCE: 369

Asp Ile Val Met Ser Gln Ser Pro Ser Ser Leu Ala Val Ser Val Gly
1               5                   10                  15

Glu Lys Val Thr Met Ser Cys Lys Ser Ser Gln Ser Leu Leu Tyr Ser
            20                  25                  30

Ser Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

```
Pro Asp Arg Phe Thr Gly Ser Gly Ser Gly Thr Asp Phe Thr Leu Thr
 65                  70                  75                  80

Ile Ser Ser Val Lys Ala Glu Asp Leu Ala Val Tyr Tyr Cys Gln Gln
                 85                  90                  95

Tyr Tyr Ser Tyr Pro Leu Thr Phe Gly Ala Gly Thr Lys Leu Glu Leu
            100                 105                 110

Lys
```

<210> SEQ ID NO 370
<211> LENGTH: 107
<212> TYPE: PRT
<213> ORGANISM: Mus musculus

<400> SEQUENCE: 370

```
Asp Ile Gln Met Thr Gln Ser Pro Ser Ser Leu Ser Ala Ser Leu Gly
  1               5                  10                  15

Glu Arg Val Ser Leu Thr Cys Arg Ala Ser Gln Glu Ile Ser Gly Tyr
                 20                  25                  30

Leu Ser Trp Leu Gln Gln Lys Pro Asp Gly Thr Ile Lys Arg Leu Ile
             35                  40                  45

Tyr Ala Ala Ser Thr Leu Asp Ser Gly Val Pro Lys Arg Phe Arg Gly
 50                  55                  60

Ser Arg Ser Gly Ser Asp Tyr Ser Leu Thr Ile Ser Ser Leu Glu Ser
 65                  70                  75                  80

Glu Asp Phe Ala Asp Tyr Tyr Cys Leu Gln Tyr Ala Ser Tyr Pro Phe
                 85                  90                  95

Thr Phe Gly Ser Gly Thr Lys Leu Glu Ile Lys
            100                 105
```

<210> SEQ ID NO 371

<400> SEQUENCE: 371

000

<210> SEQ ID NO 372
<211> LENGTH: 107
<212> TYPE: PRT
<213> ORGANISM: Mus musculus

<400> SEQUENCE: 372

```
Asp Ile Gln Met Thr Gln Thr Thr Ser Ser Leu Ser Ala Ser Leu Gly
  1               5                  10                  15

Asp Arg Val Thr Ile Ser Cys Ser Ala Ser Gln Gly Ile Ser Asn Tyr
                 20                  25                  30

Leu Asn Trp Tyr Gln Gln Lys Pro Asp Gly Thr Val Lys Leu Leu Ile
             35                  40                  45

Tyr Tyr Thr Ser Ser Leu His Ser Gly Val Pro Ser Arg Phe Ser Gly
 50                  55                  60

Ser Gly Ser Gly Thr Asp Tyr Ser Leu Thr Ile Ser Asn Leu Glu Pro
 65                  70                  75                  80

Glu Asp Ile Ala Thr Tyr Tyr Cys Gln Gln Tyr Ser Lys Leu Pro Phe
                 85                  90                  95

Thr Phe Gly Ser Gly Thr Lys Leu Glu Ile Lys
            100                 105
```

<210> SEQ ID NO 373

<400> SEQUENCE: 373

000

<210> SEQ ID NO 374
<211> LENGTH: 107
<212> TYPE: PRT
<213> ORGANISM: Mus musculus

<400> SEQUENCE: 374

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Gly Thr Ala
            20                  25                  30

Val Ala Trp Tyr Gln Gln Lys Pro Gly Gln Ser Pro Lys Leu Leu Ile
        35                  40                  45

Tyr Trp Ala Ser Thr Arg Arg Thr Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Gln Gln Tyr Ser Ser Tyr Pro Leu
                85                  90                  95

Thr Phe Gly Ala Gly Thr Lys Leu Glu Leu Lys
            100                 105

<210> SEQ ID NO 375
<211> LENGTH: 107
<212> TYPE: PRT
<213> ORGANISM: Mus musculus

<400> SEQUENCE: 375

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Ser Thr Ala
            20                  25                  30

Val Ala Trp Tyr Gln Gln Lys Pro Gly Gln Ser Pro Lys Leu Leu Ile
        35                  40                  45

Tyr Ser Ala Ser Tyr Arg Tyr Thr Gly Val Pro Asp Arg Phe Thr Gly
    50                  55                  60

Ser Gly Ser Gly Thr Asp Phe Thr Phe Thr Ile Ser Ser Val Gln Ala
65                  70                  75                  80

Glu Asp Leu Ala Val Tyr Tyr Cys Gln Gln His Tyr Ser Thr Pro Trp
                85                  90                  95

Thr Phe Gly Gly Gly Thr Lys Leu Glu Ile Lys
            100                 105

<210> SEQ ID NO 376
<211> LENGTH: 107
<212> TYPE: PRT
<213> ORGANISM: Mus musculus

<400> SEQUENCE: 376

Asp Ile Gln Met Thr Gln Thr Thr Ser Ser Leu Ser Ala Ser Leu Gly
1               5                   10                  15

Asp Arg Val Thr Ile Ser Cys Ser Ala Ser Gln Gly Ile Ser Asn Tyr
            20                  25                  30

Leu Asn Trp Tyr Gln Gln Lys Pro Asp Gly Thr Val Lys Leu Leu Ile
        35                  40                  45

```
Tyr Tyr Thr Ser Ser Leu His Ser Gly Val Pro Ser Arg Phe Ser Gly
        50                  55                  60
Ser Gly Ser Gly Thr Asp Tyr Ser Leu Thr Ile Ser Asn Leu Glu Pro
 65                  70                  75                  80
Glu Asp Ile Ala Thr Tyr Tyr Cys Gln Gln Tyr Ser Glu Leu Pro Trp
                 85                  90                  95
Thr Phe Gly Gly Gly Thr Lys Leu Glu Ile Lys
                100                 105
```

<210> SEQ ID NO 377
<211> LENGTH: 110
<212> TYPE: PRT
<213> ORGANISM: Mus musculus

<400> SEQUENCE: 377

```
Gln Ala Val Val Thr Gln Glu Ser Ala Leu Ser Thr Ser Pro Gly Glu
  1               5                  10                  15
Thr Val Thr Leu Thr Cys Arg Ser Ser Thr Gly Ala Val Thr Thr Ser
                 20                  25                  30
Asn Tyr Ala Asn Trp Val Gln Glu Lys Pro Asp His Leu Phe Thr Gly
             35                  40                  45
Leu Ile Gly Ala Thr Asn Asn Arg Ala Pro Gly Val Pro Ala Arg Phe
 50                  55                  60
Ser Gly Ser Leu Ile Gly Asp Lys Ala Ala Leu Thr Ile Thr Gly Ala
 65                  70                  75                  80
Gln Thr Glu Asp Glu Ala Ile Tyr Phe Cys Ala Leu Trp Tyr Ser Asn
                 85                  90                  95
His Leu Val Phe Gly Gly Gly Thr Lys Leu Thr Val Leu Gly
                100                 105                 110
```

<210> SEQ ID NO 378
<211> LENGTH: 112
<212> TYPE: PRT
<213> ORGANISM: Artificial Sequence
<220> FEATURE:
<223> OTHER INFORMATION: engineered humanised 6.2 VL

<400> SEQUENCE: 378

```
Asp Ile Val Met Thr Gln Ser Pro Leu Ser Leu Pro Val Thr Pro Gly
  1               5                  10                  15
Glu Pro Ala Ser Ile Ser Cys Lys Ser Ser Gln Ser Leu Leu Tyr Ser
                 20                  25                  30
Ser Asn Gln Lys Asn Tyr Leu Ala Trp Tyr Gln Gln Lys Pro Gly Gln
             35                  40                  45
Ser Pro Lys Leu Leu Ile Tyr Trp Ala Ser Thr Arg Glu Ser Gly Val
 50                  55                  60
Pro Asp Arg Phe Ser Gly Ser Gly Ser Gly Thr Asp Phe Thr Leu Lys
 65                  70                  75                  80
Ile Ser Arg Val Glu Ala Glu Asp Val Gly Val Tyr Tyr Cys Gln Gln
                 85                  90                  95
Tyr Tyr Asn Tyr Leu Thr Phe Gly Gly Gly Thr Lys Val Glu Ile Lys
                100                 105                 110
```

<210> SEQ ID NO 379

<400> SEQUENCE: 379

000

```
<210> SEQ ID NO 380
<211> LENGTH: 112
<212> TYPE: PRT
<213> ORGANISM: Mus musculus

<400> SEQUENCE: 380

Asp Ile Val Met Ser Gln Ser Pro Ser Ser Leu Pro Val Ser Val Gly
1               5                   10                  15

Glu Lys Ile Ser Met Thr Cys Lys Ser Ser Gln Ser Leu Leu Tyr Ser
            20                  25                  30

Ser Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Asp Ser Gly Val
    50                  55                  60

Pro Asp Arg Phe Ile Gly Ser Gly Ser Gly Thr Asp Phe Thr Leu Thr
65                  70                  75                  80

Ile Asn Ser Val Lys Ala Glu Asp Leu Ala Val Tyr Tyr Cys Gln Gln
                85                  90                  95

Tyr Tyr Asn Tyr Leu Thr Phe Gly Ala Gly Thr Lys Leu Glu Leu Lys
            100                 105                 110

<210> SEQ ID NO 381
<211> LENGTH: 108
<212> TYPE: PRT
<213> ORGANISM: Mus musculus

<400> SEQUENCE: 381

Glu Ile Val Leu Thr Gln Ser Pro Thr Thr Met Ala Ala Ser Pro Gly
1               5                   10                  15

Glu Lys Ile Thr Ile Thr Cys Ser Ala Ser Ser Ile Ser Ser Asn
            20                  25                  30

Tyr Leu His Trp Tyr Gln Gln Lys Pro Gly Phe Ser Pro Lys Leu Leu
        35                  40                  45

Ile Tyr Arg Thr Ser Asn Leu Ala Ser Gly Val Pro Ala Arg Phe Ser
    50                  55                  60

Gly Ser Gly Ser Gly Thr Ser Tyr Ser Leu Thr Ile Gly Thr Met Glu
65                  70                  75                  80

Ala Glu Asp Val Ala Thr Tyr Tyr Cys Gln Gln Gly Thr Asn Ile Pro
                85                  90                  95

Leu Thr Phe Gly Ala Gly Thr Lys Leu Glu Ile Lys
            100                 105

<210> SEQ ID NO 382
<211> LENGTH: 119
<212> TYPE: PRT
<213> ORGANISM: Artificial Sequence
<220> FEATURE:
<223> OTHER INFORMATION: humanised 3E8 VH

<400> SEQUENCE: 382

Gln Val Gln Leu Val Gln Ser Gly Ala Glu Leu Lys Lys Pro Gly Ala
1               5                   10                  15

Ser Val Lys Val Ser Cys Lys Ala Ser Gly Tyr Thr Phe Thr Ser Tyr
            20                  25                  30

Ala Ile Arg Trp Val Arg Gln Ala Thr Gly Gln Gly Leu Glu Trp Met
        35                  40                  45

Gly Glu Ile Tyr Pro Arg Ser Gly Asn Thr Tyr Tyr Ala Gln Lys Phe
    50                  55                  60
```

```
Gln Gly Arg Ala Thr Leu Thr Ala Asp Lys Ser Ile Ser Thr Ala Tyr
 65                  70                  75                  80

Met Glu Leu Ser Ser Leu Arg Ser Glu Asp Thr Ala Val Tyr Phe Cys
                 85                  90                  95

Ala Arg Ser Gly Gly Ala Ser Tyr Thr Met Asp Tyr Trp Gly Gln Gly
                100                 105                 110

Thr Thr Val Thr Val Ser Ser
            115

<210> SEQ ID NO 383
<211> LENGTH: 108
<212> TYPE: PRT
<213> ORGANISM: Artificial Sequence
<220> FEATURE:
<223> OTHER INFORMATION: humanised 3E8 VL

<400> SEQUENCE: 383

Glu Asn Val Leu Thr Gln Ser Pro Ala Thr Leu Ser Leu Ser Pro Gly
 1               5                  10                  15

Glu Arg Ala Thr Leu Ser Cys Ser Ala Ser Ser Ser Val Ser Ser Ser
                20                  25                  30

Tyr Leu His Trp Tyr Gln Gln Lys Pro Gly Gln Ser Pro Arg Pro Leu
             35                  40                  45

Ile His Arg Thr Ser Asn Leu Ala Ser Gly Ile Pro Ala Arg Phe Ser
 50                  55                  60

Gly Ser Gly Ser Gly Thr Asp Tyr Thr Leu Thr Ile Ser Ser Leu Glu
 65                  70                  75                  80

Pro Glu Asp Phe Ala Val Tyr Tyr Cys Gln Gln Trp Ser Gly Tyr Pro
                 85                  90                  95

Phe Thr Phe Gly Ser Gly Thr Lys Leu Glu Ile Lys
                100                 105

<210> SEQ ID NO 384
<211> LENGTH: 118
<212> TYPE: PRT
<213> ORGANISM: Artificial Sequence
<220> FEATURE:
<223> OTHER INFORMATION: humanised 6.2 VH

<400> SEQUENCE: 384

Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Leu Ser Ser Tyr
                20                  25                  30

Gly Met Ser Trp Val Arg Gln Ala Pro Gly Lys Gly Leu Glu Trp Val
             35                  40                  45

Ala Ser Ile Arg Ser Asp Gly Asn Thr Tyr Tyr Pro Asp Ser Val Lys
 50                  55                  60

Gly Arg Phe Thr Ile Ser Arg Asp Asn Ala Lys Asn Ser Leu Tyr Leu
 65                  70                  75                  80

Gln Met Ser Ser Leu Arg Ala Glu Asp Thr Ala Val Tyr Tyr Cys Thr
                 85                  90                  95

Arg Gly Gly Tyr Tyr Gly Ser Ser Pro Tyr Tyr Trp Gly Gln Gly Thr
                100                 105                 110

Thr Val Thr Val Ser Ser
            115
```

-continued

<210> SEQ ID NO 385
<211> LENGTH: 112
<212> TYPE: PRT
<213> ORGANISM: Artificial Sequence
<220> FEATURE:
<223> OTHER INFORMATION: humanised 6.2 VL

<400> SEQUENCE: 385

Asp Ile Val Met Thr Gln Ser Pro Leu Ser Leu Pro Val Thr Pro Gly
1               5                   10                  15

Glu Pro Ala Ser Ile Ser Cys Lys Ser Ser Gln Ser Leu Leu Tyr Ser
            20                  25                  30

Ser Asn Gln Lys Asn Tyr Leu Ala Trp Tyr Gln Gln Lys Pro Gly Gln
        35                  40                  45

Ser Pro Gln Leu Leu Ile Tyr Trp Ala Ser Thr Arg Asp Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Gln Gln
                85                  90                  95

Tyr Tyr Asn Tyr Leu Thr Phe Gly Gly Gly Thr Lys Val Glu Ile Lys
            100                 105                 110

<210> SEQ ID NO 386
<211> LENGTH: 17
<212> TYPE: PRT
<213> ORGANISM: Mus musculus

<400> SEQUENCE: 386

Glu Ile Tyr Pro Arg Ser Gly Asn Thr Tyr Tyr Ala Gln Lys Phe Gln
1               5                   10                  15

Gly

<210> SEQ ID NO 387
<211> LENGTH: 16
<212> TYPE: PRT
<213> ORGANISM: Mus musculus

<400> SEQUENCE: 387

Ser Ile Arg Ser Glu Gly Gln Thr Tyr Tyr Pro Asp Ser Val Lys Gly
1               5                   10                  15

<210> SEQ ID NO 388
<211> LENGTH: 17
<212> TYPE: PRT
<213> ORGANISM: Mus musculus

<400> SEQUENCE: 388

Glu Ile Tyr Pro Arg Ser Gly Asn Thr Tyr Tyr Ala Gln Ser Phe Gln
1               5                   10                  15

Gly

<210> SEQ ID NO 389
<211> LENGTH: 119
<212> TYPE: PRT
<213> ORGANISM: Artificial Sequence
<220> FEATURE:
<223> OTHER INFORMATION: engineered humanised 3E8 VH

<400> SEQUENCE: 389

Gln Val Gln Leu Val Gln Ser Gly Ala Glu Leu Lys Lys Pro Gly Ala
1               5                   10                  15

```
Ser Val Lys Val Ser Cys Lys Ala Ser Gly Tyr Thr Phe Thr Ser Tyr
            20                  25                  30

Ala Ile Arg Trp Val Arg Gln Ala Thr Gly Gln Gly Leu Glu Trp Met
        35                  40                  45

Gly Glu Ile Tyr Pro Arg Ser Gly Gln Thr Tyr Tyr Ala Gln Ser Phe
    50                  55                  60

Gln Gly Arg Ala Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Phe Cys
                85                  90                  95

Ala Arg Ser Gly Gly Ala Ser Tyr Thr Met Asp Tyr Trp Gly Gln Gly
            100                 105                 110

Thr Thr Val Thr Val Ser Ser
        115

<210> SEQ ID NO 390
<211> LENGTH: 118
<212> TYPE: PRT
<213> ORGANISM: Artificial Sequence
<220> FEATURE:
<223> OTHER INFORMATION: engineered humanised 6.2 VH 2nd

<400> SEQUENCE: 390

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Leu Ser Ser Tyr
            20                  25                  30

Gly Met Ser Trp Val Arg Gln Ala Pro Gly Lys Gly Leu Glu Trp Val
        35                  40                  45

Ala Ser Ile Arg Ser Glu Gly Gln Thr Tyr Tyr Pro Asp Ser Val Lys
    50                  55                  60

Gly Arg Phe Thr Ile Ser Arg Asp Asn Ala Lys Asn Thr Leu Tyr Leu
65                  70                  75                  80

Gln Met Ser Ser Leu Arg Ala Glu Asp Thr Ala Val Tyr Tyr Cys Thr
                85                  90                  95

Arg Gly Gly Tyr Tyr Gly Ser Ser Pro Tyr Tyr Trp Gly Gln Gly Thr
            100                 105                 110

Thr Val Thr Val Ser Ser
        115
```

BTLA ANTIBODIES

CROSS-REFERENCE

This application is a continuation of International Application No. PCT/GB2019/053569, filed Dec. 17, 2019, which claims the benefit of United Kingdom Application No. 1820554.2, filed 17 Dec. 2018, each of which is incorporated by reference in its entirety for all purposes.

REFERENCE TO A SEQUENCE LISTING

The instant application contains a Sequence Listing which has been submitted in ASCII format via EFS-Web and is hereby incorporated by reference in its entirety. Said ASCII copy, created on May 25, 2021, is named 56270-708_301_SL.txt.

FIELD OF THE INVENTION

This invention relates generally to antibodies or antigen binding fragments that bind to human B and T lymphocyte attenuator (BTLA) and uses thereof. More specifically, the invention relates to agonistic antibodies that bind human BTLA and modulate its activity, and their use in treating inflammatory, autoimmune and proliferative diseases and disorders.

BACKGROUND

The immune system must achieve a balance between the destruction of pathogens or dangerously mutated cells and tolerance of healthy self-tissue and innocuous commensals. To facilitate this balance the activity of immune cells is influenced by the integration of signals from multiple stimulatory and inhibitory receptors that attune cells to their environment. These surface-expressed receptors present attractive targets for the therapeutic modulation of immune responses. Many human diseases result from aberrant or unwanted activation of the immune system including autoimmune diseases, transplant rejection and graft-versus-host disease. Agonist agents capable of inducing signaling through inhibitory receptors could dampen these unwanted immune responses.

B and T lymphocyte attenuator (BTLA; also designated CD272) is an inhibitory member of the CD28 family of receptors that also includes CD28, CTLA-4, ICOS, and PD-1 (Watanabe et al., Nat Immunol. 4:670-679, 2003) It is widely expressed throughout the immune system on both myeloid and lymphoid cells (Han et al., J Immunol. 172: 5931-9, 2004). Following engagement by its ligand herpesvirus entry mediator (HVEM), BTLA recruits the phosphatases SHP-1 and SHP-2 to its cytoplasmic domain (Sedy et al., Nat Immunol. 6:90-8, 2005), which in turn inhibit the signaling cascades of activating receptors. Mice lacking an intact BTLA gene show hyperproliferative B and T cell responses in vitro, higher titers to DNP-KLH post-immunization and an increased sensitivity to EAE (Watanabe et al, Nat. Immunol, 4:670-679, 2003). If observed until old age BTLA knock-out mice spontaneously develop autoantibodies, an auto-immune hepatitis like disease and inflammatory cell infiltrates in multiple organs (Oya et al., Arthritis Rheum 58: 2498-2510, 2008). This evidence indicates that the BTLA inhibitory receptor plays a crucial role in maintaining immune homeostasis and inhibiting autoimmunity. Furthermore, HVEM-BTLA signaling is involved in the regulation of mucosal inflammation and infection immunity (Shui et al., J Leukoc Biol. 89:517-523, 2011).

Therapeutic agents that are capable of modulating BTLA function to inhibit autoreactive lymphocytes in the context of autoimmune disorders would be highly desirable.

It has previously been shown that monoclonal antibodies binding to mouse BTLA can act as agonists, inducing signaling through the receptor to inhibit immune cell responses. In the presence of agonist anti-BTLA antibody (mAb), anti-CD3 and anti-CD28 activated T-cells show reduced IL-2 production and proliferation (Kreig et al., J. Immunol., 175, 6420-6472, 2005).

Furthermore, anti-mouse-BTLA agonist antibodies have been shown to ameliorate disease in murine models of graft-versus-host disease (Sakoda et al., Blood. 117:2506-2514; Albring et al., J Exp Med. 207:2551-9, 2010). Agonist antibodies targeting the human BTLA receptor have been shown to inhibit T cell responses ex-vivo (see Otsuki et al., Biochem Biophys Res Commun 344:1121-7, 2006; and WO2011/014438), but have not yet been translated to the clinic.

There is a need in the art to discover new and useful agents, such as antibodies or antigen-binding antibody fragments, capable of modulating BTLA.

BRIEF SUMMARY OF THE DISCLOSURE

The present invention relates to anti-human BTLA agonist antibodies or antibody fragments thereof having one or more desirable properties, including high binding affinities, high agonist potency, high agonist efficacy, good pharmacokinetics and low antigenicity in human subjects. The invention also relates to use of the antibodies or antibody fragments of the invention in the treatment of disease.

According to a first aspect of the invention there is provided an isolated antibody or an antigen-binding fragment thereof that specifically binds BTLA, wherein the antibody has a heavy chain and/or light chain with at least one complementarity-determining region (CDR) as present in an antibody selected from the group consisting of 11.5.1, 2.8.6, 12F11, 14D4, 15B6, 15C6, 16E1, 16F10, 16H2, 1H6, 21C7, 24H7, 26B1, 26F3, 27G9, 3A9, 3E8, 4B1, 4D3, 4D5, 4E8, 4H4, 6G8, 7A1, 8B4, 8C4, 6.2 and 831, as identified in Table 1 and described herein.

According to a second aspect of the invention there is provided an isolated nucleic acid comprising a nucleotide sequence that encodes a heavy chain polypeptide or a light chain polypeptide of the isolated antibody or an antigen-binding fragment thereof of the first aspect of the invention.

According to a third aspect of the invention there is provided a vector comprising the nucleic acid of the second aspect of the invention.

According to a fourth aspect of the invention there is provided a host cell comprising the nucleic acid sequence according to the second aspect of the invention or the vector according to the third aspect of the invention.

According to a fifth aspect of the invention there is provided a method of producing an antibody or an antigen-binding fragment thereof according to the first aspect of the invention, comprising the step of culturing the host cell of the fourth aspect of the invention under conditions for production of said antibody or an antigen-binding fragment thereof, and optionally isolating and/or purifying said antibody or an antigen-binding fragment thereof.

According to a sixth aspect of the invention there is provided a pharmaceutical composition comprising a pharmaceutically acceptable carrier and a therapeutically effective amount of the antibody or antigen-binding fragment thereof of the first aspect of the invention, or that produced by the fifth aspect of the invention.

According to a seventh aspect of the invention there is provided a method of preparing a pharmaceutical composition, the method comprising formulating antibody or an antigen-binding fragment thereof in accordance with the first aspect of the invention, or one produced in accordance with the fifth aspect of the invention into a composition including at least one additional component. In a particular embodiment, the at least one additional component is a pharmaceutically acceptable excipient.

According to an eighth aspect of the invention there is provided a method of treating a BTLA-related disease in a patient, comprising administering to the patient a therapeutically effective amount of the antibody or antigen-binding fragment thereof of the first aspect of the invention or the pharmaceutical composition of the sixth aspect of the invention.

DETAILED DESCRIPTION

The inventors have identified particularly strong agonist antibodies to BTLA which are predicted to be more efficacious than current antibodies at suppressing T cell responses and thus be particularly useful in the treatment of immune mediated disorders.

As used in this specification and the appended claims, the singular forms "a", "an" and "the" include plural referents unless the content clearly dictates otherwise. Thus, for example, reference to "a molecule" optionally includes a combination of two or more such molecules, and the like.

It is understood that wherever aspects are described herein with the language "comprising," otherwise analogous aspects described in terms of "consisting of" and/or "consisting essentially of" are also provided.

It is to be understood that one, some, or all of the properties of the various embodiments described herein may be applied to any aspect unless the content clearly dictates otherwise. Furthermore, that the various embodiments may be combined to form other embodiments of the present invention. These and other aspects of the invention will become apparent to one of skill in the art. These and other embodiments of the invention are further described by the detailed description that follows.

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of ordinary skill with a general dictionary of many of the terms used in this disclosure.

The term "about" as used herein refers to the usual error range for the respective value readily known to the skilled person in this technical field. Reference to "about" a value or parameter herein includes (and describes) embodiments that are directed to that value or parameter per se.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The numbering of amino acids in the variable domain, CDRs and framework regions (FRs), of an antibody follow, unless otherwise indicated, the Kabat definition as set forth in Kabat et al. Sequences of Proteins of Immunological Interest, 5th Ed. Public Health Service, National Institutes of Health, Bethesda, Md. (1991).

The terms "B and T lymphocyte attenuator" and "BTLA" are used interchangeably and, unless the context dictates otherwise, with reference to either the protein or gene (or other nucleic acid encoding all or part of BTLA). The human BTLA sequences encompass all human isotype and variant forms. A representative example of full length human BTLA is disclosed in Genbank under accession number: AJ717664.1. Another representative polypeptide sequence of human BTLA is disclosed in SEQ ID NO: 23, which only differs from that in AJ717664.1 by two natural variant single nucleotide polymorphisms. Despite allelic variations, a human BTLA polypeptide sequence will typically have at least 90% sequence identity (such as at least 95%, 96%, 97%, 98%, 99% or 100%) to human BTLA in SEQ ID NO: 23.

A representative example of full length cynomolgus (cyno) BTLA is disclosed in Genbank under accession number: XP_005548224. A reference polypeptide sequence of cyno BTLA is disclosed in SEQ ID NO: 24. A cyno BTLA polypeptide sequence will typically have at least 90% sequence identity (such as at least 95%, 96%, 97%, 98%, 99% or 100%) to cyno BTLA as disclosed in SEQ ID NO: 24.

The term sequence identity is well known in the art. For the purposes of this invention, when determining whether a target sequence meets a defined limit (e.g. 90% identity), it is considered to meet the defined limit if it is identified as such using the BLAST (Basic local alignment search tool) algorithm (see Altschul et al. J Mol Biol 215:403-410, 1990) or Smith-Waterman algorithm (see Smith and Waterman. J Mol. Biol. 147:195-197, 1981).

Antibodies and Antigen-Binding Fragments of Antibodies

An antibody is an immunoglobulin molecule capable of specific binding to a target, such as a protein, polypeptide, peptide, carbohydrate, polynucleotide, lipid, or combinations of the foregoing through at least one antigen recognition site, located in the variable domain of the immunoglobulin molecule. In particular, as used herein, the term "antibody" encompasses intact polyclonal antibodies, intact monoclonal antibodies, multispecific antibodies such as bispecific antibodies generated from at least two intact antibodies, chimeric antibodies, humanised antibodies, human antibodies, and any other modified immunoglobulin molecule comprising an antigen recognition site so long as the antibodies exhibit the desired biological activity.

The term "antibody" as used herein, refers to an immunoglobulin molecule which specifically binds to an antigen and comprises an FcR binding site which may or may not be functional.

As used herein, a BTLA agonist antibody (or antibody fragment) refers to an antibody (or antibody fragment) that binds to BTLA and enhances its coinhibitory signal to T and/or B cells.

The antigen-binding site refers to the part of a molecule that binds to all or part of the target antigen. In an antibody molecule it may be referred to as the antibody antigen-binding site and comprises the part of the antibody that specifically binds to all or part of the target antigen. Where an antigen is large, an antibody may only bind to a particular part of the antigen, which part is termed an epitope. An antibody antigen-binding site may be provided by one or more antibody variable domains. Preferably, an antibody antigen-binding site comprises an antibody light chain variable region (VL) and an antibody heavy chain variable region (VH).

The invention also encompassed antibody-fragments that comprise an antigen-binding site. Thus, the term "antigen-binding fragment thereof", when referring to an antibody refers to antibody fragments, such as Fab, Fab', F(ab')$_2$, diabodies, Fv fragments and single chain Fv (scFv) mutants that possess an antigen recognition site, and thus, the ability to bind to an antigen. Antigen-binding immunoglobulin (antibody) fragments are well known in the art. Such fragment need not have a functional Fc receptor binding site.

As used herein the terms "antibody fragment molecules of the invention", "antibody fragment" and "antigen-binding fragment thereof", are used interchangeably herein.

The term "BTLA-binding molecule" as used herein, refers to both antibodies and binding fragments thereof capable of binding to BTLA.

There are five major classes (i.e., isotypes) of immunoglobulins: IgA, IgD, IgE, IgG, and IgM, and several of these may be further divided into subclasses (subtypes), e.g., IgG1, IgG2, IgG3, IgG4, IgA1 and IgA2. The heavy-chain constant regions that correspond to the different classes of immunoglobulins are called alpha, delta, epsilon, gamma, and mu, respectively. The subunit structures and three-dimensional configurations of different classes of immunoglobulins are well known. Unless dictated otherwise by contextual constraints the antibodies of the invention can be from one of these classes or subclasses of antibodies. Heavy-chain constant domains that correspond to the different classes of antibodies are typically denoted by the corresponding lower-case Greek letter α, δ, ε, γ, and μ, respectively. Light chains of the antibodies from any vertebrate species can be assigned to one of two clearly distinct types, called kappa (κ) and lambda (λ), based on the amino acid sequences of their constant domains.

"Native antibodies" are usually heterotetrameric Y-shaped glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain (VH) followed by a number of constant domains. Each light chain has a variable domain at one end (VL) and a constant domain at its other end; the constant domain of the light chain is aligned with the first constant domain of the heavy chain, and the light chain variable domain is aligned with the variable domain of the heavy chain. Particular amino acid residues are believed to form an interface between the light chain and heavy chain variable domains. Each heavy chain comprises one variable domain (VH) and a constant region, which in the case of IgG, IgA, and IgD antibodies, comprises three domains termed $C_H1$, $C_H2$, and $C_H3$ (IgM and IgE have a fourth domain, $C_H4$). In IgG, IgA, and IgD classes the $C_H1$ and $C_H2$ domains are separated by a flexible hinge region, which is a proline and cysteine rich segment of variable length (from about 10 to about 60 amino acids in various IgG subclasses). The variable domains in both the light and heavy chains are joined to the constant domains by a "J" region of about 12 or more amino acids and the heavy chain also has a "D" region of about 10 additional amino acids. Each class of antibody further comprises inter-chain and intra-chain disulfide bonds formed by paired cysteine residues. The heavy chain variable region (VH) and light chain variable region (VL) can each be further subdivided into regions of hypervariability, termed CDRs, interspersed with regions that are more conserved, termed framework regions (FR). Each VH and VL, comprises three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g. effector cells) and the first component (Clq) of the classical complement system.

The antibody or antigen-binding fragment thereof of the invention may be from any animal species including murine, rat, human, or any other origin (including chimeric or humanised antibodies). In some embodiments, the antibody or antigen-binding antibody fragment is monoclonal, e,g. a monoclonal antibody. In some embodiments, the antibody or antigen-binding fragment thereof is a human or humanised antibody or antigen-binding fragment thereof. A non-human antibody or antigen-binding fragment thereof may be humanised by recombinant methods to reduce its immunogenicity in man.

An antibody or antigen-binding fragment thereof of the invention may be identified using well-known methods. For example, the antigen-binding moiety may have been selected using phage display or other antigen-binding selection or panning approach. Such antigen-binding moiety could then be incorporated into an antibody framework (e.g. fused to the constant and hinge regions of, for example an IgG1 or IgG4 molecule).

The term "monoclonal antibody" ("mAb") as used herein refers to an antibody obtained from a population of substantially homogeneous antibodies, e.g., the individual antibodies comprising the population are identical except for possible mutations, e.g., naturally occurring mutations, that may be present in minor amounts. Thus, the modifier "monoclonal" indicates the character of the antibody or fragment thereof, as not being a mixture of discrete antibodies or antigen-binding fragments. A mAb is highly specific, being directed against a single antigenic site/epitope.

A mAb may be produced by hybridoma, recombinant, transgenic or other techniques known to those skilled in the art. For example, a monoclonal antibody or antigen-binding fragment thereof in accordance with the present invention may be made by the hybridoma method first described by Kohler and Milstein (Nature 256:495, 1975) or may be made by recombinant DNA methods such as described in U.S. Pat. Nos. 4,816,567 and 6,331,415. The "monoclonal antibodies" may also be isolated from phage antibody libraries using the techniques described in Clackson et al., Nature 1991; 352:624-628 and Marks et al., J. Mol. Biol. 1991; 222:581-597, for example.

The term monoclonal may also be ascribed to an antigen-binding fragment of an antibody of the invention. It merely means that the molecule is produced or present in a single clonal form.

A "human" antibody (HumAb) refers to an antibody having variable regions in which both the framework and CDR regions are derived from human germline immunoglobulin sequences. Furthermore, if the antibody contains a constant region, the constant region is also derived from human germline immunoglobulin sequences. The human antibodies may include amino acid residues not encoded by human germline immunoglobulin sequences (e.g., mutations introduced by random or site-specific mutagenesis in vitro or by somatic mutation in vivo). However, the term "human antibody," as used herein, is not intended to include antibodies in which CDR sequences derived from the germline of another mammalian species, such as a mouse, have been grafted onto human framework sequences.

Human antibodies can be prepared by administering an immunogen/antigen to a transgenic animal that has been modified to produce intact human antibodies or intact antibodies with human variable regions in response to antigenic challenge, but whose endogenous loci have been disabled, e.g., immunized xenomice (see, e.g., U.S. Pat. Nos. 6,075, 181 and 6,150,584 regarding XENOMOUSE (trade mark) technology). See also, for example, Li et al., Proc. Natl. Acad. Sci. USA, 103:3557-3562 (2006) regarding human antibodies generated via a human B-cell hybridoma technology. Such animals typically contain all or a portion of the human immunoglobulin loci, which replace the endogenous immunoglobulin loci, or which are present extra chromosomally or integrated randomly into the animal's chromosomes. In such transgenic mice, the endogenous immunoglobulin loci have generally been inactivated. For review of methods for obtaining human antibodies from transgenic animals, see Lonberg, Nat. Biotech. 23:1117-1125 (2005). See also, e.g., U.S. Pat. Nos. 6,075,181 and 6,150,584 describing XENOMOUSE™ technology; U.S. Pat. No. 5,770,429 describing HUMAB™ technology; U.S. Pat. No. 7,041,870 describing K-M MOUSE™ technology, and U.S. Patent Application Publication No. US2007/0061900, describing VELOCIMOUSE™ technology. Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor J. Immunol, 133:3001 (1984); Brodeur et al., Monoclonal Antibody Production Techniques and Applications, pp. 51-63 (Marcel Dekker, Inc., New York, 1987); and Boerner et al., J. Immunol., 147:86 (1991)) Human antibodies generated via human B-cell hybridoma technology are also described in Li et al., Proc. Natl. Acad. Sci. USA, 103:3557-3562 (2006). Additional methods include those described, for example, in U.S. Pat. No. 7,189,826 (describing production of monoclonal human IgM antibodies from hybridoma cell lines) and Ni, Xiandai Mianyixue, 26:265-268 (2006) (describing human-human hybridomas). Human hybridoma technology (Trioma technology) is also described in Vollmers and Brandlein, Histology and Histopathology, 20:927-937 (2005) and Vollmers and Brandlein, Methods and Findings in Experimental and Clinical Pharmacology, 27:185-91 (2005).

The terms "human" antibodies and "fully human" antibodies are used synonymously. This definition of a human antibody specifically excludes a humanised antibody comprising non-human antigen-binding residues.

As used herein, a "humanised antibody" refers to an antibody in which some, most or all of the amino acids outside the CDRs of a non-human antibody are replaced with corresponding amino acids derived from human immunoglobulins. In some embodiments, humanised antibodies are human immunoglobulins (recipient antibody) in which residues from a CDR of the recipient are replaced by residues from a CDR of a non-human species (donor antibody) such as mouse, rat, or rabbit having the desired specificity, affinity, and capacity. The humanised antibody may comprise residues that are found neither in the recipient antibody nor in the imported CDR or framework sequences but are included to further refine and optimize antibody performance. In one embodiment of a humanised form of an Ab, some, most or all the amino acids outside the CDRs have been replaced with amino acids from human immunoglobulins, whereas some, most or all amino acids within one or more CDR regions are unchanged. Small additions, deletions, insertions, substitutions or modifications of amino acids are permissible provided they do not abrogate the ability of the antibody to bind to a particular antigen. A "humanised" antibody retains an antigenic specificity similar to that of the original antibody. In general, a humanised antibody will comprise substantially all of at least one, and typically two, variable domains, in which all or substantially all of the hypervariable loops correspond to those of a non-human immunoglobulin, and all or substantially all of the FRs are those of a human immunoglobulin sequence. The humanised antibody optionally will also comprise at least a portion of an immunoglobulin constant region (Fc), typically that of a human immunoglobulin. For further details, see, e.g., Jones et al, Nature 321:522-525 (1986); Riechmann et al, Nature 332:323-329 (1988); and Presta, Curr. Op. Struct. Biol. 2:593-596 (1992). See also, e.g., Vaswani and Hamilton, Ann. Allergy, Asthma & Immunol. 1:105-115 (1998); Harris, Biochem. Soc. Transactions 23:1035-1038 (1995); Hurle and Gross, Curr. Op. Biotech. 5:428-433 (1994); and U.S. Pat. Nos. 6,982,321 and 7,087, 409.

As used herein, an "engineered antibody" refers to an antibody, which may be a humanized antibody, wherein particular residues have been substituted for others so as to diminish an adverse effect or property. Such substitution could be within a CD domain. For example, as described herein (see Example 21), the CDRH2 of the humanised antibody 3E8 was modified with an N57Q substitution to remove deamidation potential, and a K63S substitution to reduce predicted immunogenicity.

A "chimeric antibody" refers to an antibody in which the variable regions are derived from one species and the constant regions are derived from another species, such as an antibody in which the variable regions are derived from a mouse antibody and the constant regions are derived from a human antibody or vice versa. The term also encompasses an antibody comprising a V region from one individual from one species (e.g., a first mouse) and a constant region from another individual from the same species (e.g., a second mouse). The term "antigen (Ag)" refers to the molecular entity used for immunization of an immunocompetent vertebrate to produce the antibody (Ab) that recognizes the Ag or to screen an expression library (e.g., phage, yeast or ribosome display library, among others). Herein, Ag is termed more broadly and is generally intended to include target molecules that are specifically recognized by the Ab, thus including portions or mimics of the molecule used in an immunization process for raising the Ab or in library screening for selecting the Ab.

A "bispecific" or "bifunctional" antibody is an artificial hybrid antibody having two different heavy/light chain pairs and two different binding sites. Traditionally, the recombinant production of bispecific antibodies is based on the co-expression of two immunoglobulin heavy-chain/light-chain pairs, where the two heavy chains have different specificities (Milstein and Cuello, Nature, 305:537-539 (1983)). Methods for making bispecific antibodies are within the purview of those skilled in the art. For example, bispecific antibodies can be produced by a variety of methods including fusion of hybridomas or linking of Fab' fragments. See, e.g., Songsivilai, et al, (1990) Clin. Exp. Immunol. 79: 315-321, Kostelny, et al, (1992) J Immunol. 148:1547-1553. In addition, bispecific antibodies may be formed as "diabodies" (Holliger, et al, (1993) PNAS USA 90:6444-6448) or as "Janusins" (Traunecker, et al, (1991) EMBO J. 10:3655-3659 and Traunecker, et al, (1992) Int. J. Cancer Suppl. 7:51-52).

Generally, the term "epitope" refers to the area or region of an antigen to which an antibody specifically binds, i.e., an area or region in physical contact with the antibody. Thus, the term "epitope" refers to that portion of a molecule capable of being recognized by and bound by an antibody at one or more of the antibody's antigen-binding regions. Typically, an epitope is defined in the context of a molecular interaction between an "antibody, or antigen-binding portion thereof (Ab), and its corresponding antigen. Epitopes often consist of a surface grouping of molecules such as amino acids or sugar side chains and have specific three-dimensional structural characteristics as well as specific charge characteristics. In some embodiments, the epitope can be a protein epitope. Protein epitopes can be linear or conformational. In a linear epitope, all of the points of interaction between the protein and the interacting molecule (such as an antibody) occur linearly along the primary amino acid sequence of the protein. A "nonlinear epitope" or "conformational epitope" comprises non-contiguous polypeptides (or amino acids) within the antigenic protein to which an antibody specific to the epitope binds. The term "antigenic epitope" as used herein, is defined as a portion of an antigen to which an antibody can specifically bind as determined by any method well known in the art, for example, by conventional immunoassays.

An antibody that "specifically binds" to an epitope is a term well understood in the art, and methods to determine such specific binding are also well known in the art. A molecule is said to exhibit "specific binding" if it reacts or associates more frequently, more rapidly, with greater duration and/or with greater affinity with a particular cell, protein or substance than it does with alternative cells, proteins or substances.

A variety of assay formats may be used to select an antibody or peptide that specifically binds a molecule of interest. For example, solid-phase ELISA immunoassay, immunoprecipitation, Biacore™ (GE Healthcare, Piscataway, N.J.), KinExA, fluorescence-activated cell sorting (FACS), Octet™ (ForteBio, Inc., Menlo Park, Calif.) and Western blot analysis are among many assays that may be used to identify an antibody that specifically reacts with an antigen or a receptor, or ligand binding portion thereof, that specifically binds with a cognate ligand or binding partner. Typically, a specific or selective reaction will be at least twice the background signal or noise, more typically more than 10 times background, even more typically, more than 50 times background, more typically, more than 100 times background, yet more typically, more than 500 times background, even more typically, more than 1000 times background, and even more typically, more than 10,000 times background. Also, an antibody is said to "specifically bind" an antigen when the equilibrium dissociation constant ($K_D$ or KD, as used interchangeably herein) is <7 nM.

According to the first aspect of the invention there is provided an isolated antibody or an antigen-binding fragment thereof that specifically binds BTLA, wherein the antibody has a heavy chain and/or light chain with at least one CDR an antibody selected from the group consisting of 11.5.1, 2.8.6, 12F11, 14D4, 15B6, 15C6, 16E1, 16F10, 16H2, 1H6, 21C7, 24H7, 26B1, 26F3, 27G9, 3A9, 3E8, 4B1, 4D3, 4D5, 4E8, 4H4, 6G8, 7A1, 8B4, 8C4, 6.2 and 831, as disclosed in Table 1 and described herein. In one embodiment, the antibody or antigen-binding fragment thereof competes for binding to BTLA with its natural ligand HVEM. In another embodiment, the antibody or antigen-binding fragment thereof does not interfere with binding of HVEM.

In additional embodiments, the isolated antibody which binds human BTLA is selected from the group consisting of 11.5.1 and 2.8.6, wherein the antibody specifically binds BTLA and induces signaling through the receptor.

By an antibody selected from the group consisting of 11.5.1, 2.8.6, 12F11, 14D4, 15B6, 15C6, 16E1, 16F10, 16H2, 1H6, 21C7, 24H7, 26B1, 26F3, 27G9, 3A9, 3E8, 4B1, 4D3, 4D5, 4E8, 4H4, 6G8, 7A1, 8B4, 8C4, 6.2 and 831, as disclosed in Table 1 and described herein, means any antibody or antigen-binding fragment thereof which comprises one or more, such as VH CDR 1, 2 and 3, or VL CDR 1, 2 and 3, or VH CDR 1, 2 and 3 and VL CDR 1, 2 and 3, from any of the antibodies disclosed in Table 1 (whether murine, humanized or humanised/engineered).

According to a variation of the first aspect of the invention there is provided an isolated antibody or an antigen-binding fragment thereof that specifically binds human BTLA comprising at least one VH CDR that has an amino acid sequence as set forth in any of SEQ ID NO: 7, SEQ ID NO: 8 or SEQ ID NO: 9, with from 0 to 3 amino acid modifications, such as 0, 1, 2, or 3 amino acid modifications. In certain embodiments, the amino acid modifications include, but not limited to, amino acid substitution, addition, deletion, or chemical modification, without eliminating the antibody binding affinity or T-cell inhibitory effect of the modified amino acid sequence, as compared to the unmodified amino acid sequence.

According to a variation of the first aspect of the invention there is provided an isolated antibody or an antigen-binding fragment thereof that specifically binds human BTLA comprising at least one VH CDR with an amino acid sequence as set forth in any of SEQ ID NO: 193, SEQ ID NO: 194, or SEQ ID NO: 195, with from 0 to 3 amino acid modifications.

According to another variation of the first aspect of the invention there is provided an isolated antibody or an antigen-binding fragment thereof that specifically binds human BTLA, comprising a heavy chain and a light chain, wherein the heavy chain comprises a heavy chain variable region comprising three CDRs: CDRH1, CDRH2 and CDRH3, wherein CDRH1 has an amino acid sequence as set forth in SEQ ID NO: 7, CDRH2 has an amino acid sequence as set forth in SEQ ID NO: 8, and CDRH3 has an amino acid sequence as set forth in SEQ ID NO: 9.

According to another variation of the first aspect of the invention there is provided an isolated antibody or an antigen-binding fragment thereof that specifically binds human BTLA, comprising a heavy chain and a light chain, wherein the heavy chain comprises a heavy chain variable region comprising three CDRs: CDRH1, CDRH2 and CDRH3, wherein CDRH1 has an amino acid sequence as set forth in SEQ ID NO: 193, CDRH2 has an amino acid sequence as set forth in SEQ ID NO: 194, and CDRH3 has an amino acid sequence as set forth in SEQ ID NO: 195.

According to a variation of the first aspect of the invention there is provided an isolated antibody or an antigen-binding fragment thereof that specifically binds human BTLA comprising at least one VL CDR with an amino acid sequence as set forth in SEQ ID NO: 10, SEQ ID NO: 11 or SEQ ID NO: 12, with from 0 to 3 amino acid modifications.

According to a variation of the first aspect of the invention there is provided an isolated antibody or an antigen-binding fragment thereof that specifically binds human BTLA comprising at least one VL CDR with an amino acid sequence as set forth in SEQ ID NO: 196, SEQ ID NO: 197, or SEQ ID NO: 12, with from 0 to 3 amino acid modifications.

According to another variation of the first aspect of the invention there is provided an isolated antibody or an antigen-binding fragment thereof that specifically binds human BTLA, comprising a heavy chain and a light chain, wherein the light chain comprises a light chain variable region comprising three CDRs: CDRL1, CDRL2 and CDRL3, wherein CDRL1 has an amino acid sequence as set forth in SEQ ID NO: 10, CDRL2 has an amino acid sequence as set forth in SEQ ID NO: 11, and CDRL3 has an amino acid sequence as set forth in SEQ ID NO: 12.

According to another variation of the first aspect of the invention there is provided an isolated antibody or an antigen-binding fragment thereof that specifically binds human BTLA, comprising a heavy chain and a light chain, wherein the light chain comprises a light chain variable region comprising three CDRs: CDRL1, CDRL2 and CDRL3, wherein CDRL1 has an amino acid sequence as set forth in SEQ ID NO: 196, CDRL2 has an amino acid sequence as set forth in SEQ ID NO: 197, and CDRL3 has an amino acid sequence as set forth in SEQ ID NO: 12.

According to another variation of the first aspect of the invention there is provided an isolated antibody or an antigen-binding fragment thereof that specifically binds human BTLA, comprising a heavy chain and a light chain, wherein the heavy chain comprises a heavy chain variable region comprising three CDRs: CDRH1, CDRH2 and CDRH3, wherein CDRH1 has an amino acid sequence as set forth in SEQ ID NO: 7, CDRH2 has an amino acid sequence as set forth in SEQ ID NO: 8, and CDRH3 has an amino acid sequence as set forth in SEQ ID NO: 9, and the light chain comprises a light chain variable region comprising three CDRs: CDRL1, CDRL2 and CDRL3, wherein CDRL1 has an amino acid sequence as set forth in SEQ ID NO: 10, CDRL2 has an amino acid sequence as set forth in SEQ ID NO: 11, and CDRL3 has an amino acid sequence as set forth in SEQ ID NO: 12.

According to another variation of the first aspect of the invention there is provided an isolated antibody or an antigen-binding fragment thereof that specifically binds human BTLA, comprising a heavy chain and a light chain, wherein the heavy chain comprises a heavy chain variable region comprising three CDRs: CDRH1, CDRH2 and CDRH3, wherein CDRH1 has an amino acid sequence as set forth in SEQ ID NO: 193, CDRH2 has an amino acid sequence as set forth in SEQ ID NO: 194, and CDRH3 has an amino acid sequence as set forth in SEQ ID NO: 195, and the light chain comprises a light chain variable region comprising three CDRs: CDRL1, CDRL2 and CDRL3, wherein CDRL1 has an amino acid sequence as set forth in SEQ ID NO: 196, CDRL2 has an amino acid sequence as set forth in SEQ ID NO: 197, and CDRL3 has an amino acid sequence as set forth in SEQ ID NO: 12.

According to a variation of the first aspect of the invention there is provided an isolated antibody or an antigen-binding fragment thereof that specifically binds human BTLA comprising at least one VH CDR with an amino acid sequence as set forth in SEQ ID NO: 1, SEQ ID NO: 2 or SEQ ID NO: 3, with from 0 to 3 amino acid modifications.

According to another variation of the first aspect of the invention there is provided an isolated antibody or an antigen-binding fragment thereof that specifically binds human BTLA comprising at least one VH CDR with an amino acid sequence as set forth in SEQ ID NO: 199, SEQ ID NO: 200, or SEQ ID NO: 201, with from 0 to 3 amino acid modifications.

According to a variation of the first aspect of the invention there is provided an isolated antibody or an antigen-binding fragment thereof that specifically binds human BTLA, comprising a heavy chain and a light chain, wherein the heavy chain comprises a heavy chain variable region comprising three CDRs: CDRH1, CDRH2 and CDRH3, wherein CDRH1 has an amino acid sequence as set forth in SEQ ID NO: 1, CDRH2 has an amino acid sequence as set forth in SEQ ID NO: 2, and CDRH3 has an amino acid sequence as set forth in SEQ ID NO: 3.

According to a variation of the first aspect of the invention there is provided an isolated antibody or an antigen-binding fragment thereof that specifically binds human BTLA, comprising a heavy chain and a light chain, wherein the heavy chain comprises a heavy chain variable region comprising three CDRs: CDRH1, CDRH2 and CDRH3, wherein CDRH1 has an amino acid sequence as set forth in SEQ ID NO: 199, CDRH2 has an amino acid sequence as set forth in SEQ ID NO: 200, and CDRH3 has an amino acid sequence as set forth in SEQ ID NO: 201.

According to a variation of the first aspect of the invention there is provided an isolated antibody or an antigen-binding fragment thereof that specifically binds human BTLA comprising at least one VL CDR with an amino acid sequence as set forth in SEQ ID NO: 4, SEQ ID NO: 5 or SEQ ID NO: 6.

According to a variation of the first aspect of the invention there is provided an isolated antibody or an antigen-binding fragment thereof that specifically binds human BTLA comprising at least one VL CDR with an amino acid sequence as set forth in SEQ ID NO: 202, SEQ ID NO: 203, or SEQ ID NO: 6.

According to another variation of the first aspect of the invention there is provided an isolated antibody or an antigen-binding fragment thereof that specifically binds human BTLA, comprising a heavy chain and a light chain, wherein the light chain comprises a light chain variable region comprising three CDRs: CDRL1, CDRL2 and CDRL3, wherein CDRL1 has an amino acid sequence as set forth in SEQ ID NO: 4, CDRL2 has an amino acid sequence as set forth in SEQ ID NO: 5, and CDRL3 has an amino acid sequence as set forth in SEQ ID NO: 6.

According to another variation of the first aspect of the invention there is provided an isolated antibody or an antigen-binding fragment thereof that specifically binds human BTLA, comprising a heavy chain and a light chain, wherein the light chain comprises a light chain variable region comprising three CDRs: CDRL1, CDRL2 and CDRL3, wherein CDRL1 has an amino acid sequence as set forth in SEQ ID NO: 202, CDRL2 has an amino acid sequence as set forth in SEQ ID NO: 203, and CDRL3 has an amino acid sequence as set forth in SEQ ID NO: 6.

According to another variation of the first aspect of the invention there is provided an isolated antibody or an antigen-binding fragment thereof that specifically binds human BTLA, comprising a heavy chain and a light chain, wherein the heavy chain comprises a heavy chain variable region comprising three CDRs: CDRH1, CDRH2 and CDRH3, wherein CDRH1 has an amino acid sequence as set forth in SEQ ID NO: 1, CDRH2 has an amino acid sequence as set forth in SEQ ID NO: 2, and CDRH3 has an amino acid sequence as set forth in SEQ ID NO: 3, and the light chain comprises a light chain variable region comprising three CDRs: CDRL1, CDRL2 and CDRL3, wherein CDRL1 has an amino acid sequence as set forth in SEQ ID NO: 4, CDRL2 has an amino acid sequence as set forth in SEQ ID NO: 5, and CDRL3 has an amino acid sequence as set forth in SEQ ID NO: 6.

According to another variation of the first aspect of the invention there is provided an isolated antibody or an antigen-binding fragment thereof that specifically binds human BTLA, comprising a heavy chain and a light chain, wherein the heavy chain comprises a heavy chain variable region comprising three CDRs: CDRH1, CDRH2 and CDRH3, wherein CDRH1 has an amino acid sequence as set forth in SEQ ID NO: 199, CDRH2 has an amino acid sequence as set forth in SEQ ID NO: 200, and CDRH3 has an amino acid sequence as set forth in SEQ ID NO: 201, and the light chain comprises a light chain variable region comprising three CDRs: CDRL1, CDRL2 and CDRL3, wherein CDRL1 has an amino acid sequence as set forth in SEQ ID NO: 202, CDRL2 has an amino acid sequence as set forth in SEQ ID NO: 203, and CDRL3 has an amino acid sequence as set forth in SEQ ID NO: 6.

According to another variation of the first aspect of the invention there is provided an isolated antibody or an antigen-binding fragment thereof that specifically binds human BTLA comprising at least one VH CDR with an amino acid sequence as set forth in (1) SEQ ID NO: 31, 32, or 33, with from 0 to 3 amino acid modifications; (2) SEQ ID NO: 37, 38, or 39, with from 0 to 3 amino acid modifications; (3) SEQ ID NO: 43, 44, or 45, with from 0 to 3 amino acid modifications; (4) SEQ ID NO: 43, 56, or 57, with from 0 to 3 amino acid modifications; (5) SEQ ID NO: 61, 62, or 63, with from 0 to 3 amino acid modifications; (6) SEQ ID NO: 31, 32, or 69, with from 0 to 3 amino acid modifications; (7) SEQ ID NO: 73, 74, or 75, with from 0 to 3 amino acid modifications; (8) SEQ ID NO: 79, 80, or 81, with from 0 to 3 amino acid modifications; (9) SEQ ID NO: 85, 86, or 87, with from 0 to 3 amino acid modifications; (10) SEQ ID NO: 61, 92, or 93, with from 0 to 3 amino acid modifications; (11) SEQ ID NO: 97, 98, or 99, with from 0 to 3 amino acid modifications; (12) SEQ ID NO: 103, 104, or 105, with from 0 to 3 amino acid modifications; (13) SEQ ID NO: 109, 110, or 111, with from 0 to 3 amino acid modifications; (14) SEQ ID NO: 85, 110, or 117, with from 0 to 3 amino acid modifications; (15) SEQ ID NO: 121, 122, or 123, with from 0 to 3 amino acid modifications; (16) SEQ ID NO: 127, 128, or 129, with from 0 to 3 amino acid modifications; (17) SEQ ID NO: 133, 134, or 135, with from 0 to 3 amino acid modifications; (18) SEQ ID NO: 139, 140, or 141, with from 0 to 3 amino acid modifications; (19) SEQ ID NO: 145, 146, or 147, with from 0 to 3 amino acid modifications; (20) SEQ ID NO: 31, 32, or 33, with from 0 to 3 amino acid modifications; (21) SEQ ID NO: 31, 32, or 159, with from 0 to 3 amino acid modifications; (22) SEQ ID NO: 169, 170, or 171, with from 0 to 3 amino acid modifications; (23) SEQ ID NO: 61, 62, or 63, with from 0 to 3 amino acid modifications; (24) SEQ ID NO: 31, 182, or 183, with from 0 to 3 amino acid modifications; (25) SEQ ID NO: 187, 188, or 189, with from 0 to 3 amino acid modifications; (26) SEQ ID NO: 193, 194, or 195, with from 0 to 3 amino acid modifications; (27) SEQ ID NO: 199, 200, or 201, with from 0 to 3 amino acid modifications; (28) SEQ ID NO: 205, 206, or 207, with from 0 to 3 amino acid modifications; (29) SEQ ID NO: 211, 212, or 213, with from 0 to 3 amino acid modifications; (30) SEQ ID NO: 127, 386, or 129, with from 0 to 3 amino acid modifications; (33) SEQ ID NO: 205, 206, or 207, with from 0 to 3 amino acid modifications; (34) SEQ ID NO: 127, 388, or 129, with from 0 to 3 amino acid modifications; or (35) SEQ ID NO: 205, 387, or 207, with from 0 to 3 amino acid modifications.

According to a variation of the first aspect of the invention there is provided an isolated antibody or an antigen-binding fragment thereof that specifically binds human BTLA, comprising a heavy chain and a light chain, wherein the heavy chain comprises a heavy chain variable region comprising three CDRs: CDRH1, CDRH2 and CDRH3, wherein CDRH1, CDRH2, CDRH3 have an amino acid sequence as set forth in (1) SEQ ID NO: 31, SEQ ID NO: 32, and SEQ ID NO: 33, respectively; (2) SEQ ID NO: 37, SEQ ID NO: 38, and SEQ ID NO: 39, respectively; (3) SEQ ID NO: 43, SEQ ID NO: 44, and SEQ ID NO: 45, respectively; (4) SEQ ID NO: 43, SEQ ID NO: 56, and SEQ ID NO: 57, respectively; (5) SEQ ID NO: 61, SEQ ID NO: 62, and SEQ ID NO: 63, respectively; (6) SEQ ID NO: 31, SEQ ID NO: 32, and SEQ ID NO: 69, respectively; (7) SEQ ID NO: 73, SEQ ID NO: 74, and SEQ ID NO: 75, respectively; (8) SEQ ID NO: 79, SEQ ID NO: 80, and SEQ ID NO: 81, respectively; (9) SEQ ID NO: 85, SEQ ID NO: 86, and SEQ ID NO: 87, respectively; (10) SEQ ID NO: 61, SEQ ID NO: 92, and SEQ ID NO: 93, respectively; (11) SEQ ID NO: 97, SEQ ID NO: 98, and SEQ ID NO: 99, respectively; (12) SEQ ID NO: 103, SEQ ID NO: 104, and SEQ ID NO: 105, respectively; (13) SEQ ID NO: 109, SEQ ID NO: 110, and SEQ ID NO: 111, respectively; (14) SEQ ID NO: 85, SEQ ID NO: 110, and SEQ ID NO: 117, respectively; (15) SEQ ID NO: 121, SEQ ID NO: 122, and SEQ ID NO: 123, respectively; (16) SEQ ID NO: 127, SEQ ID NO: 128, and SEQ ID NO: 129, respectively; (17) SEQ ID NO: 133, SEQ ID NO: 134, and SEQ ID NO: 135, respectively; (18) SEQ ID NO: 139, SEQ ID NO: 140, and SEQ ID NO: 141, respectively; (19) SEQ ID NO: 145, SEQ ID NO: 146, and SEQ ID NO: 147, respectively; (20) SEQ ID NO: 31, SEQ ID NO: 32, and SEQ ID NO: 33, respectively; (21) SEQ ID NO: 31, SEQ ID NO: 32, and SEQ ID NO: 159, respectively; (22) SEQ ID NO: 169, SEQ ID NO: 170, and SEQ ID NO: 171, respectively; (23) SEQ ID NO: 61, SEQ ID NO: 62, and SEQ ID NO: 63, respectively; (24) SEQ ID NO: 31, SEQ ID NO: 182, and SEQ ID NO: 183, respectively; (25) SEQ ID NO: 187, SEQ ID NO: 188, and SEQ ID NO: 189, respectively; (26) SEQ ID NO: 193, SEQ ID NO: 194, and SEQ ID NO: 195, respectively; (27) SEQ ID NO: 199, SEQ ID NO: 200, and SEQ ID NO: 201, respectively; (28) SEQ ID NO: 205, SEQ ID NO: 206, and SEQ ID NO: 207, respectively; (29) SEQ ID NO: 211, 212, and 213, respectively; (30) SEQ ID NO: 127, 386, and 129, respectively; (31) SEQ ID NO: 205, 206, and 207, respectively; (32) SEQ ID NO: 127, 388, and 129, respectively; or (33) SEQ ID NO: 205, 387, and 207, respectively, wherein from 0 to 3 amino acid modifications can be present in any CDR/SEQ ID NO.

According to a variation of the first aspect of the invention there is provided an isolated antibody or an antigen-binding fragment thereof that specifically binds human BTLA comprising at least one VL CDR with an amino acid sequence as set forth in (1) SEQ ID NO: 34, 35, or 36; (2) SEQ ID NO: 40, 41, or 42; (3) SEQ ID NO: 46, 47, or 48; (4) SEQ ID NO: 58, 59, or 60; (5) SEQ ID NO: 64, 65, or 66; (6) SEQ ID NO: 34, 35, or 72; (7) SEQ ID NO: 76, 47, or 78; (8) SEQ ID NO: 82, 83, or 84; (9) SEQ ID NO: 88, 89, or 90; (10) SEQ ID NO: 94, 95, or 96; (11) SEQ ID NO: 100, 101, or 102; (12) SEQ ID NO: 64, 107, or 108; (13) SEQ ID NO: 88, 89, or 114; (14) SEQ ID NO: 124, 125, or 126; (15) SEQ ID NO: 34, 35, or 36; (16) SEQ ID NO: 136, 137, or 138; (17) SEQ ID NO: 142, 143, or 144; (18) SEQ ID NO: 148, 149, or 150; (19) SEQ ID NO: 136, 137, or 162; (20) SEQ ID NO: 34, 35, or 36; (21) SEQ ID NO: 172, 173, or 174; (22) SEQ ID NO: 64, 65, or 180; (23) SEQ ID NO: 136, 137, or 186; (24) SEQ ID NO: 190, 191, or 192; (25) SEQ ID NO: 196, 197, or 12; (26) SEQ ID NO: 202, 203, or 6; (27) SEQ ID NO: 142, 209, or 210; or (28) SEQ ID NO: 214, 35, or 216; (29) SEQ ID NO: 10, 11, or 12; (30) SEQ ID NO: 4, 5, or 6; or (31) SEQ ID NO: 142, 143, or 210, wherein from 0 to 3 amino acid modifications can be present in any CDR/SEQ ID NO.

According to another variation of the first aspect of the invention there is provided an isolated antibody or an antigen-binding fragment thereof that specifically binds human BTLA, comprising a heavy chain and a light chain, wherein the light chain comprises a light chain variable region comprising three CDRs: CDRL1, CDRL2 and CDRL3, wherein CDRL1, CDRL2, and CDRL3 have an amino acid sequence as set forth in (1) SEQ ID NO: 34, SEQ ID NO: 35, and SEQ ID NO: 36, respectively; (2) SEQ ID NO: 40, SEQ ID NO: 41, and SEQ ID NO: 42, respectively; (3) SEQ ID NO: 46, SEQ ID NO: 47, and SEQ ID NO: 48, respectively; (4) SEQ ID NO: 58, SEQ ID NO: 59, and SEQ ID NO: 60, respectively; (5) SEQ ID NO: 64, SEQ ID NO: 65, and SEQ ID NO: 66, respectively; (6) SEQ ID NO: 34, SEQ ID NO: 35, and SEQ ID NO: 72, respectively; (7) SEQ ID NO: 76, SEQ ID NO: 47, and SEQ ID NO: 78, respectively; (8) SEQ ID NO: 82, SEQ ID NO: 83, and SEQ ID NO: 84, respectively; (9) SEQ ID NO: 88, SEQ ID NO: 89, and SEQ ID NO: 90, respectively; (10) SEQ ID NO: 94, SEQ ID NO: 95, and SEQ ID NO: 96, respectively; (11) SEQ ID NO: 100, SEQ ID NO: 101, and SEQ ID NO: 102, respectively; (12) SEQ ID NO: 64, SEQ ID NO: 107, and SEQ ID NO: 108, respectively; (13) SEQ ID NO: 88, SEQ ID NO: 89, and SEQ ID NO: 114, respectively; (14) SEQ ID NO: 124, SEQ ID NO: 125, and SEQ ID NO: 126, respectively; (15) SEQ ID NO: 34, SEQ ID NO: 35, and SEQ ID NO: 36, respectively; (16) SEQ ID NO: 136, SEQ ID NO: 137, and SEQ ID NO: 138, respectively; (17) SEQ ID NO: 142, SEQ ID NO: 143, and SEQ ID NO: 144, respectively; (18) SEQ ID NO: 148, SEQ ID NO: 149, and SEQ ID NO: 150, respectively; (19) SEQ ID NO: 136, SEQ ID NO: 137, and SEQ ID NO: 162, respectively; (20) SEQ ID NO: 34, SEQ ID NO: 35, and SEQ ID NO: 36, respectively; (21) SEQ ID NO: 172, SEQ ID NO: 173, and SEQ ID NO: 174, respectively; (22) SEQ ID NO: 64, SEQ ID NO: 65, and SEQ ID NO: 180, respectively; (23) SEQ ID NO: 136, SEQ ID NO: 137, and SEQ ID NO: 186, respectively; (24) SEQ ID NO: 190, SEQ ID NO: 191, and SEQ ID NO: 192, respectively; (25) SEQ ID NO: 196, SEQ ID NO: 197, and SEQ ID NO: 12, respectively; (26) SEQ ID NO: 202, SEQ ID NO: 203, and SEQ ID NO: 6, respectively; (27) SEQ ID NO: 142, SEQ ID NO: 209, and SEQ ID NO: 210, respectively; (28) SEQ ID NO: 214, SEQ ID NO: 35, and SEQ ID NO: 216, respectively; (29) SEQ ID NO: 10, 11, or 12, respectively; (30) SEQ ID NO: 4, 5, or 6, respectively; or (31) SEQ ID NO: 142, 143, or 210, respectively, wherein from 0 to 3 amino acid modifications can be present in any CDR/SEQ ID NO.

According to another variation of the first aspect of the invention there is provided an isolated antibody or an antigen-binding fragment thereof that specifically binds human BTLA, comprising a heavy chain and a light chain, wherein the heavy chain comprises a heavy chain variable region comprising three CDRs: CDRH1, CDRH2 and CDRH3, and the light chain comprises a light chain variable region comprising three CDRs: CDRL1, CDRL2 and CDRL3, wherein (1) CDRH1, CDRH2, CDRH3 have an amino acid sequence as set forth in SEQ ID NO: 31, SEQ ID NO: 32, and SEQ ID NO: 33, respectively, and CDRL1, CDRL2, and CDRL3 have an amino acid sequence as set forth in SEQ ID NO: 34, SEQ ID NO: 35, and SEQ ID NO: 36, respectively; (2) CDRH1, CDRH2, CDRH3 have an amino acid sequence as set forth in SEQ ID NO: 37, SEQ ID NO: 38, and SEQ ID NO: 39, respectively, and CDRL1, CDRL2, and CDRL3 have an amino acid sequence as set forth in SEQ ID NO: 40, SEQ ID NO: 41, and SEQ ID NO: 42, respectively; (3) CDRH1, CDRH2, CDRH3 have an amino acid sequence as set forth in SEQ ID NO: 43, SEQ ID NO: 44, and SEQ ID NO: 45, respectively, and CDRL1, CDRL2, and CDRL3 have an amino acid sequence as set forth in SEQ ID NO: 46, SEQ ID NO: 47, and SEQ ID NO: 48, respectively; (4) CDRH1, CDRH2, CDRH3 have an amino acid sequence as set forth in SEQ ID NO: 43, SEQ ID NO: 56, and SEQ ID NO: 57, respectively, and CDRL1, CDRL2, and CDRL3 have an amino acid sequence as set forth in SEQ ID NO: 58, SEQ ID NO: 59, and SEQ ID NO: 60, respectively; (5) CDRH1, CDRH2, CDRH3 have an amino acid sequence as set forth in SEQ ID NO: 61, SEQ ID NO: 62, and SEQ ID NO: 63, respectively, and CDRL1, CDRL2, and CDRL3 have an amino acid sequence as set forth in SEQ ID NO: 64, SEQ ID NO: 65, and SEQ ID NO: 66, respectively; (6) CDRH1, CDRH2, CDRH3 have an amino acid sequence as set forth in SEQ ID NO: 31, SEQ ID NO: 32, and SEQ ID NO: 69, respectively, and CDRL1, CDRL2, and CDRL3 have an amino acid sequence as set forth in SEQ ID NO: 34, SEQ ID NO: 35, and SEQ ID NO: 72, respectively; (7) CDRH1, CDRH2, CDRH3 have an amino acid sequence as set forth in SEQ ID NO: 73, SEQ ID NO: 74, and SEQ ID NO: 75, respectively, and CDRL1, CDRL2, and CDRL3 have an amino acid sequence as set forth in SEQ ID NO: 76, SEQ ID NO: 47, and SEQ ID NO: 78, respectively; (8) CDRH1, CDRH2, CDRH3 have an amino acid sequence as set forth in SEQ ID NO: 79, SEQ ID NO: 80, and SEQ ID NO: 81, respectively, and CDRL1, CDRL2, and CDRL3 have an amino acid sequence as set forth in SEQ ID NO: 82, SEQ ID NO: 83, and SEQ ID NO: 84, respectively; (9) CDRH1, CDRH2, CDRH3 have an amino acid sequence as set forth in SEQ ID NO: 85, SEQ ID NO: 86, and SEQ ID NO: 87, respectively, and CDRL1, CDRL2, and CDRL3 have an amino acid sequence as set forth in SEQ ID NO: 88, SEQ ID NO: 89, and SEQ ID NO: 90, respectively; (10) CDRH1, CDRH2, CDRH3 have an amino acid sequence as set forth in SEQ ID NO: 61, SEQ ID NO: 92, and SEQ ID NO: 93, respectively, and CDRL1, CDRL2, and CDRL3 have an amino acid sequence as set forth in SEQ ID NO: 94, SEQ ID NO: 95, and SEQ ID NO: 96, respectively; (11) CDRH1, CDRH2, CDRH3 have an amino acid sequence as set forth in SEQ ID NO: 97, SEQ ID NO: 98, and SEQ ID NO: 99, respectively, and CDRL1, CDRL2, and CDRL3 have an amino acid sequence as set forth in SEQ ID NO: 100, SEQ ID NO: 101, and SEQ ID NO: 102, respectively; (12) CDRH1, CDRH2, CDRH3 have an amino acid sequence as set forth in SEQ ID NO: 103, SEQ ID NO: 104, and SEQ ID NO: 105, respectively, and CDRL1, CDRL2, and CDRL3 have an amino acid sequence as set forth in SEQ ID NO: 64, SEQ ID NO: 107, and SEQ ID NO: 108, respectively; (13) CDRH1, CDRH2, CDRH3 have an amino acid sequence as set forth in SEQ ID NO: 109, SEQ ID NO: 110, and SEQ ID NO: 111, respectively, and CDRL1, CDRL2, and CDRL3 have an amino acid sequence as set forth in SEQ ID NO: 88, SEQ ID NO: 89, and SEQ ID NO: 114, respectively; (14) CDRH1, CDRH2, CDRH3 have an amino acid sequence as set forth in SEQ ID NO: 85, SEQ ID NO: 110, and SEQ ID NO: 117, respectively, and CDRL1, CDRL2, and CDRL3 have an amino acid sequence as set forth in SEQ ID NO: 88, SEQ ID NO: 89, and SEQ ID NO: 114, respectively; (15) CDRH1, CDRH2, CDRH3 have an amino acid sequence as set forth in SEQ ID NO: 121, SEQ ID NO: 122, and SEQ ID NO: 123, respectively, and CDRL1, CDRL2, and CDRL3 have an amino acid sequence as set forth in SEQ ID NO: 124, SEQ ID NO: 125, and SEQ ID NO: 126, respectively; (16) CDRH1, CDRH2, CDRH3 have an amino acid sequence as set forth in SEQ ID NO: 127, SEQ ID NO: 128, and SEQ ID NO: 129, respectively, and CDRL1, CDRL2, and CDRL3 have an amino acid sequence as set forth in SEQ ID NO: 34, SEQ ID NO: 35, and SEQ ID NO: 36, respectively; (17) CDRH1, CDRH2, CDRH3 have an amino acid sequence as set forth in SEQ ID NO: 133, SEQ ID NO: 134, and SEQ ID NO: 135, respectively, and CDRL1, CDRL2, and CDRL3 have an amino acid sequence as set forth in SEQ ID NO: 136, SEQ ID NO: 137, and SEQ ID NO: 138, respectively; (18) CDRH1, CDRH2, CDRH3 have an amino acid sequence as set forth in SEQ ID NO: 139, SEQ ID NO: 140, and SEQ ID NO: 141, respectively, and CDRL1, CDRL2, and CDRL3 have an amino acid sequence as set forth in SEQ ID NO: 142, SEQ ID NO: 143, and SEQ ID NO: 144, respectively; (19) CDRH1, CDRH2, CDRH3 have an amino acid sequence as set forth in SEQ ID NO: 145, SEQ ID NO: 146, and SEQ ID NO: 147, respectively, and CDRL1, CDRL2, and CDRL3 have an amino acid sequence as set forth in SEQ ID NO: 148, SEQ ID NO: 149, and SEQ ID NO: 150, respectively; (20) CDRH1, CDRH2, CDRH3 have an amino acid sequence as set forth in SEQ ID NO: 31, SEQ ID NO: 32, and SEQ ID NO: 33, respectively, and CDRL1, CDRL2, and CDRL3 have an amino acid sequence as set forth in SEQ ID NO: 148, SEQ ID NO: 149, and SEQ ID NO: 150, respectively; (21) CDRH1, CDRH2, CDRH3 have an amino acid sequence as set forth in SEQ ID NO: 31, SEQ ID NO: 32, and SEQ ID NO: 159, respectively, and CDRL1, CDRL2, and CDRL3 have an amino acid sequence as set forth in SEQ ID NO: 136, SEQ ID NO: 137, and SEQ ID NO: 162, respectively; (22) CDRH1, CDRH2, CDRH3 have an amino acid sequence as set forth in SEQ ID NO: 169, SEQ ID NO: 170, and SEQ ID NO: 171, respectively, and CDRL1, CDRL2, and CDRL3 have an amino acid sequence as set forth in SEQ ID NO: 172, SEQ ID NO: 173, and SEQ ID NO: 174, respectively; (23) CDRH1, CDRH2, CDRH3 have an amino acid sequence as set forth in SEQ ID NO: 61, SEQ ID NO: 62, and SEQ ID NO: 63, respectively, and CDRL1, CDRL2, and CDRL3 have an amino acid sequence as set forth in SEQ ID NO: 64, SEQ ID NO: 65, and SEQ ID NO: 180, respectively; (24) CDRH1, CDRH2, CDRH3 have an amino acid sequence as set forth in SEQ ID NO: 31, SEQ ID NO: 182, and SEQ ID NO: 183, respectively, and CDRL1, CDRL2, and CDRL3 have an amino acid sequence as set forth in SEQ ID NO: 136, SEQ ID NO: 137, and SEQ ID NO: 186, respectively; (25) CDRH1, CDRH2, CDRH3 have an amino acid sequence as set forth in SEQ ID NO: 187, SEQ ID NO: 188, and SEQ ID NO: 189, respectively, and CDRL1, CDRL2, and CDRL3 have an amino acid sequence as set forth in SEQ ID NO: 190, SEQ ID NO: 191, and SEQ ID NO: 192, respectively; (26) CDRH1, CDRH2, CDRH3 have an amino acid sequence as set forth in SEQ ID NO: 193, SEQ ID NO: 194, and SEQ ID NO: 195, respectively, and CDRL1, CDRL2, and CDRL3 have an amino acid sequence as set forth in SEQ ID NO: 196, SEQ ID NO: 197, and SEQ ID NO: 12, respectively; (27) CDRH1, CDRH2, CDRH3 have an amino acid sequence as set forth in SEQ ID NO: 199, SEQ ID NO: 200, and SEQ ID NO: 201, respectively, and CDRL1, CDRL2, and CDRL3 have an amino acid sequence as set forth in SEQ ID NO: 202, SEQ ID NO: 203, and SEQ ID NO: 6, respectively; (28) CDRH1, CDRH2, CDRH3 have an amino acid sequence as set forth in SEQ ID NO: 205, SEQ ID NO: 206, and SEQ ID NO: 207, respectively, and CDRL1, CDRL2, and CDRL3 have an amino acid sequence as set forth in SEQ ID NO: 142, SEQ ID NO: 209, and SEQ ID NO: 210, respectively; (29) CDRH1, CDRH2, CDRH3 have an amino acid sequence as set forth in SEQ ID NO: 211, SEQ ID NO: 212, and SEQ ID NO: 213, respectively, and CDRL1, CDRL2, and CDRL3 have an amino acid sequence as set forth in SEQ ID NO: 214, SEQ ID NO: 35, and SEQ ID NO: 216, respectively; (30) CDRH1, CDRH2, CDRH3 have an amino acid sequence as set forth in SEQ ID NO: 127, SEQ ID NO: 386, and SEQ ID NO: 129, respectively, and CDRL1, CDRL2, and CDRL3 have an amino acid sequence as set forth in SEQ ID NO: 34, SEQ ID NO: 35, and SEQ ID NO: 36, respectively; (31) CDRH1, CDRH2, CDRH3 have an amino acid sequence as set forth in SEQ ID NO: 205, SEQ ID NO: 206, and SEQ ID NO: 207, respectively, and CDRL1, CDRL2, and CDRL3 have an amino acid sequence as set forth in SEQ ID NO: 142, SEQ ID NO: 209, and SEQ ID NO: 210, respectively; (32) CDRH1, CDRH2, CDRH3 have an amino acid sequence as set forth in SEQ ID NO: 127, SEQ ID NO: 388, and SEQ ID NO: 129, respectively, and CDRL1, CDRL2, and CDRL3 have an amino acid sequence as set forth in SEQ ID NO: 34, SEQ ID NO: 35, and SEQ ID NO: 36, respectively; (33) CDRH1, CDRH2, CDRH3 have an amino acid sequence as set forth in SEQ ID NO: 205, SEQ ID NO: 387, and SEQ ID NO: 207, respectively, and CDRL1, CDRL2, and CDRL3 have an amino acid sequence as set forth in SEQ ID NO: 142, SEQ ID NO: 209, and SEQ ID NO: 210, respectively; or (34) CDRH1, CDRH2, CDRH3 have an amino acid sequence as set forth in SEQ ID NO: 205, SEQ ID NO: 387, and SEQ ID NO: 207, respectively, and CDRL1, CDRL2, and CDRL3 have an amino acid sequence as set forth in SEQ ID NO: 142, SEQ ID NO: 143, and SEQ ID NO: 210, respectively; wherein from 0 to 3 amino acid modifications can be present in any CDR/SEQ ID NO.

According to another variation of the first aspect of the invention there is provided an isolated antibody or an antigen-binding fragment thereof that specifically binds human BTLA, comprising: (1) at least one VH CDR with an amino acid sequence as set forth in SEQ ID NO: 31, SEQ ID NO: 32, or SEQ ID NO: 33, and at least one VL CDR with an amino acid sequence as set forth in SEQ ID NO: 34, SEQ ID NO: 35, or SEQ ID NO: 36; (2) at least one VH CDR with an amino acid sequence as set forth in SEQ ID NO: 37, SEQ ID NO: 38, or SEQ ID NO: 39, and at least one VL CDR with an amino acid sequence as set forth in SEQ ID NO: 40, SEQ ID NO: 41, or SEQ ID NO: 42; (3) at least one VH CDR with an amino acid sequence as set forth in SEQ ID NO: 43, SEQ ID NO: 44, or SEQ ID NO: 45, and at least one VL CDR with an amino acid sequence as set forth in SEQ ID NO: 46, SEQ ID NO: 47, or SEQ ID NO: 48; (4) at least one VH CDR with an amino acid sequence as set forth in SEQ ID NO: 43, SEQ ID NO: 56, or SEQ ID NO: 57, and at least one VL CDR with an amino acid sequence as set forth in SEQ ID NO: 58, SEQ ID NO: 59, or SEQ ID NO: 60; (5) at least one VH CDR with an amino acid sequence as set forth in SEQ ID NO: 61, SEQ ID NO: 62, or SEQ ID NO: 63, and at least one VL CDR with an amino acid sequence as set forth in SEQ ID NO: 64, SEQ ID NO: 65, or SEQ ID NO: 66; (6) at least one VH CDR with an amino acid sequence as set forth in SEQ ID NO: 31, SEQ ID NO: 32, or SEQ ID NO: 69, and at least one VL CDR with an amino acid sequence as set forth in SEQ ID NO: 34, SEQ ID NO: 35, or SEQ ID NO: 72; (7) at least one VH CDR with an amino acid sequence as set forth in SEQ ID NO: 73, SEQ ID NO: 74, or SEQ ID NO: 75, and at least one VL CDR with an amino acid sequence as set forth in SEQ ID NO: 76, SEQ ID NO: 47, or SEQ ID NO: 78; (8) at least one VH CDR with an amino acid sequence as set forth in SEQ ID NO: 79, SEQ ID NO: 80, or SEQ ID NO: 81, and at least one VL CDR with an amino acid sequence as set forth in SEQ ID NO: 82, SEQ ID NO: 83, or SEQ ID NO: 84; (9) at least one VH CDR with an amino acid sequence as set forth in SEQ ID NO: 85, SEQ ID NO: 86, or SEQ ID NO: 87, and at least one VL CDR with an amino acid sequence as set forth in SEQ ID NO: 88, SEQ ID NO: 89, or SEQ ID NO: 90; (10) at least one VH CDR with an amino acid sequence as set forth in SEQ ID NO: 61, SEQ ID NO: 92, or SEQ ID NO: 93, and at least one VL CDR with an amino acid sequence as set forth in SEQ ID NO: 94, SEQ ID NO: 95, or SEQ ID NO: 96; (11) at least one VH CDR with an amino acid sequence as set forth in SEQ ID NO: 97, SEQ ID NO: 98, or SEQ ID NO: 99, and at least one VL CDR with an amino acid sequence as set forth in SEQ ID NO: 100, SEQ ID NO: 101, or SEQ ID NO: 102; (12) at least one VH CDR with an amino acid sequence as set forth in SEQ ID NO: 103, SEQ ID NO: 104, or SEQ ID NO: 105, and at least one VL CDR with an amino acid sequence as set forth in SEQ ID NO: 64, SEQ ID NO: 107, or SEQ ID NO: 108; (13) at least one VH CDR with an amino acid sequence as set forth in SEQ ID NO: 109, SEQ ID NO: 110, or SEQ ID NO: 111, and at least one VL CDR with an amino acid sequence as set forth in SEQ ID NO: 88, SEQ ID NO: 89, or SEQ ID NO: 114; (14) at least one VH CDR with an amino acid sequence as set forth in SEQ ID NO: 85, SEQ ID NO: 110, or SEQ ID NO: 117, and at least one VL CDR with an amino acid sequence as set forth in SEQ ID NO: 88, SEQ ID NO: 89, or SEQ ID NO: 114; (15) at least one VH CDR with an amino acid sequence as set forth in SEQ ID NO: 121, SEQ ID NO: 122, or SEQ ID NO: 123, and at least one VL CDR with an amino acid sequence as set forth in SEQ ID NO: 124, SEQ ID NO: 125, or SEQ ID NO: 126; (16) at least one VH CDR with an amino acid sequence as set forth in SEQ ID NO: 127, SEQ ID NO: 128, or SEQ ID NO: 129, and at least one VL CDR with an amino acid sequence as set forth in SEQ ID NO: 34, SEQ ID NO: 35, or SEQ ID NO: 36; (17) at least one VH CDR with an amino acid sequence as set forth in SEQ ID NO: 133, SEQ ID NO: 134, or SEQ ID NO: 135, and at least one VL CDR with an amino acid sequence as set forth in SEQ ID NO: 136, SEQ ID NO: 137, or SEQ ID NO: 138; (18) at least one VH CDR with an amino acid sequence as set forth in SEQ ID NO: 139, SEQ ID NO: 140, or SEQ ID NO: 141, and at least one VL CDR with an amino acid sequence as set forth in SEQ ID NO: 142, SEQ ID NO: 143, or SEQ ID NO: 144; (19) at least one VH CDR with an amino acid sequence as set forth in SEQ ID NO: 145, SEQ ID NO: 146, or SEQ ID NO: 147, and at least one VL CDR with an amino acid sequence as set forth in SEQ ID NO: 148, SEQ ID NO: 149, or SEQ ID NO: 150; (20) at least one VH CDR with an amino acid sequence as set forth in SEQ ID NO: 31, SEQ ID NO: 32, or SEQ ID NO: 33, and at least one VL CDR with an amino acid sequence as set forth in SEQ ID NO: 148, SEQ ID NO: 149, or SEQ ID NO: 150; (21) at least one VH CDR with an amino acid sequence as set forth in SEQ ID NO: 31, SEQ ID NO: 32, or SEQ ID NO: 159, and at least one VL CDR with an amino acid sequence as set forth in SEQ ID NO: 136, SEQ ID NO: 137, or SEQ ID NO: 162; (22) at least one VH CDR with an amino acid sequence as set forth in SEQ ID NO: 169, SEQ ID NO: 170, or SEQ ID NO: 171, and at least one VL CDR with an amino acid sequence as set forth in SEQ ID NO: 172, SEQ ID NO: 173, or SEQ ID NO: 174; (23) at least one VH CDR with an amino acid sequence as set forth in SEQ ID NO: 61, SEQ ID NO: 62, or SEQ ID NO: 63, and at least one VL CDR with an amino acid sequence as set forth in SEQ ID NO: 64, SEQ ID NO: 65, or SEQ ID NO: 180; (24) at least one VH CDR with an amino acid sequence as set forth in SEQ ID NO: 31, SEQ ID NO: 182, or SEQ ID NO: 183, and at least one VL CDR with an amino acid sequence as set forth in SEQ ID NO: 136, SEQ ID NO: 137, or SEQ ID NO: 186; (25) at least one VH CDR with an amino acid sequence as set forth in SEQ ID NO: 187, SEQ ID NO: 188, or SEQ ID NO: 189, and at least one VL CDR with an amino acid sequence as set forth in SEQ ID NO: 190, SEQ ID NO: 191, or SEQ ID NO: 192; (26) at least one VH CDR with an amino acid sequence as set forth in SEQ ID NO: 193, SEQ ID NO: 194, or SEQ ID NO: 195, and at least one VL CDR with an amino acid sequence as set forth in SEQ ID NO: 196, SEQ ID NO: 197, or SEQ ID NO: 12; (27) at least one VH CDR with an amino acid sequence as set forth in SEQ ID NO: 199, SEQ ID NO: 200, or SEQ ID NO: 201, and at least one VL CDR with an amino acid sequence as set forth in SEQ ID NO: 202, SEQ ID NO: 203, or SEQ ID NO: 6; (28) at least one VH CDR with an amino acid sequence as set forth in SEQ ID NO: 205, SEQ ID NO: 206, or SEQ ID NO: 207, and at least one VL CDR with an amino acid sequence as set forth in SEQ ID NO: 142, SEQ ID NO: 209, or SEQ ID NO: 210; (29) at least one VH CDR with an amino acid sequence as set forth in SEQ ID NO: 211, SEQ ID NO: 212, or SEQ ID NO: 213, and at least one VL CDR with an amino acid sequence as set forth in SEQ ID NO: 214, SEQ ID NO: 35, or SEQ ID NO: 216; (30) at least one VH CDR with an amino acid sequence as set forth in SEQ ID NO: 127, SEQ ID NO: 386, or SEQ ID NO: 129, and at least one VL CDR with an amino acid sequence as set forth in SEQ ID NO: 34, SEQ ID NO: 35, or SEQ ID NO: 36; (31) at least one VH CDR with an amino acid sequence as set forth in SEQ ID NO: 205, SEQ ID NO: 206, or SEQ ID NO: 207, and at least one VL CDR with an amino acid sequence as set forth in SEQ ID NO:142, SEQ ID NO: 209, or SEQ ID NO:210; (32) at least one VH CDR with an amino acid sequence as set forth in SEQ ID NO: 127, SEQ ID NO: 388, or SEQ ID NO: 129, and at least one VL CDR with an amino acid sequence as set forth in SEQ ID NO: 34, SEQ ID NO: 35, or SEQ ID NO: 36; (33) at least one VH CDR with an amino acid sequence as set forth in SEQ ID NO: 205, SEQ ID NO: 387, or SEQ ID NO: 207, and at least one VL CDR with an amino acid sequence as set forth in SEQ ID NO:142, SEQ ID NO: 209, or SEQ ID NO:210; or (34) at least one VH CDR with an amino acid sequence as set forth in SEQ ID NO: 205, SEQ ID NO: 387, or SEQ ID NO: 207, and at least one VL CDR with an amino acid sequence as set forth in SEQ ID NO:142, SEQ ID NO: 143, or SEQ ID NO:210; wherein from 0 to 3 amino acid modifications can be present in any CDR/SEQ ID NO.

According to another variation of the first aspect of the invention there is provided an isolated antibody or an antigen-binding fragment thereof that specifically binds human BTLA, comprising a heavy chain and a light chain, wherein the heavy chain comprises a heavy chain variable region comprising an amino acid sequence as set forth in SEQ ID NO: 13, or a sequence with at least 90% sequence identity thereto. In other embodiments, the heavy chain variable region comprises an amino acid sequence that has at least 90% sequence identity to the amino acid sequence as set forth in SEQ ID NO: 17 or 21.

For any embodiment disclosed herein that refers to at least 90% sequence identity it is understood that this includes any sequence identity from 90% to 100%, i.e. at least 90% at least 91%, at least 92%, at least 93%, at least 94%, at least 95%, at least 96%, at least 97%, at least 98%, at least 99% and 100%.

In other embodiments, the heavy chain variable region comprises an amino acid sequence that has at least 90% sequence identity to the amino acid sequence as set forth in SEQ ID NO: 301, 302, 303, 305, 306, 307, 308, 309, 310, 311, 312, 313, 314, 315, 316, 317, 318, 319, 320, 321, 322, 324, 306, 326, 327, 330, 331, 13, 17, 21, 382, 384, 389, 390 and 378.

In other embodiments, the heavy chain variable region comprises an amino acid sequence as set forth in SEQ ID NO: 301, 302, 303, 305, 306, 307, 308, 309, 310, 311, 312, 313, 314, 315, 316, 317, 318, 319, 320, 321, 322, 324, 306, 326, 327, 330, 331, 13, 17, 21, 382, 384, 389, 390 and 378, with up to 10 modifications, such as 1, 2, 3, 4, 5, 6, 7, 8, 9 or 10 amino acid modifications therein.

According to another variation of the first aspect of the invention there is provided an isolated antibody or an antigen-binding fragment thereof that specifically binds human BTLA, comprising a heavy chain and a light chain, wherein the light chain comprises a light chain variable region comprising an amino acid sequence as set forth in SEQ ID NO: 14, or a sequence with at least 90% sequence identity thereto. In other embodiments, the light chain variable region comprises an amino acid sequence that has at least 90% sequence identity to the amino acid sequence as set forth in SEQ ID NO: 15 or 19.

In other embodiments, the light chain variable region comprises an amino acid sequence that has at least 90% sequence identity to the amino acid sequence as set forth in SEQ ID NO: 351, 352, 353, 355, 356, 357, 358, 359, 360, 361, 362, 363, 364, 366, 367, 368, 369, 370, 372, 351, 374, 375, 376, 377, 380, 381, 14, 15, 19, 383, 385 or 378.

According to another variation of the first aspect of the invention there is provided an isolated antibody or an antigen-binding fragment thereof that specifically binds human BTLA, comprising a heavy chain and a light chain, wherein the heavy chain comprises a heavy chain variable region comprising an amino acid sequence as set forth in SEQ ID NO: 13, and the light chain comprises a light chain variable region comprising an amino acid sequence as set forth in SEQ ID NO: 14.

According to another variation of the first aspect of the invention there is provided an isolated antibody or an antigen-binding fragment thereof that specifically binds human BTLA, comprising a heavy chain and a light chain, wherein the heavy chain comprises a heavy chain variable region comprising an amino acid sequence that has at least 90% sequence identity to the amino acid sequence as set forth in SEQ ID NO: 13, and the light chain comprises a light chain variable region comprising an amino acid sequence that has at least 90% sequence identity to the amino acid sequence as set forth in SEQ ID NO: 14.

According to another variation of the first aspect of the invention there is provided an isolated antibody or an antigen-binding fragment thereof that specifically binds human BTLA, comprising a heavy chain and a light chain, wherein: (1) the heavy chain comprises a heavy chain variable region comprising an amino acid sequence that has at least 90% sequence identity to the amino acid sequence as set forth in SEQ ID NO: 17, and the light chain comprises a light chain variable region comprising an amino acid sequence that has at least 90% sequence identity to the amino acid sequence as set forth in SEQ ID NO: 15; or (2) the heavy chain comprises a heavy chain variable region comprising an amino acid sequence that has at least 90% sequence identity to the amino acid sequence as set forth in SEQ ID NO: 21, and the light chain comprises a light chain variable region comprising an amino acid sequence that has at least 90% sequence identity to the amino acid sequence as set forth in SEQ ID NO: 19.

According to another variation of the first aspect of the invention there is provided an isolated antibody or an antigen-binding fragment thereof that specifically binds human BTLA, comprising a heavy chain and a light chain, wherein: (1) the heavy chain comprises a heavy chain variable region comprising an amino acid sequence that has at least 90% sequence identity to the amino acid sequence as set forth in SEQ ID NO: 301, and the light chain comprises a light chain variable region comprising an amino acid sequence that has at least 90% sequence identity to the amino acid sequence as set forth in SEQ ID NO: 351; (2) the heavy chain comprises a heavy chain variable region comprising an amino acid sequence that has at least 90% sequence identity to the amino acid sequence as set forth in SEQ ID NO: 302, and the light chain comprises a light chain variable region comprising an amino acid sequence that has at least 90% sequence identity to the amino acid sequence as set forth in SEQ ID NO: 352; (3) the heavy chain comprises a heavy chain variable region comprising an amino acid sequence as set forth in SEQ ID NO: 303, and the light chain comprises a light chain variable region comprising an amino acid sequence that has at least 90% sequence identity to the amino acid sequence as set forth in SEQ ID NO: 353; (4) the heavy chain comprises a heavy chain variable region comprising an amino acid sequence that has at least 90% sequence identity to the amino acid sequence as set forth in SEQ ID NO: 305, and the light chain comprises a light chain variable region comprising an amino acid sequence that has at least 90% sequence identity to the amino acid sequence as set forth in SEQ ID NO: 355; (5) the heavy chain comprises a heavy chain variable region comprising an amino acid sequence that has at least 90% sequence identity to the amino acid sequence as set forth in SEQ ID NO: 306, and the light chain comprises a light chain variable region comprising an amino acid sequence that has at least 90% sequence identity to the amino acid sequence as set forth in SEQ ID NO: 356; (6) the heavy chain comprises a heavy chain variable region comprising an amino acid sequence that has at least 90% sequence identity to the amino acid sequence as set forth in SEQ ID NO: 307, and the light chain comprises a light chain variable region comprising an amino acid sequence that has at least 90% sequence identity to the amino acid sequence as set forth in SEQ ID NO: 357; (7) the heavy chain comprises a heavy chain variable region comprising an amino acid sequence that has at least 90% sequence identity to the amino acid sequence as set forth in SEQ ID NO: 308, and the light chain comprises a light chain variable region comprising an amino acid sequence that has at least 90% sequence identity to the amino acid sequence as set forth in SEQ ID NO: 358; (8) the heavy chain comprises a heavy chain variable region comprising an amino acid sequence that has at least 90% sequence identity to the amino acid sequence as set forth in SEQ ID NO: 309, and the light chain comprises a light chain variable region comprising an amino acid sequence that has at least 90% sequence identity to the amino acid sequence as set forth in SEQ ID NO: 359; (9) the heavy chain comprises a heavy chain variable region comprising an amino acid sequence that has at least 90% sequence identity to the amino acid sequence as set forth in SEQ ID NO: 310, and the light chain comprises a light chain variable region comprising an amino acid sequence that has at least 90% sequence identity to the amino acid sequence as set forth in SEQ ID NO: 360; (10) the heavy chain comprises a heavy chain variable region comprising an amino acid sequence that has at least 90% sequence identity to the amino acid sequence as set forth in SEQ ID NO: 311, and the light chain comprises a light chain variable region comprising an amino acid sequence that has at least 90% sequence identity to the amino acid sequence as set forth in SEQ ID NO: 361; (11) the heavy chain comprises a heavy chain variable region comprising an amino acid sequence that has at least 90% sequence identity to the amino acid sequence as set forth in SEQ ID NO: 312, and the light chain comprises a light chain variable region comprising an amino acid sequence that has at least 90% sequence identity to the amino acid sequence as set forth in SEQ ID NO: 362; (12) the heavy chain comprises a heavy chain variable region comprising an amino acid sequence that has at least 90% sequence identity to the amino acid sequence as set forth in SEQ ID NO: 313, and the light chain comprises a light chain variable region comprising an amino acid sequence that has at least 90% sequence identity to the amino acid sequence as set forth in SEQ ID NO: 363; (13) the heavy chain comprises a heavy chain variable region comprising an amino acid sequence that has at least 90% sequence identity to the amino acid sequence as set forth in SEQ ID NO: 314, and the light chain comprises a light chain variable region comprising an amino acid sequence that has at least 90% sequence identity to the amino acid sequence as set forth in SEQ ID NO: 364; (14) the heavy chain comprises a heavy chain variable region comprising an amino acid sequence that has at least 90% sequence identity to the amino acid sequence as set forth in SEQ ID NO: 315, and the light chain comprises a light chain variable region comprising an amino acid sequence that has at least 90% sequence identity to the amino acid sequence as set forth in SEQ ID NO: 364; (15) the heavy chain comprises a heavy chain variable region comprising an amino acid sequence that has at least 90% sequence identity to the amino acid sequence as set forth in SEQ ID NO: 316, and the light chain comprises a light chain variable region comprising an amino acid sequence that has at least 90% sequence identity to the amino acid sequence as set forth in SEQ ID NO: 366; (16) the heavy chain comprises a heavy chain variable region comprising an amino acid sequence that has at least 90% sequence identity to the amino acid sequence as set forth in SEQ ID NO: 317, and the light chain comprises a light chain variable region comprising an amino acid sequence that has at least 90% sequence identity to the amino acid sequence as set forth in SEQ ID NO: 367; (17) the heavy chain comprises a heavy chain variable region comprising an amino acid sequence that has at least 90% sequence identity to the amino acid sequence as set forth in SEQ ID NO: 318, and the light chain comprises a light chain variable region comprising an amino acid sequence that has at least 90% sequence identity to the amino acid sequence as set forth in SEQ ID NO: 368; (18) the heavy chain comprises a heavy chain variable region comprising an amino acid sequence that has at least 90% sequence identity to the amino acid sequence as set forth in SEQ ID NO: 319, and the light chain comprises a light chain variable region comprising an amino acid sequence that has at least 90% sequence identity to the amino acid sequence as set forth in SEQ ID NO: 369; (19) the heavy chain comprises a heavy chain variable region comprising an amino acid sequence that has at least 90% sequence identity to the amino acid sequence as set forth in SEQ ID NO: 320, and the light chain comprises a light chain variable region comprising an amino acid sequence that has at least 90% sequence identity to the amino acid sequence as set forth in SEQ ID NO: 370; (20) the heavy chain comprises a heavy chain variable region comprising an amino acid sequence that has at least 90% sequence identity to the amino acid sequence as set forth in SEQ ID NO: 321, and the light chain comprises a light chain variable region comprising an amino acid sequence that has at least 90% sequence identity to the amino acid sequence as set forth in SEQ ID NO: 370; (21) the heavy chain comprises a heavy chain variable region comprising an amino acid sequence that has at least 90% sequence identity to the amino acid sequence as set forth in SEQ ID NO: 322, and the light chain comprises a light chain variable region comprising an amino acid sequence that has at least 90% sequence identity to the amino acid sequence as set forth in SEQ ID NO: 372; (22) the heavy chain comprises a heavy chain variable region comprising an amino acid sequence that has at least 90% sequence identity to the amino acid sequence as set forth in SEQ ID NO: 324, and the light chain comprises a light chain variable region comprising an amino acid sequence that has at least 90% sequence identity to the amino acid sequence as set forth in SEQ ID NO: 374; (23) the heavy chain comprises a heavy chain variable region comprising an amino acid sequence that has at least 90% sequence identity to the amino acid sequence as set forth in SEQ ID NO: 306, and the light chain comprises a light chain variable region comprising an amino acid sequence that has at least 90% sequence identity to the amino acid sequence as set forth in SEQ ID NO: 375; (24) the heavy chain comprises a heavy chain variable region comprising an amino acid sequence that has at least 90% sequence identity to the amino acid sequence as set forth in SEQ ID NO: 326, and the light chain comprises a light chain variable region comprising an amino acid sequence that has at least 90% sequence identity to the amino acid sequence as set forth in SEQ ID NO: 376; (25) the heavy chain comprises a heavy chain variable region comprising an amino acid sequence that has at least 90% sequence identity to the amino acid sequence as set forth in SEQ ID NO: 327, and the light chain comprises a light chain variable region comprising an amino acid sequence that has at least 90% sequence identity to the amino acid sequence as set forth in SEQ ID NO: 377; (26) the heavy chain comprises a heavy chain variable region comprising an amino acid sequence that has at least 90% sequence identity to the amino acid sequence as set forth in SEQ ID NO: 17, and the light chain comprises a light chain variable region comprising an amino acid sequence that has at least 90% sequence identity to the amino acid sequence as set forth in SEQ ID NO: 15; (27) the heavy chain comprises a heavy chain variable region comprising an amino acid sequence that has at least 90% sequence identity to the amino acid sequence as set forth in SEQ ID NO: 21, and the light chain comprises a light chain variable region comprising an amino acid sequence that has at least 90% sequence identity to the amino acid sequence as set forth in SEQ ID NO: 19; (28) the heavy chain comprises a heavy chain variable region comprising an amino acid sequence that has at least 90% sequence identity to the amino acid sequence as set forth in SEQ ID NO: 330, and the light chain comprises a light chain variable region comprising an amino acid sequence that has at least 90% sequence identity to the amino acid sequence as set forth in SEQ ID NO: 380; (29) the heavy chain comprises a heavy chain variable region comprising an amino acid sequence that has at least 90% sequence identity to the amino acid sequence as set forth in SEQ ID NO: 331, and the light chain comprises a light chain variable region comprising an amino acid sequence that has at least 90% sequence identity to the amino acid sequence as set forth in SEQ ID NO: 381; (30) the heavy chain comprises a heavy chain variable region comprising an amino acid sequence that has at least 90% sequence identity to the amino acid sequence as set forth in SEQ ID NO: 382, and the light chain comprises a light chain variable region comprising an amino acid sequence that has at least 90% sequence identity to the amino acid sequence as set forth in SEQ ID NO: 383; (31) the heavy chain comprises a heavy chain variable region comprising an amino acid sequence that has at least 90% sequence identity to the amino acid sequence as set forth in SEQ ID NO: 384, and the light chain comprises a light chain variable region comprising an amino acid sequence that has at least 90% sequence identity to the amino acid sequence as set forth in SEQ ID NO: 385; (32) the heavy chain comprises a heavy chain variable region comprising an amino acid sequence that has at least 90% sequence identity to the amino acid sequence as set forth in SEQ ID NO: 389, and the light chain comprises a light chain variable region comprising an amino acid sequence that has at least 90% sequence identity to the amino acid sequence as set forth in SEQ ID NO: 383; (33) the heavy chain comprises a heavy chain variable region comprising an amino acid sequence that has at least 90% sequence identity to the amino acid sequence as set forth in SEQ ID NO: 390, and the light chain comprises a light chain variable region comprising an amino acid sequence that has at least 90% sequence identity to the amino acid sequence as set forth in SEQ ID NO: 385; or (34) the heavy chain comprises a heavy chain variable region comprising an amino acid sequence that has at least 90% sequence identity to the amino acid sequence as set forth in SEQ ID NO: 390, and the light chain comprises a light chain variable region comprising an amino acid sequence that has at least 90% sequence identity to the amino acid sequence as set forth in SEQ ID NO: 378.

In one embodiment, the heavy chain variable region comprises an amino acid sequence that has at least 90% sequence identity to the amino acid sequence as set forth in SEQ ID NO: 13 and the light chain variable region comprises an amino acid sequence that has at least 90% sequence identity to the amino acid sequence as set forth in SEQ ID NO: 14.

In one embodiment, the heavy chain variable region comprises an amino acid sequence that has at least 90% sequence identity to the amino acid sequence as set forth in SEQ ID NO: 17 and the light chain variable region comprises an amino acid sequence that has at least 90% sequence identity to the amino acid sequence as set forth in SEQ ID NO: 15.

In one embodiment, the heavy chain variable region comprises an amino acid sequence that has at least 90% sequence identity to the amino acid sequence as set forth in SEQ ID NO: 21 and the light chain variable region comprises an amino acid sequence that has at least 90% sequence identity to the amino acid sequence as set forth in SEQ ID NO: 19.

In one embodiment, the heavy chain variable region comprises an amino acid sequence that has at least 90% sequence identity to the amino acid sequence as set forth in SEQ ID NO: 301 and the light chain variable region comprises an amino acid sequence that has at least 90% sequence identity to the amino acid sequence as set forth in SEQ ID NO: 351.

In one embodiment, the heavy chain variable region comprises an amino acid sequence that has at least 90% sequence identity to the amino acid sequence as set forth in SEQ ID NO: 302 and the light chain variable region comprises an amino acid sequence that has at least 90% sequence identity to the amino acid sequence as set forth in SEQ ID NO: 352.

In one embodiment, the heavy chain variable region comprises an amino acid sequence that has at least 90% sequence identity to the amino acid sequence as set forth in SEQ ID NO: 303 and the light chain variable region comprises an amino acid sequence that has at least 90% sequence identity to the amino acid sequence as set forth in SEQ ID NO: 353.

In one embodiment, the heavy chain variable region comprises an amino acid sequence that has at least 90% sequence identity to the amino acid sequence as set forth in SEQ ID NO: 305 and the light chain variable region comprises an amino acid sequence that has at least 90% sequence identity to the amino acid sequence as set forth in SEQ ID NO: 355.

In one embodiment, the heavy chain variable region comprises an amino acid sequence that has at least 90% sequence identity to the amino acid sequence as set forth in SEQ ID NO: 306 and the light chain variable region comprises an amino acid sequence that has at least 90% sequence identity to the amino acid sequence as set forth in SEQ ID NO: 356.

In one embodiment, the heavy chain variable region comprises an amino acid sequence that has at least 90% sequence identity to the amino acid sequence as set forth in SEQ ID NO: 307 and the light chain variable region comprises an amino acid sequence that has at least 90% sequence identity to the amino acid sequence as set forth in SEQ ID NO: 357.

In one embodiment, the heavy chain variable region comprises an amino acid sequence that has at least 90% sequence identity to the amino acid sequence as set forth in SEQ ID NO: 308 and the light chain variable region comprises an amino acid sequence that has at least 90% sequence identity to the amino acid sequence as set forth in SEQ ID NO: 358.

In one embodiment, the heavy chain variable region comprises an amino acid sequence that has at least 90% sequence identity to the amino acid sequence as set forth in SEQ ID NO: 309 and the light chain variable region comprises an amino acid sequence that has at least 90% sequence identity to the amino acid sequence as set forth in SEQ ID NO: 359.

In one embodiment, the heavy chain variable region comprises an amino acid sequence that has at least 90% sequence identity to the amino acid sequence as set forth in SEQ ID NO: 310 and the light chain variable region comprises an amino acid sequence that has at least 90% sequence identity to the amino acid sequence as set forth in SEQ ID NO: 360.

In one embodiment, the heavy chain variable region comprises an amino acid sequence that has at least 90% sequence identity to the amino acid sequence as set forth in SEQ ID NO: 311 and the light chain variable region comprises an amino acid sequence that has at least 90% sequence identity to the amino acid sequence as set forth in SEQ ID NO: 361.

In one embodiment, the heavy chain variable region comprises an amino acid sequence that has at least 90% sequence identity to the amino acid sequence as set forth in SEQ ID NO: 312 and the light chain variable region comprises an amino acid sequence that has at least 90% sequence identity to the amino acid sequence as set forth in SEQ ID NO: 362.

In one embodiment, the heavy chain variable region comprises an amino acid sequence that has at least 90% sequence identity to the amino acid sequence as set forth in SEQ ID NO: 313 and the light chain variable region comprises an amino acid sequence that has at least 90% sequence identity to the amino acid sequence as set forth in SEQ ID NO: 363.

In one embodiment, the heavy chain variable region comprises an amino acid sequence that has at least 90% sequence identity to the amino acid sequence as set forth in SEQ ID NO: 314 and the light chain variable region comprises an amino acid sequence that has at least 90% sequence identity to the amino acid sequence as set forth in SEQ ID NO: 364.

In one embodiment, the heavy chain variable region comprises an amino acid sequence that has at least 90% sequence identity to the amino acid sequence as set forth in SEQ ID NO: 315 and the light chain variable region comprises an amino acid sequence that has at least 90% sequence identity to the amino acid sequence as set forth in SEQ ID NO: 364.

In one embodiment, the heavy chain variable region comprises an amino acid sequence that has at least 90% sequence identity to the amino acid sequence as set forth in SEQ ID NO: 316 and the light chain variable region comprises an amino acid sequence that has at least 90% sequence identity to the amino acid sequence as set forth in SEQ ID NO: 366.

In one embodiment, the heavy chain variable region comprises an amino acid sequence that has at least 90% sequence identity to the amino acid sequence as set forth in SEQ ID NO: 317 and the light chain variable region comprises an amino acid sequence that has at least 90% sequence identity to the amino acid sequence as set forth in SEQ ID NO: 367.

In one embodiment, the heavy chain variable region comprises an amino acid sequence that has at least 90% sequence identity to the amino acid sequence as set forth in SEQ ID NO: 318 and the light chain variable region comprises an amino acid sequence that has at least 90% sequence identity to the amino acid sequence as set forth in SEQ ID NO: 368.

In one embodiment, the heavy chain variable region comprises an amino acid sequence that has at least 90% sequence identity to the amino acid sequence as set forth in SEQ ID NO: 319 and the light chain variable region comprises an amino acid sequence that has at least 90% sequence identity to the amino acid sequence as set forth in SEQ ID NO: 369.

In one embodiment, the heavy chain variable region comprises an amino acid sequence that has at least 90% sequence identity to the amino acid sequence as set forth in SEQ ID NO: 320 and the light chain variable region comprises an amino acid sequence that has at least 90% sequence identity to the amino acid sequence as set forth in SEQ ID NO: 370.

In one embodiment, the heavy chain variable region comprises an amino acid sequence that has at least 90% sequence identity to the amino acid sequence as set forth in SEQ ID NO: 321 and the light chain variable region comprises an amino acid sequence that has at least 90% sequence identity to the amino acid sequence as set forth in SEQ ID NO: 370.

In one embodiment, the heavy chain variable region comprises an amino acid sequence that has at least 90% sequence identity to the amino acid sequence as set forth in SEQ ID NO: 322 and the light chain variable region comprises an amino acid sequence that has at least 90% sequence identity to the amino acid sequence as set forth in SEQ ID NO: 372.

In one embodiment, the heavy chain variable region comprises an amino acid sequence that has at least 90% sequence identity to the amino acid sequence as set forth in SEQ ID NO: 324 and the light chain variable region comprises an amino acid sequence that has at least 90% sequence identity to the amino acid sequence as set forth in SEQ ID NO: 374.

In one embodiment, the heavy chain variable region comprises an amino acid sequence that has at least 90% sequence identity to the amino acid sequence as set forth in SEQ ID NO: 306 and the light chain variable region comprises an amino acid sequence that has at least 90% sequence identity to the amino acid sequence as set forth in SEQ ID NO: 375.

In one embodiment, the heavy chain variable region comprises an amino acid sequence that has at least 90% sequence identity to the amino acid sequence as set forth in SEQ ID NO: 326 and the light chain variable region comprises an amino acid sequence that has at least 90% sequence identity to the amino acid sequence as set forth in SEQ ID NO: 376.

In one embodiment, the heavy chain variable region comprises an amino acid sequence that has at least 90% sequence identity to the amino acid sequence as set forth in SEQ ID NO: 327 and the light chain variable region comprises an amino acid sequence that has at least 90% sequence identity to the amino acid sequence as set forth in SEQ ID NO: 377.

In one embodiment, the heavy chain variable region comprises an amino acid sequence that has at least 90% sequence identity to the amino acid sequence as set forth in SEQ ID NO: 17 and the light chain variable region comprises an amino acid sequence that has at least 90% sequence identity to the amino acid sequence as set forth in SEQ ID NO: 15.

In one embodiment, the heavy chain variable region comprises an amino acid sequence that has at least 90% sequence identity to the amino acid sequence as set forth in SEQ ID NO: 21 and the light chain variable region comprises an amino acid sequence that has at least 90% sequence identity to the amino acid sequence as set forth in SEQ ID NO: 19.

In one embodiment, the heavy chain variable region comprises an amino acid sequence that has at least 90% sequence identity to the amino acid sequence as set forth in SEQ ID NO: 330 and the light chain variable region comprises an amino acid sequence that has at least 90% sequence identity to the amino acid sequence as set forth in SEQ ID NO: 380.

In one embodiment, the heavy chain variable region comprises an amino acid sequence that has at least 90% sequence identity to the amino acid sequence as set forth in SEQ ID NO: 331 and the light chain variable region comprises an amino acid sequence that has at least 90% sequence identity to the amino acid sequence as set forth in SEQ ID NO: 381.

In one embodiment, the heavy chain variable region comprises an amino acid sequence that has at least 90% sequence identity to the amino acid sequence as set forth in SEQ ID NO: 382 and the light chain variable region comprises an amino acid sequence that has at least 90% sequence identity to the amino acid sequence as set forth in SEQ ID NO: 383.

In one embodiment, the heavy chain variable region comprises an amino acid sequence that has at least 90% sequence identity to the amino acid sequence as set forth in SEQ ID NO: 384 and the light chain variable region comprises an amino acid sequence that has at least 90% sequence identity to the amino acid sequence as set forth in SEQ ID NO: 385.

In one embodiment, the heavy chain variable region comprises an amino acid sequence that has at least 90% sequence identity to the amino acid sequence as set forth in SEQ ID NO: 389 and the light chain variable region comprises an amino acid sequence that has at least 90% sequence identity to the amino acid sequence as set forth in SEQ ID NO: 383.

In one embodiment, the heavy chain variable region comprises an amino acid sequence that has at least 90% sequence identity to the amino acid sequence as set forth in SEQ ID NO: 390 and the light chain variable region comprises an amino acid sequence that has at least 90% sequence identity to the amino acid sequence as set forth in SEQ ID NO: 385.

In one embodiment, the heavy chain variable region comprises an amino acid sequence that has at least 90% sequence identity to the amino acid sequence as set forth in SEQ ID NO: 390 and the light chain variable region comprises an amino acid sequence that has at least 90% sequence identity to the amino acid sequence as set forth in SEQ ID NO: 378.

In other embodiments, the heavy chain variable region polypeptide has at least 92%, at least 95%, at least 97%, at least 98% or at least 99% identity with the sequence disclosed in SEQ ID NO: 13.

In other embodiments, the heavy chain variable region polypeptide has at least 92%, at least 95%, at least 97%, at least 98% or at least 99% identity with the sequence disclosed in SEQ ID NO: 17.

In other embodiments, the heavy chain variable region polypeptide has at least 92%, at least 95%, at least 97%, at least 98% or at least 99% identity with the sequence disclosed in SEQ ID NO: 21.

In other embodiments, the heavy chain variable region polypeptide has at least 92%, at least 95%, at least 97%, at least 98% or at least 99% identity with the sequence disclosed in SEQ ID NO: 301, 302, 303, 305, 306, 307, 308, 309, 310, 311, 312, 313, 314, 315, 316, 317, 318, 319, 320, 321, 322, 324, 306, 326, 327, 330, 331, 382, 384, 389, or 390.

In other embodiments, the light chain variable region polypeptide has at least 92%, at least 95%, at least 97%, at least 98% or at least 99% identity with the sequence disclosed in SEQ ID NO: 14.

In other embodiments, the light chain variable region polypeptide has at least 92%, at least 95%, at least 97%, at least 98% or at least 99% identity with the sequence disclosed in SEQ ID NO: 15.

In other embodiments, the light chain variable region polypeptide has at least 92%, at least 95%, at least 97%, at least 98% or at least 99% identity with the sequence disclosed in SEQ ID NO: 19.

In other embodiments, the light chain variable region polypeptide has at least 92%, at least 95%, at least 97%, at least 98% or at least 99% identity with the sequence disclosed in SEQ ID NO: 351, 352, 353, 355, 356, 357, 358, 359, 360, 361, 362, 363, 364, 364, 366, 367, 368, 369, 370, 372, 374, 375, 376, 377, 380, 381, 383, 385, or 378.

According to another variation of the first aspect of the invention there is provided an isolated antibody or an antigen-binding fragment thereof having primary VH domain, primary VL domain, CDRH1, CDRH2, CDRH3, CDRL1, CDRL2, and CDRL3 of any antibody clone as set forth in Table 1. In certain embodiments, provided herein is an isolated antibody selected from the antibody clones as set forth in Table 1.

TABLE 1

Exemplary BTLA Agonistic Antibodies

| Clone | Scheme | CDR H1 | CDR H2 | CDR H3 | CDR L1 | CDR L2 | CDR L3 | VH | VL |
|---|---|---|---|---|---|---|---|---|---|
| 10B1 | Kabat | 31 | 32 | 33 | 34 | 35 | 36 | 301 | 351 |
| 12F11 | Kabat | 37 | 38 | 39 | 40 | 41 | 42 | 302 | 352 |
| 14D4 | Kabat | 43 | 44 | 45 | 46 | 47 | 48 | 303 | 353 |
| 15B6 | Kabat | 43 | 56 | 57 | 58 | 59 | 60 | 305 | 355 |
| 15C6 | Kabat | 61 | 62 | 63 | 64 | 65 | 66 | 306 | 356 |
| 16E1 | Kabat | 31 | 32 | 69 | 34 | 35 | 72 | 307 | 357 |
| 16F10 | Kabat | 73 | 74 | 75 | 76 | 47 | 78 | 308 | 358 |
| 16H2 | Kabat | 79 | 80 | 81 | 82 | 83 | 84 | 309 | 359 |
| 1H6 | Kabat | 85 | 86 | 87 | 88 | 89 | 90 | 310 | 360 |
| 21C7 | Kabat | 61 | 92 | 93 | 94 | 95 | 96 | 311 | 361 |
| 24H7 | Kabat | 97 | 98 | 99 | 100 | 101 | 102 | 312 | 362 |
| 26B1 | Kabat | 103 | 104 | 105 | 64 | 107 | 108 | 313 | 363 |
| 26F3 | Kabat | 109 | 110 | 111 | 88 | 89 | 114 | 314 | 364 |
| 27G9 | Kabat | 85 | 110 | 117 | 88 | 89 | 114 | 315 | 364 |
| 3A9 | Kabat | 121 | 122 | 123 | 124 | 125 | 126 | 316 | 366 |
| 3E8 | Kabat | 127 | 128 | 129 | 34 | 35 | 36 | 317 | 367 |
| 4B1 | Kabat | 133 | 134 | 135 | 136 | 137 | 138 | 318 | 368 |
| 4D3 | Kabat | 139 | 140 | 141 | 142 | 143 | 144 | 319 | 369 |
| 4D5 | Kabat | 145 | 146 | 147 | 148 | 149 | 150 | 320 | 370 |
| 4E8 | Kabat | 31 | 32 | 33 | 148 | 149 | 150 | 321 | 370 |
| 4H4 | Kabat | 31 | 32 | 159 | 136 | 137 | 162 | 322 | 372 |
| 6G8 | Kabat | 169 | 170 | 171 | 172 | 173 | 174 | 324 | 374 |
| 7A1 | Kabat | 61 | 62 | 63 | 64 | 65 | 180 | 306 | 375 |
| 8B4 | Kabat | 31 | 182 | 183 | 136 | 137 | 186 | 326 | 376 |
| 8C4 | Kabat | 187 | 188 | 189 | 190 | 191 | 192 | 327 | 377 |
| 2.8.6 | Kabat | 193 | 194 | 195 | 196 | 197 | 12 | 17 | 15 |
| 11.5.1 | Kabat | 199 | 200 | 201 | 202 | 203 | 6 | 21 | 19 |
| 6.2 | Kabat | 205 | 206 | 207 | 142 | 209 | 210 | 330 | 380 |
| 831 | Kabat | 211 | 212 | 213 | 214 | 35 | 216 | 331 | 381 |
| humanised 2.8.6 | IMGT | 7 | 8 | 9 | 10 | 11 | 12 | 13 | 14 |
| 2.8.6 | IMGT | 7 | 8 | 9 | 10 | 11 | 12 | 17 | 15 |
| 11.5.1 | IMGT | 1 | 2 | 3 | 4 | 5 | 6 | 21 | 19 |
| Humanised 3E8 | Kabat | 127 | 386 | 129 | 34 | 35 | 36 | 382 | 383 |
| Humanised 6.2 | Kabat | 205 | 206 | 207 | 142 | 209 | 210 | 384 | 385 |
| Engineered humanised 3E8 | Kabat | 127 | 388 | 129 | 34 | 35 | 36 | 389 | 383 |
| Engineered humanised 6.2 (2$^{nd}$) | Kabat | 205 | 387 | 207 | 142 | 209 | 210 | 390 | 385 |
| Engineered humanised 6.2 | Kabat | 205 | 387 | 207 | 142 | 143 | 210 | 390 | 378 |

In particular embodiments, the heavy chain or light chain also comprise a constant region. If the molecule is a full-length IgG-type antibody molecule, the heavy chain may comprise three constant domains.

In certain embodiments the isolated antibody or an antigen-binding fragment thereof that specifically binds human BTLA exhibits a $K_D$ for binding to human BTLA of at most about $10 \times 10^{-9}$ M. In certain embodiments the isolated antibody or an antigen-binding fragment thereof that specifically binds human BTLA exhibits a $K_D$ for binding to human BTLA of at most about $4\times10^{-9}$ M. In certain embodiments the isolated antibody or an antigen-binding fragment thereof that specifically binds human BTLA exhibits a $K_D$ for binding to human BTLA of at most about $1\times10^{-9}$ M.

In certain embodiments, an isolated antibody (e.g., humanised) of the invention binds human BTLA at 37° C. with a $K_D$ of no more than about 10 nM ($1\times10^{-8}$ M); suitably no more than about 1 nM; more suitably are embodiments in which the antibodies have $K_D$ values at 37° C. of no more than about 500 pM ($5\times10^{-10}$ M), 200 pM, 100 pM, 50 pM, 20 pM, 10 pM, 5 pM or even 2 pM. The term "about", as used in this context means+/−10%.

In certain embodiments, an isolated antibody (e.g., humanised) of the invention binds human BTLA at 37° C. with an on rate of at least $1.0\times10^5$ (1/Ms). In certain embodiments, an isolated antibody (e.g., humanised) of the invention binds human BTLA at 37° C. with an on rate of at least $2.0\times10^5$ (1/Ms), $3.0\times10^5$ (1/Ms), $4.0\times10^5$ (1/Ms), $5.0\times10^5$ (1/Ms), $6.0\times10^5$ (1/Ms), or $7.0\times10^5$ (1/Ms).

In certain embodiments, an isolated antibody (e.g., humanised) of the invention binds human BTLA at 37° C. with an off rate of no more than or less than $1.0\times10^{-3}$ (1/s). In certain embodiments, an isolated antibody (e.g., humanised) of the invention binds human BTLA at 37° C. with an off rate of no more than or less than $3.0\times10^{-4}$ (1/s). In certain embodiments, an isolated antibody (e.g., humanised) of the invention binds human BTLA at 37° C. with an off rate of no more than or less than $2.0\times10^4$ (1/s), or $1.0\times10^{-4}$ (1/s).

In particular embodiments of the first aspect of the invention, provided herein are isolated agonistic antibodies or antigen binding fragments thereof that specifically binds human B and T Lymphocyte Attenuator (BTLA) with a KD of less than 10 nM, as determined by surface plasmon resonance (SPR) at 37° C. using a method such as that described in Example 2, and wherein said antibody binds cynomolgus BTLA with a KD of less than 20 nM, as determined by surface plasmon resonance (SPR) at 37° C. using a method such as that described in Example 2; does not inhibit binding of BTLA to herpes virus entry mediator (HVEM), as determined for example by surface plasmon resonance (SPR) using a method such as that described in Example 4; and inhibits proliferation of T cells in vitro, as determined for example by a mixed lymphocyte reaction assay using a method such as that described in Example 9. In some embodiments, said antibody or antigen binding fragment thereof binds human B and T Lymphocyte Attenuator (BTLA) with an on rate of at least $5.0\times10^5$ (1/Ms) as determined by surface plasmon resonance (SPR) at 37° C. using a method such as that described in Example 2. In some embodiments, said antibody or antigen binding fragment thereof binds human B and T Lymphocyte Attenuator (BTLA) with an off rate of less than $3.0\times10^4$ (1/s) as determined by surface plasmon resonance (SPR) at 37° C. using a method such as that described in Example 2. In some embodiments, said antibody or antigen binding fragment thereof binds human B and T Lymphocyte Attenuator (BTLA) with an off rate from $3.0\times10^{-4}$ (1/s) to $1.0\times10^{-3}$ (1/s) as determined by surface plasmon resonance (SPR) at 37° C. using a method such as that described in Example 2. In some embodiments, the antibody or antigen-binding fragment thereof binds a residue of human BTLA selected from: Y39, K41, R42, Q43, E45 and S47. In some embodiments, the antibody or antigen-binding fragment thereof binds a residue of human BTLA selected from: D35, T78, K81, S121 and L123. In some embodiments, the antibody or antigen-binding fragment thereof binds residue H68 of human BTLA. In some embodiments, the antibody or antigen-binding fragment thereof binds a residue of human BTLA selected from: N65 and A64.

Methods for characterizing the properties of an antibody or antigen-binding fragment thereof of the invention are well known in the art. A suitable method for determining binding specificity using surface plasmon resonance (SPR) at 37° C. is described in Example 2. A suitable method for determining whether the tested antibody/fragment thereof inhibits binding of BTLA to herpes virus entry mediator (HVEM) is described in Example 4; this also employs surface plasmon resonance (SPR). A suitable method for determining whether the tested antibody/fragment thereof inhibits proliferation of T cells in vitro, is a mixed lymphocyte reaction assay such as that described in Example 9. Suitable methods for determining the site of binding of an antibody/fragment thereof to BTLA can utilise x-ray crystallography or flow cytometry of mutated receptors, such as by the method described in Example 5

In particular embodiments of the first aspect of the invention, provided herein are isolated agonistic antibodies or antigen binding fragments thereof that specifically binds human B and T Lymphocyte Attenuator (BTLA) with an on rate of at least $5.0\times10^5$ (1/Ms), as determined by surface plasmon resonance (SPR) at 37° C. using a method such as that described in Example 2, wherein said antibody does not inhibit binding of BTLA to herpes virus entry mediator (HVEM) as determined for example by surface plasmon resonance (SPR) using a method such as that described in Example 4; and wherein said antibody inhibits proliferation of T cells in vitro, as determined for example by a mixed lymphocyte reaction assay using a method such as that described in Example 9. In some embodiments, said antibody or antigen binding fragment thereof binds human B and T Lymphocyte Attenuator (BTLA) with an off rate of less than $3.0\times10^{-4}$ (1/s) as determined by surface plasmon resonance (SPR) at 37° C. using a method such as that described in Example 2. In some embodiments, said antibody or antigen binding fragment thereof binds human B and T Lymphocyte Attenuator (BTLA) with a KD of less than 10 nM, as determined by surface plasmon resonance (SPR) at 37° C. using a method such as that described in Example 2. In some embodiments, said antibody or antigen binding fragment thereof binds cynomolgus BTLA with a KD of less than 20 nM, as determined by surface plasmon resonance (SPR) at 37° C. using a method such as that described in Example 2. In some embodiments, the antibody or antigen-binding fragment thereof binds a residue of human BTLA selected from: D52, P53, E55, E57, E83, Q86, E103, L106 and E92 as determined by x-ray crystallography or by flow cytometry of mutated receptors using a method such as that described in Example 5. In some embodiments, the antibody or antigen-binding fragment thereof binds a residue of human BTLA selected from: Y39, K41, R42, Q43, E45 and S47. In some embodiments, the antibody or antigen-binding fragment thereof binds a residue of human BTLA selected from: D35, T78, K81, S121 and L123. In some embodiments, the antibody or antigen-binding fragment thereof binds residue H68 of human BTLA. In some embodiments, the antibody or antigen-binding fragment thereof binds a residue of BTLA selected from: N65 and A64.

In particular embodiments of the first aspect of the invention, provided herein are isolated agonistic antibody or antigen binding fragment thereof that specifically binds human B and T Lymphocyte Attenuator (BTLA) with an off rate from $3.0 \times 10^4$ (1/s) to $1.0 \times 10^{-3}$ (1/s) as determined by surface plasmon resonance (SPR) at 37° C. using a method such as that described in Example 2, wherein said antibody does not inhibit binding of BTLA to herpes virus entry mediator (HVEM) as determined for example by surface plasmon resonance (SPR) using a method such as that described in Example 4; and wherein said antibody inhibits proliferation of T cells in vitro, as determined for example by a mixed lymphocyte reaction assay using a method such as that described in Example 9. In some embodiments, said antibody or antigen binding fragment thereof binds human B and T Lymphocyte Attenuator (BTLA) with a KD of less than 10 nM, as determined by surface plasmon resonance (SPR) at 37° C. using a method such as that described in Example 2. In some embodiments, said antibody or antigen binding fragment thereof binds cynomolgus BTLA with a KD of less than 20 nM, as determined by surface plasmon resonance (SPR) at 37° C. using a method such as that described in Example 2. In some embodiments, said antibody or antigen binding fragment thereof binds human B and T Lymphocyte Attenuator (BTLA) with an on rate of at least $5.0 \times 10^5$ (1/Ms) as determined by surface plasmon resonance (SPR) at 37° C. using a method such as that described in Example 2. In some embodiments, the antibody or antigen-binding fragment thereof binds a residue of human BTLA selected from: D52, P53, E55, E57, E83, Q86, E103, L106 and E92 as determined by x-ray crystallography or by flow cytometry of mutated receptors using a method such as that described in Example 5. In some embodiments, the antibody or antigen-binding fragment thereof binds a residue of human BTLA selected from: Y39, K41, R42, Q43, E45 and S47. In some embodiments, the antibody or antigen-binding fragment thereof binds a residue of human BTLA selected from: D35, T78, K81, S121 and L123. In some embodiments, the antibody or antigen-binding fragment thereof binds residue H68 of human BTLA. In some embodiments, the antibody or antigen-binding fragment thereof binds a residue of human BTLA selected from: N65 and A64.

In particular embodiments of the first aspect of the invention, provided herein are isolated agonistic antibodies or antigen binding fragments thereof that specifically binds human B and T Lymphocyte Attenuator (BTLA) with an off rate of less than $1.0 \times 10^{-3}$ (1/s) and an on rate of at least $5.0 \times 10^5$ (1/Ms), each as measured by surface plasmon resonance (SPR) at 37° C. using a method such as that described in Example 2, wherein said antibody does not inhibit binding of BTLA to herpes virus entry mediator (HVEM) as determined for example by surface plasmon resonance (SPR) using a method such as that described in Example 4; and wherein said antibody inhibits proliferation of T cells in vitro, as determined for example by a mixed lymphocyte reaction assay using a method such as that described in Example 9. In some embodiments, said antibody or antigen binding fragment thereof binds human B and T Lymphocyte Attenuator (BTLA) with a KD of less than 10 nM, as determined by surface plasmon resonance (SPR) at 37° C. using a method such as that described in Example 2. In some embodiments, said antibody or antigen binding fragment thereof binds cynomolgus BTLA with a KD of less than 20 nM, as determined by surface plasmon resonance (SPR) at 37° C. using a method such as that described in Example 2. In some embodiments, the antibody or antigen-binding fragment thereof binds a residue of human BTLA selected from: D52, P53, E55, E57, E83, Q86, E103, L106 and E92 as determined by x-ray crystallography or by flow cytometry of mutated receptors using a method such as that described in Example 5. In some embodiments, the antibody or antigen-binding fragment thereof binds a residue of BTLA selected from: Y39, K41, R42, Q43, E45 and S47. In some embodiments, the antibody or antigen-binding fragment thereof binds a residue of human BTLA selected from: D35, T78, K81, S121 and L123. In some embodiments, the antibody or antigen-binding fragment thereof binds residue H68 of human BTLA. In some embodiments, the antibody or antigen-binding fragment thereof binds a residue of human BTLA selected from: N65 and A64.

In particular embodiments of the first aspect of the invention, provided herein are isolated agonistic antibodies or antigen binding fragments thereof that specifically binds human B and T Lymphocyte Attenuator (BTLA) with a KD of less than 2 nM, as determined by surface plasmon resonance (SPR) at 37° C. using a method such as that described in Example 2, wherein said antibody inhibits binding of BTLA to herpes virus entry mediator (HVEM) as determined by surface plasmon resonance (SPR) using a method such as that described in Example 4; and inhibits proliferation of T cells in vitro, as determined for example by a mixed lymphocyte reaction assay using a method such as that described in Example 9. In some embodiments, said antibody or antigen binding fragment thereof binds human B and T Lymphocyte Attenuator (BTLA) with an on rate of less than $1.0 \times 10^6$ (1/Ms), as determined by surface plasmon resonance (SPR) at 37° C. using a method such as that described in Example 2. In some embodiments, said antibody or antigen binding fragment thereof binds human B and T Lymphocyte Attenuator (BTLA) with an off rate of less than $1.0 \times 10^{-3}$ (1/s), as determined by surface plasmon resonance (SPR) at 37° C. using a method such as that described in Example 2. In some embodiments, said antibody or antigen binding fragment thereof binds cynomolgus B and T Lymphocyte Attenuator (BTLA) with a KD of less than 10 nM, as determined by surface plasmon resonance (SPR) at 37° C. using a method such as that described in Example 2. In some embodiments, the antibody or antigen-binding fragment thereof binds a residue of human BTLA selected from: D52, P53, E55, E57, E83, Q86, E103, L106 and E92 as determined by x-ray crystallography or by flow cytometry of mutated receptors using a method such as that described in Example 5. In some embodiments, the antibody or antigen-binding fragment thereof binds a residue of human BTLA selected from: Y39, K41, R42, Q43, E45 and S47. In some embodiments, the antibody or antigen-binding fragment thereof binds a residue of human BTLA selected from: D35, T78, K81, S121 and L123. In some embodiments, the antibody or antigen-binding fragment thereof binds residue H68 of BTLA. In some embodiments, the antibody or antigen-binding fragment thereof binds a residue of human BTLA selected from: N65 and A64.

In particular embodiments of the first aspect of the invention, provided herein are isolated agonistic antibodies or antigen binding fragments thereof that specifically binds human B and T Lymphocyte Attenuator (BTLA) with an on off rate of less than $1 \times 10^{-3}$ (1/s) as determined by surface plasmon resonance (SPR) at 37° C. using a method such as that described in Example 2, wherein said antibody inhibits binding of BTLA to herpes virus entry mediator (HVEM) as determined by surface plasmon resonance (SPR) using a method such as that described in Example 4; and inhibits proliferation of T cells in vitro, as determined for example by a mixed lymphocyte reaction assay using a method such as that described in Example 9. In some embodiments, said antibody or antigen binding fragment thereof binds cynomolgus B and T Lymphocyte Attenuator (BTLA) with a KD of less than 10 nM, as determined by surface plasmon resonance (SPR) at 37° C. using a method such as that described in Example 2. In some embodiments, said antibody or antigen binding fragment thereof binds human B and T Lymphocyte Attenuator (BTLA) with a KD of less than 2 nM, as determined by surface plasmon resonance (SPR) at 37° C. using a method such as that described in Example 2. In some embodiments, the antibody or antigen-binding fragment thereof binds a residue of human BTLA selected from: D52, P53, E55, E57, E83, Q86, E103, L106 and E92 as determined by x-ray crystallography or by flow cytometry of mutated receptors using a method such as that described in Example 5. In some embodiments, the antibody or antigen-binding fragment thereof binds a residue of human BTLA selected from: Y39, K41, R42, Q43, E45 and S47. In some embodiments, the antibody or antigen-binding fragment thereof binds a residue of human BTLA selected from: D35, T78, K81, S121 and L123. In some embodiments, the antibody or antigen-binding fragment thereof binds residue H68 of human BTLA. In some embodiments, the antibody or antigen-binding fragment thereof binds a residue of human BTLA selected from: N65 and A64.

In particular embodiments of the first aspect of the invention, provided herein are isolated agonistic antibodies or antigen binding fragments thereof that specifically binds human B and T Lymphocyte Attenuator (BTLA), wherein said antibody binds cynomolgus BTLA with a KD of at least 5 nM, as determined by surface plasmon resonance (SPR) at 37° C. using a method such as that described in Example 2; and wherein said antibody inhibits binding of BTLA to herpes virus entry mediator (HVEM) as determined by surface plasmon resonance (SPR) using a method such as that described in Example 4; and inhibits proliferation of T cells in vitro, as determined for example by a mixed lymphocyte reaction assay using a method such as that described in Example 9. In some embodiments, the antibody or antigen-binding fragment thereof binds a residue of human BTLA selected from: D52, P53, E55, E57, E83, Q86, E103, L106 and E92 as determined by x-ray crystallography or by flow cytometry of mutated receptors using a method such as that described in Example 5. In some embodiments, the antibody or antigen-binding fragment thereof binds a residue of human BTLA selected from: Y39, K41, R42, Q43, E45 and S47. In some embodiments, the antibody or antigen-binding fragment thereof binds a residue of human BTLA selected from: D35, T78, K81, S121 and L123. In some embodiments, the antibody or antigen-binding fragment thereof binds residue H68 of human BTLA. In some embodiments, the antibody or antigen-binding fragment thereof binds a residue of human BTLA selected from: N65 and A64.

In particular embodiments of the first aspect of the invention, provided herein are isolated agonistic antibodies or antigen binding fragments thereof that specifically binds human B and T Lymphocyte Attenuator (BTLA), wherein said antibody binds cynomolgus BTLA with a KD of at least than 50 nM, as determined by surface plasmon resonance (SPR) at 37° C. using a method such as that described in Example 2; and wherein said antibody does not inhibit binding of BTLA to herpes virus entry mediator (HVEM) as determined by surface plasmon resonance (SPR) using a method such as that described in Example 4; and inhibits proliferation of T cells in vitro, as determined for example by a mixed lymphocyte reaction assay using a method such as that described in Example 9. In some embodiments, the antibody or antigen-binding fragment thereof binds a residue of human BTLA selected from: D52, P53, E55, E57, E83, Q86, E103, L106 and E92 as determined by x-ray crystallography or by flow cytometry of mutated receptors using a method such as that described in Example 5. In some embodiments, the antibody or antigen-binding fragment thereof binds a residue of human BTLA selected from: Y39, K41, R42, Q43, E45 and S47. In some embodiments, the antibody or antigen-binding fragment thereof binds a residue of human BTLA selected from: D35, T78, K81, S121 and L123. In some embodiments, the antibody or antigen-binding fragment thereof binds residue H68 of human BTLA. In some embodiments, the antibody or antigen-binding fragment thereof binds a residue of human BTLA selected from: N65 and A64.

In particular embodiments of the first aspect of the invention, provided herein are isolated agonistic antibodies or antigen binding fragments thereof that specifically binds human B and T Lymphocyte Attenuator (BTLA) with a KD from 1400 nM to 3500 nM, as determined by surface plasmon resonance (SPR) at 37° C. using a method such as that described in Example 2; and wherein said antibody does not inhibit binding of BTLA to herpes virus entry mediator (HVEM) as determined by surface plasmon resonance (SPR) using a method such as that described in Example 4; and inhibits proliferation of T cells in in vitro, as determined for example by a mixed lymphocyte reaction assay using a method such as that described in Example 9. In some embodiments, said antibody or antigen binding fragment thereof binds human BTLA with an on rate of at least $2.0 \times 10^5$ (1/Ms), as determined by surface plasmon resonance (SPR) at 37° C. using a method such as that described in Example 2. In some embodiments, said antibody or antigen binding fragment thereof binds human BTLA with an off rate of less than $10.0 \times 10^{-1}$ (1/s), as determined by surface plasmon resonance (SPR) at 37° C. using a method such as that described in Example 2. In some embodiments, the antibody or antigen-binding fragment thereof binds a residue of human BTLA selected from: D52, P53, E55, E57, E83, Q86, E103, L106 and E92 as determined by x-ray crystallography or by flow cytometry of mutated receptors using a method such as that described in Example 5. In some embodiments, the antibody or antigen-binding fragment thereof binds a residue of human BTLA selected from: Y39, K41, R42, Q43, E45 and S47. In some embodiments, the antibody or antigen-binding fragment thereof binds a residue of human BTLA selected from: D35, T78, K81, S121 and L123. In some embodiments, the antibody or antigen-binding fragment thereof binds residue H68 of human BTLA. In some embodiments, the antibody or antigen-binding fragment thereof binds a residue of human BTLA selected from: N65 and A64.

In particular embodiments of the first aspect of the invention, provided herein are isolated agonistic antibodies or antigen binding fragments thereof that specifically binds human B and T Lymphocyte Attenuator (BTLA) with an on rate from $1.7 \times 10^5$ (1/Ms) to $2.5 \times 10^5$ (1/Ms), as determined by surface plasmon resonance (SPR) at 37° C. using a method such as that described in Example 2; and wherein said antibody does not inhibit binding of BTLA to herpes virus entry mediator (HVEM) as determined by surface plasmon resonance (SPR) using a method such as that described in Example 4; and inhibits proliferation of T cells in in vitro, as determined for example by a mixed lymphocyte reaction assay using a method such as that described in Example 9. In some embodiments, said antibody or antigen binding fragment thereof binds human BTLA with an off rate of less than $3.0 \times 10^{-1}$ (1/s), as determined by surface plasmon resonance (SPR) at 37° C. using a method such as that described in Example 2. In some embodiments, said antibody or antigen binding fragment thereof binds human BTLA with an off rate from $3.0 \times 10^{-1}$ (1/s) to $5.0 \times 10^{-1}$ (1/s), as determined by surface plasmon resonance (SPR) at 37° C. using a method such as that described in Example 2. In some embodiments, said antibody or antigen binding fragment thereof binds human BTLA with a KD of at least 150 nM, as determined by surface plasmon resonance (SPR) at 37° C. using a method such as that described in Example 2. In some embodiments, said antibody or antigen binding fragment thereof binds human BTLA with a KD from 150 nM to 1500 nM, as determined by surface plasmon resonance (SPR) at 37° C. using a method such as that described in Example 2. In some embodiments, said antibody or antigen binding fragment thereof binds to an epitope that blocks binding of 286 antibody. In some embodiments, the antibody or antigen-binding fragment thereof binds a residue of human BTLA selected from: D52, P53, E55, E57, E83, Q86, E103, L106 and E92 as determined by x-ray crystallography or by flow cytometry of mutated receptors using a method such as that described in Example 5. In some embodiments, the antibody or antigen-binding fragment thereof binds a residue of human BTLA selected from: Y39, K41, R42, Q43, E45 and S47. In some embodiments, the antibody or antigen-binding fragment thereof binds a residue of human BTLA selected from: D35, T78, K81, S121 and L123. In some embodiments, the antibody or antigen-binding fragment thereof binds residue H68 of human BTLA. In some embodiments, the antibody or antigen-binding fragment thereof binds a residue of human BTLA selected from: N65 and A64.

In particular embodiments of the first aspect of the invention, provided herein are isolated agonistic antibodies or antigen binding fragments thereof that specifically binds human B and T Lymphocyte Attenuator (BTLA) with a KD from 40 nM to 1200 nM, as determined by surface plasmon resonance (SPR) at 37° C. using a method such as that described in Example 2; and wherein said antibody does not inhibit binding of BTLA to herpes virus entry mediator (HVEM) as determined by surface plasmon resonance (SPR) using a method such as that described in Example 4; and inhibits proliferation of T cells in in vitro, as determined for example by a mixed lymphocyte reaction assay using a method such as that described in Example 9. In some embodiments, said antibody or antigen binding fragment thereof binds human BTLA with an on rate of at least $1.0 \times 10^5$ (1/Ms), as determined by surface plasmon resonance (SPR) at 37° C. using a method such as that described in Example 2. In some embodiments, said antibody or antigen binding fragment thereof binds human BTLA with an on rate from $1.0 \times 10^5$ (1/Ms) to $10 \times 10^5$ (1/Ms), as determined by surface plasmon resonance (SPR) at 37° C. using a method such as that described in Example 2. In some embodiments, said antibody or antigen binding fragment thereof binds human BTLA with an off rate of less than $6.0 \times 10^{-1}$ (1/s), as determined by surface plasmon resonance (SPR) at 37° C. using a method such as that described in Example 2. In some embodiments, said antibody or antigen binding fragment thereof binds human BTLA with an off rate from $6.0 \times 10^{-1}$ (1/s) to $10.0 \times 10^{-2}$ (1/s), as determined by surface plasmon resonance (SPR) at 37° C. using a method such as that described in Example 2. In some embodiments, the antibody or antigen-binding fragment thereof binds a residue of human BTLA selected from: D52, P53, E55, E57, E83, Q86, E103, L106 and E92 as determined by x-ray crystallography or by flow cytometry of mutated receptors using a method such as that described in Example 5. In some embodiments, the antibody or antigen-binding fragment thereof binds a residue of human BTLA selected from: Y39, K41, R42, Q43, E45 and S47. In some embodiments, the antibody or antigen-binding fragment thereof binds a residue of human BTLA selected from: D35, T78, K81, S121 and L123. In some embodiments, the antibody or antigen-binding fragment thereof binds residue H68 of human BTLA. In some embodiments, the antibody or antigen-binding fragment thereof binds a residue of human BTLA selected from: N65 and A64.

In certain embodiments the isolated antibody or an antigen-binding fragment thereof of the invention that specifically binds human BTLA increases BTLA activity and/or signaling through the receptor.

In particular embodiments, the antibody of the invention is selected from the group consisting of: a human antibody, a humanised antibody, a chimeric antibody, a multispecific antibody (such as a bispecific antibody).

In particular embodiments, the antigen-binding fragment of the invention is selected from the group consisting of: scFv, sc(Fv)$^2$, dsFv, Fab, Fab', (Fab')2 and diabody.

In particular embodiments, the heavy chain and light chain molecules that form the antigen-binding fragment are connected by a flexible linker. There are many commonly used flexible linkers and the choice of linker can be made by a person of skill in the art.

The peptide linker connecting scFv VH and VL domains joins the carboxyl terminus of one variable region domain to the amino terminus of another variable domain without significantly compromising the fidelity of the VH-VL pairing and antigen-binding sites. Peptide linkers can vary from 10 to 25 amino acids in length and are typically, but not always, composed of hydrophilic amino acids such as glycine (G) and serine (S). The linker can be one that is found in natural multi-domain proteins (e.g. see Argos P. J Mol Biol. 211:943-958, 1990; and. Heringa G. Protein Eng. 15:871-879, 2002), or adapted therefrom.

Commonly used flexible linkers have sequences consisting primarily of stretches of Gly and Ser residues ("GS" linker). An example of the most widely used flexible linker has the sequence of (Gly-Gly-Gly-Gly-Ser). By adjusting the copy number "n", the length of this GS linker can be altered to achieve appropriate separation of the functional domains, or to maintain necessary inter-domain interactions. Generally, the (GGGGS)3 peptide is used as an scFv peptide linker (Leith et al., Int. J. Oncol. 24:765-771, 2004; Holiger et al. Proc. Natl. Acad. Sci. U.S.A. 90:6444-6448, 1993). This 15-amino acid linker sequence [designated as the (GGGGS)3 linker] is used in the Recombinant Phage Antibody System (RPAS kit) commercially available from Amersham. Several other linkers have also been used to create scFV molecules (e.g. KESGSVSSEQLAQFRSLD and EGKSSGSGSESKST; Bird et al., Science 242:432-426, 1988).

The inventors have mapped the epitopes on BTLA where the potent 2.8.6 and 11.5.1 agonist and the other antibodies disclosed herein bind.

In particular embodiments, the antibody or antigen-binding fragment thereof of the invention binds a residue of human BTLA selected from: D52, P53, E55, E57, E83, Q86, E103, L106, E92, Y39, K41, R42, Q43, E45, S47, D35, T78, K81, 5121, L123, H68, N65, A64.

In particular embodiments, the antibody or antigen-binding fragment thereof of the invention binds a residue of human BTLA selected from: D52, P53, E55, E57, E83, Q86, E103, L106, E92.

In particular embodiments, the antibody or antigen-binding fragment thereof of the invention binds at least two residues of human BTLA selected from: D52, P53, E55, E57, E83, Q86, E103, L106, E92.

In particular embodiments, the antibody or antigen-binding fragment thereof of the invention binds at least three residues of human BTLA selected from: D52, P53, E55, E57, E83, Q86, E103, L106 and E92.

In particular embodiments, the antibody or antigen-binding fragment thereof of the invention binds at least five residues of human BTLA selected from: D52, P53, E55, E57, E83, Q86, E103, L106 and E92.

In particular embodiments, the antibody or antigen-binding fragment thereof of the invention binds all of the residues of human BTLA selected from: D52, P53, E55, E57, E83, Q86, E103, L106 and E92.

In particular embodiments, the antibody or antigen-binding fragment thereof of the invention binds a residue of human BTLA selected from: Y39, K41, R42, Q43, E45 and S47.

In a particular embodiment, the antibody or antigen-binding fragment thereof of the invention binds at least two residues of human BTLA selected from: Y39, K41, R42, Q43, E45 and S47.

In particular embodiments, the antibody or antigen-binding fragment thereof of the invention binds all of the residues of human BTLA selected from: Y39, K41, R42, Q43, E45 and S47.

In particular embodiments, the antibody or antigen-binding fragment thereof of the invention binds a residue of human BTLA selected from: D35, T78, K81, S121 and L123.

In a particular embodiment, the antibody or antigen-binding fragment thereof of the invention binds at least two residues of human BTLA selected from: D35, T78, K81, S121 and L123.

In particular embodiments, the antibody or antigen-binding fragment thereof of the invention binds residue H68 of human BTLA In particular embodiments, the antibody or antigen-binding fragment thereof of the invention binds a residue of human BTLA selected from: N65 and A64.

In particular embodiments, the antibody or antigen-binding fragment thereof of the invention binds both the N65 and A64 residues of human BTLA.

The numbering of the residues, such as K41 refers to the amino acid (K; lysine) at position 41; wherein the numbering refers to the position in human BTLA polypeptide as disclosed in SEQ ID NO: 23.

In particular embodiments, the antibody of the invention is an IgG1, IgG2 or IgG4 antibody. In particular embodiments the antibody is a murine or human antibody.

In a particular embodiment, the antibody or antigen-binding fragment thereof of the invention is a humanised antibody.

In a particular embodiment, the antibody or antigen-binding fragment thereof of the invention is a fully human antibody.

In a particular embodiment, the antibody or antigen-binding fragment thereof of the invention acts as an agonist inducing signaling through the BTLA receptor.

The antibodies (or antigen-binding fragments thereof) of the invention are particularly potent agonists.

In a particular embodiment, the antibody or antigen-binding fragment thereof of the invention have EC50s of not more than 1 nM.

The agonist antibodies (or antigen-binding fragments thereof) of the invention have particularly high efficacy.

In a particular embodiment the antibody or antigen-binding fragment thereof of the invention inhibits T cell proliferation by at least 20%, suitably by at least 30%, more suitably by at least 40%.

In a particular embodiment the antibody or antigen-binding fragment thereof of the invention inhibits T cell IFN-gamma production by at least 50%, suitably by at least 75%, more suitably by at least 95%, as measured for example by ELISA of supernatants in an in vitro mixed lymphocyte reaction.

In a particular embodiment the antibody or antigen-binding fragment thereof of the invention inhibits T cell IL-2 production by at least 50%, suitably by at least 75%, more suitably by at least 95%, as measured for example by ELISA of supernatants in an in vitro mixed lymphocyte reaction.

In a particular embodiment the antibody or antigen-binding fragment thereof of the invention inhibits T cell IL-17 production by at least 50%, suitably by at least 75%, more suitably by at least 95%, as measured for example by ELISA of supernatants in an in vitro mixed lymphocyte reaction.

In a particular embodiment the antibody or antigen-binding fragment thereof of the invention reduces mortality in a murine GVHD model by at least 50%, suitably by at least 75%, more suitably by at least 95%, using a method such as that described in Example 12.

In a particular embodiment the antibody or antigen-binding fragment thereof of the invention reduces weight loss in a murine T-cell colitis model by at least 50%, suitably by at least 75%, more suitably by at least 95%, using a method such as that described in Example 11.

In a particular embodiment the antibody or antigen-binding fragment thereof of the invention reduces colon inflammation in a murine T-cell colitis model by at least 50%, suitably by at least 75%, more suitably by at least 95%, using a method such as that described in Example 11.

In certain aspects, the invention also relates to an isolated polypeptide comprising the VL domains or the VH domains of any of the antibodies or antigen-binding fragments thereof described herein.

In a particular embodiment, the isolated polypeptide comprises an amino acid sequence as set forth in SEQ ID NO: 13 or 14, or a sequence with at least 90% identity thereto.

Nucleic Acid Molecules

The antibody or antigen-binding fragment thereof of the invention will be encoded by nucleic acid. The antibody or antigen-binding fragment thereof may be encoded by a single nucleic acid molecule or it may be encoded by two or more nucleic acid molecules. For example, as the antigen binding site is typically formed by the coming together of a heavy chain variable polypeptide region and a light chain variable polypeptide region, the two variable (heavy and light) polypeptide regions may be encoded by separate nucleic acid molecules. Alternatively, for example in the case of an ScFv, they may be encoded by the same nucleic acid molecule.

According to a second aspect of the invention there is provided one or more nucleic acid molecules that encode an antibody or antigen-binding fragment thereof in accordance with the first aspect of the invention.

From the primary amino acid sequence of the polypeptide(s) encoding an antibody or antigen-binding fragment thereof of the invention the person of skill in the art is able to determine suitable nucleotide sequence(s) that encodes the polypeptide(s) and, if desired, one that is codon-optimised (e.g. see Mauro and Chappell. Trends Mol Med. 20(11):604-613, 2014).

As used herein, when there is reference to a previous aspect of the invention, e.g. "in accordance with the first (or second etc.) aspect of the invention", it is understood to also cover any recited variation of said aspect (e.g. variation of the first (or second etc.) aspect).

According to a variation of the second aspect of the invention there is provided an isolated nucleic acid comprising a nucleotide sequence that encodes a heavy chain variable region polypeptide or a light chain variable region polypeptide of the invention. A heavy chain variable polypeptide or a light chain variable polypeptide of the invention refers to the individual polypeptide chains that include amino acids that make up part of the antigen-binding site. Of course, the said polypeptides may also comprise other domains such as constant domains, hinge regions, and an Fc region, such as one comprising one or more Fc receptor binding sites.

According to another variation of the second aspect of the invention there is provided an isolated nucleic acid which comprises one or more nucleotide sequence encoding polypeptides capable of forming an antibody or antigen-binding fragment of the invention. In particular embodiments, the said polypeptides may also comprise other domains such as constant domains, hinge regions, and an Fc region, such as one comprising one or more Fc receptor binding sites.

One of the nucleic acid molecules may encode just the polypeptide sequence that comprises the VL domain of the antibody or fragment thereof. One of the nucleic acid molecules may encode just the polypeptide sequence that comprises the VH domain of the antibody or fragment thereof However, the nucleic acid molecule may also encode both VH and VL domain containing polypeptide sequences capable of forming the antibody or antibody fragment thereof of the invention.

The nucleic acid molecule(s) that encode the antibody or antigen-binding fragment thereof of the invention, such as according to the first aspect of the invention, may be, or may be part of, a vector (such as a plasmid vector, cosmid vector or viral vector, or an artificial chromosome) that may comprise other functional regions (elements) such as one or more promoters, one or more origins or replication, one or more selectable marker(s), and one or more other elements typically found in expression vectors. The cloning and expression of nucleic acids that encode proteins, including antibodies, is well established and well within the skill of the person in the art.

According to a third aspect of the invention there is provided a vector comprising the nucleic acid of the second aspect of the invention. In particular embodiments, the vector is a plasmid vector, cosmid vector, viral vector, or an artificial chromosome.

The nucleic acids of the invention, including vector nucleic acids that comprise nucleotide sequences that encode the polypeptides capable of forming an antibody of the invention or an antigen-binding fragments thereof, may be in purified/isolated form.

Isolated/purified nucleic acids that encode an antibody or antigen-binding fragment thereof of the invention will be free or substantially free of material with which they are naturally associated, such as other proteins or nucleic acids with which they are found in their natural environment, or the environment in which they are prepared (e.g. cell culture) when such preparation is by recombinant DNA technology practised in vitro or in vivo.

In particular embodiments, the nucleic acids of the invention are greater than 80%, such as greater than 90%, greater than 95%, greater than 97% and greater than 99% pure.

Thus, according to another variation of the third aspect of the invention there is provided a vector comprising a nucleic acid or nucleotide sequence that encodes a heavy chain variable polypeptide or a light chain variable polypeptide of the invention. In a particular embodiment, the vector comprises nucleic acid that encodes both the heavy and light chain variable regions. In particular embodiments, the said polypeptides may also comprise other domains such as constant domains, hinge regions, and an Fc region, such as one comprising one or more Fc receptor binding sites.

The nucleic acid and/or vector of the invention may be introduced into a host cell. The introduction may employ any available technique. For eukaryotic cells, suitable techniques may include calcium phosphate transfection, DEAE-Dextran, electroporation, liposome-mediated transfection and transduction using retrovirus or other virus, e.g. vaccinia or, for insect cells, baculovirus. Introducing nucleic acid in the host cell, in particular a eukaryotic cell may use a viral or a plasmid-based system. The plasmid system may be maintained episomally or may incorporated into the host cell or into an artificial chromosome. Incorporation may be either by random or targeted integration of one or more copies at single or multiple loci. For bacterial cells, suitable techniques may include calcium chloride transformation, electroporation and transfection using bacteriophage.

In one embodiment, the nucleic acid of the invention is integrated into the genome (e.g. chromosome) of the host cell. Integration may be promoted by inclusion of sequences that promote recombination with the genome, in accordance with standard techniques.

Host Cells

A further aspect of the present invention provides a host cell containing nucleic acid as disclosed herein. Such a host cell may be in vitro and may be in culture.

The host cell can be from any species, such as a bacterium or yeast but suitably the host cell is an mammalian cell such as a human cell or rodent cell, for example a HEK293T cell or CHO-K1 cell.

Thus, according to a fourth aspect of the invention there is provided a host cell comprising the nucleic acid sequence according to the second aspect of the invention or the vector according to third aspect of the invention.

The host cell can be treated so as to cause or allow expression of the protein of the invention from the nucleic acid, e.g. by culturing host cells under conditions for expression of the encoding nucleic acid. The purification of the expressed product may be achieved by methods known to one of skill in the art.

Thus, the nucleic acids of the invention, including vector nucleic acids that comprise nucleotide sequences that encode the polypeptides capable of forming the antibodies of the invention or antigen-binding fragments thereof, may be present in an isolated host cell. The host cell is typically part of a clonal population of host cells. As used herein, reference to a host cell also encompasses a clonal population of said cell. A clonal population is one that has been grown from a single parent host cell. The host cell can be from any suitable organism. Suitable host cells include bacterial, fungal or mammalian cells.

The host cell may serve to assist in amplifying the vector nucleic acid (such as with a plasmid) or it may serve as the biological factory to express the polypeptide(s) of the invention that form the BTLA antibody or antigen-binding fragment thereof of the invention. A suitable host for amplifying the vector nucleic acid could be a bacterial or fungal cell, such as an *Escherichia coli* cell or *Saccharomyces cerevisiae* cell. A suitable host for expressing the proteins of the invention (i.e. the polypeptides making up the human BTLA-binding antibody or antigen-binding fragment thereof of the invention would be a mammalian cell such as a HEK293T or CHO-K1 cell. In a particular embodiment, the host cell is a mammalian cell, such as a HEK293T or CHO-K1 cell.

A variety of host-expression vector systems may be utilized to express a BTLA-binding molecule as described herein (see e.g. U.S. Pat. No. 5,807,715). For example, mammalian cells such as Chinese hamster ovary cells (CHO), in conjunction with a vector such as the major intermediate early gene promoter element from human cytomegalovirus is an effective expression system for CEA proteins (Foecking et al., Gene, 45:101 (1986); and Cockett et al., Bio/Technology, 8:2 (1990)). Different host cells have characteristic and specific mechanisms for the post-translational processing and modification of proteins and gene products. Appropriate cell lines or host systems can be chosen to ensure the correct modification and processing of the protein of the disclosure. To this end, eukaryotic host cells which possess the cellular machinery for proper processing of the primary transcript, glycosylation, and phosphorylation of the gene product may be used. Such mammalian host cells include but are not limited to CHO, HEK, VERY, BHK, Hela, COS, MDCK, 293, 3T3, W138, BT483, Hs578T, HTB2, BT2O and T47D, NS0, CRL7O3O and HsS78Bst cells.

Antibody Production

According to a fifth aspect of the invention there is provided a method of producing an antibody or an antigen-binding fragment thereof according to the first aspect of the invention, comprising the step of culturing the host cell of the fourth aspect of the invention under conditions for production of said an antibody or antigen-binding fragment thereof, and optionally isolating and/or purifying said antibody or antigen-binding fragment thereof.

According to a variation of the fifth aspect of the invention there is provided a method of producing an antibody or an antigen-binding fragment thereof that binds to human BTLA, comprising the step of culturing the host cell that comprises nucleic acid encoding the polypeptide(s) that form the antibody or the antigen-binding fragment thereof that binds to human BTLA under conditions for production of said antibody or antigen-binding fragment thereof, optionally further comprising isolating/purifying said antibody or antigen-binding fragment thereof.

By isolated/purified we mean that the antibody or antigen-binding fragment thereof of the invention, or polypeptides that make up these molecules, will be free or substantially free of material with which they are naturally associated, such as other proteins or nucleic acids with which they are found in their natural environment, or the environment in which they are prepared (e.g. cell culture) when such preparation is by recombinant DNA technology practised in vitro or in vivo.

According to a variation of the fifth of the invention there is provided a method for preparing an antibody or antigen-binding fragment thereof that specifically binds human BTLA, the method comprising the steps of:

a) providing a host cell comprising one or more nucleic acid molecules encoding the amino acid sequence of a heavy chain variable domain and a light chain variable domain which when expressed are capable of combining to create a human BTLA-binding molecule;

b) culturing the host cell expressing the encoded amino acid sequence; and c) isolating the antibody or antigen-binding fragment molecule.

The one or more nucleic acid molecules are those describe above that encode for polypeptides capable of forming an antibody or antigen-binding fragment thereof of the invention that specifically binds human BTLA.

In a particular embodiment, the antibody or antigen-binding fragment thereof comprises: i) a heavy chain variable region comprising three CDRs: CDRH1, CDRH2 and CDRH3, wherein CDRH1 has an amino acid sequence as set forth in SEQ ID NO: 1, CDRH2 has an amino acid sequence as set forth in SEQ ID NO: 2, and CDRH3 has an amino acid sequence as set forth in SEQ ID NO: 3; and ii) a light chain variable region comprising three CDRs: CDRL1, CDRL2 and CDRL3, wherein CDRL1 has an amino acid sequence as set forth in SEQ ID NO: 4, CDRL2 has an amino acid sequence as set forth in SEQ ID NO: 5, and CDRL3 has an amino acid sequence as set forth in SEQ ID NO: 6.

In a particular embodiment, the antibody or antigen-binding fragment thereof comprises: i) a heavy chain variable region comprising three CDRs: CDRH1, CDRH2 and CDRH3, wherein CDRH1 has an amino acid sequence as set forth in SEQ ID NO: 7, CDRH2 has an amino acid sequence as set forth in SEQ ID NO: 8, and CDRH3 has an amino acid sequence as set forth in SEQ ID NO: 9; and ii) a light chain variable region comprising three CDRs: CDRL1, CDRL2 and CDRL3, wherein CDRL1 has an amino acid sequence as set forth in SEQ ID NO: 10, CDRL2 has an amino acid sequence as set forth in SEQ ID NO: 11, and CDRL3 has an amino acid sequence as set forth in SEQ ID NO: 12.

In a particular embodiment, the antibody or antigen-binding fragment thereof comprises:

i) a heavy chain variable region comprising an amino acid sequence disclosed in SEQ ID NO: 13, or a sequence with at least 90% sequence identity thereto; and ii) a light chain variable region comprising an amino acid sequence disclosed in SEQ ID NO:14, or a sequence with at least 90% sequence identity thereto.

In various embodiments, the antibody or antigen-binding fragment thereof comprises a heavy chain and a light chain, wherein the heavy chain comprises a heavy chain variable region comprising three CDRs: CDRH1, CDRH2 and CDRH3, and the light chain comprises a light chain variable region comprising three CDRs: CDRL1, CDRL2 and CDRL3, wherein (1) CDRH1, CDRH2, CDRH3 have an amino acid sequence as set forth in SEQ ID NO: 31, SEQ ID NO: 32, and SEQ ID NO: 33, respectively, and CDRL1, CDRL2, and CDRL3 have an amino acid sequence as set forth in SEQ ID NO: 34, SEQ ID NO: 35, and SEQ ID NO: 36, respectively; (2) CDRH1, CDRH2, CDRH3 have an amino acid sequence as set forth in SEQ ID NO: 37, SEQ ID NO: 38, and SEQ ID NO: 39, respectively, and CDRL1, CDRL2, and CDRL3 have an amino acid sequence as set forth in SEQ ID NO: 40, SEQ ID NO: 41, and SEQ ID NO: 42, respectively; (3) CDRH1, CDRH2, CDRH3 have an amino acid sequence as set forth in SEQ ID NO: 43, SEQ ID NO: 44, and SEQ ID NO: 45, respectively, and CDRL1, CDRL2, and CDRL3 have an amino acid sequence as set forth in SEQ ID NO: 46, SEQ ID NO: 47, and SEQ ID NO:

48, respectively; (4) CDRH1, CDRH2, CDRH3 have an amino acid sequence as set forth in SEQ ID NO: 43, SEQ ID NO: 56, and SEQ ID NO: 57, respectively, and CDRL1, CDRL2, and CDRL3 have an amino acid sequence as set forth in SEQ ID NO: 58, SEQ ID NO: 59, and SEQ ID NO: 60, respectively; (5) CDRH1, CDRH2, CDRH3 have an amino acid sequence as set forth in SEQ ID NO: 61, SEQ ID NO: 62, and SEQ ID NO: 63, respectively, and CDRL1, CDRL2, and CDRL3 have an amino acid sequence as set forth in SEQ ID NO: 64, SEQ ID NO: 65, and SEQ ID NO: 66, respectively; (6) CDRH1, CDRH2, CDRH3 have an amino acid sequence as set forth in SEQ ID NO: 31, SEQ ID NO: 32, and SEQ ID NO: 69, respectively, and CDRL1, CDRL2, and CDRL3 have an amino acid sequence as set forth in SEQ ID NO: 34, SEQ ID NO: 35, and SEQ ID NO: 72, respectively; (7) CDRH1, CDRH2, CDRH3 have an amino acid sequence as set forth in SEQ ID NO: 73, SEQ ID NO: 74, and SEQ ID NO: 75, respectively, and CDRL1, CDRL2, and CDRL3 have an amino acid sequence as set forth in SEQ ID NO: 76, SEQ ID NO: 47, and SEQ ID NO: 78, respectively; (8) CDRH1, CDRH2, CDRH3 have an amino acid sequence as set forth in SEQ ID NO: 79, SEQ ID NO: 80, and SEQ ID NO: 81, respectively, and CDRL1, CDRL2, and CDRL3 have an amino acid sequence as set forth in SEQ ID NO: 82, SEQ ID NO: 83, and SEQ ID NO: 84, respectively; (9) CDRH1, CDRH2, CDRH3 have an amino acid sequence as set forth in SEQ ID NO: 85, SEQ ID NO: 86, and SEQ ID NO: 87, respectively, and CDRL1, CDRL2, and CDRL3 have an amino acid sequence as set forth in SEQ ID NO: 88, SEQ ID NO: 89, and SEQ ID NO: 90, respectively; (10) CDRH1, CDRH2, CDRH3 have an amino acid sequence as set forth in SEQ ID NO: 61, SEQ ID NO: 92, and SEQ ID NO: 93, respectively, and CDRL1, CDRL2, and CDRL3 have an amino acid sequence as set forth in SEQ ID NO: 94, SEQ ID NO: 95, and SEQ ID NO: 96, respectively; (11) CDRH1, CDRH2, CDRH3 have an amino acid sequence as set forth in SEQ ID NO: 97, SEQ ID NO: 98, and SEQ ID NO: 99, respectively, and CDRL1, CDRL2, and CDRL3 have an amino acid sequence as set forth in SEQ ID NO: 100, SEQ ID NO: 101, and SEQ ID NO: 102, respectively; (12) CDRH1, CDRH2, CDRH3 have an amino acid sequence as set forth in SEQ ID NO: 103, SEQ ID NO: 104, and SEQ ID NO: 105, respectively, and CDRL1, CDRL2, and CDRL3 have an amino acid sequence as set forth in SEQ ID NO: 64, SEQ ID NO: 107, and SEQ ID NO: 108, respectively; (13) CDRH1, CDRH2, CDRH3 have an amino acid sequence as set forth in SEQ ID NO: 109, SEQ ID NO: 110, and SEQ ID NO: 111, respectively, and CDRL1, CDRL2, and CDRL3 have an amino acid sequence as set forth in SEQ ID NO: 88, SEQ ID NO: 89, and SEQ ID NO: 114, respectively; (14) CDRH1, CDRH2, CDRH3 have an amino acid sequence as set forth in SEQ ID NO: 85, SEQ ID NO: 110, and SEQ ID NO: 117, respectively, and CDRL1, CDRL2, and CDRL3 have an amino acid sequence as set forth in SEQ ID NO: 88, SEQ ID NO: 89, and SEQ ID NO: 114, respectively; (15) CDRH1, CDRH2, CDRH3 have an amino acid sequence as set forth in SEQ ID NO: 121, SEQ ID NO: 122, and SEQ ID NO: 123, respectively, and CDRL1, CDRL2, and CDRL3 have an amino acid sequence as set forth in SEQ ID NO: 124, SEQ ID NO: 125, and SEQ ID NO: 126, respectively; (16) CDRH1, CDRH2, CDRH3 have an amino acid sequence as set forth in SEQ ID NO: 127, SEQ ID NO: 128, and SEQ ID NO: 129, respectively, and CDRL1, CDRL2, and CDRL3 have an amino acid sequence as set forth in SEQ ID NO: 34, SEQ ID NO: 35, and SEQ ID NO: 36, respectively; (17) CDRH1, CDRH2, CDRH3 have an amino acid sequence as set forth in SEQ ID NO: 133, SEQ ID NO: 134, and SEQ ID NO: 135, respectively, and CDRL1, CDRL2, and CDRL3 have an amino acid sequence as set forth in SEQ ID NO: 136, SEQ ID NO: 137, and SEQ ID NO: 138, respectively; (18) CDRH1, CDRH2, CDRH3 have an amino acid sequence as set forth in SEQ ID NO: 139, SEQ ID NO: 140, and SEQ ID NO: 141, respectively, and CDRL1, CDRL2, and CDRL3 have an amino acid sequence as set forth in SEQ ID NO: 142, SEQ ID NO: 143, and SEQ ID NO: 144, respectively; (19) CDRH1, CDRH2, CDRH3 have an amino acid sequence as set forth in SEQ ID NO: 145, SEQ ID NO: 146, and SEQ ID NO: 147, respectively, and CDRL1, CDRL2, and CDRL3 have an amino acid sequence as set forth in SEQ ID NO: 148, SEQ ID NO: 149, and SEQ ID NO: 150, respectively; (20) CDRH1, CDRH2, CDRH3 have an amino acid sequence as set forth in SEQ ID NO: 31, SEQ ID NO: 32, and SEQ ID NO: 33, respectively, and CDRL1, CDRL2, and CDRL3 have an amino acid sequence as set forth in SEQ ID NO: 148, SEQ ID NO: 149, and SEQ ID NO: 150, respectively; (21) CDRH1, CDRH2, CDRH3 have an amino acid sequence as set forth in SEQ ID NO: 31, SEQ ID NO: 32, and SEQ ID NO: 159, respectively, and CDRL1, CDRL2, and CDRL3 have an amino acid sequence as set forth in SEQ ID NO: 136, SEQ ID NO: 137, and SEQ ID NO: 162, respectively; (22) CDRH1, CDRH2, CDRH3 have an amino acid sequence as set forth in SEQ ID NO: 169, SEQ ID NO: 170, and SEQ ID NO: 171, respectively, and CDRL1, CDRL2, and CDRL3 have an amino acid sequence as set forth in SEQ ID NO: 172, SEQ ID NO: 173, and SEQ ID NO: 174, respectively; (23) CDRH1, CDRH2, CDRH3 have an amino acid sequence as set forth in SEQ ID NO: 61, SEQ ID NO: 62, and SEQ ID NO: 63, respectively, and CDRL1, CDRL2, and CDRL3 have an amino acid sequence as set forth in SEQ ID NO: 64, SEQ ID NO: 65, and SEQ ID NO: 180, respectively; (24) CDRH1, CDRH2, CDRH3 have an amino acid sequence as set forth in SEQ ID NO: 31, SEQ ID NO: 182, and SEQ ID NO: 183, respectively, and CDRL1, CDRL2, and CDRL3 have an amino acid sequence as set forth in SEQ ID NO: 136, SEQ ID NO: 137, and SEQ ID NO: 186, respectively; (25) CDRH1, CDRH2, CDRH3 have an amino acid sequence as set forth in SEQ ID NO: 187, SEQ ID NO: 188, and SEQ ID NO: 189, respectively, and CDRL1, CDRL2, and CDRL3 have an amino acid sequence as set forth in SEQ ID NO: 190, SEQ ID NO: 191, and SEQ ID NO: 192, respectively; (26) CDRH1, CDRH2, CDRH3 have an amino acid sequence as set forth in SEQ ID NO: 193, SEQ ID NO: 194, and SEQ ID NO: 195, respectively, and CDRL1, CDRL2, and CDRL3 have an amino acid sequence as set forth in SEQ ID NO: 196, SEQ ID NO: 197, and SEQ ID NO: 12, respectively; (27) CDRH1, CDRH2, CDRH3 have an amino acid sequence as set forth in SEQ ID NO: 199, SEQ ID NO: 200, and SEQ ID NO: 201, respectively, and CDRL1, CDRL2, and CDRL3 have an amino acid sequence as set forth in SEQ ID NO: 202, SEQ ID NO: 203, and SEQ ID NO: 6, respectively; (28) CDRH1, CDRH2, CDRH3 have an amino acid sequence as set forth in SEQ ID NO: 205, SEQ ID NO: 206, and SEQ ID NO: 207, respectively, and CDRL1, CDRL2, and CDRL3 have an amino acid sequence as set forth in SEQ ID NO: 142, SEQ ID NO: 209, and SEQ ID NO: 210, respectively; (29) CDRH1, CDRH2, CDRH3 have an amino acid sequence as set forth in SEQ ID NO: 211, SEQ ID NO: 212, and SEQ ID NO: 213, respectively, and CDRL1, CDRL2, and CDRL3 have an amino acid sequence as set forth in SEQ ID NO: 214, SEQ ID NO: 35, and SEQ ID NO: 216, respectively; (30) CDRH1, CDRH2, CDRH3 have an amino acid sequence as set forth in SEQ ID NO: 127, SEQ ID NO:

386, and SEQ ID NO: 129, respectively, and CDRL1, CDRL2, and CDRL3 have an amino acid sequence as set forth in SEQ ID NO: 34, SEQ ID NO: 35, and SEQ ID NO: 36, respectively; (31) CDRH1, CDRH2, CDRH3 have an amino acid sequence as set forth in SEQ ID NO: 205, SEQ ID NO: 206, and SEQ ID NO: 207, respectively, and CDRL1, CDRL2, and CDRL3 have an amino acid sequence as set forth in SEQ ID NO: 142, SEQ ID NO: 209, and SEQ ID NO: 210, respectively; (32) CDRH1, CDRH2, CDRH3 have an amino acid sequence as set forth in SEQ ID NO: 127, SEQ ID NO: 388, and SEQ ID NO: 129, respectively, and CDRL1, CDRL2, and CDRL3 have an amino acid sequence as set forth in SEQ ID NO: 34, SEQ ID NO: 35, and SEQ ID NO: 36, respectively; (33) CDRH1, CDRH2, CDRH3 have an amino acid sequence as set forth in SEQ ID NO: 205, SEQ ID NO: 387, and SEQ ID NO: 207, respectively, and CDRL1, CDRL2, and CDRL3 have an amino acid sequence as set forth in SEQ ID NO: 142, SEQ ID NO: 209, and SEQ ID NO: 210, respectively; or (34) CDRH1, CDRH2, CDRH3 have an amino acid sequence as set forth in SEQ ID NO: 205, SEQ ID NO: 387, and SEQ ID NO: 207, respectively, and CDRL1, CDRL2, and CDRL3 have an amino acid sequence as set forth in SEQ ID NO: 142, SEQ ID NO: 143, and SEQ ID NO: 210, respectively; wherein from 0 to 3 amino acid modifications can be present in any CDR/SEQ ID NO:

Conditions for the production of the antibody or an antigen-binding fragment thereof of the invention and purification of said molecules are well-known in the art.

One way of attending to this is to prepare a clonal population of cells capable of expressing the antibody or fragment thereof of the invention and culturing these in a suitable growth medium for a period of time and at a temperature conducive to allow for expansion/growth of the cell population and expression of the protein(s) of interest. If the protein(s) of interest (e.g. antibody of invention) is expressed within the host cells then the cells may be lysed (e.g. using a mild detergent or sonication) to release the contents of the cell (and thus the protein of interest) into the surrounding medium (which could be the culture medium or another medium that the cells have been reconstituted in) and this medium is then subjected to purification processes. If the protein(s) of interest (e.g. antibody of invention) is secreted into the growth medium, then the medium is subjected to purification processes. Antibody purification typically involves isolation of antibody from, for example the medium or from the culture supernatant of a hybridoma cell line using well-established methods typically involving chromatography (e.g., using affinity chromatography, anionic and/or cationic exchange chromatography, size-exclusion chromatography or other separation techniques) to separate the protein of interest from unwanted host-derived proteins and other cellular contaminants (e.g. nucleic acids, carbohydrates etc.).

The purified proteins may also be subjected to a virus inactivation step. Finally, the purified protein of interest may, for example, be lyophilised or formulated ready for storage, shipment and subsequent use. Preferably the protein of interest (e.g. antibody or antigen-binding fragment thereof of the invention) will be substantially free from contaminating proteins which were originally present in the culture medium following expression or cell-lysis.

In certain embodiments, the antibody or antigen-binding fragment thereof of the invention will be at least 90%, at least 95%, at least 96%, at least 97%, at least 98% or at least 99% pure.

The proteins of the invention (antibody or antigen-binding fragment thereof of the invention) can be formulated into a suitable composition.

Compositions

While the BTLA-binding molecule may be administered alone, in certain embodiments administration is of a pharmaceutical composition wherein the BTLA-binding molecule is formulated with at least one pharmaceutically-acceptable excipient. The excipient may be a suitable pharmaceutical carrier solute. Such carriers are well known in the art and include phosphate buffered saline solutions, water, liposomes, various types of wetting agents, sterile solutions, etc. Compositions comprising such carriers can be formulated by well-known conventional methods. These pharmaceutical compositions can be administered to the subject at a suitable dose. The dosage regimen will be determined by the attending physician and clinical factors.

According to a sixth aspect of the invention there is provided a pharmaceutical composition comprising a pharmaceutically acceptable excipient and a therapeutically effective amount of the antibody or antigen-binding fragment thereof of the first aspect of the invention, or that produced by the fifth aspect of the invention. In a particular embodiment, the composition comprises phosphate buffered saline.

A "pharmaceutical composition" refers to a preparation which is in such form as to permit the biological activity of the active ingredient to be effective, and which contains no additional components which are unacceptably toxic to a subject to which the formulation would be administered. The pharmaceutical composition will include one or more pharmaceutically acceptable excipients. The term excipient in this context refers to any additive, such as fillers, solubilisers, carriers, vehicles, additives and the like.

The pharmaceutical compositions can comprise one or more pharmaceutically acceptable excipients, including, e.g., water, ion exchangers, proteins, buffer substances, and salts. Preservatives and other additives can also be present. The excipient can be a solvent or dispersion medium. Suitable formulations for use in therapeutic methods disclosed herein are described in Remington's Pharmaceutical Sciences 16th edition, Osol, A. Ed. (1980).

"Pharmaceutically acceptable" excipients are those which can reasonably be administered to a subject mammal to provide an effective dose of the active ingredient employed. Pharmaceutical compositions of the invention are prepared for storage by mixing the composition with optional pharmaceutically acceptable carriers, excipients or stabilizers (Remington's Pharmaceutical Sciences 16th edition, Osol, A. Ed. (1980)), in the form of lyophilized formulations or aqueous solutions. Acceptable excipients are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG). Lyophilized HER2 antibody formulations are described in WO 97/04801.

The pharmaceutical compositions to be used for in vivo administration must be sterile. This can be readily accomplished by filtration through sterile filtration membranes.

The route of administration of the BTLA binding moiety molecule, e.g., an antibody, or antigen-binding fragment thereof can be, for example, oral, parenteral, by inhalation or topical. The term parenteral as used herein includes, e.g., intravenous, intraarterial, intraperitoneal, intramuscular, subcutaneous, rectal, or vaginal administration.

Pharmaceutical compositions for parenteral administration include sterile aqueous or non-aqueous solutions, and suspensions. Examples of non-aqueous solvents are propylene glycol, polyethylene glycol, and injectable organic esters such as ethyl oleate. Aqueous carriers include water, aqueous solutions, or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like. In addition, the composition might comprise proteinaceous carriers, like, e.g., serum albumin or immunoglobulin, in certain embodiments of human origin. For intravenous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required. As noted above, these are all referred to herein as excipients.

Compositions for injection can be administered with medical devices known in the art. For example, with a hypodermic needle. Needleless injection devices, such as those disclosed in U.S. Pat. Nos. 6,620,135 and 5,312,335 could also be utilised.

Pharmaceutical compositions for oral administration may be in tablet, capsule, powder, liquid or semi-solid form. A tablet may comprise a solid carrier such as gelatin or an adjuvant. Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included as required.

An antibody or antigen-binding fragment thereof of the present invention may be formulated in liquid, semi-solid or solid forms depending on the physicochemical properties of the molecule and the route of delivery. Formulations may include excipients, or combinations of excipients, for example: sugars, amino acids and surfactants. Liquid formulations may include a wide range of antibody concentrations and pH. Solid formulations may be produced by lyophilisation, spray drying, or drying by supercritical fluid technology, for example.

The pharmaceutical composition can be administered as a single dose, multiple doses or over an established period of time in an infusion. Dosage regimens also can be adjusted to provide the optimum desired response (e.g., a therapeutic or prophylactic response). In particular, parenteral formulations can be a single bolus dose, an infusion or a loading bolus dose followed with one or more maintenance doses. These compositions can be administered at specific fixed or variable intervals, e.g., once a day, or on an "as needed" basis.

Dosages

The amount of the BTLA-binding molecule, or the pharmaceutical formulation containing such molecule, which will be therapeutically effective can be determined by standard clinical techniques, such as through dose ranging clinical trials. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses may be extrapolated from dose-response curves derived from in vitro or animal model test systems. The dosage of the compositions to be administered can be determined by the skilled artisan without undue experimentation in conjunction with standard dose-response studies. Relevant circumstances to be considered in making those determinations include the condition or conditions to be treated, the choice of composition to be administered, the age, weight, and response of the individual patient, and the severity of the patient's symptoms. For example, the actual patient body weight may be used to calculate the dose of the formulations in milliliters (mL) to be administered. There may be no downward adjustment to "ideal" weight. In such a situation, an appropriate dose may be calculated by the following formula:

$$\text{Dose(ml.)} = [\text{patient weight (kg)} \times \text{dose level (mg/kg)} / \text{drug concentration (mg/mL)}]$$

Therapeutically effective doses of the pharmaceutical compositions for the treatment of BTLA-related diseases or disorders, as discussed herein, will vary depending upon many different factors, including means of administration, target site, physiological state of the patient, weight or patient, sex of patient, age of patient, whether the patient is human or an animal, other medications administered, and whether treatment is prophylactic or therapeutic. The therapeutically effective dose is likely to have been determined from clinical trials and is something that the attending physician can determine using treatment guidelines. Usually, the patient is a human, but non-human mammals can also be treated. Treatment dosages can be titrated using routine methods known to those of skill in the art to optimize safety and efficacy.

In various embodiments, the BTLA-binding molecule is administered at a concentration of about 1 mg/kg, about 2 mg/kg, about 3 mg/kg, about 4 mg/kg, about 5 mg/kg, about 6 mg/kg, about 7 mg/kg, about 8 mg/kg, about 9 mg/kg, about 10 mg/kg, about 11 mg/kg, about 12 mg/kg, about 13 mg/kg, about 14 mg/kg, about 15 mg/kg, about 16 mg/kg, about 17 mg/kg, about 18 mg/kg, about 19 mg/kg, or about 20 mg/kg.

A pharmaceutical composition of the invention may be administered alone or in combination with other treatments, either simultaneously or sequentially dependent upon the condition to be treated. Such combination would likely be with other immunosuppressives such as one selected from: corticosteroids, cyclosporine, azathioprine, sulfasalazine, methotrexate, mycophenolate, tacrolimus and fingolimod, or other biologics such as infliximab, adalimumab, ustekinumab, tocilizumab and rituximab.

According to a seventh aspect of the invention there is provided a method of preparing a pharmaceutical composition, the method comprising formulating an antibody or an antigen-binding fragment thereof in accordance with the first aspect of the invention, or one produced in accordance with the fifth aspect of the invention into a composition including at least one additional component. In a particular embodiment, the at least one additional component is a pharmaceutically acceptable excipient.

Kits

Further, the product (e.g. BTLA binding molecule or a pharmaceutical composition thereof) can be packaged and sold in the form of a kit. Such articles of manufacture can have labels or package inserts indicating instructions about the product and the appropriate use of the product for the treatment of a subject suffering from or predisposed to a disease or disorder.

Thus, according to one aspect of the invention there is provided a kit comprising an antibody or antigen-binding fragment thereof in accordance with the first aspect of the invention or the pharmaceutical composition in accordance with the sixth aspect of the invention. Suitably, such a kit includes a package insert comprising instructions for use.

Therapy/Medical Uses

An antibody or antigen-binding fragment thereof of the invention or a pharmaceutical composition comprising said antibody or antigen-binding fragment thereof may be used in therapy, typically as a medicament.

In certain embodiments, an antibody or antigen-binding fragment thereof of the invention or a pharmaceutical composition comprising said antibody or antigen-binding fragment thereof may be used for treating or preventing any disease or condition in a subject in need thereof.

BTLA is involved in down-regulating immune responses and there are many diseases or conditions that could be treated by suppressing host T-cells and/or B-cells (e.g. see Crawford & Wherry. Editorial: Therapeutic potential of targeting BTLA. J Leukocyte Biol. 86:5-8, 2009). Diseases or conditions that could benefit from treatment with an anti-BTLA agonist are referred to herein as "BTLA-related diseases". BTLA-related diseases include inflammatory or autoimmune diseases, and disorders of excessive immune cell proliferation.

Specific BTLA-related diseases that can be treated with the BTLA-binding molecules of the invention include: Addison's disease, allergy, alopecia areata, amyotrophic lateral sclerosis, ankylosing spondylitis, anti-phospholipid syndrome, asthma (including allergic asthma), autoimmune haemolytic anaemia, autoimmune hepatitis, autoimmune pancreatitis, autoimmune polyendocrine syndrome, Behcet's disease, bullous pemphigoid, cerebral malaria, chronic inflammatory demyelinating polyneuropathy, coeliac disease, Crohn's disease, Cushing's Syndrome, dermatomyositis, diabetes mellitus type 1, eosinophilic granulomatosis with polyangiitis, graft versus host disease, Graves' disease, Guillain-Barre syndrome, Hashimoto's thyroiditis, Hidradenitis Suppurativa, inflammatory fibrosis (e.g., scleroderma, lung fibrosis, and cirrhosis), juvenile arthritis, Kawasaki disease, leukemia, lymphoma, lymphoproliferative disorders, multiple sclerosis, myasthenia gravis, myeloma, neuromyelitis optica, pemphigus, polymyositis, primary biliary cholangitis, primary sclerosing cholangitis, psoriasis, psoriatic arthritis, rheumatoid arthritis, sarcoidosis, Sjögren's syndrome, systemic lupus erythematosus, Takayasu's arteritis, temporal arteritis, transplant rejection, transverse myelitis, ulcerative colitis, uveitis, vasculitis, vitiligo and Vogt-Koyanagi-Harada Disease.

According to an eighth aspect of the invention there is provided an antibody or antigen-binding fragment thereof in accordance with the first aspect of the invention or the pharmaceutical composition in accordance with the sixth aspect of the invention for use in therapy.

In a particular embodiment, the therapy is treatment or prevention of a BTLA-related disease.

In a particular embodiment, the BTLA-related disease is one caused by decreased expression and/or activity of BTLA in a subject. In particular, any disease or disorder characterised by the presence or activity of T or B cells can be treated with a BTLA agonist antibody or antigen-binding fragment of the invention.

In one embodiment, the BTLA-related disease is an inflammatory disease (such as rheumatoid arthritis), an autoimmune disease or disorder (such as graft versus host) or a proliferative disease or disorder (such as cancer).

In a particular embodiment, the therapy is treatment or prevention of inflammatory or autoimmune diseases, and disorders of excessive immune cell proliferation.

According to a variation of the eighth aspect of the invention there is provided a method of treating a patient in need thereof, comprising administering to the patient an antibody or antigen-binding fragment thereof in accordance with the first aspect of the invention or the pharmaceutical composition in accordance with the sixth aspect of the invention. In a particular embodiment the patient in need of treatment, or to be treated, has (or is suffering from) a BTLA-related disease. In a particular embodiment, the patient in need of treatment, or to be treated, has (or is suffering from) an inflammatory disease, an autoimmune disease, or a disorder of excessive immune cell proliferation.

In a particular embodiment, the antibody or antigen-binding fragment thereof in accordance with the first aspect of the invention or the pharmaceutical composition in accordance with the sixth aspect of the invention is administered to a patient in need thereof in a pharmaceutically acceptable amount.

In a variation of this aspect there is provided an antibody or antigen-binding fragment thereof in accordance with the first aspect of the invention or the pharmaceutical composition in accordance with the sixth aspect of the invention for use in a method of treating a patient in need thereof. In a particular embodiment, the method is for treating or preventing a BTLA-related disease. In particular embodiments, the method is for treating or preventing inflammatory or autoimmune diseases, and disorders of excessive immune cell proliferation.

In a further variation of this aspect there is provided use of an antibody or antigen-binding fragment thereof in accordance with the first aspect of the invention or the pharmaceutical composition in accordance with the sixth aspect of the invention in the manufacture of a medicament for the treatment of a patient in need thereof.

In one embodiment, the therapy is for treating a BTLA-related disease. Suitably, the BTLA-related disease is an inflammatory disease (such as asthma), an autoimmune disease or disorder (such as rheumatoid arthritis) or an immunoproliferative disease or disorder (such as lymphoma).

In particular embodiments, the antibody or antigen-binding fragment thereof of the invention or a pharmaceutical composition comprising said antibody or antigen-binding fragment thereof is used to suppress T-cells and/or B-cells.

In particular embodiments, the antibody or antigen-binding fragment thereof of the invention or a pharmaceutical composition comprising said antibody or antigen-binding fragment thereof is used for treating or preventing a disease or condition in a subject in need thereof selected from the group consisting of: Addison's disease, allergy, alopecia areata, amyotrophic lateral sclerosis, ankylosing spondylitis, anti-phospholipid syndrome, asthma (including allergic asthma), autoimmune haemolytic anaemia, autoimmune hepatitis, autoimmune pancreatitis, autoimmune polyendocrine syndrome, Behcet's disease, bullous pemphigoid, cerebral malaria, chronic inflammatory demyelinating polyneuropathy, coeliac disease, Crohn's disease, Cushing's Syndrome, dermatomyositis, diabetes mellitus type 1, eosinophilic granulomatosis with polyangiitis, graft versus host disease (GVHD), Graves' disease, Guillain-Barre syndrome, Hashimoto's thyroiditis, Hidradenitis Suppurativa, inflammatory fibrosis (e.g., scleroderma, lung fibrosis, and cirrhosis), juvenile arthritis, Kawasaki disease, leukemia, lymphoma, lymphoproliferative disorders, multiple sclerosis (MS), myasthenia gravis, myeloma, neuromyelitis optica, pemphigus, polymyositis, primary biliary cholangitis, primary sclerosing cholangitis, psoriasis, psoriatic arthritis, rheumatoid arthritis, sarcoidosis, Sjögren's syndrome, systemic lupus erythematosus, Takayasu's arteritis, temporal arteritis, transplant rejection, transverse myelitis, ulcerative colitis, uveitis, vasculitis, vitiligo and Vogt-Koyanagi-Harada Disease.

In particular embodiments, the antibody or antigen-binding fragment thereof of the invention or a pharmaceutical composition comprising said antibody or antigen-binding fragment thereof is used for treating or preventing a disease or condition in a subject in need thereof selected from the group consisting of: GVHD, colitis, rheumatoid arthritis, psoriasis and MS. In one embodiment, the immunoproliferative disease is cancer. Suitably the cancer is a leukemia or a lymphoma.

In another embodiment, the antibody or antigen-binding fragment thereof of the invention or a pharmaceutical composition comprising said antibody or antigen-binding fragment thereof is for use in the prevention or treatment of transplant rejection.

In another embodiment, the invention relates to the prevention or treatment of graft versus host disease.

In another embodiment, the antibody or antigen-binding fragment thereof of the invention or a pharmaceutical composition comprising said antibody or antigen-binding fragment thereof is for use in the treatment of rheumatoid arthritis.

In other embodiments, the antibody or antigen-binding fragment thereof of the invention or a pharmaceutical composition comprising said antibody or antigen-binding fragment thereof is for use in the treatment of diabetes, such as type 1 diabetes.

In another embodiment, the antibody or antigen-binding fragment thereof of the invention or a pharmaceutical composition comprising said antibody or antigen-binding fragment thereof is for use in the treatment of psoriasis.

In another embodiment, the antibody or antigen-binding fragment thereof of the invention or a pharmaceutical composition comprising said antibody or antigen-binding fragment thereof is for use in the treatment of multiple sclerosis.

In another embodiment, the antibody or antigen-binding fragment thereof of the invention or a pharmaceutical composition comprising said antibody or antigen-binding fragment thereof is for use in the treatment of colitis.

The term "effective amount" or "therapeutically effective amount" refers to a dosage or an amount of a drug that is sufficient to ameliorate the symptoms in a patient or to achieve a desired biological outcome, e.g., with cancer, an increased death of tumour cells, reduced tumour size, increased progression free survival or overall survival etc. As disclosed elsewhere herein, the effective amount will typically be assessed through extensive human clinical studies.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

The invention will now be further described with reference to the following non-limiting Examples and accompanying Figures.

Figure 1:
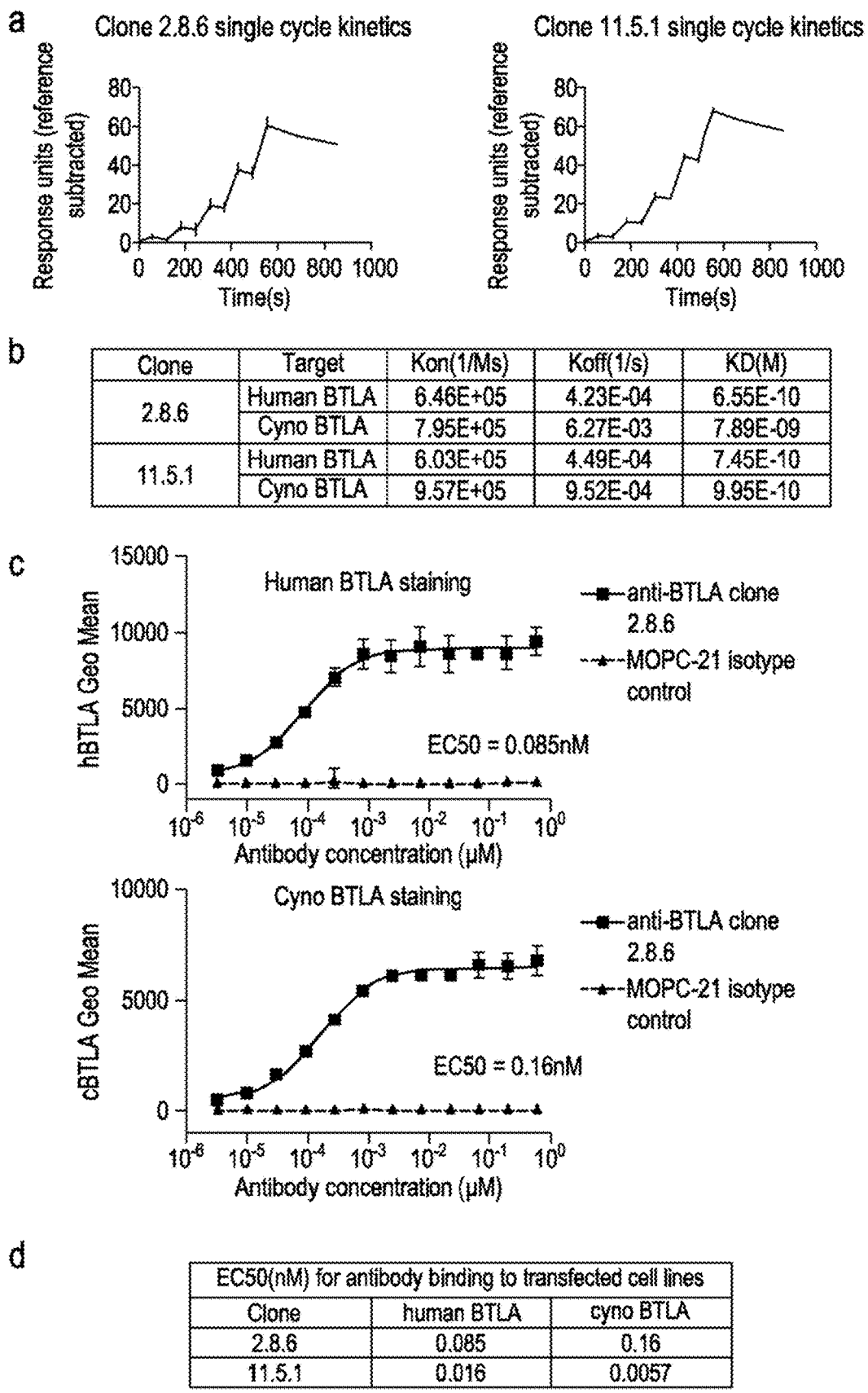
FIG. 1

Binding of antibodies to human and cynomolgus BTLA in soluble and cell expressed forms. (a) Surface plasmon resonance (SPR) binding curves for soluble monomeric human BTLA extracellular domain injected at increasing concentrations over immobilized anti-BTLA antibody; graphs show SPR signal after reference and blank subtraction. (b) Association and dissociation rates for binding to human or cynomolgus BTLA as calculated by curve fitting using BiaEvaluation software. (c) Binding of antibody 2.8.6, compared to isotype control antibody, to a human BTLA or cynomolgus BTLA expressing Jurkat cell line. (d) EC50s for antibody binding to transfected cell lines, as calculated by non-linear curve fitting using GraphPad Prism software

FIG. 2

(a) Blockade of ligand binding by anti-BTLA antibodies was assessed by SPR. Human BTLA extracellular domain was immobilized on the sensor chip. Human HVEM was injected to confirm binding, then allowed to fully dissociate.

A saturating concentration of anti-BTLA antibody was then injected, followed immediately by a second injection of HVEM. (b) Equilibrium binding of HVEM after injection of antibody was expressed as a percent of HVEM binding prior to antibody injection. Saturation of BTLA with clone 11.5.1, but not with clone 2.8.6, blocked subsequent binding of ligand.

FIG. 3

Epitope mapping of anti-BTLA antibodies. (a) HEK293T cells transfected with BTLA constructs in a bicistronic vector also expressing GFP were stained with Pacific Blue conjugated anti-BTLA antibody. Clone 11.5.1 binds to cells transfected with wild-type receptor (left) but not to cells transfected with BTLA having a Y39R mutation (right). (b) Binding to each BTLA mutant construct was expressed as a percentage of binding to wild-type BTLA for clones 2.8.6 and 11.5.1. (c) Mutations Y39R and K41E which selectively eliminate binding of clone 11.5.1 were mapped onto the crystal structure of human BTLA (black residues). Residues critical for binding of the ligand HVEM are highlighted in grey.

FIG. 4

(a) The crystal structure of human BTLA extracellular domain in complex with the Fab' fragment of clone 2.8.6. Residues on BTLA which are buried at the interface are highlighted in black. (b) The epitope of antibody 2.8.6 is shown (black residues) in relation to the HVEM binding site (grey residues).

FIG. 5

(a) Strategy for creation of a chimeric BTLA gene in humanised-BTLA mice. A section of human genomic DNA from the beginning of exon 2 to the end of exon 3 was inserted into the mouse locus replacing the mouse sequence from the beginning of exon 2 to the end of exon 4. The sequences at the exon-intron junction at the beginning of mouse exon 2 and end of mouse exon 4 were left intact to ensure proper splicing.

FIG. 6

(a) Protocol for T cell transfer assay to assess anti-BTLA antibodies in vivo. A mixture of humanised and wild-type OVA specific CD4 T cells was injected into recipient mice. The next day mice were immunised with ovalbumin in Alum to activate the transferred cells and 24 hours later were dosed with anti-human-BTLA antibody or isotype control. Eight days after initial cell transfer the ratio of humanised to wild-type cells in the transferred population in the spleen was assessed by flow cytometry. (b) Clone 11.5.1 and to a lesser extent 2.8.6 both reduced expansion of the humanised cells relative to the wild-type. Graph shows pooled data from two (for 11.5.1) or three (for 2.8.6) repeat experiments.

FIG. 7

Effect of anti-BTLA clone 2.8.6 on CD4 T-cell proliferation in a mixed lymphocyte reaction in vitro. T cells from humanised C57BL/6 mice were stained with CellTraceViolet and added to Mitomycin C treated Balb/c stimulator cells in the presence of anti-BTLA antibody or isotype control. After 96 hours, proliferation of humanised CD4 cells was assessed and normalised to proliferation in the absence of antibody. Clone 2.8.6 inhibited proliferation of humanised cells with an IC50 of 0.029 nM and had a maximal effect of 42% inhibition of proliferation.

FIG. 8

(a) Effect of clone 2.8.6 in a T cell colitis model. RAG knockout recipient mice were injected with CD45RBhiCD25-CD4+ T cells from humanised BTLA mice and treated with 200 μg 2.8.6 or isotype control antibody on days 7, 21 and 35. Isotype control treated mice progressively lost weight from 3 weeks onwards, whilst 2.8.6 treated mice were spared. (b) 8 weeks after cell transfer colons were processed to extract lamina propria lymphocytes and the total number of inflammatory cells extracted per colon was calculated. Isotype control treated mice had significantly more infiltrating immune cells than 2.8.6 treated mice. (c) Colon weight to length ratios were calculated as a marker of inflammation and thickening. 2.8.6 treatment prevented the increase in weight to length ratio seen in isotype control treated mice.

FIG. 9

(a) Effect of BTLA antibodies in a parent-to-Ft model of GVHD. C57BL/6 splenocytes and bone marrow cells from humanised-BTLA mice were injected into CB6F1 recipient mice, which were then treated with anti-BTLA antibody or isotype control. Untreated mice developed clinical GVHD with progressive weight loss, dermatitis and diarrhea and were culled when they reached pre-specified humane endpoints. 2.8.6 and 11.5.1 antibody treated mice were relatively spared, with survival comparable to control mice reconstituted with syngeneic cells. (b) 5 weeks after cell transfer mice were culled and colon weight to length ratio was calculated as a marker of gut inflammation. 2.8.6 and 11.5.1 treatment prevented the colon thickening seen in untreated mice.

FIG. 10

(a) Effect of D265A mutated clone 11.5.1 in a T cell transfer assay in vivo. This mutated antibody, which does not bind Fc receptors, no longer inhibited proliferation of humanised BTLA cells, instead lead to enhanced proliferation due to receptor blockade. (b) The D265A mutated 11.5.1 antibody no longer inhibited T cell proliferation in a mixed lymphocyte reaction.

FIG. 11

Anti-BTLA antibodies do not fix complement. Splenocytes from humanised BTLA mice were incubated with 10% rabbit complement for 1 hour at 37° C. in the presence of 20 μg/ml BTLA antibody, isotype control or positive control (a depleting CD20 antibody). Anti-CD20 antibody depleted the majority of B cells confirming the activity of the rabbit complement, but BTLA antibodies did not deplete either B or T cells, even though both these populations stain positive for BTLA.

FIG. 12

Anti-BTLA antibodies do not cause antibody-dependent-cell-mediated cytotoxicity. Splenocytes from humanised BTLA mice were incubated for 24 hours at 37° C. in the presence of 20 μg/ml BTLA antibody, isotype control or positive control (a depleting CD20 antibody). Anti-CD20 antibody depleted the majority of B cells by inducing ADCC by effector cells in the mixture, but BTLA antibodies did not deplete either B or T cells, even though both these populations stain positive for BTLA.

FIG. 13

Anti-BTLA antibodies do not deplete B or T cells in vivo. Humanised BTLA mice were injected with 200 μg of 2.8.6 antibody. At 24 hours spleens and bone marrow were collected and cell populations assessed by flow cytometry. 2.8.6 did not deplete B or T cells in the spleen or affect the frequency of different B cell precursor populations in the bone marrow.

FIG. 14

BTLA expression levels on B cells or CD4+ T cells from humanised mice following 6 days of in vivo incubation with antibodies 2.8.6 or 11.5.1, compared to BTLA expression on cells from mice injected with isotype control antibody.

EXAMPLES

In the examples that follow it is shown that antibodies 11.5.1 and 2.8.6 bind to human BTLA with high affinity. Using transgenic mice expressing the human receptor it is shown that, following binding to BTLA, these antibodies inhibit T cell responses in vitro and in vivo and are able to ameliorate disease in murine models of inflammatory bowel disease and graft-versus-host disease. Whilst these agonist effects are dependent on Fc-receptor binding, the antibodies do not cause depletion of BTLA expressing cells via cytotoxicity and do not induce receptor down-modulation.

Example 1. Generation and Sequencing of Anti-BTLA Antibodies

Antibodies recognizing the human immune cell receptor BTLA were generated by BioGenes GmbH via immunizing mice with the extracellular region of human BTLA (BTLA$^{K31-R151}$). Splenocytes from immunized mice were fused with Sp2/0-Ag14 myeloma cells and resulting hybridomas selected for reactivity with human BTLA by ELISA of supernatants, in conjunction with dilution cloning. Antibodies were isotyped from hybridoma supernatant using a Rapid Mouse Isotyping Kit (RayBiotech). The antibodies produced by clones 2.8.6 and 11.5.1 were both found to be IgG1k.

To sequence the immunoglobulin variable domains, RNA was extracted from hybridomas using TRIzol Reagent (ThermoFisher) as per the manufacturer's instructions. RNA was reverse transcribed to produce cDNA using primers specific for the first constant domain of the heavy chain or for the constant domain of the light chain, and Super Script II Reverse Transcriptase (Invitrogen) as per manufacturer's instructions.

PCR was then performed using primers targeting conserved regions of the immunoglobulin locus as previously described (Tiller et al., J Immunol Methods. 350:183-193, 2009) and PCR products were sequenced. In some cases identification of functional light chain was complicated by abundant non-functional kappa light chain cDNA from the fusion myeloma cell line, and to resolve this a previously described technique was employed, adding excess primer specific for the non-functional chain CDR3 to force truncation of the aberrant chain product (Yuan et al. J Immunol Methods. 294:39553-61, 2005).

Variable domain sequences were assessed using the NCBI IgBlast tool to determine the location of the CDRs.

Example 2. Binding to Soluble Human and Cynomolgus BTLA

The binding affinity and kinetics of the BTLA agonist antibodies of the present invention (2.8.6 and 11.5.1) to human or cynomolgus BTLA were determined by surface plasmon resonance using the Biacore T200 (GE Healthcare). Mouse antibody capture kit (GE Healthcare) was used to coat a Series S CM5 Sensor Chip (GE Healthcare) with polyclonal anti-mouse IgG. Anti-BTLA antibody was then captured onto the biosensor surface and a negative control antibody (clone Mopc21; Biolegend) captured in the reference channel. Various concentrations of monomeric soluble human BTLA extracellular domain (BTLA$^{K31-R151}$) (from SEQ ID NO: 23) or soluble cynomolgus macaque BTLA extracellular domain (BTLA$^{K31-R151}$) (from SEQ ID NO: 24) were then injected over the immobilized antibodies in the buffer 10 mM Hepes, 150 mM NaCl, 0.005% v/v Surfactant P20, pH 7.4 (HBS-P) at 37° C., in a single cycle kinetics analysis (FIG. 1a). Association and dissociation rates were fitted using BiaEvaluation Software (GE Healthcare) after reference and blank subtractions, and dissociation constants were calculated (FIG. 1b). Clone 2.8.6 binds human BTLA with a KD of 0.65 nM and cynomolgus BTLA with a KD of 7.89 nM. Clone 11.5.1 binds human BTLA with a KD of 0.75 nM and cynomolgus BTLA with a KD of 0.99 nM. In a separate experiment against human BTLA only, Clone 2.8.6 bound human BTLA with a KD of 0.37 nM and Clone 11.5.1 bounds human BTLA with a KD of 0.53 nM.

Example 3. Binding to BTLA on Cells

The ability of the BTLA agonist antibodies of the present invention (2.8.6 and 11.5.1) to bind to human or cynomolgus BTLA expressed on the cell surface was assessed by flow cytometry. A lentiviral transfection system was used to express full length human or cynomolgus BTLA in a Jurkat T cell line. 1×10$^5$ cells per well were plated in 96 well U-bottom plates. BTLA antibody binding versus mIgG1 isotype control (clone MOPC-21, Biolegend #400165) was assessed at twelve concentrations by 1 in 3 serial dilution in FACS buffer (PBS, 2% FCS, 0.05% sodium azide), starting at a concentration of 90 µg/ml. Non-specific antibody binding was prevented by addition of Fc block (Biolegend #101319). Antibodies were incubated with cells for 30 minutes on ice, then cells were washed twice with FACS buffer prior to staining with an AF647 conjugated anti-mIgG1 secondary antibody (Biolegend #406618). Secondary antibody was incubated for 30 minutes on ice, then cells were washed and resuspended in FACS buffer for analysis on a flow cytometer. The geometric mean fluorescent intensity of secondary antibody was plotted for each concentration and the EC50 for receptor binding calculated by non-linear curve fitting using GraphPad Prism software. Clone 11.5.1 binds to human BTLA expressing cells with an EC50 of 0.016 nM and cynomolgus BTLA expressing cells with an EC50 of 0.0057 nM. Clone 2.8.6 binds to human BTLA expressing cells with an EC50 of 0.085 nM and cynomolgus BTLA expressing cells with an EC50 of 0.16 nM (FIG. 1c-d).

Example 4. Competition with the Natural Ligand HVEM for Binding to BTLA

Figure 2:
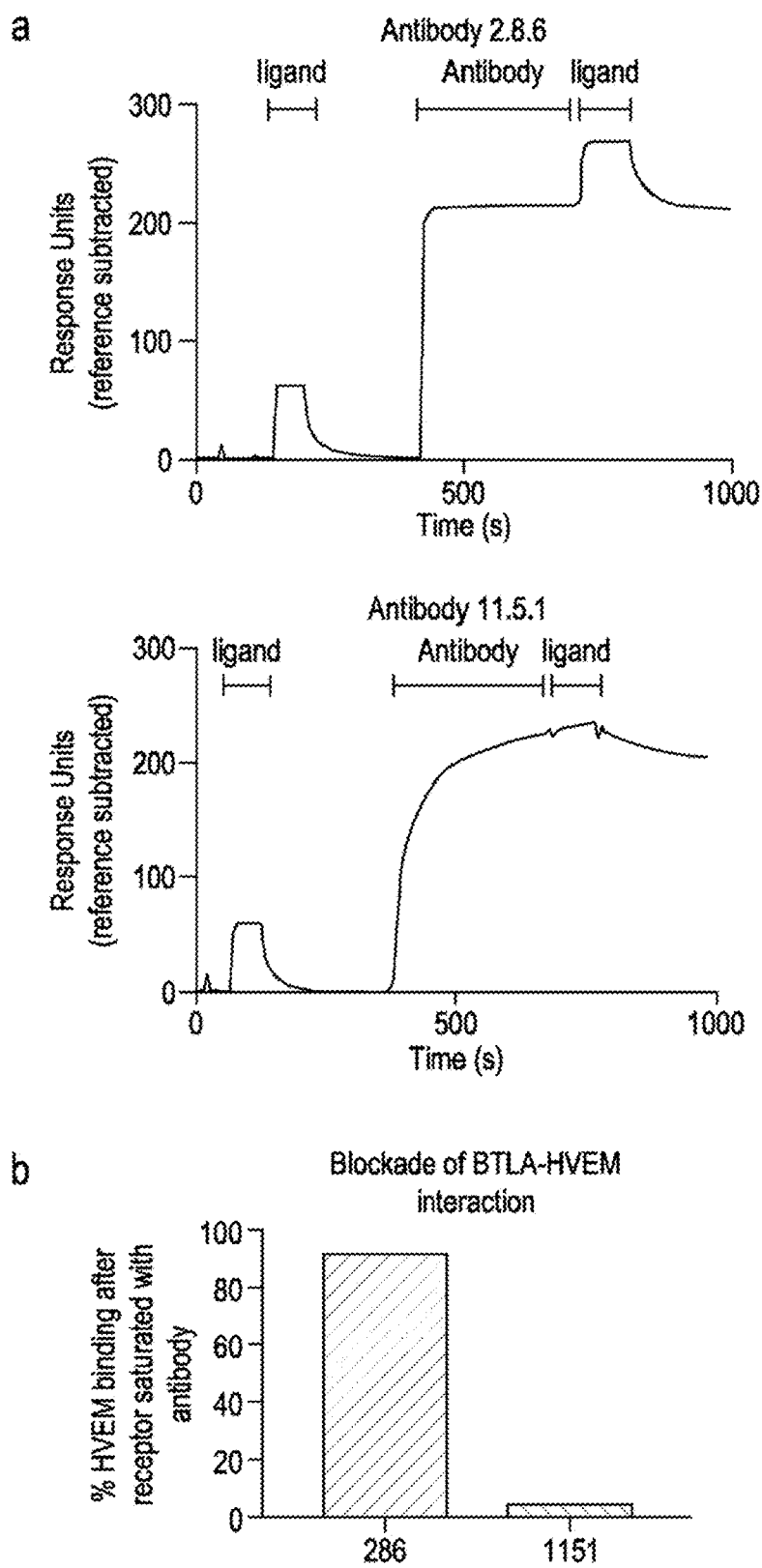

The ability of the BTLA agonist antibodies of the present invention (2.8.6 and 11.5.1) to block natural ligand binding to BTLA was assessed by surface plasmon resonance using the Biacore T200 (GE Healthcare). Human BTLA extracellular domain (BTLA$^{31K-151R}$) was covalently coupled to a CM5 Sensor chip using amine coupling. Human HVEM extracellular domain, fused to mouse IgG1 Fc, was then injected over the immobilized hBTLA in HBS-P buffer at 37° C., and allowed to fully dissociate. A saturating amount of anti-BTLA antibody (2.8.6 or 11.5.1) was then injected, followed immediately by a second injection of human HVEM-mFc at the same concentration as the initial injection (FIG. 2a). Equilibrium HVEM binding (in Resonance Units) after saturation of BTLA with antibody was expressed as a percentage of binding prior to antibody injection (FIG. 2b). If HVEM binding following saturation with antibody was >90% of the binding prior to antibody injection then the antibody was considered non-blocking.

Example 5. Binding Epitope of Antibody 11.5.1 on Human BTLA

Figure 3:
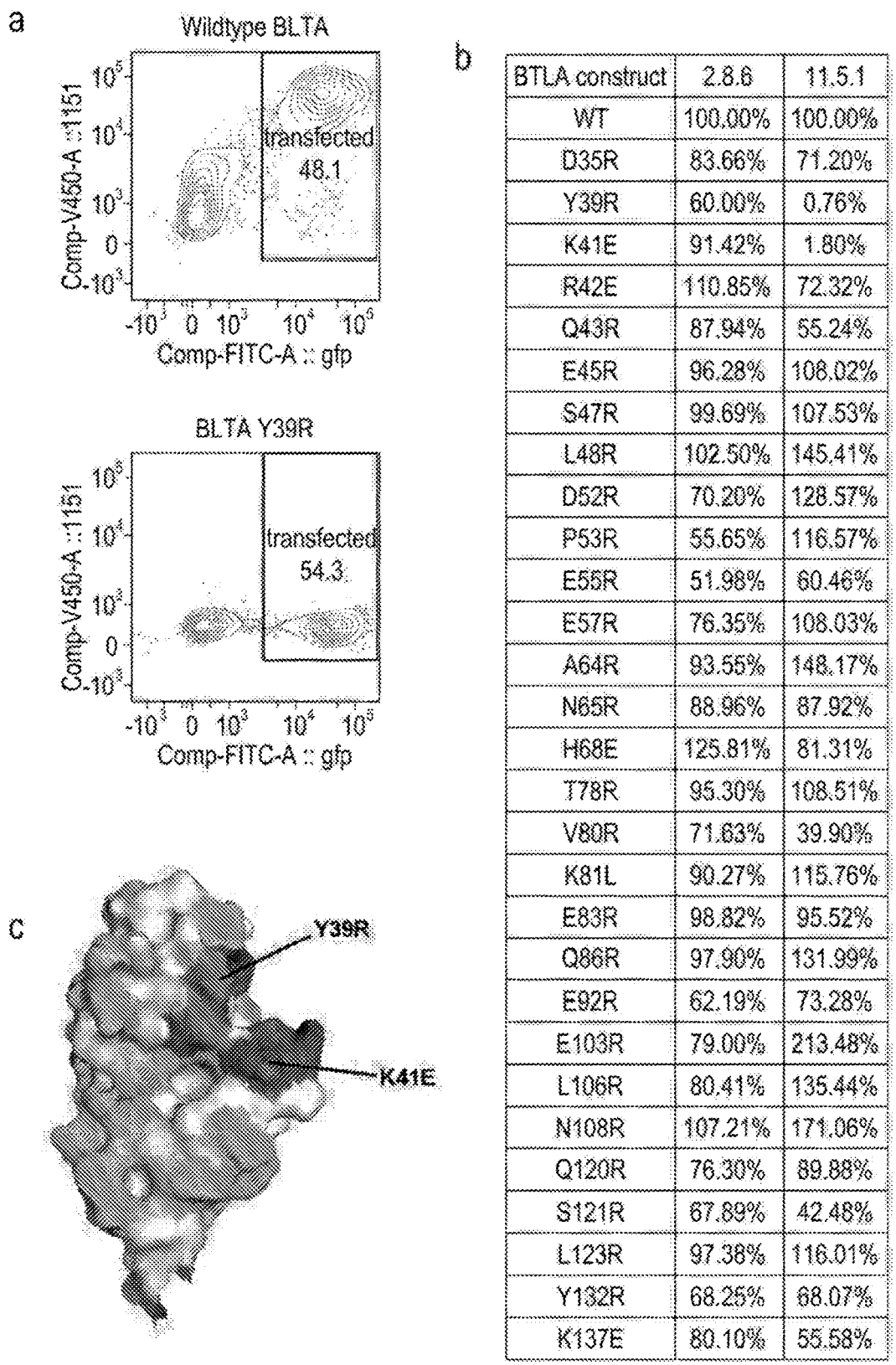
Figure 4:
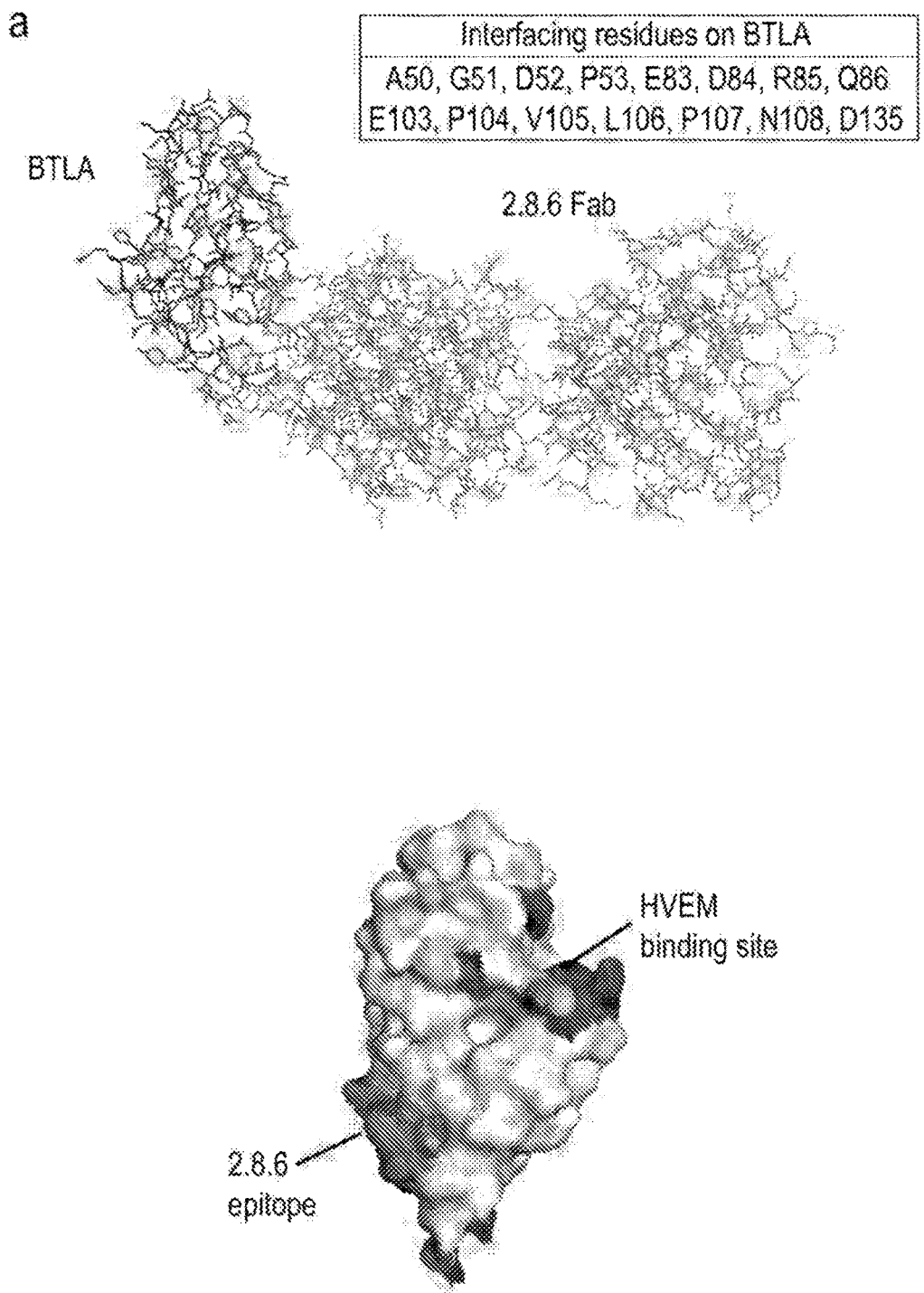

The functional epitope of the antibody 11.5.1 on human BTLA was determined by flow cytometry assessment of binding to a panel of single residue mutants of the receptor expressed on the cell surface. Constructs encoding the human extracellular region of BTLA with the transmembrane and intracellular regions of murine CD28 were cloned into the bi-cistronic mammalian expression vector pGFP2-n2 (BioSignal Packard Ltd), which also encodes GFP. Mutant constructs varying by one amino acid were prepared using the "drastic" mutagenesis approach (Davis et al. Proc Natl Acad Sci USA. 95, 5490-4 (1998)). Plasmids (2 µg/well) were transfected into HEK-293T cells in 6 well plates using Genejuice transfection reagent (Novagen; 6 µl/well). Mock and no-transfection controls were included with each experiment. Cells were harvested at 48 hours and stained with fluorochrome-conjugated anti-BTLA antibody at 10 µg/ml, alongside a Live/Dead marker, in PBS, 0.05% azide, 2% FCS (FACS buffer) for 1 h at 4° C. Cells were washed, pelleted and resuspended in 200 µl FACS buffer before being analysed on a BD FACSCanto flow cytometer. GFP-positive (transfected) viable cells were gated and analysed for binding of anti-BTLA antibodies (an example of the binding analysis for clone 11.5.1 is shown in FIG. 3a). For each mutant the Geo-mean of anti-BTLA antibody binding to transfected cells was expressed as a percentage of binding to the wild-type receptor (FIG. 3b). A panel of anti-BTLA antibodies was assessed and any mutation that eliminated binding of all antibodies was excluded from the analysis, on the assumption that such mutations lead to drastic changes in protein folding or expression rather than indicating an antibody epitope. The mutations Y39R and K41E completely abolish binding of antibody 11.5.1 whilst leaving binding of 2.8.6 unaffected. These mutations are mapped onto the human BTLA crystal structure (Compaan et al., J Biol Chem. 280:39553-61, 2005) in FIG. 3c (black residues), indicating the binding epitope of 11.5.1. Residues required for HVEM binding (Gln37, Arg42, Pro59, His127; from patent publication number WO2017004213) are also mapped onto the structure in grey demonstrating that 11.5.1 binds to an epitope very close to the HVEM binding site.

Example 6. Crystal Structure of the Fab' Fragment of 2.8.6 in Complex with Human BTLA The structural epitope of antibody 2.8.6 on human BTLA was determined by solving the crystal structure of antibody Fab in complex with human BTLA extracellular domain. The heavy and light variable domains of antibody 2.8.6 were cloned into the pOPINVH and pOPINVL expression vectors (Addgene), which encode the first constant domain of the mouse IgG1 heavy chain (with a 6×Histidine tag) and the constant domain of the mouse Ig kappa chain, respectively. These vectors were transiently co-transfected into HEK293T cells to produce the Fab' fragment of anti-BTLA 2.8.6, which was purified by Ni-NTA purification. Human BTLA Ig-V set domain ($BTLA^{S33-D135}$) was cloned into the pGMT7 vector and expressed in BL21(DE3)pLysS E. coli cells (Novagen) to produce inclusion bodies. The inclusion bodies were isolated from the cell pellet by sonication and washed repeatedly with a wash solution containing 0.5% Triton X-100. The purified BTLA inclusion bodies were solubilized in a denaturant solution containing 6 M guanidine hydrochloride. The solubilized protein solution was diluted slowly in refolding buffer [0.1 M Tris-HCl (pH 8.0), 0.6 M L-arginine, 2 mM ethylenediaminetetraacetic acid, 3.73 mM cystamine, and 6.73 mM cysteamine] to a final protein concentration of 1-2 µM and then stirred for 48 h at 4° C. The refolded mixture of BTLA was then concentrated with a VIVA FLOW50 system (Sartorius). BTLA was purified by gel filtration on a Superdex 75 column (GE Healthcare).

The purified BTLA and Fab' were mixed and purified as a complex by size exclusion chromatography. The crystal suitable for data collection was obtained in 0.2 M calcium acetate, 0.1 M imidazole pH 8.0, 10% (w/v) PEG 8000 at 293° K by the hanging drop vapor-diffusion method. The final dataset was collected at the Photon Factory, and the structure was determined by molecular replacement using the structure of BTLA (PDB ID; 2AW2 chain A) and anti-PD1-Fab (PDB ID: 5GGS chain C, D) as search probes.

The residues on BTLA at the interface with antibody 2.8.6 are A50, G51, D52, P53, E83, D84, R85, Q86, E103, P104, V105, L106, P107, N108, D135.

Example 7. Development of Humanised BTLA Mice

Figure 5:
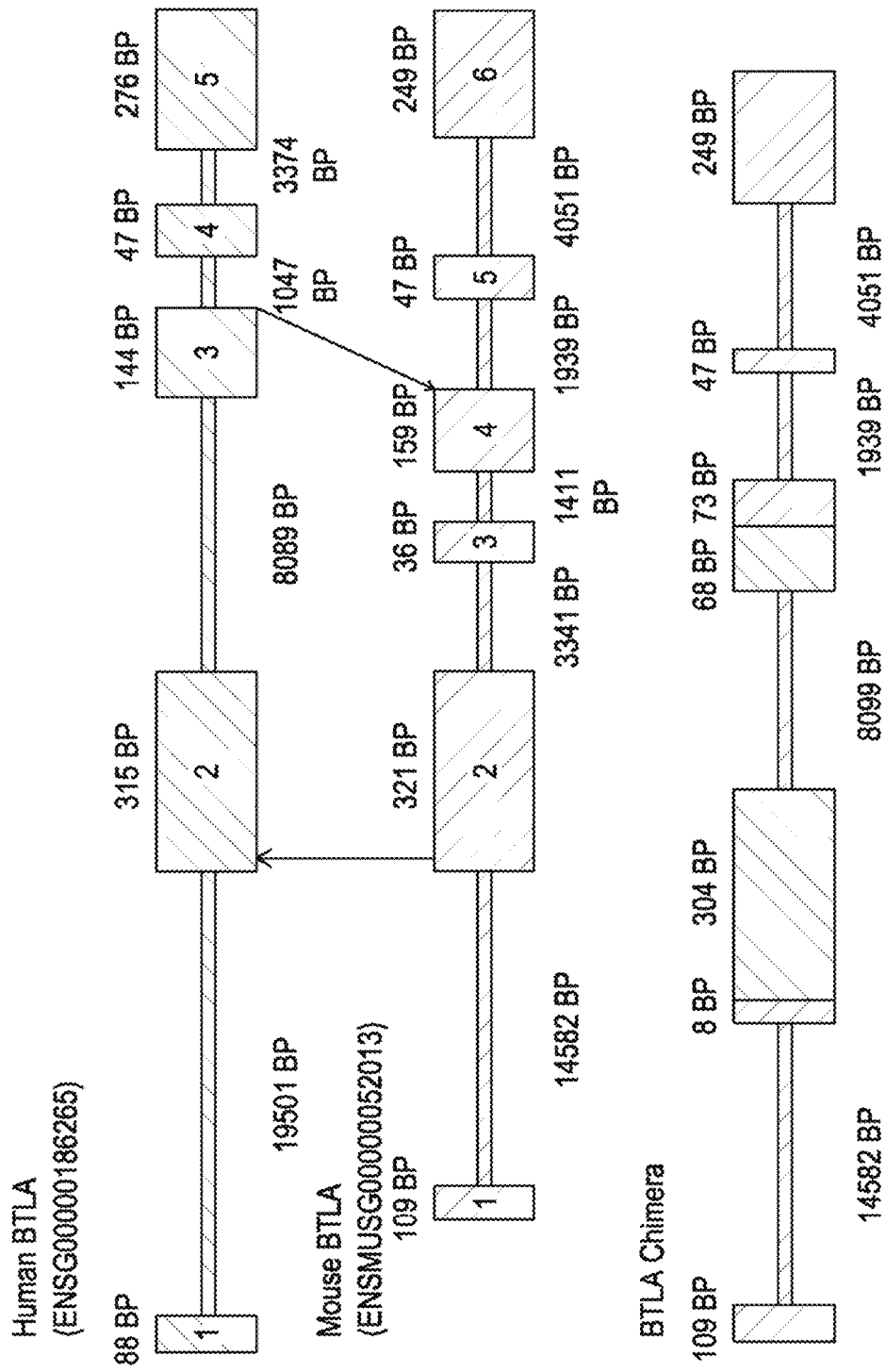

To provide a platform to assess anti human-BTLA antibodies in mouse models, a knock-in strain of C57Bl/6 mice was developed expressing a chimeric form of BTLA with the human extracellular region and the murine transmembrane and signaling regions. A section of human genomic DNA from the beginning of exon 2 to the end of exon 3 was inserted into the mouse locus replacing the mouse sequence from the beginning of exon 2 to the end of exon 4. The sequences at the exon-intron junction at the beginning of mouse exon 2 and end of mouse exon 4 were left intact to ensure proper splicing (FIG. 5).

Example 8. Inhibition of Antigen-Specific T Cell Proliferation In Vivo

Figure 6:
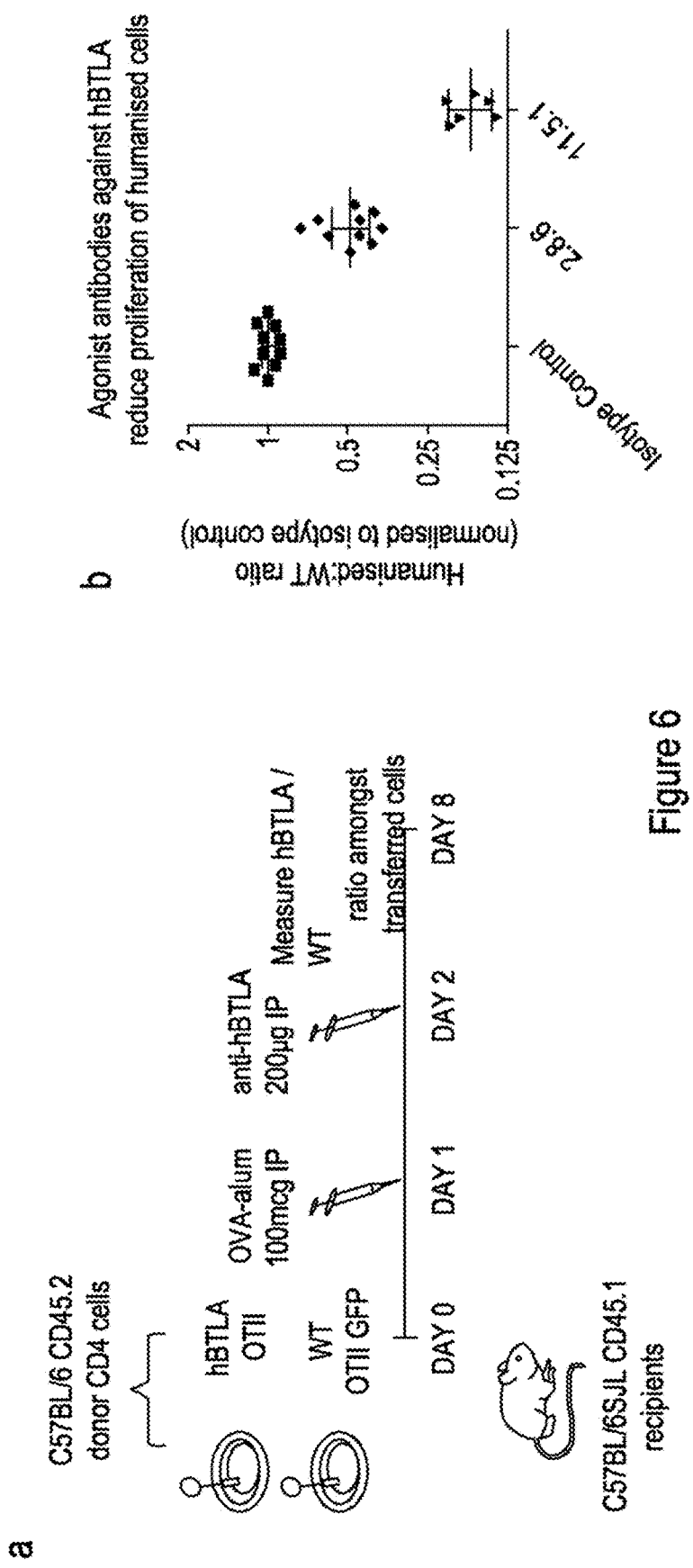

The ability of the BTLA agonist antibodies of the present invention (2.8.6 and 11.5.1) to inhibit antigen specific T cell proliferation in vivo was assessed using a sensitive T-cell transfer assay (FIG. 6a). In this assay, $5 \times 10^5$ T-cells, comprising a mixture of purified OTII (TCR transgenic) $CD4^+$ T cells specific for ovalbumin (OVA) from mice expressing homozygous human BTLA (hBTLA), and from OT-II mice expressing the wild-type murine BTLA receptor (The Jackson Laboratory), were transferred into non-transgenic C57BL/6 recipients. The transferred cells were distinguished from host cells using the CD45.2 (versus CD45.1) allotypic marker. The wild-type donor cells also expressed green fluorescent protein under the control of the human ubiquitin C promoter to allow them to be distinguished from the humanised donor cells by flow cytometry. The day after T cell transfer, the recipient mice were immunised with 100 µg ovalbumin (Sigma-Aldrich) in 100 µl PBS mixed with 100 µl Imject Alum (ThermoFisher), to induce expansion of the T cells. On the second day, the mice were dosed with 200 µg of antibody, intraperitoneally. Eight days following the initial transfer of the T cells, the ratio of the humanised BTLA-expressing and wild-type OVA-specific T-cells in the spleen was determined by flow cytometry. In this way, it was possible to track the expansion or contraction of the humanised cells, which bind the anti-human BTLA antibodies, relative to the wild-type controls, which do not. Both antibodies 2.8.6 and 11.5.1 led to reduced expansion of the humanised BTLA cells relative to the wild-type controls indicating that they are inducing signaling through the inhibitory BTLA receptor, which leads to reduced T cell proliferation (FIG. 6b).

Example 9. Inhibition of T Cell Proliferation in a Mixed Lymphocyte Reaction

Figure 7:
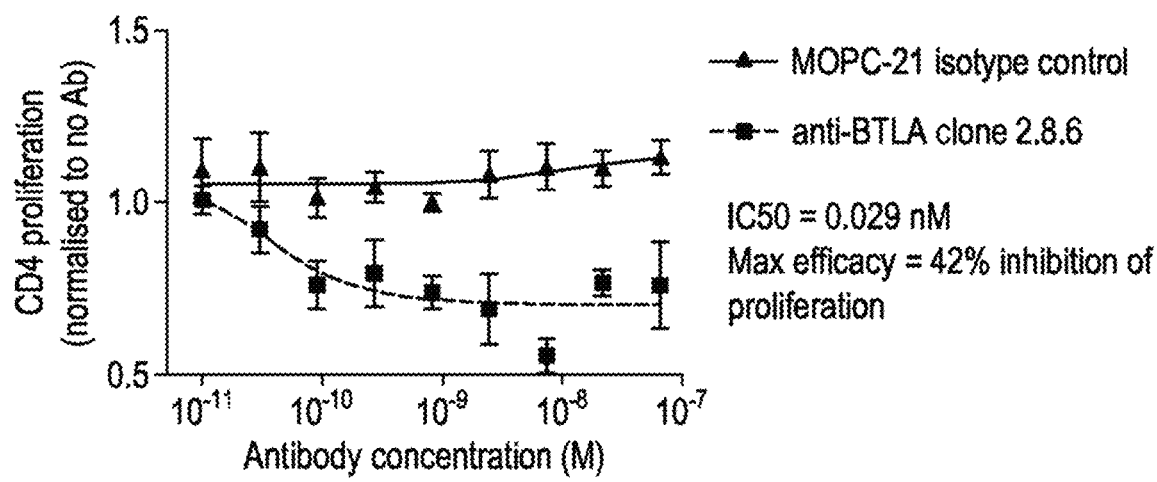

The ability of the BTLA agonist antibodies of the present invention (2.8.6 and 11.5.1) to inhibit proliferation of primary T cells from the humanised mice in vitro was assessed using a mixed lymphocyte reaction (MLR). Splenocytes from Balb/c mice were treated with Mitomycin C for 30 mins at 37° C. then washed and used as stimulator cells. T cells were purified from the spleens of humanised BTLA mice, by negative selection using magnetic-activated cell sorting (Mojosort Mouse CD3 T cell isolation kit, Biolegend #480023), and stained with CellTrace Violet Cell Proliferation Kit (ThermoFisher) to use as responder cells. $4 \times 10^5$ stimulator cells and $2 \times 10^5$ responder cells per well were mixed in 96-well U-bottom plates with various concentrations of anti-BTLA or isotype control antibody (clone MOPC-21, Biolegend #400165). Serial 1 in 3 dilutions of antibody were assessed starting at a concentration of 1 μg/ml for a total of 10 concentrations. Polyclonal anti-mHVEM antibody (R&D systems #AF2516) was also added to all wells at 1 μg/ml to block any baseline signaling through the BTLA pathway and accentuate the effects of agonist antibodies. After 96 hours, dilution of CellTrace Violet in responder cells was assessed by flow cytometry as a marker of proliferation. Proliferation in the presence of anti-BTLA antibody or isotype control was compared to proliferation in the absence of antibody. $CD4^+$ and $CD8^+$ populations were gated out and analysed separately. Both antibodies 2.8.6 and 11.5.1 reduced proliferation of human-BTLA expressing T cells, indicating that they induce inhibitory signaling through the human BTLA receptor. Clone 2.8.6 inhibited CD4 T cells with an IC50 of 0.029 nM and had a maximal effect of 42% inhibition of proliferation (FIG. 7). Clone 11.5.1 inhibited CD4 T cells with an IC50 of 0.016 nM and had a maximal effect of 33% inhibition of proliferation.

Example 10. Inhibition of NFkB Signalling in Human BTLA or Cynomolgus BTLA Transfected Jurkat T Cell Lines The ability of the BTLA agonist antibodies of the present invention (2.8.6 and 11.5.1) to inhibit NFkB signalling was assessed using a BTLA transfected reporter T cell line. A Jurkat T cell line stably transfected with an expression cassette that includes NF-κB-responsive transcriptional elements upstream of a minimal CMV promoter (mCMV)-GFP cassette (Source BioSciences #TR850A-1) was used as a reporter cell line for NFkB signalling. A lentiviral transfection system was used to express full length human or cynomolgus BTLA in this reporter cell line. These cells were mixed with a stimulator cell line comprised of bw5147 cells expressing an anti-CD3 ScFv construct on their surface as described by Leitner et al. J Immunol Methods. 2010 Oct. 31; 362(1-2):131-41. The stimulator cell line was also transfected with murine FcγRIIB to provide Fc receptors for presentation of the agonist BTLA antibodies. $5 \times 10^4$ reporter cells per well were mixed in 96 well U-bottom plates with $5 \times 10^4$ stimulator cells in the presence of various concentrations of BTLA antibody or isotype control (clone MOPC-21, Biolegend #400165). After 24 hours incubation at 37° C., cells were pelleted and stained for flow cytometry with a viability dye (Zombie Aqua, Biolegend #423101) and a mouse CD45 antibody (Pe-Cy7 conjugated clone 104, Biolegend #109830) to separate stimulator (murine) from responder (human) cells. Geometric mean of GFP expression was assessed for each antibody concentration and normalized to GFP expression in the absence of antibody. Clone 2.8.6 inhibited human BTLA transfected cells with an IC50 of 0.06 nM and cynomolgus BTLA transfected cells with an IC50 of 0.22 nM. Clone 11.5.1 inhibited human BTLA transfected cells with an IC50 of 0.033 nM and cynomolgus BTLA transfected cells with an IC50 of 0.14 nM.

Example 11. Treatment of a T Cell Driven Mouse Model of Colitis by Antibody 2.8.6

Figure 8:
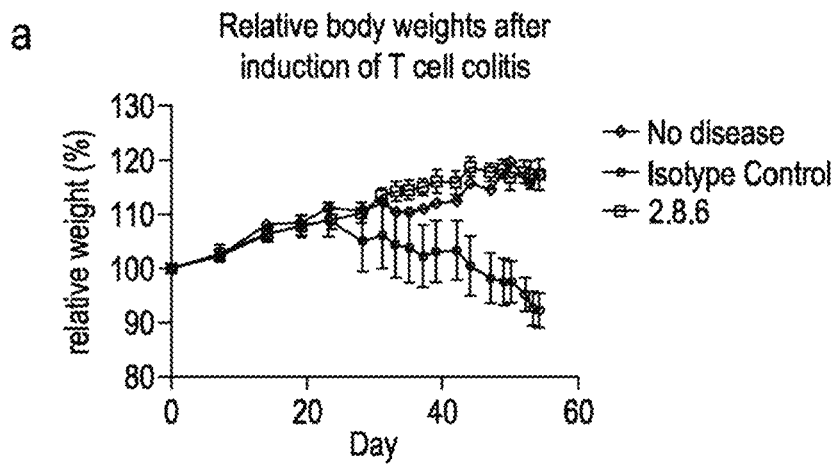
Figure 8:
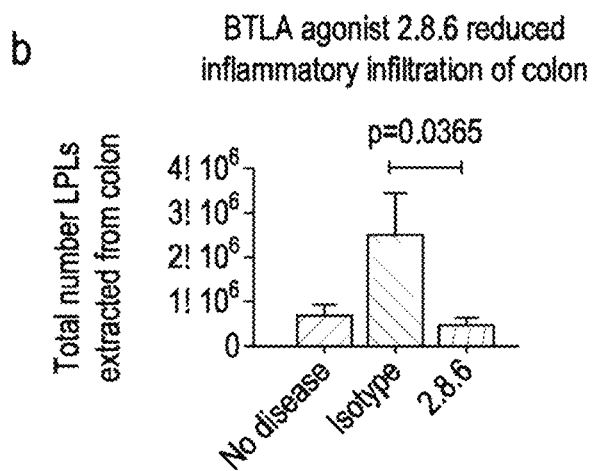
Figure 8:
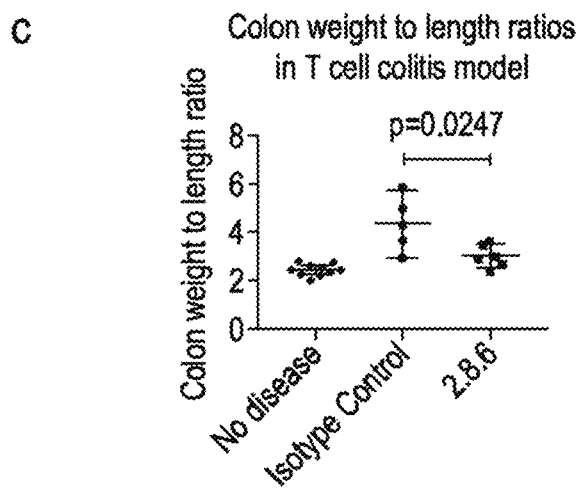

The ability of the BTLA agonist antibody 2.8.6 to ameliorate a T cell driven model of colitis was assessed using the humanised mice. This T cell transfer model has previously been described as a murine model of inflammatory bowel disease (Ostanin et al., Am J Physiol Gastrointest Liver Physiol. 296:G135-46, 2009). $CD45RB^{hi}CD25$-CD4+ T cells sorted from spleens and lymph nodes of humanised BTLA mice were injected intraperitoneally into Rag1 KO recipients, ($Rag1^{tm1Mom}$; The Jackson Laboratory), at a dose of $5 \times 10^5$ cells per mouse. The transferred T cells cause an inflammatory colitis that develops after approximately 3 weeks and leads to diarrhea and weight loss. Rag1 KO cagemates that did not receive transferred T cells serve as non-diseased controls. On days 7, 21 and 35 after T cell transfer the recipient mice were injected intraperitoneally with 200 μg of 2.8.6 or isotype control antibody. All mice were weighed regularly, and at 8 weeks colons were weighed and measured and inflammatory infiltration assessed by histology, as well as by cell counting and flow cytometry of extracted lamina propria leucocytes. Antibody 2.8.6 prevented weight loss (FIG. 8a) and significantly reduced inflammatory infiltration of colons (FIG. 8b). Colon inflammation in diseased mice led to an increased colon weight:length ratio that was not seen in 2.8.6 treated mice (FIG. 8c).

Example 12. Treatment of a Mouse Model of Graft-Versus-Host Disease (GVHD)

Figure 9:
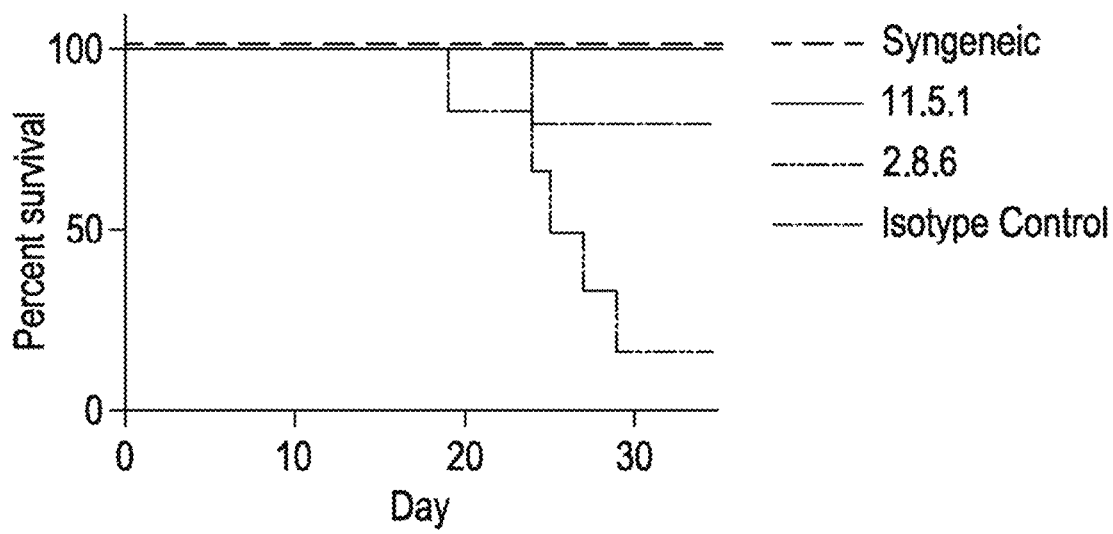
Figure 9:
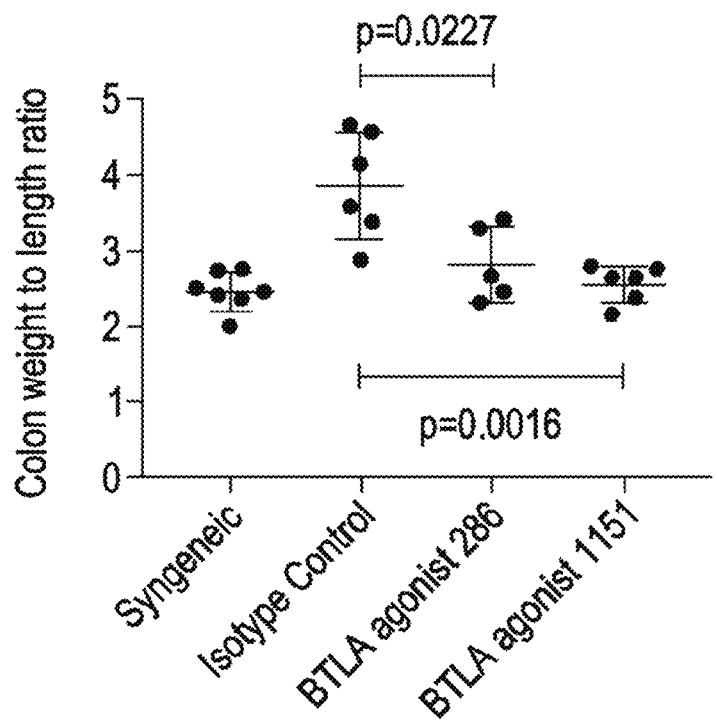

The effects of the anti-BTLA agonist antibodies were assessed in a non-lethal parent-into-F1 model of GVHD. Bone marrow cells (BMCs) and splenocytes were harvested from humanised BTLA donor mice (C57BL/6 background; $H2^b$). $2 \times 10^7$ BMCs and 107 splenocytes were injected intravenously into CB6F1 ($H2^{b/d}$) recipients that had been lethally irradiated with 9 Gy total body irradiation. Irradiated CB6F1 mice reconstituted with syngeneic BMCs and splenocytes served as non-diseased controls. On the day of immune cell transfer mice were injected intraperitoneally with 200 μg anti-BTLA antibody or isotype control. Mice were weighed regularly and GVHD was monitored by calculating relative loss of body weight and by clinical observation. Mice were culled 5 weeks after immune cell transfer or when they reached a humane endpoint (which included >20% weight loss relative to starting weight in the first 14 days, or >15% weight loss at any other time). At the time of death colons were weighed and measured and a colon weight:length ratio calculated as a marker of colon inflammation, which is a prominent clinical feature of GVHD. Both antibodies 2.8.6 and 11.5.1 significantly reduced weight loss, leading to increased survival (FIG. 9a) and prevented colon inflammation (FIG. 9b).

Figure 10:
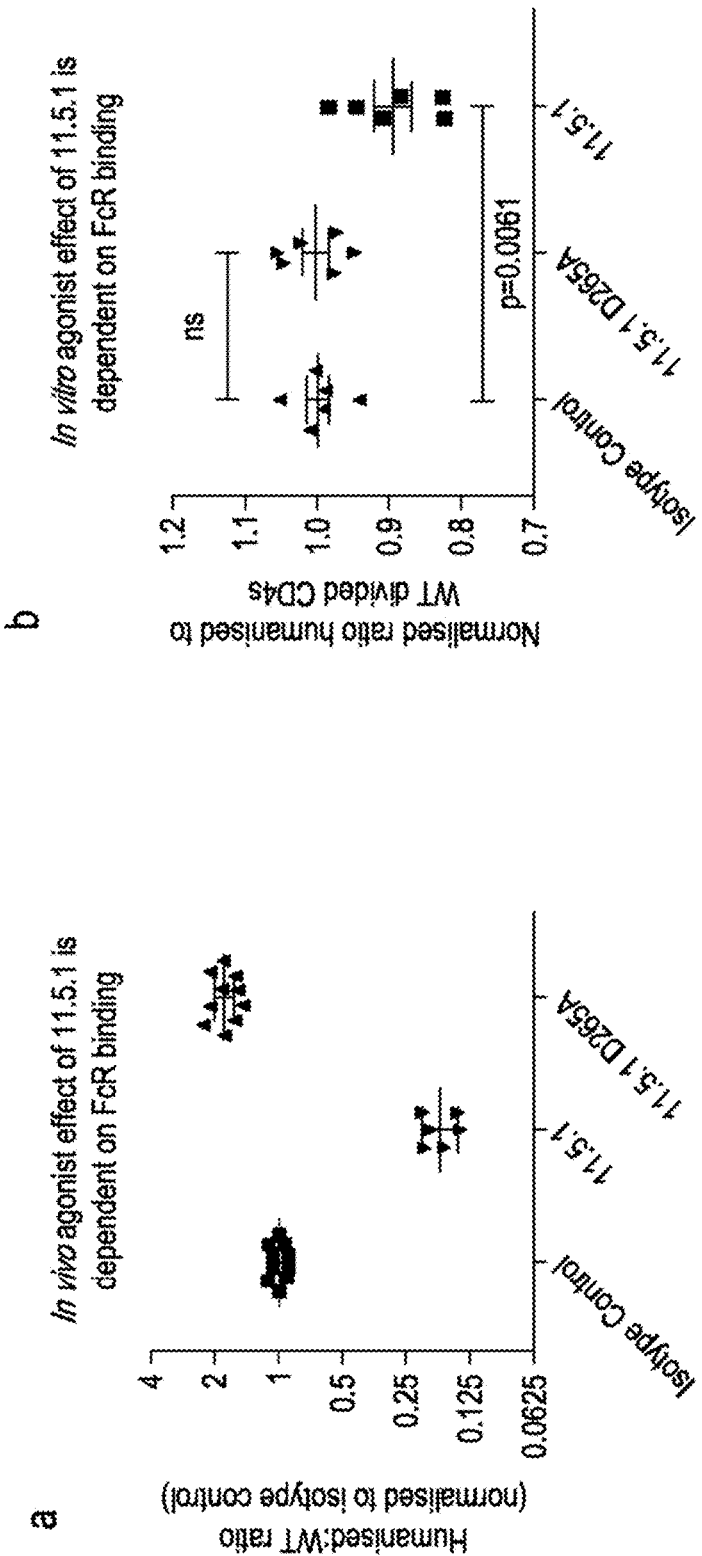

Example 13. Agonist Activity of Antibody 11.5.1 is Dependent on Fc Receptor Binding Antibody 11.5.1 was recombinantly expressed as a mIgG1k containing a D265A mutation which has previously been described as significantly reducing Fc receptor binding (Clynes et al., Nat Med. 6:443-446, 2000). This mutated antibody was assessed in the T cell transfer assay described in Example 8. The parental 11.5.1 antibody inhibited proliferation of humanised T cells as its net effect is agonism of the BTLA receptor. The FcR-null D265A mutation, however, led to enhanced proliferation of humanised T cells suggesting that the FcR-null mutation removes the antibody's agonistic effect, leaving only the effect of receptor blockade (FIG. 10a). The D265A mutated 11.5.1 antibody was also assessed in the in vitro MLR assay described in Example 9. Again, the parental 11.5.1 antibody inhibited proliferation of humanised T cells as its net effect is agonism of the BTLA receptor. The FcR-null D265A mutation removes the antibody's agonistic effect, so this antibody showed no effect in this assay (FIG. 10b). The FcR null 11.5.1 antibody did not enhance proliferation of humanised cells in this assay as HVEM was blocked (by the addition of polyclonal anti-HVEM antibody) so there was no baseline signaling through the pathway to be blocked by the BTLA blocking antibody.

Example 14. Antibodies 2.8.6 and 11.5.1 do not Fix Complement In Vitro

Figure 11:
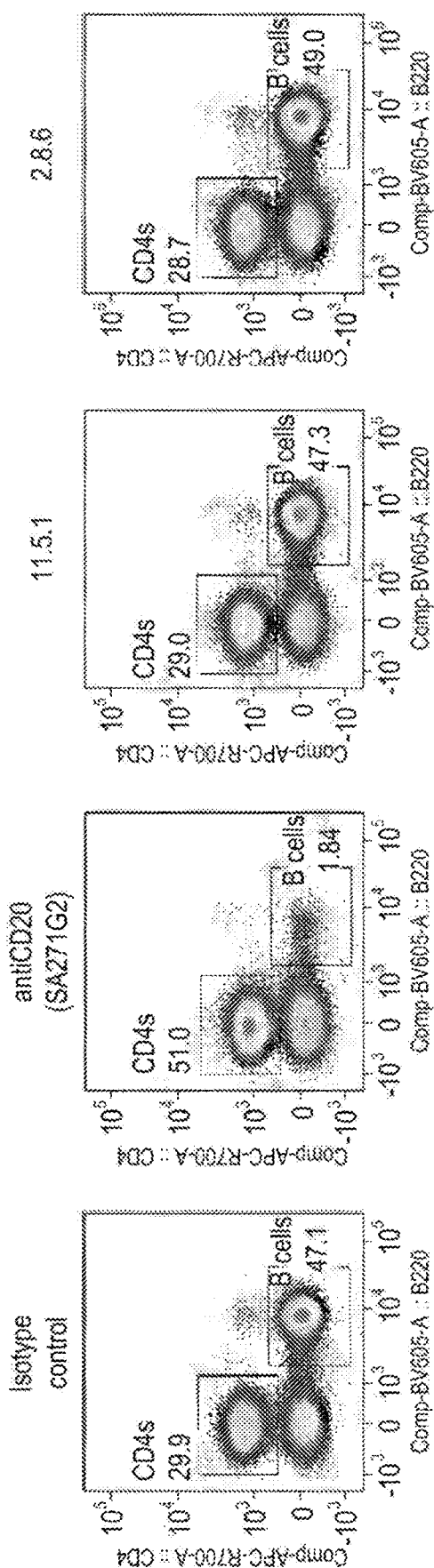

Splenocytes from humanised mice were incubated with 10% baby rabbit complement (BioRad) and anti-BTLA antibodies (or an isotype control or a positive control depleting anti-CD20 antibody; clone SA271G2 from Biolegend) at 20 µg/ml for 15 min at 37° C. Whilst anti-CD20 antibody depleted the majority of B220+ B cells, anti-BTLA antibodies did not deplete either B220+ or CD4+ cells (FIG. 11), even though both these populations stain positively for BTLA.

Example 15. Antibodies 2.8.6 and 11.5.1 do not Induce ADCC In Vitro

Figure 12:
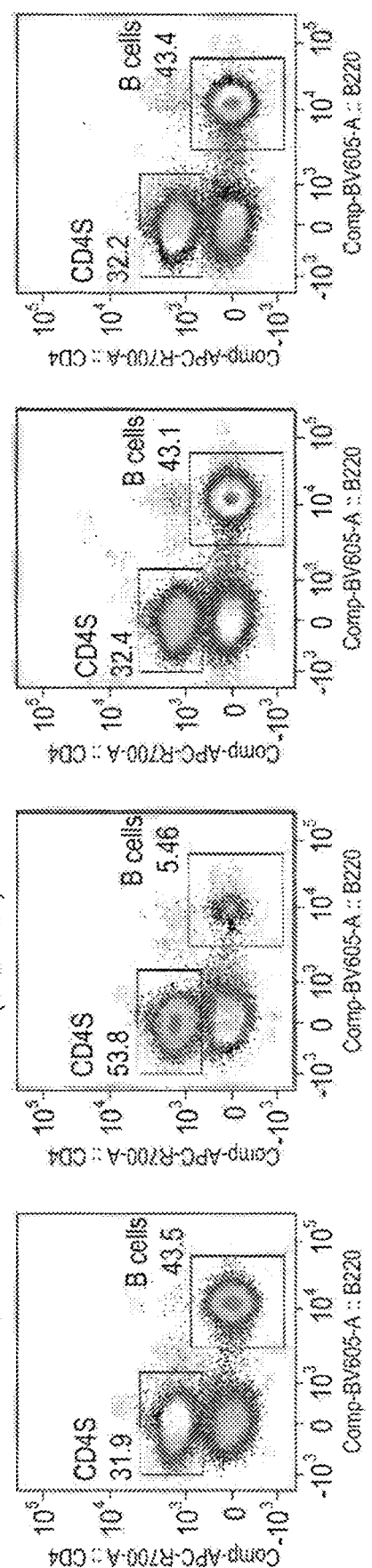

Whole splenocytes (including myeloid effector cells) from humanised mice were incubated with anti-BTLA antibodies (or isotype control or depleting anti-CD20 antibody SA271G2) at 20 µg/ml for 24 hours at 37° C. Whilst anti-CD20 antibody depleted the majority of B220+ cells, anti-BTLA antibodies did not deplete either B220+ or CD4+ cells (FIG. 12), even though both these populations stain positively for BTLA.

Figure 13:
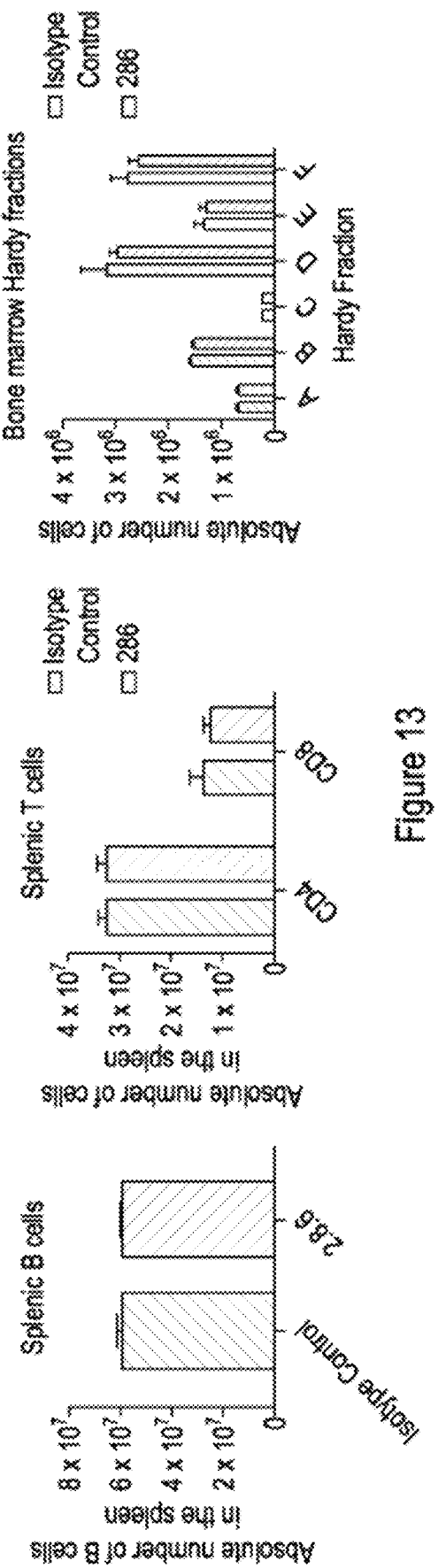

Example 16. Antibodies 2.8.6 and 11.5.1 do not Deplete BTLA Expressing Cells In Vivo Humanised BTLA mice were injected intraperitoneally with 200 µg anti-BTLA antibody or isotype control. At 24 hours spleens were harvested and the frequency of different cell populations identified by flow cytometry. Anti-BTLA antibody had no effect on the frequency or absolute number of B or T cells in the spleen or on the number of B cell precursors in the bone marrow (FIG. 13).

Figure 14:
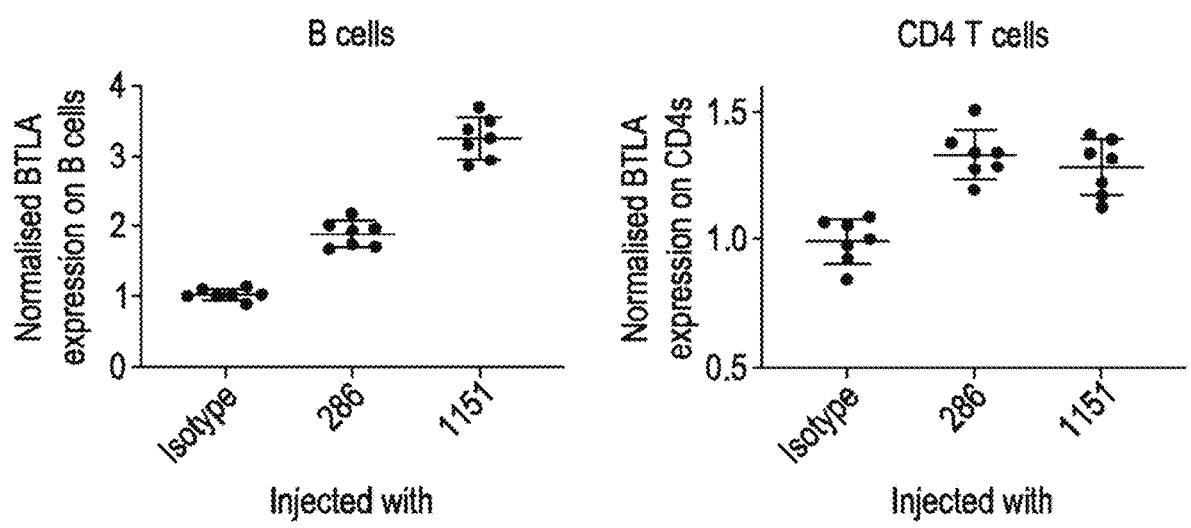

Example 17. Antibodies 2.8.6 and 11.5.1 Stabilize Expression of BTLA on Immune Cells in Vivo Humanised mice were injected intraperitoneally with 10 mg/kg of antibody 2.8.6 or 11.5.1. Six days after injection mice were humanely sacrificed and spleens harvested and processed to single cell suspension for assessment by flow cytometry. Cells were stained with a cocktail of antibodies to identify immune cell subsets and with fluorescently conjugated anti-BTLA antibody that had a non-competing epitope with the antibody that had been injected. The geometric mean of BTLA staining following in vivo incubation with anti-BTLA antibody was normalized to the geometric mean of BTLA staining (using the same staining antibody) following incubation with isotype control. BTLA expression was significantly higher on B cells and CD4 T cells from mice that had been injected with either clone 2.8.6 or 11.5.1, compared to mice that had been injected with isotype control (FIG. 14). This suggests that clones 2.8.6 and 11.5.1 stabilise expression of BTLA on the cell surface in vivo, rather than inducing receptor down-modulation, as has been observed with other BTLA antibodies in the prior art (M.-L. del Rio et al./Immunobiology 215 (2010) 570-578). For the purposes of immunosuppression an agonist antibody that stabilizes expression of the receptor presents the benefit of enabling prolonged high levels of inhibitory signaling through the pathway compared to a downmodulating antibody.

Example 18. Tolerability and Side Effects in Animal Models

There were no tolerability issues or side effects noted in any animal studies with antibodies 2.8.6 or 11.5.1.

Example 19. Humanisation of Antibody 2.8.6

Antibody 2.8.6 was humanised by CDR grafting on to homologous human germline framework regions (See SEQ ID NO: 13-14). IGHV2-5*08 was used for the heavy chain and IGKV3-11*01 for the light chain. After humanisation, binding to BTLA was assessed by SPR. Humanised 2.8.6 bound to monomeric BTLA with a $K_D$ of 0.73 nM.

Example 20. Characterisation of Exemplary BTLA Antibodies

Described in this example is characterisation of exemplary mIgG1 BTLA antibodies provided herein in addition to 2.8.6 and 11.5.1. Various clones listed in Table 1 were evaluated for their binding affinity to BTLA and inhibition efficiency of lymphocytes (Table 2). For each antibody, the association rate ("on rate") and dissociation rate ("off rate") for binding human BTLA, and KD for binding human or cynomolgus BTLA were measured according to the method described in Example 2, fitting curves for injection of BTLA extracellular domain at a single concentration. Inhibition efficiency of individual antibodies on T cells was also evaluated at a single concentration of 10 µg/ml. MLR assay was performed for each individual antibody according to the method as described in Example 9 (two biological repeats as shown in Table 3); anti-CD3 assay was performed according to the method described below (two biological repeats, Table 3); and inhibition of NFkB signalling in human BTLA transfected Jurkat T cell line by each antibody was determined according to the method as described in Example 10 (Table 3). The average inhibition of T cells relative to isotype control in various in vitro stimulation assays for each exemplary antibody was calculated as a mean of the percentage inhibition of all assay results (Table 2 and Table 3).

The ability of the BTLA agonist antibodies to inhibit anti-CD3 and anti-CD28 induced T cell activation was assessed as follows. Splenocytes from humanised BTLA mice were processed to single cell suspension and treated with ACK buffer to lyse red blood cells. Cells were stained with CFSE (Biolegend Cat #423801) to enable tracking of cell proliferation. $2\times10^5$ cells per well were plated in 96 well U-bottom plates with soluble anti-CD3 antibody (clone 145.2C11; Biolegend #100339) and anti-CD28 (clone 37.51; Biolegend #102115) each at a concentration of 50 ng/ml, and soluble anti-BTLA antibody or isotype control at a concentration of 10 µg/ml. After 72 hours cells were analysed by flow cytometry to assess proliferation ("antiCD3/CD28 (CD4 T cell proliferation)") and T cell activation by staining of surface expressed activation markers ("antiCD3/CD28 (CD69+CD4 T cells)"). For each BTLA antibody the percentage inhibition compared to isotype control antibody was calculated.

Further, for each BTLA antibody, their ligand blocking capability, e.g., competition with HVEM for binding to BTLA, was assessed according to the method as described in Example 4, and the results are presented as "Yes" for more than 90% inhibition of HVEM-BTLA binding, and "No" for less than 10% inhibition of HVEM-BTLA binding. Functional epitope of each BTLA antibody was also determined according to the method as described in Example 5. The "epitope" column in Table 2 summarizes the epitope group that each individual BTLA antibody binds to. Antibodies 2.8.6, 6.2, 831, 16H2, 7A1, 16F10, 6G8, 3E8, 4E8, 15C6, 12F11, 10B1, 15B6, 4D3, 16E1, 4D5 and 3A9 all bind to a first epitope (named "epitope 1" in the table) comprising at least one critical residue selected from the list: D52, P53, E55, E57, E83, Q86, E103, L106 and E92. Antibodies binding to epitope 1 do not compete with the ligand HVEM for binding to BTLA.

Antibodies 11.5.1, 14D4, 1H6, 8C4, 27G9, 26F3 all bind to a different second epitope ("epitope 2") comprising at least one critical residue selected from the list: Y39, K41, R42, Q43, E45 and S47. Antibodies binding to epitope 2 do compete with the ligand HVEM for binding to BTLA. Antibody 26B1 binds to a third epitope ("epitope 3") comprising at least one critical residue selected from the list: D35, T78, K81, S121 and L123. Antibodies binding to epitope 3 do compete with the ligand HVEM for binding to BTLA. Antibodies 24H7, 4B1, 8B4, 4H4 all bind to a different fourth epitope ("epitope 4") comprising the critical residue H68. Antibodies binding to epitope 4 do not compete with the ligand HVEM for binding to BTLA. Antibody 21C7 binds to a different fifth epitope ("epitope 5") comprising at least one critical residue selected from the list: N65 and A64. Antibodies binding to epitope 5 do not compete with the ligand HVEM for binding to BTLA.

Example 21. Humanisation and CDR Engineering of BTLA Antibodies 3E8 and 6.2

The variable domains of 3E8 and 6.2 were humanised by germlining to homologous human germline framework regions (Seq ID No. 382-385). For 3E8 the acceptor frameworks selected were VH1-1-08 and JH6 for the heavy chain and VK3-L6 and JK2 for the light chain. For 6.2 the acceptor frameworks selected were VH3-3-21 and JH6 for the heavy chain and VK2-A19 and JK4 for the light chain.

It is sometimes possible to substitute certain residues in the CDRs of an antibody to remove undesirable characteristics without significantly impacting target binding. The CDRH2 of the humanised antibody 6.2 was modified with D54E and N56Q substitutions (Seq ID No. 387) to remove deamidation potential (the engineered humanised VH sequence of 6.2 is given in Seq ID No. 390). Similarly, the CDRH2 of the humanised antibody 3E8 was modified with an N57Q substitution (Seq ID No. 388) to remove deamidation potential, and a K63S substitution to reduce predicted immunogenicity, as determined by Lonza's Epibase analysis (the engineered humanised VH sequence of 3E8 is given in Seq ID No. 389).

TABLE 2

Characterisation of binding affinity and inhibitory effect of exemplary antibodies

| Clone | Ligand Blocking | Human BTLA On rate (1/Ms) | Human BTLA Off rate (1/s) | Human BTLA KD (nM) | Cyno BTLA KD (nM) | Average inhibitory effect in vitro | Epitope |
|---|---|---|---|---|---|---|---|
| 2.8.6 | No | 6.46E+05 | 4.23E−04 | 0.65 | 7.89 | 39% | 1 |
| 24H7 | No | 2.43E+05 | 1.60E−04 | 0.66 | — | 30% | 4 |
| 11.5.1 | Yes | 6.03E+05 | 4.49E−04 | 0.75 | 0.99 | 30% | 2 |
| 14D4 | Yes | 2.54E+05 | 3.77E−04 | 1.49 | 1.83 | 33% | 2 |
| 6.2 | No | 6.30E+05 | 1.07E−03 | 1.70 | 9.71 | 35% | 1 |
| 4B1 | No | 5.77E+05 | 1.85E−03 | 3.21 | — | 29% | 4 |
| 8B4 | No | 5.38E+05 | 4.40E−03 | 8.17 | — | 29% | 4 |
| 16H2 | No | 3.97E+05 | 3.27E−03 | 8.25 | 160.1 | 34% | 1 |
| 1H6 | Yes | 7.72E+05 | 6.90E−03 | 8.94 | 6.08 | 31% | 2 |
| 8C4 | Yes | 3.63E+05 | 5.76E−03 | 15.89 | 161.48 | 19% | 2 |
| 26B1 | Yes | 3.23E+05 | 9.70E−03 | 30.03 | 167.66 | 21% | 3 |
| 7A1 | No | 4.13E+05 | 1.66E−02 | 40.17 | — | 24% | 1 |
| 21C7 | No | 9.30E+05 | 4.06E−02 | 43.65 | — | 18% | 5 |
| 16F10 | No | 5.81E+05 | 2.83E−02 | 48.78 | — | — | 1 |
| 6G8 | No | 3.18E+05 | 1.67E−02 | 52.42 | — | — | 1 |
| 3E8 | No | 5.43E+05 | 6.08E−02 | 111.98 | 607.46 | 41% | 1 |
| 4E8 | No | 1.75E+05 | 3.14E−02 | 180.00 | — | — | 1 |
| 27G9 | Yes | 1.92E+05 | 8.38E−02 | 436.86 | 653.63 | 16% | 2 |
| 15C6 | No | 1.93E+05 | 1.38E−01 | 718.44 | — | — | 1 |
| 12F11 | No | 2.15E+05 | 1.55E−01 | 722.33 | — | 24% | 1 |
| 10B1 | No | 4.22E+05 | 5.21E−01 | 1233.36 | — | 21% | 1 |

TABLE 2-continued

Characterisation of binding affinity and inhibitory effect of exemplary antibodies

| Clone | Ligand Blocking | Human BTLA On rate (1/Ms) | Human BTLA Off rate (1/s) | Human BTLA KD (nM) | Cyno BTLA KD (nM) | Average inhibitory effect in vitro | Epitope |
|---|---|---|---|---|---|---|---|
| 15B6 | No | 4.47E+05 | 5.76E−01 | 1287.18 | — | 14% | 1 |
| 4D3 | No | 1.52E+05 | 2.51E−01 | 1651.32 | — | — | 1 |
| 4H4 | No | 2.03E+05 | 3.47E−01 | 1708.23 | — | 26% | 4 |
| 26F3 | Yes | 9.21E+05 | 2.02E+00 | 2195.81 | 809.75 | 9% | 2 |
| 16E1 | No | 7.30E+05 | 2.13E+00 | 2923.69 | — | 15% | 1 |
| 4D5 | No | 2.70E+05 | 7.90E−01 | 2929.18 | — | — | 1 |
| 3A9 | No | 4.06E+05 | 1.63E+00 | 4006.90 | — | 19% | 1 |

TABLE 3

Inhibitory effect assay results of exemplary antibodies

| Clone | MLR (CD4 T cell proliferation) | | AntiCD3/CD28 (CD4 T cell proliferation) | | AntiCD3/CD28 (CD69 + CD4 T cells) | | T cell reporter (NFκB signaling) | Average |
|---|---|---|---|---|---|---|---|---|
| | repeat 1 | repeat 2 | repeat 1 | repeat 2 | repeat 1 | repeat 2 | | |
| 2.8.6 | 30% | 36% | 23% | 35% | 58% | 67% | 22% | 39% |
| 24H7 | 23% | 31% | 13% | 23% | 52% | 44% | 22% | 30% |
| 6.2 | 31% | 35% | 19% | 21% | 53% | 61% | 26% | 35% |
| 11.5.1 | 23% | 18% | 21% | 28% | 50% | 47% | 19% | 30% |
| 11.5.1 D265A | −3% | 1% | −3% | −9% | −47% | −26% | −13% | −14% |
| 4B1 | 33% | 30% | 14% | 18% | 47% | 41% | 23% | 29% |
| 14D4 | 39% | 26% | 24% | 29% | 43% | 52% | 16% | 33% |
| 831 | 25% | 34% | 10% | 8% | 50% | 53% | 24% | 29% |
| 16H2 | 40% | 26% | 11% | 23% | 51% | 60% | 29% | 34% |
| 1H6 | 31% | 16% | 26% | 19% | 47% | 53% | 26% | 31% |
| 8B4 | 33% | 23% | 20% | 4% | 51% | 47% | 24% | 29% |
| 21C7 | 8% | 17% | 10% | −4% | 39% | 35% | 23% | 18% |
| 3E8 | 43% | 35% | 27% | 35% | 52% | 64% | 30% | 41% |
| 7A1 | 23% | 29% | 14% | 17% | 28% | 38% | 20% | 24% |
| 26B1 | 12% | 10% | 11% | 19% | 35% | 30% | 29% | 21% |
| 8C4 | 42% | −2% | 12% | 4% | 29% | 29% | 21% | 19% |
| 27G9 | 9% | 8% | 10% | 13% | 24% | 22% | 24% | 16% |
| 12F11 | 28% | 23% | 5% | 9% | 30% | 40% | 30% | 24% |
| 15C6 | 19% | 8% | 2% | −2% | 12% | 19% | 9% | 10% |
| 26F3 | 9% | −5% | 4% | 0% | 19% | 17% | 20% | 9% |
| 4D3 | 12% | 9% | −4% | −2% | 6% | 2% | 26% | 7% |
| 10B1 | 16% | 25% | 8% | 14% | 24% | 36% | 27% | 21% |
| 16E1 | 33% | 8% | 4% | 8% | 9% | 23% | 22% | 15% |
| 15B6 | 7% | 13% | 9% | 16% | 13% | 20% | 21% | 14% |
| 3A9 | 7% | 24% | 9% | 9% | 22% | 34% | 27% | 19% |
| 4H4 | 10% | 17% | 14% | 22% | 43% | 52% | 25% | 26% |
| No antibody | 3% | −3% | 1% | −6% | 2% | −9% | 2% | −1% |

SEQUENCE LISTING:

SEQ ID NO: 1
GDSITSAY

SEQ ID NO: 2
ISYSGST

SEQ ID NO: 3
ARSHYYGYYFDY

SEQ ID NO: 4
ETIDSYGDSL

SEQ ID NO: 5
RAS

SEQ ID NO: 6
QQTDEDPYT

SEQ ID NO: 7
GFSLTTYG

SEQ ID NO: 8
MWPGGRT

SEQ ID NO: 9
VRGDYEYDYYAMDY

SEQ ID NO: 10
SSVSY

SEQ ID NO: 11
ATS

SEQ ID NO: 12
HQWSSNPYT

SEQUENCE LISTING:

SEQ ID NO: 13-Humanised antibody 2.8.6 VH region
QVTLKESGPALVKPTQTLTLTCTVSGFSLTTYGVHWIRQPPGKALEWLGV
MWPGGRTSYNPSLKSRLTITKDNSKSQVVLTMTNMDPVDTATYYCVRGDY
EYDYYAMDYWGQGTLVTVSS SEQ ID NO: 14-Humanised antibody 2.8.6 VL region
EIVLTQSPATLSLSPGERATLSCRASSSVSYMHWYQQKPGQAPRPLIYAT
SNRATGIPARFSGSGSGTDYTLTISSLEPEDFAVYYCHQWSSNPYTFGQG
TKLEIK SEQ ID NO: 15-Mouse Ab 2.8.6 VL region
QIVLSQSPAILSASPGEKVTMTCRASSSVSYMHWYQQKPGSSPKPWIYAT
SNLASGVPARFSGSGSGTSYSLTISRMEAEDAATYYCHQWSSNPYTFGGG
TKLEIK SEQ ID NO: 16
caaattgttctctcccagtctccagcaatcctgtctgcatctccagggga
gaaggtcacaatgacttgcagggcagttcaagtgtaagttacatgcact
ggtaccagcagaagccaggatcctccccaaaccctggattatgccaca
tccaacctggcttctggagtccctgctcgcttcagtggcagtgggtctgg
gacctcttactctctcacaatcagcagaatggaggctgaagatgctgcca
cttattactgccaccagtggagtagtaacccgtacacgttcggagggggg
accaagctggaaataaaac SEQ ID NO: 17 = Mouse Ab 2.8.6 VH region
QVQLKESGPGLVAPSQSLSITCTVSGFSLTTYGVHWVRQSPGKGLEWLGV
MWPGGRTSYNPAPMSRLSISKDNSKSQVFLKMNSLQTDDTAMYYCVRGDY
EYDYYAMDYWGQGTSVTVSS SEQ ID NO: 18
caggtgcagctgaaggagtctggacctggcctggtggcgccctcacagag
cctgtccatcacttgcactgtctctgggttttcattaaccacctatggtg
tacactgggttcgccagtctccaggaaagggtctggagtggctgggagta
atgtggcctggtggaagaacaagttataatccggctcccatgtccagact
gagcatcagcaaagacaactccaagagccaagttttcttaaaaatgaaca
gtctgcaaactgatgacacggccatgtactactgtgtcagaggggactat
gaatacgattactatgctatggactactggggtcaaggaacctcagtcac
cgtctcctcag SEQ ID NO: 19 Mouse Ab 11.5.1 VL region
DIVLTQSPASLAVSLGQRATISCRASETIDSYGDSLMHWYQQKAGQPPKL
LIYRASNLESGIPARFSGSGSRTDFTLTINPVEADDVATYYCQQTDEDPY
TFGGGTKLEIK SEQ ID NO: 20
gacattgtgctgacccaatctccagcttctttggctgtgtctctagggca
gagggccaccatatcctgcagagccagtgaaactattgatagttatggcg
atagtttgatgcactggtaccagcagaaagcaggacagccacccaaactcc
tcatctatcgtgcatccaacctagaatctgggatcccgtgccaggttcagt
ggcagtgggtctcggacagacttcaccctcaccattaatcctgtggaggc
tgatgatgttgcaacctattactgtcagcaaactgatgaggatccgtaca
cgttcggaggggggaccaagctggaaataaaa SEQ ID NO: 21-Mouse Ab 11.5.1 VH region
EVQLQESGPSLVKPSQTLSLTCSVTGDSITSAYWNVVIRKFPGNKLEYMG
YISYSGSTYFNPSLKSRISITRNTSKNQYYLQLNSVTTEDTATYYCARSH
YYGYYFDYWGHGTTLTVSS SEQ ID NO: 22
gaggtgcagcttcaggagtcaggacctagcctcgtgaaaccttctcagac
tctgtccctcacctgttctgtcactggcgactccatcaccagtgcttact
ggaactggatccggaaattcccagggaataaacttgagtacatgggtac
ataagctacagtggtagcacttacttcaatccatctctcaaaagtcgaat
ctccatcactcgaaacacatccaagaaccagtactacctgcagttgaatt
ctgtgactactgaggacacagccacatattactgtgcaagatctcattac
tacggctactactttgactactggggccatggcaccactctcacagtctc
ctca SEQ ID NO: 23-Human (Homo sapiens) BTLA
polypeptide. Positions 1-30 is signal sequence,
31-151 is extracellular region, 152-178 is
transmembrane region and 179 to end is
intracellular region
MKTLPAMLGTGKLFWVFFLIPYLDIWNIHGKESCDVQLYIKRQSEHSILA
GDPFELECPVKYCANRPHVTWCKLNGTTCVKLEDRQTSWEEKNISFFIL
HFEPVLPNDNGSYRCSANFQSNLIESHSTTLYVTDVKSASERPSKDEMAS
RPWLLYRLLPLGGLPLLITTCFCLFCCLRRHQGKQNELSDTAGREINLVD
AHLKSEQTEASTRQNSQVLLSETGIYDNDPDLCFRMQEG-
SEVYSNPCLEENKPGIVYASLNHSVIGPNSRLARNVKEAPTEYASICVRS SEQ ID NO: 24-cynomolgus monkey (Macaca fascicularis) BTLA polypeptide.
MKTLPAMLGSGRLFWVVFLIPYLDIWNIHGKESCDVQLYIKRQSYHSIFA
GDPFKLECPVKYCAHRPQVTWCKLEGRHTSWKQEKNLSFFIL
HFEPVLPSDNGSYRCSANFLSAIIESHSTTLYVTDVKSASERPSKDEMAS
RPWLLYSLLPLGGLPLLITTCFCLFCFLRRHQGKQNELSDTTGREITLVD
VPFKSEQTEASTRQNSQVLLSETGIYDNEPDFCFRMQEG-
SEVYSNPCLEENKPGIIYASLNHSIIGLNSRQARNVKEAPTEYASICVRS

TABLE 4

Exemplary CDR Sequences

| SEQ ID NOs | Amino Acid Sequences | SEQ ID NOs | Amino Acid Sequences |
|---|---|---|---|
| 31 | SYGIS | 114 | WQGTHFPQT |
| 32 | EIYPRSGNTYYNEKFKG | 117 | TYYGSSQYYFDY |
| 33 | NYGSSYPFAY | 121 | DYYIN |
| 34 | SASSSVSSSYLH | 122 | RIYPGSGNTYYNEKFKG |
| 35 | RTSNLAS | 123 | GYGNSDY |
| 36 | QQWSGYPFT | 124 | RASQSIGTRIH |
| 37 | DYYMN | 125 | YASESIS |
| 38 | DINPNNGGTSYNQKFKG | 126 | QQSNSWPYT |
| 39 | WRQLRSDY | 127 | SYAIR |
| 40 | LASQTIGTWLA | 128 | EIYPRSGNTYYNENFKG |
| 41 | AATSLAD | 129 | SGGASYTMDY |
| 42 | QQLYSTPLT | 133 | SYGLI |
| 43 | SYWMH | 134 | EIYPRSGSTYYNEWFKG |
| 44 | MIHPNNGIPNYNEKFKS | 135 | RRGTGDGFDY |
| 45 | EGYYGSEGYFDV | 136 | SASQGISNYLN |
| 46 | SASSSISYIH | 137 | YTSSLHS |
| 47 | DTSKLAS | 138 | QQYIELPFT |
| 48 | HQRSTYPYT | 139 | DYYMH |
| 56 | MIHPNSGSTNYNEKFKS | 140 | YIYPNNGGNGYNQKFKG |
| 57 | KRGGLGDY | 141 | GDYYGSLRLTFAY |
| 58 | RASKSVSTSGYSYMH | 142 | KSSQSLLYSSNQKNYLA |
| 59 | LASNLES | 143 | WASTRES |
| 60 | QHSRELPYT | 144 | QQYYSYPLT |
| 61 | SSWMN | 145 | TYGVS |
| 62 | RIYPGDGDTNYNGKFKG | 146 | WINTYSGVPTYADDFKG |
| 63 | RGYGYLAY | 147 | VTTILHWYFDV |

TABLE 4-continued

Exemplary CDR Sequences

| SEQ ID NOs | Amino Acid Sequences | SEQ ID NOs | Amino Acid Sequences |
|---|---|---|---|
| 64 | KASQDVSTAVA | 148 | RASQEISGYLS |
| 65 | SASYRYT | 149 | AASTLDS |
| 66 | QQHYSTPYT | 150 | LQYASYPFT |
| 69 | GYGSSYGFAY | 159 | RRGAGDGFDY |
| 72 | QQWSGYPWT | 162 | QQYSKLPFT |
| 73 | SGYYWN | 169 | DHTIH |
| 74 | YISYDGSNNYNPSLKN | 170 | YIYPRDGSTKYNEKFKG |
| 75 | IYGNYYAMDY | 171 | SNWNFDY |
| 76 | SASSSVSYMH | 172 | KASQDVGTAVA |
| 78 | QQWSSNPPT | 173 | WASTRRT |
| 79 | DYYMI | 174 | QQYSSYPLT |
| 80 | NINPNNGGTTYNQKFKG | 180 | QQHYSTPWT |
| 81 | GGLRPLYFDY | 182 | EIYPRSGTTYYNEKFKG |
| 82 | KASENVDTYVS | 183 | RISSGSGVDY |
| 83 | GASNRYT | 186 | QQYSELPWT |
| 84 | GQSYSYPLT | 187 | SGYDWH |
| 85 | NTYMH | 188 | YISYSGSTNYNPSLKS |
| 86 | RIDPANGNTKYDPKFQG | 189 | GTPVVAEDYFDY |
| 87 | TYYGSSQHYFDY | 190 | RSSTGAVTTSNYAN |
| 88 | KSSQSLLDSDGKTYLN | 191 | ATNNRAP |
| 89 | LVSKLDS | 192 | ALWYSNHLV |
| 90 | WQDTHFPQT | 193 | TYGVH |
| 92 | RIYPGDGDANYNGKFKG | 194 | VMWPGGRTSYNPAPMS |
| 93 | EGHYYGSGYRWYLDV | 195 | GDYEYDYYAMDY |
| 94 | RASENIYSNLA | 196 | RASSSVSYMH |
| 95 | AATNLAD | 197 | ATSNLAS |
| 96 | QHFRGAPFT | 199 | SAYWN |
| 97 | DYEIH | 200 | YISYSGSTYFNPSLKS |
| 98 | PIDPDTGNTAYNQNLKG | 201 | SHYYGYYFDY |
| 99 | GGYDSDWGFAY | 202 | RASETIDSYGDSLMH |
| 100 | RSSKSLLHSNGNTFLF | 203 | RASNLES |
| 101 | RMSDLAS | 205 | SYGMS |
| 102 | MQHLEYPFT | 206 | SIRSDGNTYYPDSVKG |
| 103 | DYYLN | 207 | GGYYGSSPYY |
| 104 | LIDPYNGGSSCNQKFKG | 209 | WASTRDS |
| 105 | GNAMDY | 210 | QQYYNYLT |
| 107 | WASTRHT | 211 | SGYSWH |

TABLE 4-continued

Exemplary CDR Sequences

| SEQ ID NOs | Amino Acid Sequences | SEQ ID NOs | Amino Acid Sequences |
|---|---|---|---|
| 108 | QQHYIIPYM | 212 | YIHYSGSTNYNPSLKS |
| 109 | NTYMY | 213 | GPHRYDGVWFAY |
| 110 | RIDPANGNTKYAPKFQG | 214 | SASSSISSNYLH |
| 111 | LYYGSSYDYFDY | 216 | QQGTNIPLT |
| 386 | EIYPRSGNTYYAQKFQG | 388 | EIYPRSGQTYYAQSFQG |
| 387 | SIRSEGQTYYPDSVKG | | |

TABLE 5

Exemplary Primary VH and VL Sequences

| SEQ ID NOs | Amino Acid Sequences |
|---|---|
| 301 | QVQLQQSGAELARPGASVKLSCKASGYTFTSYGISWVKQRTGQGLEWIGEIYPRSGNTYYNEKFKGKATLTADKSSTAYMELRSLTSEDSAVYFCARNYGSSYPFAYWGQGTLVTVSA |
| 302 | EVQLQQSGPELVKPGASVKISCKASGYTFTDYYMNWVKQSHGKSLEWIGDINPNNGGTSYNQKFKGKATLTVDKSSTAYMELRSLTSEDSAVYYCARWRQLRSDYWGQGTTLTVSS |
| 303 | QVQLQQPGAELVKPRASVKLSCKASGYTFTSYWMHWVKQRPGQGLEWIGMIHPNNGIPNYNEKFKSKATLTVDKSSTAYMQLSSLTSEDSAVYHCAREGYYGSEGYFDVWGTGTTVTSS |
| 305 | QVQLQQPGAELVKPGASVKLSCKASGYTFTSYWMHWVKQRPGQGLEWIGMIHPNSGSTNYNEKFKSKATLTVDKSSSTAYMQLSSLTSEDSAVYYCARKRGGLGDYWGQGTSVTVSS |
| 306 | QVQLQQSGPELVKPGASVKISCKASGYAFSSSWMNWVKQRPGKGLEWIGRIYPGDGDTNYNGKFKGKATLTADKSSSTAYMQLSSLTSEDSAVYFCARRGYGYLAYWGQGTLVTVSA |
| 307 | QVQLQQSGAELARPGASVKLSCKASGYTFTSYGISWVKQRTGQGLEWIGEIYPRSGNTYYNEKFKGKATLTADKSSSTAYMELRSLTSEDSAVYFCARGYGSSYGFAYWGQGTLVTVSA |
| 308 | DVQLQESGPGLVKPSQSLSLTCSVTGYSITSGYYWNWIRQFPGNKLEWMGYISYDGSNNYNPSLKNRISITRDTSKNQFFLKLNSVTTEDTATYYCASIYGNYYAMDYWGQGTSVTVSS |
| 309 | EVQLQQSGPELVQPGASVKISCKASGYTFTDYYMIWVKQSHGKSLEWIGNINPNNGGTTYNQKFKGKATLTVDKSSTAYMGLPSLTSEDSAVYYCARGGLRPLYFDYWGQGTTLTVSS |
| 310 | EVQLQQSVAELVRPGASVKLSCTASGFNIKNTYMHWVKQRPEQGLEWIGRIDPANGNTKYDPKFQGKATITADTSSNTAYVQLSSLTSEDTAIYYCALTYYGSSQHYFDYWGQGTTLTVSS |
| 311 | QIQLQQSGPELVKPGASVKISCKASGYAFSSSWMNWVKKRPGKGLEWIGRIYPGDGDANYNGKFKGKATLTADKSSSTAYMQLSSLTSEDSAVYFCAGEGHYYGSGYRWYLDVWGTGTTVTVSS |
| 312 | QVQLQQSGAELVRPGASVTLSCKASGYTFTDYEIHWVKQTLVHGLEWIGPIDPDTGNTAYNQNLKGKAILTADKSSSTAYMELRSLTSEDSAVYYCTRGGYDSDWGFAYWGQGTLVTVSA |
| 313 | EVQLQQSGPVLVKPGASVKMSCKASGYTFTDYYLNWVKQSHGKSLEWIGLIDPYNGGSSCNQKFKGKATLTVDKSSTAYMDLNSLTSEDSAVYYCARGNAMDYWGQGTSVTVSS |
| 314 | EVQLQQSVAELVRPGASVKLSCTASGFNIKNTYMYWVKQRPEQGLEWIGRIDPANGNTKYAPKFQGKATITADTSSNTAYLQLSSLTSEDTAIYYCALLYYGSSYDYFDYWGQGTTLTVSS |

TABLE 5-continued

Exemplary Primary VH and VL Sequences

| SEQ ID NOs | Amino Acid Sequences |
|---|---|
| 315 | EVQLQQSVAELVRPGASVKLSCTASGFNIKNTYMHWVKQRP EQGLEWIGRIDPANGNTKYAPKFQGKATITADTSSNTAYLQ LSSLTSEDTAIYYCALTYYGSSQYYFDYWGQTTLTVSS |
| 316 | QVQLKQSGAELVRPGASVKLSCKASGYTFTDYYINWVKQRP GQGLEWIARIYPGSGNTYYNEKFKGKATLTAEKSSSTAYMQ LSSLTSEDSAVYFCARGYGNSDYWGQGTTLTVSS |
| 317 | QVQLQQSGAELARPGASVRLSCKASGYTFTSYAIRWVKQRT YGQGLEWIGEIPRSGNTYYNENFKGKATLTADKSSSTAYME LRSLTSEDSAVYFCARSGGASYTMDYWGQGTSVTVSS |
| 318 | QVQLQQSGAELARPGASVRLSCKASGYTFTSYGLIWLKQRT GQGLEWIGEIYPRSGSTYYNEWFKGKATLTADKSSNTAFME LRSLTSEDSAVYFCARRGTGDGFDYWGQGTILTVSS |
| 319 | EVQLQQSGPELVKPGASVKMSCKASGYTFTDYYMHWVKQSH GKSLEWIGYIYPNNGGNGYNQKFKGKATLTVDKSSSTAYME LRSLTSEDSAVYYCAIGDYYGSLRLTFAYWGQGTLVTVSA |
| 320 | QIQLVQSGPELKKPGETVKISCKASGYTFTTYGVSWVKQAP GKVLKWMGWINTYSGVPTYADDFKGRFAFSLETSASTAYLQ ISNLKNEDTATYFCAPVTTILHWYFDVWGTGTTVTVSS |
| 321 | QVQLQQSGAELARPGASVRLSCKASGYTFTSYGISWVKQRT GQGLEWIGEIYPRSGNTYYNEKFKGKATLTADKSSSTAYME LRSLTSEDSAVYFCARNYGSSYPFAYWGQGTLVTVSA |
| 322 | QVQLQQSGAELARPGASVKLSCKASGYTFTSYGISWVKQRT GQGLEWIGEIYPRSGNTYYNEKFKGKATLTADKSSSTAYME LRSLTSEDSAVYFCARRGAGDGFDYWGQGTTLTVSS |
| 324 | QDQLQQSDAELVKPGASVKISCKVSGYTFTDHTIHWMKQRP EQGLEWIGYIYPRDGSTKYNEKFKGKATLTADKSSSTAYMQ LNSLTSEDSAVYFCASSNWNFDYWGQGTTLTVSS |
| 326 | QVQLQQSGAELARPGASVKLPCKASGYTFTSYGISWVKQRT GQGLEWIGEIYPRSGTTYYNEKFKGKATLTADKSSSTAYME LRSLTSEDSAVYFCARRISSGSGVDYVVGQGTTLTVSS |
| 327 | DVQLQESGPGMVKPSQSLSLTCTVTGYSITSGYDWHWIRHF PGNKLEWMGYISYSGSTNYNPSLKSRISITHDTSKNHFFLK LNSVTTEDTATYYCARGTPVVAEDYFDYWGQGTTLTVSS |
| 330 | EVKLVESGGGLVKPGGSLKLSCAASGFTLSSYGMSWVRQIP EKRLEWVASIRSDGNTYYPDSVKGRFIISRDNARNILYLQM SSLRSEDTAMYYCTRGGYYGSSPYYWGQGTTLTVSS |
| 331 | DVQLQESGPDLVKPSQSLSVTCTVTGYSITSGYSWHWIRQF PGNKLEWMGYIHYSGSTNYNPSLKSRISITRDTSKNQFFLQ LSSVTTEDTATYYCASGPHRYDGVWFAYWGQGTLVTVSS |
| 351 | ENVLTQSPAIMAASLGQKVTMTCSASSSVSSSYLHWYQQKS GASPKPLIHRTSNLASGVPARFSGSGSGTSYSLTISSVEAE DDATYYCQQWSGYPFTFGGGTKLEIK |
| 352 | DIQMTQSPASQSASLGESVTITCLASQTIGTWLAWYQQKPG KSPQLLIYAATSLADGVPSRFSGSGSGTKFSFKISSLQAED FVSYYCQQLYSTPLTFGAGTKLELK |
| 353 | QIVLTQSPAIMSASPGEKVTMTCSASSSISYIHWYQQKPGT SPKRWIYDTSKLASGVPARFSGSGSGTSYSLTISSMEAEDA ATYYCHQRSTYPYTFGGGTKLEIK |
| 355 | DIVLTQSPASLAVSLGQRATISCRASKSVSTSGYSYMHWYQ QKPGQPPKLLIYLASNLESGVPARFSGSGSGTDFTLNIHPV EEEDAATYYCQHSRELPYTFGGGTKLEIK |
| 356 | DIVMTQSHKFMSTSVGDRVSITCKASQDVSTAVAWYQQKPG QSPKLLIYSASYRTGVPDRFTGSGSGTDFTFTISSVQAED LAVYYCQQHYSTPYTFGGGTKLEIK |
| 357 | ENVLTQSPAIMAASLGQKVTMTCSASSSVSSSYLHWYQQKS GASPKPLIHRTSNLASGVPARFSGSGSGTSYSLTISSVEAE DDATYYCQQWSGYPWTFGGGTKLEIK |
| 358 | QIVLTQSPAIMSASPGEKVTMTCSASSSVSYMHWYQQKSGT SPKRWIYDTSKLASGVPARFSGSGSGTSYSLTISSMEAEDA ATYYCQQWSSNPPTFGSGTKLEIK |
| 359 | NIVMTQSPKSMSMSVGERVTLSCKASENVDTYVSWYQQKPE QSPKLLIYGASNRYTGVPDRFTGSGSATDFTLTISSVQAED LADYHCGQSYSYPLTFGAGTKLELI |
| 360 | DVVMTQTPLTLSVTIGQPASISCKSSQSLLDSDGKTYLNWL LQRPGQSPKRLIYLVSKLDSGVPDRFTGSGSGTDFTLKISR VEAEDLGVYYCWQDTHFPQTFGGGTKLEIK |
| 361 | DIQMTQSPASLSVSVGETVTITCRASENIYSNLAWYQQKQG KSPQLLVYAATNLADGVPSRFSGSGSGTQYSLKINSLQSED FGSYYCQHFRGAPFTFGSGTKLEIK |
| 362 | DIVMTQATPSVPVTPGESVSISCRSSKSLLHSNGNTFLFWF LQRPGQSPQLLIYRMSDLASGVPDRFSGSGSGTAFTLRISR VEAEDVGIYYCMQHLEYPFTFGSGTKLEIK |
| 363 | DIVMTQSHKFMSTSVGDRVSITCKASQDVSTAVAWYQEKPG QSPKLLIYWASTRHTGVPDRFTGSGSGTDYILNISSVQAED LALYYCQQHYIIPYMFGGGTKLEIK |
| 364 | DVVMTQTPLTLSVTIGQPASISCKSSQSLLDSDGKTYLNWL LQRPGQSPKRLIYLVSKLDSGVPDRFTGSGSGTDFTLKISR VEAEDLGVYYCWQGTHFPQTFGGGTKLEIK |
| 366 | DILLTQSPAILSVSPGERVSFSCRASQSIGTRIHWYQQRTN GSPRLLIKYASESISGIPSRFSGSGSGTDFTLSINSVESED IADYYCQQSNSWPYTFGGGTKLEIK |
| 367 | ENVLTQSPAIMAASLGQKVTMTCSASSSVSSSYLHWYQQKS GASPKPLIHRTSNLASGVPARFSGSGSGTSYSLTISSVEAE DDATYYCQQWSGYPPFTFGSGTKLEIK |
| 368 | DIQMTQTTSSLSASLGDRVTISCSASQGISNYLNWYQQKPD GTVKLLIYYTSSLHSGVPSRFSGSGSGTDYSLTISNLEPED IATYYCQQYIELPFTFGSGTKLEIK |
| 369 | DIVMSQSPSSLAVSVGEKVTMSCKSSQSLLYSSNQKNYLAW YQQKPGQSPKLLIYWASTRESGVPDRFTGSGSGTDFTLTIS SVKAEDLAVYYCQQYYSYPLTFGAGTKLELK |
| 370 | DIQMTQSPSSLSASLGERVSLTCRASQEISGYLSWLQQKPD GTIKRLIYAASTLDSGVPKRFRGSRSGSDYSLTISSLESED FADYYCLQYASYPFTFGSGTKLEIK |
| 372 | DIQMTQTTSSLSASLGDRVTISCSASQGISNYLNWYQQKPD GTVKLLIYYTSSLHSGVPSRFSGSGSGTDYSLTISNLEPED IATYYCQQYSKLPFTFGSGTKLEIK |
| 374 | DIVMTQSHKFMSTSVGDRVSITCKASQDVGTAVAWYQQKPG QSPKLLIYWASTRRTGVPDRFTGSGSGTDFTLTISNVQSED LADYFCQQYSSYPTFGGGTKLELK |
| 375 | DIVMTQSHKFMSTSVGDRVSITCKASQDVSTAVAWYQQKPG QSPKLLIYSASYRTGVPDRFTGSGSGTDFTFTISSVQAED LAVYYCQQHYSTPWTFGGGTKLEIK |
| 376 | DIQMTQTTSSLSASLGDRVTISCSASQGISNYLNWYQQKPD GTVKLLIYYTSSLHSGVPSRFSGSGSGTDYSLTISNLEPED IATYYCQQYSELPWTFGGGTKLEIK |
| 377 | QAVVTQESALSTSPGETVTLTCRSSTGAVTTSNYANWVQEK PDHLFTGLIGATNNRAPGVPARFSGSLIGDKAALTITGAQT EDEAIYFCALWYSNHLVFGGGTKLTVLG |

TABLE 5-continued

Exemplary Primary VH and VL Sequences

| SEQ ID NOs | Amino Acid Sequences |
|---|---|
| 378 | DIVMTQSPLSLPVTPGEPASISCKSSQSLLYSSNQKNYLAW YQQKPGQSPKLLIYWASTRESGVPDRFSGSGSGTDFTLKIS RVEAEDVGVYYCQQYYNYLTFGGGTKVEIK |
| 380 | DIVMSQSPSSLPVSVGEKISMTCKSSQSLLYSSNQKNYLAW YQQKPGQSPKLLIYWASTRDSGVPDRFIGSGSGTDFTLTIN SVKAEDLAVYYCQQYYNYLTFGAGTKLELK |
| 381 | EIVLTQSPTTMAASPGEKITITCSASSSISSNYLHWYQQKP GFSPKWYRTSNLASGVPARFSGSGSGTSYSLTIGTMEAEDV ATYYCQQGTNIPLTFGAGTKLEIK |
| 382 | QVQLVQSGAELKKPGASVKVSCKASGYTFTSYAIRWVRQAT GQGLEWMGEIYPRSGNTYYAQKFQGRATLTADKSISTAYME LSSLRSEDTAVYFCARSGGASYTMDYWGQGTTVTVSS |
| 383 | ENVLTQSPATLSLSPGERATLSCSASSSVSSSYLHWYQQKP GQSPRPLIHRTSNLASGIPARFSGSGSGTDYTLTISSLEPE DFAVYYCQQWSGYPFTFGSGTKLEIK |
| 384 | EVQLVESGGGLVKPGGSLRLSCAASGFTLSSYGMSWVRQAP GKGLEWVASIRSDGNTYYPDSVKGRFTISRDNAKNSLYLQM SSLRAEDTAVYYCTRGGYYGSSPYYWGQGTTVTVSS |
| 385 | DIVMTQSPLSLPVTPGEPASISCKSSQSLLYSSNQKNYLAW YQQKPGQSPQLLIYWASTRDSGVPDRFSGSGSGTDFTLKIS RVEAEDVGVYYCQQYYNYLTFGGGTKVEIK |
| 389 | QVQLVQSGAELKKPGASVKVSCKASGYTFTSYAIRWVRQAT GQGLEWMGEIYPRSGTYYAQSFQGRATLTADKSTSTAYME LSSLRSEDTAVYFCARSGGASYTMDYWGQGTTVTVSS |
| 390 | EVQLVESGGGLVKPGGSLRLSCAASGFTLSSYGMSWVRQAP GKGLEWVASIRSEGQTYYPDSVKGRFTISRDNAKNTLYLQM SSLRAEDTAVYYCTRGGYYGSSPYYWGQGTTVTVSS |

What is claimed is:

1. An antibody or an antigen-binding fragment thereof that specifically binds B and T Lymphocyte Attenuator (BTLA), wherein the antibody or antigen-binding fragment thereof comprises a heavy chain and a light chain, wherein:
   (i) the light chain comprises a light chain variable region comprising three CDRs: CDRL1, CDRL2, and CDRL3, wherein (a) CDRL1 has the amino acid sequence as set forth in SEQ ID NO: 142; (b) CDRL2 has the amino acid sequence as set forth in SEQ ID NO: 143, with 0 to 1 amino acid modification at position 6 numbered according to SEQ ID NO: 143; and (c) CDRL3 has the amino acid sequence as set forth in SEQ ID NO: 210; and
   (ii) the heavy chain comprises a heavy chain variable region comprising three CDRs: CDRH1, CDRH2, and CDRH3, wherein (a) CDRH1 has the amino acid sequence as set forth in SEQ ID NO: 205; (b) CDRH2 has the amino acid sequence as set forth in SEQ ID NO: 387, with 0 to 2 amino acid modifications at positions 5 and 7 numbered according to SEQ ID NO: 387; and (c) CDRH3 has the amino acid sequence as set forth in SEQ ID NO: 207.

2. The antibody or antigen-binding fragment thereof of claim 1, wherein the antibody or antigen-binding fragment thereof binds a residue of BTLA selected from the group consisting of: D52, P53, E55, E57, E83, Q86, E103, L106 and E92.

3. The antibody or antigen-binding fragment thereof of claim 1, wherein the antibody or antigen-binding fragment thereof agonizes human BTLA expressed on the surface of an immune cell.

4. The antibody or antigen-binding fragment thereof of claim 1, wherein the light chain variable region comprises an amino acid sequence having at least 90% identity to the amino acid sequence as set forth in SEQ ID NO: 378.

5. The antibody or antigen-binding fragment thereof of claim 4, wherein the heavy chain variable region comprises an amino acid sequence having at least 90% identity to the amino acid sequence as set forth in SEQ ID NO: 390.

6. The antibody or antigen-binding fragment thereof of claim 1, wherein the antibody or antigen-binding fragment thereof binds human BTLA at a $K_D$ of less than 10 nM, as determined by surface plasmon resonance at 37° C.

7. The antibody or antigen-binding fragment thereof of claim 1, wherein the antibody or antigen-binding fragment thereof binds human BTLA at a $K_D$ of less than 2 nM, as determined by surface plasmon resonance at 37° C.

8. The antibody or antigen-binding fragment thereof of claim 1, wherein the antibody or antigen-binding fragment thereof binds cynomolgus BTLA at a $K_D$ of less than 20 nM, as determined by surface plasmon resonance at 37° C.

9. The antibody or antigen-binding fragment thereof of claim 1, wherein the antibody or antigen-binding fragment thereof inhibits proliferation of T cells in vitro, as determined by a mixed lymphocyte reaction assay.

10. The antibody or antigen-binding fragment thereof of claim 1, wherein the antibody or antigen-binding fragment thereof does not inhibit binding of BTLA to herpes virus entry mediator (HVEM).

11. The antibody or antigen-binding fragment thereof of claim 1, further comprising a domain that binds to an Fc receptor.

12. The antibody or antigen-binding fragment thereof of claim 11, wherein said Fc receptor is FcγRIIB.

13. The antibody or antigen-binding fragment thereof of claim 1, wherein the antibody or antigen-binding fragment thereof is a humanized antibody.

14. The antibody or antigen-binding fragment thereof of claim 1, wherein the antibody or antigen-binding fragment thereof is a monoclonal antibody.

15. An isolated nucleic acid that comprises one or more nucleotide sequences encoding polypeptides capable of forming the antibody or antigen-binding fragment thereof of claim 1.

16. A host cell comprising one or more nucleic acid molecules encoding the amino acid sequence of a heavy chain and the amino acid sequence of a light chain, which when expressed are capable of forming the antibody or antigen-binding fragment thereof of claim 1.

17. A method, comprising culturing the host cell of claim 16 under conditions for production of the antibody or antigen-binding fragment thereof.

18. A method, comprising:
(1) providing a host cell comprising one or more nucleic acid molecules encoding the amino acid sequence of a heavy chain and the amino acid sequence of a light chain, which when expressed are capable of forming the antibody or antigen-binding fragment thereof of claim 1;
(2) culturing the host cell expressing the encoded amino acid sequences; and
(3) isolating the antibody or antigen-binding fragment thereof.

19. A pharmaceutical composition comprising a therapeutically effective amount of the antibody or antigen-binding fragment thereof of claim 1 and at least one pharmaceutically acceptable excipient.

20. A method of treating a BTLA-related disease or condition in a patient in need thereof, comprising administering to the patient a therapeutically effective amount of the antibody or antigen-binding fragment thereof of claim 1.

21. The method of claim 20, wherein the disease or condition comprises an inflammatory disease, an autoimmune disease or disorder, or a proliferative disease or disorder.

22. The method of claim 20, wherein the disease or condition comprises Addison's disease, allergy, alopecia areata, amyotrophic lateral sclerosis, ankylosing spondylitis, anti-phospholipid syndrome, asthma, autoimmune haemolytic anaemia, autoimmune hepatitis, autoimmune pancreatitis, autoimmune polyendocrine syndrome, Behcet's disease, bullous pemphigoid, cerebral malaria, chronic inflammatory demyelinating polyneuropathy, coeliac disease, Crohn's disease, Cushing's Syndrome, dermatomyositis, diabetes mellitus type 1, eosinophilic granulomatosis with polyangiitis, graft versus host disease, Graves' disease, Guillain-Barre syndrome, Hashimoto's thyroiditis, Hidradenitis Suppurativa, inflammatory fibrosis, inflammatory bowel disease, juvenile arthritis, Kawasaki disease, leukemia, lymphoma, lymphoproliferative disorders, multiple sclerosis, myasthenia gravis, myeloma, neuromyelitis optica, pemphigus, polymyositis, primary biliary cholangitis, primary sclerosing cholangitis, psoriasis, psoriatic arthritis, rheumatoid arthritis, sarcoidosis, Sjögren's syndrome, systemic lupus erythematosus, Takayasu's arteritis, temporal arteritis, transplant rejection, transverse myelitis, ulcerative colitis, uveitis, vasculitis, vitiligo, or Vogt-Koyanagi-Harada Disease.

23. The method of claim 20, wherein the disease or condition comprises vasculitis, systemic lupus erythematosus, ulcerative colitis, inflammatory bowel disease, or graft versus host disease.

24. The antibody or antigen-binding fragment thereof of claim 1, wherein CRDL2 has no amino acid modifications as compared to SEQ ID NO: 143.

25. The antibody or antigen-binding fragment thereof of claim 1, wherein CRDH2 has an amino acid modification at position 5, position 7, or both, numbered according to SEQ ID NO: 387.

26. The antibody or antigen-binding fragment thereof of claim 25, wherein CDRL2 has no amino acid modifications as compared to SEQ ID NO: 143.

27. The antibody or antigen-binding fragment thereof of claim 25, wherein CDRH2 has Aspartic acid (D) at position 5, and Asparagine (N) at position 7, numbered according to SEQ ID NO: 387.

28. The antibody or antigen-binding fragment thereof of claim 1, wherein the light chain variable region comprises the amino acid sequence as set forth in SEQ ID NO: 378.

* * * * *